United States Patent

Shiosaki et al.

Patent Number: 5,270,302
Date of Patent: Dec. 14, 1993

[54] DERIVATIVES OF TETRAPEPTIDES AS CCK AGONISTS

[75] Inventors: Kazumi Shiosaki; Alex M. Nadzan, both of Libertyville; Hana Kopecka, Vernon Hills; Youe-Kong Shue, Vernon Hills; Mark W. Holladay, Vernon Hills; Chun W. Lin, Wood Dale; Hugh N. Nellans, Mundelein, all of Ill.

[73] Assignee: Abbott Laboratories, Abbott Park, Ill.

[21] Appl. No.: 713,010

[22] Filed: Jun. 17, 1991

Related U.S. Application Data

[63] Continuation-in-part of Ser. No. 541,230, Jun. 20, 1990, abandoned, which is a continuation-in-part of Ser. No. 5,673, Dec. 18, 1989, which is a continuation-in-part of Ser. No. 287,955, Dec. 21, 1988, abandoned.

[51] Int. Cl.$^5$ ............ A61K 37/02; C07K 5/08; C07K 5/10
[52] U.S. Cl. ............................ 514/18; 514/17; 514/19; 530/330; 530/331
[58] Field of Search .............. 530/330, 331; 514/17, 514/18, 19

[56] References Cited

U.S. PATENT DOCUMENTS

| | | | |
|---|---|---|---|
| 2,932,635 | 4/1960 | Amiard et al. | 530/331 |
| 4,687,760 | 8/1987 | Martinez et al. | 514/18 |
| 4,808,701 | 2/1989 | Darho et al. | 530/317 |
| 4,818,748 | 4/1989 | Bender et al. | 514/17 |

FOREIGN PATENT DOCUMENTS

| | | |
|---|---|---|
| 0175617 | 3/1986 | European Pat. Off. |
| 2945239 | 5/1981 | Fed. Rep. of Germany ........ 514/18 |
| 45-10506 | 4/1970 | Japan |
| 1063728 | 3/1967 | United Kingdom |

OTHER PUBLICATIONS

Vanderhaeger et al., *Neuronal Cholecystokinin*, 1985 pp. 461–462, 593, 599.

Miyamoto et al.,-*Chem. Pharm. Bull.*, 1986, 34(2) pp. 694–700.

Stewart et al., (*Solid Phase Peptide Synthesis*, 2nd Ed, 1984, Pierce Chemical Company, Rockford, Ill., pp. 27 and 28.

Martinez, et al., *J. Med., Chem.* 1985, 28:1874.

Yabe et al., *Chem. Pharm. Bull.*, 1977, 25:2731.

Kovacs et al., "Cholesystokinin Analogs Containing Non-Coded Amino Acids", Pept Synthesis, Structure and Function, Proc. 9th Am. Pept. Symp., 1985, pp. 583–586.

*Primary Examiner*—Lester L. Lee
*Attorney, Agent, or Firm*—Richard A. Elder; Steven R. Crowley; Steven F. Weinstock

[57] ABSTRACT

Selective and potent Type-A CCK receptor agonists of formula (I):

$$X-Y-Z-Q \qquad (I)$$

or a pharmaceutically acceptable salt thereof, wherein, X is selected from

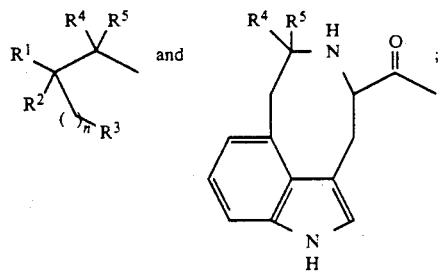

Y is selected from

Z is (Abstract continued on next page.)

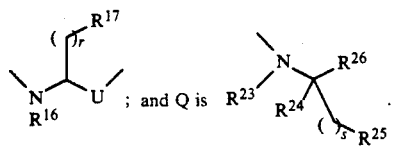
or pharmaceutically-acceptable salts thereof, useful in the treatment of gastrointestinal disorders (including gallbladder disorders), central nervous system disorders, insulin-related disorders and pain, as well as in appetite regulation.
10 Claims, 2 Drawing Sheets

DERIVATIVES OF TETRAPEPTIDES AS CCK AGONISTS

CROSS REFERENCE TO RELATED APPLICATIONS

This is a continuation-in-part of copending U.S. patent application Ser. No. 541,230, filed Jun. 20, 1990 and now abandoned, which is a continuation-in-part of PCT patent application Ser. No. PCT/US89/05673, filed Dec. 18, 1989, which is a continuation-in-part of U.S. patent application Ser. No. 287,955, filed Dec. 21, 1988, now abandoned.

TECHNICAL FIELD

The present invention relates to novel organic compounds and compositions which mimic the effects of cholecystokinin, to processes for preparing such compounds, to synthetic intermediates employed in these processes and to a method of treating gastrointestinal disorders (including gallbladder disorders), central nervous system disorders, insulin-related disorders and pain, or of regulating appetite with such compounds.

BACKGROUND OF THE INVENTION

Cholecystokinin (CCK) is a polypeptide hormone found in both the periphery and the brain that plays a major role in gut function, in the digestive process and in the control of feeding behaviors. Relative to other neuropeptides, high concentrations of CCK and CCK receptors are found in the brain and CCK meets many of the criteria for consideration as a neurotransmitter (J. F. Rehfeld, *J. Neurochem*, 1985, 448:1-8), suggesting important CNS functions for this peptide. CCK exists in multiple biologically active forms (CCK-58, CCK-39, CCK-33, CCK-8 and CCK-4), with CCK-33, CCK-8 and CCK-4 predominating in the periphery (J. Martinez in *Comprehensive Medicinal Chemistry*, Vol. 3, J. C. Emmett, ed, Pergamon Press, Oxford, England, 1990, p. 925) and the C-terminal octapeptide, CCK-8, predominating in the brain.

CCK has a variety of regulatory roles in the periphery including gallbladder contraction and pancreatic enzyme secretion (V. Mutt in *Gastrointestinal Hormones*, G. B. J. Glass, ed, Raven Press, New York, 1980, p. 169; J. A. Williams, *Biomed. Res.*, 1982, 3:107), inhibition of gastric emptying and suppression of food intake. CCK and its fragments are believed to play an important role in appetite regulation and satiety (Della-Fera, *Science* 1979, 206:471; Saito et al., *Nature* 1981, 289:599; and Smith, *Eating and Its Disorders*, A. J. Stunkard and E. Stellar, eds., Raven Press, New York, 1984, p. 67) and recently, patients with bulimia were shown to have lower than normal CCK levels in their plasma (Geracioti et al., *New England Journal of Medicine*, 1988, 319:683). An additional role for CCK in the periphery is to regulate the release of insulin. CCK has been shown to increase the levels of insulin when administered to mammals (Rushakoff et al., *J. Clin. Endocrinol. Metab.* 1987, 65:395).

CCK in the brain has been suggested to have a role in schizophrenia (N.P.V. Nair et al, *Prog. Brain Res.*, 1986, 65:237), memory and cognition (S. Itoh and H. Lal, *Drug Dev. Res.*, 1990, 21:257), and CCK antagonists have been suggested to be potentially useful in drug abuse therapy (B. Costall et al. in "Proceedings of the Cambridge Symposia, The Neurological Basis of Anxiety," Robinson College, Cambridge, U.K., Sep. 7 and 8, 1990).

Two sub-types of the CCK receptor have been identified. Type-A CCK receptors, commonly referred to as the "peripheral-type" receptor, are primarily found in the pancreas, gall bladder, ileum and on vagal afferent nerve fibers. Type-A CCK receptors bind CCK-8 with high affinity but have low affinity for desulfated CCK-8 and CCK-4. The brain contains predominantly the Type-B receptors that bind CCK-8, desulfated CCK-8 and CCK-4 with high affinity. Type-A CCK receptors are found in the brain, although in low abundance (D. R. Hill et al., *Brain Res*, 1988, 454:101-5; D. R. Hill et al., *Neurosci Lett.*, 1988, 89:133-9; R. W. Barrett et al., *Mol. Pharmacol*, 1989, 36:285-90; and D. R. Hill et al., *J. Neurosci*, 1990, 10:1070-81), and play an important role there also (V. Dauge et al., *Pharmacol Biochem Behav.*, 1989, 34:157-63; J. Soar et al., *Pharmacol. Biochem. Behav*, 1989, 33:637-40). Type-A receptor-selective CCK agonists are currently of particular interest as potential anorectic agents because of the ability of CCK-8 and Type-A CCK-selective agonists to suppress food intake in several animal species (Della-Fera et al., *Science*, 1979, 206:471; K. E. Asin et al., *Intl Conference on Obesity.*, 1990, Abstract p. 40).

Obesity is a major disorder affecting as much as one third of the North American population. Several studies have shown that such individuals are at increased risk in developing cardiovascular disease (hypertension and hypercholesterolemia), diabetes and several types of cancer. The effective treatment of obesity, however, remains a largely unachieved goal. Existing phamacotherapeutic approaches to weight loss involve the use of amphetamine-based agents such as amphetamine, diethylpropion, mazindol and fenfluramine which act directly on the CNS to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions other drugs such as MAO inhibitors and antihypertensives. There is also a subpopulation of obese patients that is refractory to present anorectic drug treatments. The medical need is high for an effective anorectic agent which overcomes the above disadvantages of existing therapies. Of particular need are agents which act by alternative mechanisms to modulate food intake and/or metabolism.

Several references have disclosed CCK agonists or analogs of CCK-8. For example, U.S. Pat. No. 4,490,364, issued Dec. 25, 1984 to Rivier, discloses heptapeptide, octapeptide and nonapeptide analogs of CCK-8 as CCK agonists for stimulating gallbladder contractions, arresting the secretion of gastric acid and treating convulsions. J. D. Rosamond in European Patent Application EP381,340, published Aug. 8, 1990, and in European Patent Application EP268,297, published May 25, 1988, discloses hepta- and octapeptides with sulfate ester groups which are useful for treating obesity.

C-terminal fragments of CCK have recently been reported to function as CCK receptor antagonists or gastrin receptor antagonists (Jensen et al., *Biochem. Biophys. Acta*, 1983, 757:250; Spanarkel, *J. Biol. Chem.* 1983, 258:6746). Japanese Patent Application 45/10506 to Miyao et al., discloses a tetrapeptide derivative of the carboxy terminal sequence of gastrin (L-Trp-L-Lys-L-Asp-L-PheNH$_2$) which act as antagonists of gastrin.

In contrast, the present invention relates to tetrapeptide analogs which function as agonists of CCK Type-A receptor activity. These CCK agonists are useful in the treatment and prevention of CCK-related disorders of the gastrointestinal, appetite and insulin regulatory systems of animals, especially man. They are also useful as central nervous system suppressants which can exhibit antipsychotic, neuroleptic, anxiolytic, and anticonvulsant effects, among other effects on central nervous system disorders.

SUMMARY OF THE INVENTION

The present invention is directed to cholecystokinin receptor agonists of the formula:

$$X-Y-Z-Q \quad (I)$$

or a pharmaceutically acceptable salt thereof, wherein, X is selected from

[Chemical structures shown]

Y is selected from

[Chemical structures shown]

Z is

[Chemical structures shown]; and Q is [Chemical structure shown]

The present invention is also directed to pharmaceutical compositions comprising a therapeutically-effective amount of a compound of formula (I) and a pharmaceutically-acceptable carrier or diluent, as well as to a method of treating gastrointestinal disorders (including gallbladder disorders), central nervous system disorders, insulin-related disorders and pain, or of regulating appetite in humans and lower mammals, by administration of a compound of formula (I).

DETAILED DESCRIPTION OF THE INVENTION

Figure 1:
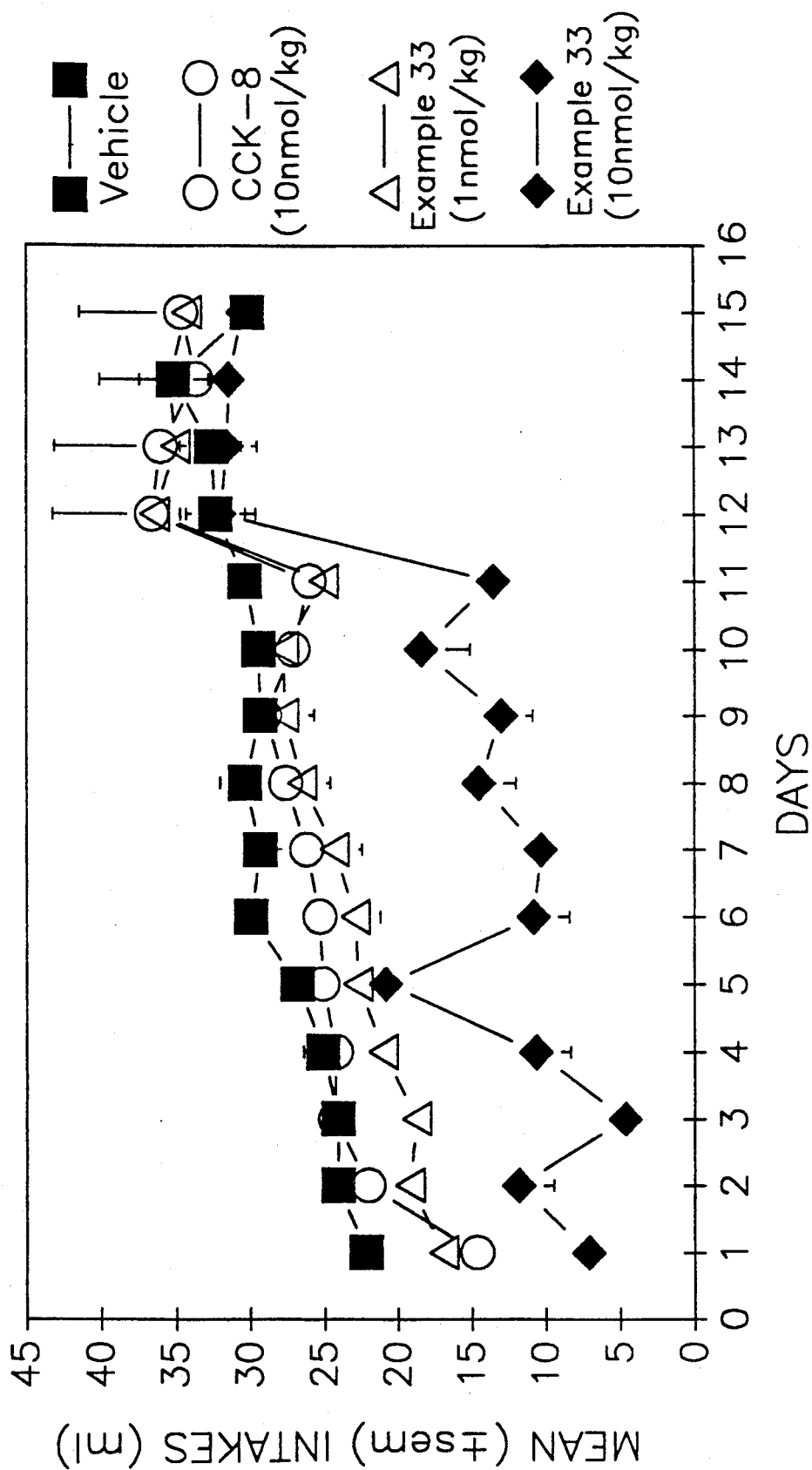
FIG. 1 is a plot comparing the mean level of liquid food intake (mLs.) for rats after chronic administration of vehicle, CCK-8 (10 nmol/kg) or the compound of Example 33 (1 nmol/kg or 10 nmol/kg).

This invention relates to novel tetrapeptide compounds of formula (I) which are selective and potent Type-A CCK receptor agonists and, therefore, may be used in the treatment of gastrointestinal disorders (including gallbladder disorders), central nervous system disorders, insulin-related disorders and pain, as well as in appetite regulation.

In particular, the invention relates to compounds of formula (I):

$$X-Y-Z-Q$$

or a pharmaceutically-acceptable salt thereof, wherein, X is selected from the group consisting of

[Chemical structure (A) shown]

wherein n is 1 or 2;
R$^1$ is selected from the group consisting of
  (1) hydrogen,
  (2) hydroxy,
  (3) halogen,
  (4) C$_1$-C$_4$-alkyl,
  (5) C$_1$-C$_4$-alkoxy,
  (6) halo-C$_1$-C$_4$-alkyl,
  (7) C$_1$-C$_4$-alkanoyl,
  (8) C$_1$-C$_4$-alkoxycarbonyl,
  (9) C$_1$-C$_4$-alkoxycarbonyloxy,
  (10) aminocarbonyl,
  (11) C$_1$-C$_4$-alkylaminocarbonyl,
  (12) cyano,
  (13) R$^6$HN— wherein
    R$^6$ is selected from the group consisting of
      (a) hydrogen,
      (b) C$_1$-C$_6$-alkyl,
      (c) —C(O)—R$^7$, wherein
        R$^7$ is selected from the group consisting of
          (i) C$_1$-C$_6$-alkyl, wherein the alkyl group may be substituted with from 1 to 3 halogens or 1 substituent selected from carboxy, C$_1$-C$_4$-alkoxycarbonyl, aminocarbonyl, C$_1$-C$_4$-alkylaminocarbonyl, (C$_1$-C$_4$-alkyl)$_2$-aminocarbonyl and cyano,
          (ii) cyclo-C$_3$-C$_{10}$-alkyl,
          (iii) C$_6$-C$_{10}$-aryl unsubstituted or substituted with 1 to 3 substituents selected from halogen, hydroxy and C$_1$-C$_4$-alkoxy,
          (iv) C$_7$-C$_{14}$-arylalkyl unsubstituted or substituted with 1 to 3 substituents selected from halogen, hydroxy and C$_1$-C$_4$-alkoxy,
          (v) diphenyl-(C$_1$-C$_4$-alkyl),
          (vi) C$_1$-C$_6$-alkoxy, wherein the alkyl group may be substituted with from 1 to 3 halogens or with a substituent selected from carboxy, $C_1$–$C_4$-alkoxycarbonyl, aminocarbonyl, $C_1$–$C_4$-alkylaminocarbonyl, ($C_1$–$C_4$-alkyl)$_2$aminocarbonyl, hydroxy-$C_1$–$C_4$-alkylaminocarbonyl, morpholinocarbonyl, thiomorpholinocarbonyl, piperidinylcarbonyl, 4-methyl-1-piperazinylcarbonyl, hydroxy or $C_1$–$C_4$-alkoxy,
(vii) cyclo-$C_3$–$C_{10}$-alkoxy,
(viii) $C_6$–$C_{10}$-aryl unsubstituted or substituted with 1 to 3 substituents selected from halogen, hydroxy and $C_1$–$C_4$-alkoxy,
(ix) $C_7$–$C_{14}$-arylalkyl, wherein the aryl may be substituted with 1 to 3 substituents selected from halogen, hydroxy and $C_1$–$C_4$-alkoxy,
(x) $C_1$–$C_6$-alkylamino,
(xi) cyclo-$C_3$–$C_{10}$-alkylamino,
(xii) $C_6$–$C_{10}$-arylamino, wherein the aryl may be substituted with 1 to 3 substituents selected from halogen, hydroxy and $C_1$–$C_4$-alkoxy, and
(xiii) $C_6$–$C_{10}$-aryl-$C_1$–$C_4$-alkylamino, wherein the aryl may be substituted with 1 to 3 substituents selected from halogen, hydroxy and $C_1$–$C_4$-alkoxy, and
(d) —S(O)$_2$R$^8$, wherein
R$^8$ is selected from
(i) $C_1$–$C_4$-alkyl, unsubstituted or mono-, di- or trisubstituted substituted with from 1 to 3 halogens,
(ii) $C_6$–$C_{10}$-aryl, and
(iii) $C_7$–$C_{14}$-arylalkyl;
R$^2$ is hydrogen or $C_1$–$C_4$-alkyl;
R$^3$ is bicyclic carbocycle or bicyclic heterocycle as defined below; and
R$^4$ and R$^5$ are each hydrogen or taken together are =O; and

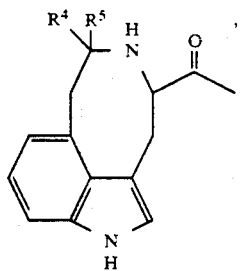
(B)

wherein R$^4$ and R$^5$ are as defined above, and the indole ring is unsubstituted or substituted with a substituent selected from the group consisting of hydroxy, halo, $C_1$–$C_4$-alkylamino, ($C_1$–$C_4$-alkyl)$_2$amino, $C_1$–$C_4$-alkoxy, thio-$C_1$–$C_4$-alkoxy, carboxy, $C_1$–$C_4$-alkoxycarbonyl, $C_1$–$C_4$-alkyl, $C_3$–$C_8$-cycloalkyl, —OSO$_3$H and halo-$C_1$–$C_4$-alkyl;
Y is selected from

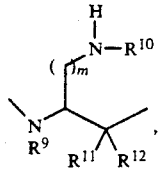
(A)

wherein m is 3, 4 or 5;
R$^9$ is hydrogen or $C_1$–$C_4$-alkyl;

R$^{10}$ is selected from the group consisting of

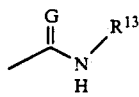
(1)

wherein G is O or S; and
R$^{13}$ is selected from the group consisting of
(i) $C_1$–$C_6$-alkyl,
(ii) $C_2$–$C_6$-alkenyl,
(iii) cyclo-$C_3$–$C_{10}$-alkyl
(iv) monocyclic heterocycle, as defined below,
(v) bicyclic heterocycle, as defined below,
(vi) $C_6$–$C_{10}$-aryl, and
(vii) mono- or disubstituted $C_6$–$C_{10}$-aryl wherein the 1 or 2 substituents on the aryl are selected from the group consisting of
(a) hydroxy,
(b) halogen,
(c) —OSO$_3$H,
(d) nitro,
(e) cyano,
(f) amino,
(g) $C_1$–$C_4$-alkylamino,
(h) ($C_1$–$C_4$-alkyl)$_2$amino,
(i) $C_1$–$C_4$-alkyl,
(j) halo-$C_1$–$C_4$-alkyl,
(k) $C_1$–$C_4$-alkoxy,
(l) $C_1$–$C_4$-alkanoyl,
(m) $C_1$–$C_4$-alkoxycarbonyl, and
(n) phenoxy;
(2) —C(O)—(CH$_2$)$_p$—R$^{14}$, wherein p is 0, 1 or 2 and R$^{14}$ is selected from the group consisting of
(i) cyclo-$C_3$–$C_{10}$-alkyl,
(ii) monocyclic heterocycle, as defined below
(iii) bicyclic heterocycle, as defined below
(iv) $C_6$–$C_{10}$-aryl, and
(v) mono- or disubstituted $C_6$–$C_{10}$-aryl, wherein the 1 or 2 substituents on the aryl are selected from the group consisting of
(a) hydroxy,
(b) halogen,
(c) —OSO$_3$H,
(d) nitro,
(e) cyano,
(f) amino,
(g) $C_1$–$C_4$-alkylamino,
(h) ($C_1$–$C_4$-alkyl)$_2$amino,
(i) $C_1$–$C_4$-alkyl,
(j) halo-$C_1$–$C_4$-alkyl,
(k) $C_1$–$C_4$-alkoxy,
(l) $C_1$–$C_4$-alkanoyl,
(m) $C_1$–$C_4$-alkoxycarbonyl, and
(n) phenoxy;
(3) —C(O)—(CH$_2$)$_q$—CR$^{15}$=CH—R$^{14}$, wherein R$^{14}$ is as defined above,
q is 0 or 1, and
R$^{15}$ is hydrogen or cyano; and
R$^{11}$ and R$^{12}$ are each hydrogen or taken together are =O, and

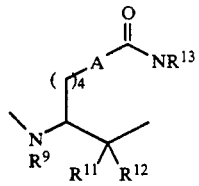
(B)

wherein A is —O— or —CH$_2$—; and
R$^9$, R$^{11}$, R$^{12}$ and R$^{13}$ are as independently defined above;
Z is

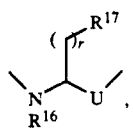

wherein U is —C(O)—, —CH$_2$, or —CH$_2$C(O)—;
r is 1 when U is —C(O)— or —CH$_2$— and r is 0 when U is —CH$_2$C(O)—;
R$^{16}$ is hydrogen or C$_1$-C$_4$ alkyl; and
R$^{17}$ is selected from
(A) —COOH,
(B) prodrug ester groups of the formula:

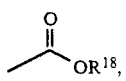

wherein R$^{18}$ is selected from
(1) C$_1$-C$_6$-alkyl,
(2) C$_2$-C$_6$-alkenyl,
(3) cyclo-C$_3$-C$_{10}$-alkyl,
(4) —(CH$_2$)$_t$—NR$^{19}$R$^{20}$ wherein t is 1, 2 or 3, and R$^{19}$ and R$^{20}$ are independently selected from hydrogen, C$_1$-C$_4$-alkyl, C$_2$-C$_4$-alkenyl and hydroxy-C$_1$-C$_4$-alkyl, or R$^{20}$ and R$^{21}$ are taken together with the nitrogen atom to which they are attached to form

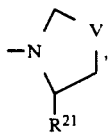

wherein V is —CH$_2$—, —CH$_2$CH$_2$—, —CH$_2$—O—, —CH$_2$—S— or —CH$_2$—N(CH$_3$)—, and R$^{21}$ is hydrogen or carboxy, and
(5) —(CH$_2$)$_t$—OR$^{22}$ wherein t is as defined above and R$^{22}$ is hydrogen or C$_1$-C$_4$-alkyl,
(6) —CH$_2$—C(O)NR$^{19}$R$^{20}$, wherein R$^{19}$ and R$^{20}$ are as independently defined above,
(7) —CH$_2$—C(O)OR$^{19}$, wherein R$^{19}$ is selected from hydrogen, C$_1$-C$_4$-alkyl, C$_2$-C$_4$-alkenyl and hydroxy-C$_1$-C$_4$-alkyl, and
(8) benzyl; and
(C) 5-tetrazolyl; and
Q is

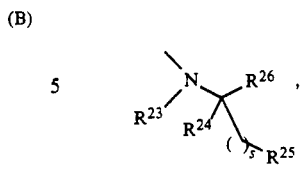

wherein s is 1 or 2;
R$^{23}$ is hydrogen or C$_1$-C$_4$-alkyl;
R$^{24}$ is hydrogen or methyl; or
R$^{23}$ and R$^{24}$ taken together from —CH$_2$CH$_2$CH$_2$—;
R$^{25}$ is selected from (1) C$_6$-C$_{10}$-aryl, (2) monocyclic or bicyclic heterocycle, as defined below and (3) cyclo-C$_3$-C$_{10}$-alkyl; and
R$^{26}$ is selected from the group consisting of

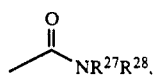

wherein R$^{27}$ and R$^{28}$ are independently hydrogen or methyl,
(2) —C(O)O—C$_1$-C$_4$-alkyl,
(3) —CH$_2$OH,
(4) —C≡N,
(5) —C≡CH, and
(6) C(O)NHNH$_2$.

In one preferred embodiment of the present invention are compounds, represented by the formula:

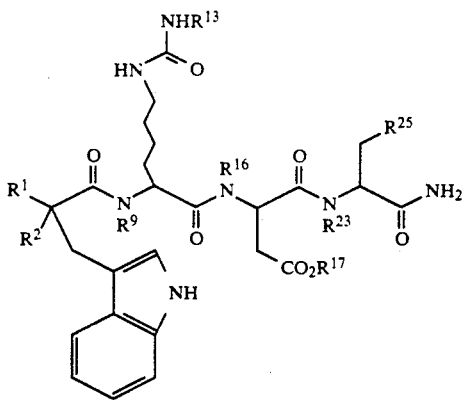

wherein R$^1$, R$^2$, R$^{13}$, R$^{16}$ and R$^{25}$ are as defined above and R$^9$, R$^{16}$ and R$^{23}$ are independently hydrogen or methyl.

In a second preferred embodiment of the present invention are compounds, represented by the formula:

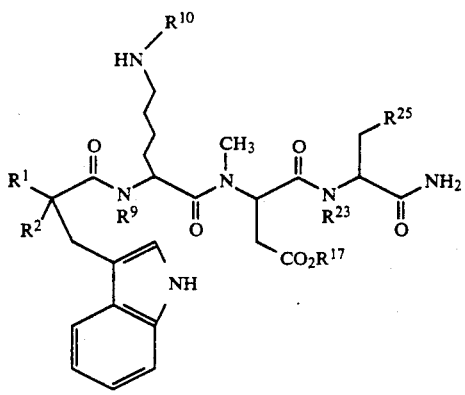

wherein R¹⁰ is selected from options 2 and 3 in its definition above, R¹, R², R¹⁰, R¹⁷ and R²⁵ are as defined above, and R⁹ and R²³ are independently hydrogen or methyl.

The terms "$C_2$-$C_4$-alkenyl" and "$C_2$-$C_6$-alkenyl" as used herein refer to a 2 to 4 to 6 straight- or branched-chain of carbon atoms which contains a carbon-carbon double bond, such as allyl, propenyl, butenyl, isoprenyl and the like.

The terms "$C_1$-$C_4$-alkyl" and "$C_1$-$C_6$-alkyl" as used herein refer to straight or branched chain alkyl radicals having from 1 to 4 or 1 to 6 carbon atoms including, but not limited to, methyl, ethyl, propyl, isopropyl, butyl, isobutyl, sec-butyl, pentyl, neopentyl hexyl, and the like.

The term "$C_6$-$C_{10}$-aryl" as used herein refers to phenyl or to a "bicyclic carbocyclic" group or "bicyclic carbocycle" having two fused carbocyclic rings, each ring having 5, 6 or 7 carbon atoms, and each ring being fully saturated, partially saturated or aromatic. Bicyclic carbocyclic groups include, but are not limited to, naphthyl, tetrahydronaphthyl, decalin, indanyl, indenyl and the like.

The term "$C_7$-$C_{14}$-arylalkyl" as used herein refers to an aryl group appended to a $C_1$-$C_4$-alkyl radical including, but not limited to, benzyl, phenethyl, naphthylmethyl and the like.

The term "bicyclic heterocycle" as used herein refers to a group having two fused rings, one or both of which are heterocyclic rings as defined herein. When both rings are not heterocyclic, the other ring is carbocyclic and is saturated, partially saturated or aromatic, preferably a benzene ring. Bicyclic heterocyclic groups can be unsubstituted or monosubstituted or disubstituted with substituents independently selected from hydroxy, halo, oxo (=O), amino, $C_1$-$C_4$-alkylamino, di-($C_1$-$C_4$)-alkylamino, $C_1$-$C_4$-alkoxy, thio-$C_1$-$C_4$-alkoxy, carboxy, $C_1$-$C_4$-alkoxycarbonyl, $C_1$-$C_4$-alkyl, $C_3$-$C_8$-cycloalkyl, —OSO₃H and halo-$C_1$-$C_4$-alkyl. Examples of bicyclic heterocycles include indole, 5-hydroxyindole, quinoline, isoquinoline, tetrahydroisoquinoline, quinoxaline, benzimidazole, benzofuran, and the like.

The term "cyclo-$C_3$-$C_{10}$-alkyl" as used herein refers to an aliphatic monocyclic of 3 to 10 or bicyclic group having 6 to 10 carbon atoms including, but not limited to, cyclopropyl, cyclobutyl, cyclopentyl, cyclohexyl, cyclooctyl, adamantyl, and the like.

The term "halo" or "halogen" as used herein refers to chloro, bromo, iodo or fluoro.

The term "halo-$C_1$-$C_4$-alkyl" as used herein refers to a loweralkyl radical in which one to three hydrogen atoms have been replaced by a halogen including, but not limited to, chloromethyl, 2-fluoroethyl, trifluoromethyl and the like.

The term "monocyclic heterocyclic group" or "monocyclic heterocycle" as used herein refers to any 3- or 4-membered ring containing a heteroatom selected from oxygen, nitrogen and sulfur, or a 5- or 6-membered ring containing carbon atoms and one, two or three nitrogen atoms; one nitrogen and one sulfur atom; or one nitrogen and one oxygen atom; wherein the 5-membered ring has 0–2 double bonds and the 6-membered ring has 0–3 double bonds; wherein the nitrogen and sulfur heteroatoms may optionally be oxidized; and wherein the nitrogen heteroatom may optionally be quaternized. Heterocycles include, but are not limited to, pyridyl, imidazolyl, furyl, thienyl, pyrazinyl, pyrrolyl, pyrimidyl and the like. Heterocyclics may be unsubstituted or mono- or disubstituted with substituents independently selected from hydroxy, halo, oxo (=O), amino, $C_1$-$C_4$-alkylamino, ($C_1$-$C_4$)₂-alkylamino, $C_1$-$C_4$-alkoxy, thio-$C_1$-$C_4$-alkoxy, carboxy, $C_1$-$C_4$-alkoxycarbonyl, $C_1$-$C_4$-alkyl, $C_3$-$C_8$-cycloalkyl, —OSO₃H and halo-$C_1$-$C_4$-alkyl.

All amino acid residues identified herein are in the natural L-configuration unless otherwise designated with "D-", (e.g., D-Trp). The compounds of formula (I) contain two or more asymmetric carbon atoms and thus can exist as pure diastereomers, mixtures of distereomers, diastereomeric racemates or mixtures of diastereomeric racemates. The present invention includes within its scope all of the isomeric forms. In keeping with standard peptide nomenclature, *J. Biol. Chem.*, 1969, 243:3557–59, abbreviations for amino acid residues are used herein. Abbreviations used herein are as shown in the following Table of Correspondence:

| TABLE OF CORRESPONDENCE | |
|---|---|
| SYMBOL | REPRESENTS |
| Ala | L-alanine |
| Arg | L-arginine |
| Asp | L-aspartic acid |
| Cha | L-cyclohexylalanine |
| Cys | L-cysteine |
| Gln | L-glutamine |
| Glu | L-glutamic acid |
| Gly | glycine |
| His | L-histidine |
| hLys | homo-L-lysine |
| Ile | L-isoleucine |
| Leu | L-leucine |
| Lys | L-lysine |
| Met | L-methionine |
| α-Nal | alpha-naphthylalanine |
| β-Nal | beta-naphthylalanine |
| Nle | norleucine |
| Orn | L-ornithine |
| Phe | L-phenylanlanine |
| hPhe | homo-L-phenylalanine |
| Pro | L-proline |
| Ser | L-serine |
| Thr | L-threonine |
| Trp | L-tryptophan |
| Tyr | L-tyrosine |
| Val | L-valine |

TABLE OF CORRESPONDENCE
| SYMBOL | REPRESENTS |
|---|---|
| Ctp | 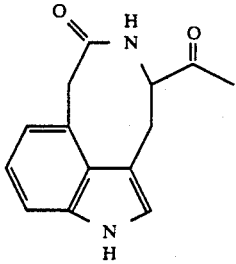 |

The abbreviation ψ(CH₂NH) indicates that the amide (—C(O)NH—) bond of a peptide has been replaced by the reduced form —CH₂NH—. For example, Trpψ(CH₂NH)Lys represents a tryptophan residue bonded to a lysine residue wherein the amide bond is reduced as shown below.

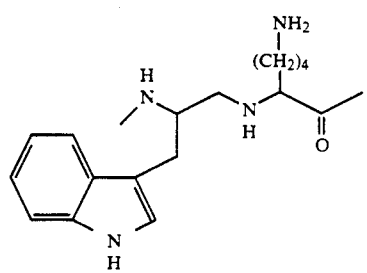

It is noted that all amino acid residue sequences are represented herein by formulae whose left to right orientation is in the conventional direction of amino-terminus to carboxy-terminus.

t-BOC is the standard abbreviation for a t-butoxycarbonyl group.

Exemplary compounds of the present invention include:

t-BOC-Trp-Lys(ε-N-(3-(4-hydroxyphenyl)propionyl))-Asp-PheNH₂;
t-BOC-Trp-Lys(ε-N-(3-phenylpropionyl))-Asp-PheNH₂;
t-BOC-β-Nal-Lys(ε-N-(3-(4-hydroxyphenyl)propionyl))-Asp-PheNH₂;
t-BOC-Trp-Lys(ε-N-(3-(4-sulfatylphenyl)propionyl))-Asp-PheNH₂;
t-BOC-Trp-Lys(ε-N-(3-carboxyquinolyl))-Asp-PheNH₂;
t-BOC-Trp-Lys(ε-N-(4-hydroxyphenylacetyl))-Asp-PheNH₂;
t-BOC-Trp-Lys(ε-N-(4-hydroxycinnamoyl))-Asp-PheNH₂;
t-BOC-Trp-Lys(ε-N-(4-sulfatylcinnamoyl))-Asp-PheNH₂;
t-BOC-Trp-Lys(ε-N-(3-(3-hydroxyphenyl)propionyl))-Asp-PheNH₂;
t-BOC-Trp-Lys(ε-N-(3-(3-sulfatylphenyl)propionyl))-Asp-PheNH₂;
t-BOC-Trp-Lys(ε-N-(3-(4-chlorophenyl)propionyl))-Asp-PheNH₂;
t-BOC-Trp-Lys(ε-N-(4-phenylbutyryl))-Asp-PheNH₂;
t-BOC-Trp-Lys(ε-N-(3-(4-methoxyphenyl)propionyl))-Asp-PheNH₂;
t-BOC-Trp-Lys(ε-N-(3-(4-methylphenyl)propionyl))-Asp-PheNH₂;
t-BOC-Trp-Lys(ε-N-(3-hydroxycinnamoyl))-Asp-PheNH₂;
t-BOC-Trp-Lys(ε-N-(3-sulfatylcinnamoyl))-Asp-PheNH₂;
t-BOC-Trp-Lys(ε-N-(4-methylcinnamoyl))-Asp-PheNH₂;
t-BOC-Trp-Lys(ε-N-(4-fluorocinnamoyl))-Asp-PheNH₂;
t-BOC-Trp-Lys(ε-N-(4-trifluoromethylcinnamoyl))-Asp-PheNH₂;
t-BOC-Trp-Lys(ε-N-(3-(3-pyridyl)acrylyl))-Asp-PheNH₂;
t-BOC-Trp-Lys(ε-N-(3-(4-fluorophenyl)propionyl))-Asp-PheNH₂;
t-BOC-Trp-Lys(ε-N-(3-(4-trifluoromethylphenyl)propionyl))-Asp-PheNH₂;
t-BOC-Trp-Lys(ε-N-(3-(3-indolyl)acrylyl))-Asp-PheNH₂;
t-BOC-Trp-Lys(ε-N-(α-naphthoyl))-Asp-PheNH₂;
t-BOC-Trp-Lys(ε-N-(3-(2-thienyl)acrylyl))-Asp-PheNH₂;
t-BOC-Trp-Lys(ε-N-(β-naphthoyl))-Asp-PheNH₂;
t-BOC-Trp-Lys(ε-N-(4-chlorocinnamoyl))-Asp-PheNH₂;
t-BOC-Trp-Lys(ε-N-(3-(3,4-dihydroxyphenyl)propionyl))-Asp-PheNH₂;
t-BOC-Trp-Lys(ε-N-(6-acetoxy-β-naphthoyl))-Asp-PheNH₂;
t-BOC-Trp-Lys(ε-N-(α-cyano-3-hydroxycinnamoyl))-Asp-PheNH₂;
t-BOC-Trp-Lys(ε-N-(cinnamoyl))-Asp-PheNH₂;
t-BOC-Trp-Lys(ε-N-(1-adamantanoyl))-Asp-PheNH₂;
t-BOC-Trp-Lys(ε-N-(1-adamantaneacetyl))-Asp-PheNH₂;
t-BOC-Trp-Lys(ε-N-(4-methoxycinnamoyl))-Asp-PheNH₂;
t-BOC-Trp-Lys(ε-N-(4-dimethylaminocinnamoyl))-Asp-PheNH₂;
t-BOC-Trp-Lys(ε-N-(4-bromocinnamoyl))-Asp-PheNH₂;
t-BOC-Trp-Lys(ε-N-(6-hydroxy-β-naphthoyl))-Asp-PheNH₂;
t-BOC-Trp-Lys(ε-N-(2,4-dichlorocinnamoyl))-Asp-PheNH₂;
t-BOC-Trp-Lys(ε-N-(4-nitrocinnamoyl))-Asp-PheNH₂;
t-BOC-Trp-Lys(ε-N-(3,4-dimethoxycinnamoyl))-Asp-PheNH₂;
t-BOC-Trp-Lys(ε-N-(4-(3-quinolyl)-3-butenoyl))-Asp-PheNH₂;
t-BOC-Trp-Lys(ε-N-(3,4-dihydroxycinnamoyl))-Asp-PheNH₂;
t-BOC-Trp-Lys(ε-N-(3,4-dichlorocinnamoyl))-Asp-PheNH₂;
t-BOC-D-Trp-Lys(ε-N-(3-(4-hydroxyphenyl)propionyl))-Asp-PheNH₂;
t-BOC-D-Trp-Lys(ε-N-(4-hydroxycinnamoyl))-Asp-PheNH₂;
t-BOC-α-Nal-Lys(ε-N-(3-(4-hydroxyphenyl)propionyl))-Asp-PheNH₂;
t-BOC-α-Nal-Lys(ε-N-(4-hydroxycinnamoyl))-Asp-PheNH₂;
t-BOC-β-Nal-Lys(ε-N-(3-(4-hydroxyphenyl)propionyl))-Asp-PheNH₂;
t-BOC-β-Nal-Lys(ε-N-(4-hydroxycinnamoyl))-Asp-PheNH₂;

t-BOC-Trp-Lys(ε-N-(3-(4-hydroxyphenyl)propionyl))-Asp-(NMe)PheNH$_2$;
t-BOC-Trp-Lys(ε-N-(4-hydroxycinnamoyl))-Asp-(NME)PheNH$_2$;
t-BOC-Trp-Lys(ε-N-(4-chlorocinnamoyl))-Asp-(NME)PheNH$_2$;
t-BOC-Trp-Lys(ε-N-(6-hydroxy-β-naphthoyl))-Asp-(NMe)PheNH$_2$;
t-BOC-Trp-Lys(ε-N-(6-acetoxy-β-naphthoyl))-Asp-(NMe)PheNH$_2$;
t-BOC-D-Trp-Lys(ε-N-(3-(4-hydroxyphenyl)propionyl))-Asp-(NMe)PheNH$_2$;
t-BOC-D-Trp-Lys(ε-N-(4-hydroxycinnamoyl))-Asp-(NMe)PheNH$_2$;
t-BOC-Trp-Lys(ε-N-(3-(4-hydroxyphenyl)propionyl))-Asp-α-NalNH$_2$;
t-BOC-Trp-Lys(ε-N-(2-hydroxycinnamoyl))-Asp-PheNH$_2$;
t-BOC-Trp-Lys(ε-N-(3-chlorocinnamoyl))-Asp-PheNH$_2$;
t-BOC-Trp-Lys(ε-N-((6-sulfatyl-β-naphthoyl))-Asp-PheNH$_2$;
t-BOC-Trp-Lys(ε-N-(2,4-dimethoxycinnamoyl))-Asp-PheNH$_2$;
t-BOC-Trp-Lys(ε-N-(4-(β-naphthyl)-3-butenoyl))-Asp-PheNH$_2$;
Ctp-Lys(ε-N-(3-(4-hydroxyphenyl)-propionyl))-Asp-PheNH$_2$;
β-Naphthoxyacetyl-Lys(ε-N-(4-hydroxycinnamoyl))-Asp-PheNH$_2$;
3-(3-Indolyl)propionyl-Lys(ε-N-(3-(4-hydroxyphenyl)-propionyl))-Asp-PheNH$_2$;
t-BOC-Trp-Lys(ε-N-(3-(3-indolyl)propionyl))-Asp-PheNH$_2$;
t-BOC-Trp-Lys(ε-N-(t-BOC-Tyr))-Asp-PheNH$_2$;
t-BOC-Trp-Lys(ε-N-(t-BOC-O-sulfatyl-tyrosyl))-Asp-PheNH$_2$;
t-BOC-Trp-Lys(ε-N-(t-BOC-Trp))-Asp-PheNH$_2$;
t-BOC-Trp-(2-aminopimelic acid(7-tyramide))-Asp-PheNH$_2$;
t-BOC-Trp-Lys(ε-N-(2-methylphenyl)aminocarbonyl)-Asp-PheNH$_2$;
t-BOC-Trp-Lys(ε-N-(3-cyclohexylpropionyl))-Asp-PheNH$_2$;
t-BOC-Trp-Lys(ε-N-(8-hydroxyquinolyl-2-carbonyl))-Asp-PheNH$_2$;
t-BOC-Trp-Lys(ε-N-(5-methoxyindolyl-2-carbonyl))-Asp-PheNH$_2$;
t-BOC-Trp-Lys(ε-N-t-BOC-D-Trp)-Asp-PheNH$_2$;
t-BOC-Trp-Lys(ε-N-t-BOC-D-Tyr)-Asp-PheNH$_2$;
t-BOC-Trp-Lys(ε-N-(5-(benzyloxy)indole-2-carbonyl)Asp-PheNH$_2$;
t-BOC-Trp-Lys(ε-N-(5-chlorindole-2-carbonyl))-Asp-PheNH$_2$;
t-BOC-Trp-Lys(ε-N-(5-hydroxyindole-2-carbonyl))-Asp-PheNH$_2$;
t-BOC-Trp-Lys(ε-N-(3-methylphenyl)aminocarbonyl)-Asp-PheNH$_2$;
t-BOC-Trp-Lys(ε-N-(4-chlorophenyl)aminocarbonyl)-Asp-PheNH$_2$;
t-BOC-Trp-Lys(ε-N-(2-chlorophenyl)aminocarbonyl)-Asp-PheNH$_2$;
t-BOC-Trp-Lys(ε-N-(α-naphthylaminocarbonyl))-Asp-PheNH$_2$;
t-BOC-Trp-Lys(ε-N-(phenylaminocarbonyl))-Asp-PheNH$_2$;
t-BOC-Trp-Lys(ε-N-(cyclohexylaminocarbonyl))-Asp-PheNH$_2$;
t-BOC-Trp-Lys(ε-N-(3-chlorophenyl)aminocarbonyl)-Asp-PheNH$_2$;
t-BOC-Trp-Lys(ε-N-(3-methylphenyl)aminothiocarbonyl)-Asp-PheNH$_2$;
t-BOC-Trp-Lys(ε-N-(t-butylaminocarbonyl))-Asp-PheNH$_2$;
t-BOC-Trp-Lys(ε-N-(2-methylphenyl)aminocarbonyl)-Asp-(NMe)PheNH$_2$;
t-BOC-Trpψ(CH$_2$NH)Lys(ε-N-4-hydroxycinnamoyl)-Asp-PheNH$_2$;
t-BOC-Trp-Lys(ε-N-4-hydroxycinnamoyl)ψ(CH$_2$NH)Asp-PheNH$_2$;
t-BOC-Trp-Lys(ε-N-(2-nitrophenyl)aminocarbonyl)-Asp-PheNH$_2$;
t-BOC-Trp-Lys(ε-N-(2-triflurormethylphenyl)aminocarbonyl)-Asp-PheNH$_2$;
t-BOC-Trp-Lys(ε-N-(2-bromophenyl)aminocarbonyl)-Asp-PheNH$_2$;
t-BOC-Trp-Lys(ε-N-(2-chlorophenyl)aminothiocarbonyl)-Asp-PheNH$_2$;
t-BOC-Trp-Lys(ε-N-(2-methylphenyl)aminothiocarbonyl)-Asp-PheNH$_2$;
t-BOC-Trp-Lys(ε-N-(3-acetylphenyl)aminocarbonyl)-Asp-PheNH$_2$;
t-BOC-Trp-Lys(ε-N-(4-acetylphenyl)aminocarbonyl)-Asp-PheNH$_2$;
t-BOC-Trp-Lys(ε-N-(4-phenoxyphenyl)aminocarbonyl)-Asp-PheNH$_2$;
t-BOC-Trp-Lys(ε-N-(2-isopropylphenyl)aminocarbonyl)-Asp-PheNH$_2$;
t-BOC-Trp-Lys(α-N-(S-2-(α-naphthyl)ethylaminocarbonyl))-Asp-PheNH$_2$;
t-BOC-Trp-Lys(ε-N-(4-methylphenyl)aminocarbonyl)-Asp-PheNH$_2$;
t-BOC-Trp-Lys(ε-N-(2-methoxyphenyl)aminocarbonyl)-Asp-PheNH$_2$;
t-BOC-Trp-Lys(ε-N-(β-naphthyl)aminocarbonyl)-Asp-PheNH$_2$;
t-BOC-Trp-Lys(ε-N-(2-(methoxycarbonylphenyl)aminocarbonyl))-Asp-PheNH$_2$;
t-BOC-Trp-Lys(ε-N-(3-(methoxycarbonyl)phenyl)aminocarbonyl)-Asp-PheNH$_2$;
t-BOC-Trp-Lys(ε-N-(2,6-dichlorophenyl)aminocarbonyl)-Asp-PheNH$_2$;
t-BOC-Trp-Lys(ε-N-(2,6-dimethylphenyl)aminocarbonyl)-Asp-PheNH$_2$;
t-BOC-Trp-Lys(ε-N-(allylaminocarbonyl))-Asp-PheNH$_2$;
t-BOC-Trp-Lys(ε-N-(4-nitrophenyl)aminocarbonyl)-Asp-PheNH$_2$;
t-BOC-Trp-Lys(ε-N-(benzylaminocarbonyl))-Asp-PheNH$_2$;
t-BOC-Trp-Lys(ε-N-(2-methylphenyl)aminocarbonyl)-Asp-hPheNH$_2$;
t-BOC-Trp-Lys(ε-N-(2-methylphenyl)aminocarbonyl)-Asp-phenylalaninol;
t-BOC-Trp-Lys(ε-N-(2-methylphenyl)aminocarbonyl)-Asp-(NMe)phenylalaninol;
(Isobutoxycarbonyl)indolelactoyl-Lys(ε-N-(2-methylphenyl)aminocarbonyl)-Asp-PheNH$_2$;
Indolelactoyl-Lys(ε-N-(2-methylphenyl)aminocarbonyl)-Asp-PheNH$_2$;
t-BOC-Trp-Lys(ε-N-(4-hydroxycinnamoyl))-Asp-TrpNH$_2$;
t-BOC-Trp-Orn(δ-N-(2-methylphenyl)aminocarbonyl)-Asp-PheNH$_2$;
t-BOC-Trp-Orn(δ-N-(4-hydroxycinnamoyl))-Asp-PheNH$_2$;

t-BOC-Trp-hLys(ω-N-(2-methylphenyl)aminocarbonyl)-Asp-PheNH$_2$;
t-BOC-Trp-hLys(ω-N-(4-hydroxyphenylcinnamoyl))-Asp-PheNH$_2$;
t-BOC-Trp-Lys(ε-N-(3-pyridyl-3-acrylyl))-Asp-(NMe)-PheNH$_2$;
t-BOC-Trp-(6-amino-1-(4-hydroxyphenethylamido)-hept-2-enoyl)-Asp-PheNH$_2$;
t-BOC-Trp-Lys(ε-N-(4-sulphatylcinnamoyl))-Asp-(NMe)PheNH$_2$;
t-BOC-Trp-Lys(ε-N-(2-methylphenyl)aminocarbonyl)-Asp(β-Me)-PheNH$_2$;
Trp-Lys(ε-N-(2-methylphenyl)aminocarbonyl)-Asp-(NMe)PheNH$_2$;
D-Trp-Lys(ε-N-(2-methylphenyl)aminocarbonyl)-Asp-(NMe)PheNH$_2$;
t-BOC-Trp-Lys(ε-N-(2-methylphenyl)aminocarbonyl)-β-Asp-PheNH$_2$;
Acetyl-Trp-Lys(ε-N-(2-methylphenyl)aminocarbonyl)-Asp-PheNH$_2$;
t-BOC-Trp-(NMe)Lys(ε-N-(2-methylphenyl)aminocarbonyl)-Asp-PheNH$_2$;
t-BOC-Trp-(NMe)Lys(ε-N-(2-methylphenyl)aminocarbonyl)-Asp-(NMe)PheNH$_2$;
t-BOC-Trp-Lys(ε-N-(2-methylphenyl)aminocarbonyl)-(NMe)Asp-PheNH$_2$;
t-BOC-Trp-Lys(ε-N-(2-methylphenyl)aminocarbonyl)-(NMe)Asp-(NMe)PheNH$_2$;
t-BOC-Trp-Lys(ε-N-(2-methylphenyl)aminocarbonyl)-Asp-PheNHMe;
t-BOC-Trp-Lys(ε-N-(2-methylphenyl)aminocarbonyl)-Asp-PheNMe$_2$;
t-BOC-Trp-Lys(ε-N-(2-methylphenyl)aminocarbonyl)ψ(CH$_2$NH)Asp-PheNH$_2$;
2-Fluoro-3-(indol-3-yl)propionyl-Lys(ε-N-(2-methylphenyl)aminocarbonyl)-Asp-PheNH$_2$;
2-Cyano-3-(indol-3-yl)-propionyl-Lys(ε-N-(2-methylphenyl)aminocarbonyl)-Asp-PheNH$_2$;
t-BOC-Trp-Lys(ε-N-(2-methylphenyl)aminocarbonyl)-Asp-PheOMe.
3-(3-Indolyl)propionyl-Lys(ε-N-(2-methylphenyl)aminocarbonyl)-(NMe)Asp-PheNH$_2$;
t-BOC-Trp-Lys(ε-N-3-(2-thienyl)acrylyl)-(NMe)Asp-PheNH$_2$;
t-BOC-Trp-Lys(ε-N-3-(3-pyridyl)acrylyl)-(NMe)Asp-PheNH$_2$;
t-BOC-Trp-Lys(ε-N-3-(3-pyridyl)acrylyl)-(NMe)Asp-(N-Me)PheNH$_2$;
(NMe)Trp-Lys(ε-N-(ε-N-(2-methylphenyl)aminocarbonyl)-(NMe)Asp-PheNH$_2$;
3-(Indol-3-yl)propionyl-Lys(ε-N-(2-methylphenylaminocarbonyl))-Asp-(NMe)PheNH$_2$;
t-BOC-Trp-Lys(ε-N-(4-hydroxycinnamoyl))-(NMe)Asp-PheNH$_2$;
t-BOC-Trp-Lys(ε-N-(4-hydroxycinnamoyl))-(NMe)Asp-(NMe)PheNH$_2$;
t-BOC-Trp-Lys(ε-N-(6-hydroxy-β-naphthoyl)-(NMe)Asp-(NMe)PheNH$_2$;
2-Adamantyloxycarbonyl-Trp-Lys(ε-N-(2-methylphenyl)aminocarbonyl)-Asp-(NMe)PheNH$_2$;
1-Adamantyloxycarbonyl-Trp-Lys(ε-N-(2-methylphenyl)aminocarbonyl)-Asp-(NMe)PheNH$_2$;
Benzyloxycarbonyl-Trp-Lys(ε-N-(2-methylphenyl)aminocarbonyl)-Asp-(NMe)PheNH$_2$;
Isobutyloxycarbonyl-Trp-Lys(ε-N-(2-methylphenyl)aminocarbonyl)-Asp-(NMe)PheNH$_2$;
Isopropyloxycarbonyl-Trp-Lys(ε-N-(2-methylphenyl)aminocarbonyl)-Asp-(NMe)PheNH$_2$;
Phenoxycarbonyl-Trp-Lys(ε-N-(2-methylphenyl)aminocarbonyl)-Asp-(NMe)PheNH$_2$;
Methoxycarbonyl-Trp-Lys(ε-N-(2-methylphenyl)aminocarbonyl)-Asp-(NMe)PheNH$_2$;
Methoxycarbonyl-Trp-Lys(ε-N-(2-methylphenyl)aminocarbonyl)(NMe)Asp-PheNH$_2$;
t-Butylaminocarbonyl-Trp-Lys(ε-N-(2-methylphenyl)aminocarbonyl)-Asp-(NMe)PheNH$_2$;
Methylaminocarbonyl-Trp-Lys(ε-N-(2-methylphenyl)aminocarbonyl)-Asp-(NMe)PheNH$_2$;
Phenylaminocarbonyl-Trp-Lys(ε-N-(2-methylphenyl)aminocarbonyl)-Asp-(NMe)PheNH$_2$;
Acetyl-Trp-Lys(ε-N-(2-methylphenyl)aminocarbonyl)-Asp-(NMe)PheNH$_2$;
Acetyl-Trp-Lys(ε-N-(2-methylphenyl)aminocarbonyl)-(NMe)Asp-PheNH$_2$;
t-Butylacetyl-Trp-Lys(ε-N-(2-methylphenyl)aminocarbonyl)-Asp-(NMe)PheNH$_2$;
Trifluoroacetyl-Trp-Lys(ε-N-(2-methylphenyl)aminocarbonyl)-(NMe)Asp-PheNH$_2$;
t-Butylacetyl-Trp-Lys(ε-N-(2-methylphenyl)aminocarbonyl)-(NMe)Asp-PheNH$_2$;
Benzoyl-Trp-Lys(ε-N-(2-methylphenyl)aminocarbonyl)-Asp-(NMe)PheNH$_2$;
Benzoyl-Trp-Lys(ε-N-(2-methylphenyl)aminocarbonyl)-(NMe)Asp-PheNH$_2$;
Phenylacetyl-Trp-Lys(ε-N-(2-methylphenyl)aminocarbonyl)-Asp-(NMe)PheNH$_2$;
(3,3-Diphenylpropionyl)-Trp-Lys(ε-N-(2-methylphenyl)aminocarbonyl)-Asp-(NMe)PheNH$_2$;
(3-(4-Hydroxy-3-iodophenyl)propionyl)-Trp-Lys(ε-N-(2-methylphenyl)aminocarbonyl)-Asp-(NMe)PheNH$_2$;
(3-Carboxylpropionyl)-Trp-Lys(ε-N-(2-methylphenyl)aminocarbonyl)-Asp-(NMe)PheNH$_2$;
Methylsulfonamyl-Trp-Lys(ε-N-(2-methylphenyl)aminocarbonyl)-Asp-(NMe)PheNH$_2$;
t-BOC-D,L-(α-methyl)Trp-Lys(ε-N-(2-methylphenyl)aminocarbonyl)-Asp-PheNH$_2$;
D,L-(α-Methyl)-Trp-Lys(ε-N-(2-methylphenyl)aminocarbonyl)-Asp-PheNH$_2$;
t-BOC-(α-Methyl)Trp-Lys(ε-N-(2-methylphenyl)aminocarbonyl)-Asp-(NMe)PheNH$_2$ (Isomer A);
t-BOC-(α-Methyl)Trp-Lys(ε-N-(2-methylphenyl)aminocarbonyl)-Asp-(NMe)PheNH$_2$ (Isomer B);
(NMe)Trp-Lys(ε-N-(2-methylphenyl)aminocarbonyl)-(NMe)Asp-α-NalNH$_2$;
(NMe)Trp-Lys(ε-N-(2-methylphenyl)aminocarbonyl)-Asp-(NMe)PheNH$_2$;
(3-(3-Indolyl)propionyl)-Lys(ε-N-(2-methylphenyl)aminocarbonyl)(NMe)Asp-(NMe)PheNH$_2$;
(3-(3-Indolyl)propionyl)-Lys(ε-N-(2-methylphenyl)aminocarbonyl)(NMe)Asp-α-NalNH$_2$;
(2-Methyl-3-(3-indolyl)propionyl)-Lys(ε-N-(2-methylphenyl)aminocarbonyl)-Asp-(NMe)PheNH$_2$;
(2-Cyano-3-(3-indolyl)propionyl)-Lys(ε-N-(2-methylphenyl)aminocarbonyl)-Asp-(NMe)PheNH$_2$;
(2-Aminocarbonyl-3-(3-indolyl)propionyl)-Lys(ε-N-(2-methylphenyl)aminocarbonyl)-Asp-(NMe)PheNH$_2$;
(2-Carbomethoxy-3-(3-indolyl)propionyl)-Lys(ε-N-(2-methylphenyl)aminocarbonyl)-Asp-(NMe)PheNH$_2$;
(2-Carboxy-3-(3-indolyl)propionyl)-Lys(ε-N-(2-methylphenyl)aminocarbonyl)-Asp-(NMe)PheNH$_2$;
(2-Carboethoxy-2-methyl-3-(3-indolyl)propionyl)-Lys(ε-N-(2-methylphenyl)aminocarbonyl)-Asp-(NMe)PheNH$_2$;
(2-Fluoro-3-(3-indolyl)propionyl)-Lys(ε-N-(2-methylphenyl)aminocarbonyl)-Asp-(NMe)PheNH$_2$;

(2-Fluoro-3-(3-indolyl)propionyl)-Lys(ε-N-(2-methylphenyl)aminocarbonyl)(NMe)Asp-PheNH₂;
(3-(β-Naphthyl)propionyl)-Lys(ε-N-(2-methylphenyl)aminocarbonyl)-Asp-PheNH₂;
(3-(α-Naphthyl)propionyl)-Lys(ε-N-(2-methylphenyl)aminocarbonyl)(NMe)Asp-PheNH₂;
Ctp-Lys(ε-N-(2-methylphenyl)aminocarbonyl)-Asp-(NMe)PheNH₂;
t-BOC-Trp-Lys(ε-N-(3-trifluoromethylphenyl)aminocarbonyl)-Asp-PheNH₂;
t-BOC-Trp-Nle(6-((2-methylphenyl)aminocarbonyl)oxy)-Asp-(NMe)PheNH₂;
t-BOC-Trp-Lys(ε-N-(2-methylphenyl)aminocarbonyl)-Asp-(S)-α-benzylprolinamide;
t-BOC-Trp-Lys(ε-N-(2-methylphenyl)aminocarbonyl)-Asp-ChaNH₂;
t-BOC-Trp-Lys-(ε-N-3-(3-pyridyl)acrylyl))-(NMe)Asp-(OMe)-(NMe)PheNH₂;
(NMe)Trp-Lys(ε-N-(2-methylphenyl)aminocarbonyl)-(NMe)Asp(OMe)(NMe)Phe-NH₂;
Isobutyloxycarbonyl-Trp-Lys(ε-N-(2-methylphenyl)aminocarbonyl)-Asp(β-benzyl ester)-(NMe)PheNH₂;
t-BOC-Trp-Lys(ε-N-(2-methylphenyl)aminocarbonyl)-Asp(β-2-(1-morpholino)ethyl)-(NMe)PheNH₂;
t-BOC-Trp-Lys(ε-N-(2-methylphenyl)aminocarbonyl)-Asp(β-(OCH₂-CO-N(CH₃)₂))-(NMe)PheNH₂;
(N-((morpholinocarbonylmethyl)oxycarbonyl)-Trp-Lys(ε-N-(2-methylphenyl)aminocarbonyl)-Asp(OMe)-(NMe)PheNH₂;
α-Methyl-Trp-Lys((ε-N-(2-methylphenyl)aminocarbonyl)-(NMe)Asp(β-methyl)-PheNH₂;
Methoxycarbonyl-Trp-Lys((ε-N-(2-methylphenyl)aminocarbonyl)-(NMe)Asp-(NMe)PheNH₂;
Methoxycarbonyl-Trp-Lys((ε-N-3-(thienyl)acrylyl)-(NMe)Asp-(NMe)PheNH₂;
t-BOC-Trp-Lys(ε-N-(2,3-dichlorophenyl)aminocarbonyl)-Asp-PheNH₂;
Methoxycarbonyl-Trp-Lys((ε-N-3-(thienyl)acrylyl)-(NMe)Asp-PheNH₂;
(2-Carboethoxy-2-methyl-3-(3-indolyl)propionyl)-Lys(ε-N-(2-methylphenyl)aminocarbonyl)-Asp(OBn)-(NMe)PheNH₂;
t-BOC-Trp-Lys(ε-N-(4-trifluoromethylphenyl)aminocarbonyl)-Asp-PheNH₂;
t-BOC-Trp-Lys(ε-N-(2,4-dichlorophenyl)aminocarbonyl)-Asp-PheNH₂;
(3-Carboxylpropionyl)-Trp-Lys(ε-N-(2-methylphenyl)aminocarbonyl)-Asp(OBn)-(NMe)PheNH₂;
t-BOC-Trp-Lys(ε-N-(2-methylphenyl)aminocarbonyl)-(R)-α-benzylprolamide;
3-(3-Indolyl)propionyl-Lys(ε-N-(2-methylphenyl)aminocarbonyl)-Asp-PheNH₂;
(NMe)Trp-Lys(ε-N-(2-methylphenyl)aminocarbonyl)-Asp-(NMe)Phe-NH₂;
t-BOC-Trp-hLys(ω-N-(6-hydroxy-2-naphthyl)carbonyl)-Asp-PheNH₂;
t-BOC-Trp-Lys(3-quinolinecarbonyl)-(NMe)Asp-PheNH₂;
t-BOC-Trp-Lys(ε-N-(2-thienylacryloyl)-(NMe)Asp-(NMe)PheNH₂;
t-BOC-Trp-Lys(ε-N-(2-methylphenyl)aminocarbonyl)-Asp(OBn)(NMe)PheNH₂;
Propionyl-Trp-Lys(ε-N-(2-methylphenyl)aminocarbonyl)-Asp-(NMe)PheNH₂;
t-BOC-Trp-Lys(ε-N-(2-methylphenyl)aminocarbonyl)-Asp-(2S)-2-benzyl-2-aminoacetonitrile;
t-BOC-Trp-Lys(ε-N-(2-methylphenyl)aminocarbonyl)-Asp-(2S)-2-benzyl-2-(N-methylamino)acetonitrile;
t-BOC-Trp-Lys(ε-N-(2-methylphenyl)aminocarbonyl)-(NMe)Asp-(2S)-2-benzyl-2-aminoacetonitrile;
t-BOC-Trp-Lys(ε-N-(2-methylphenyl)-aminocarbonyl)-Asp-(2S)-2-benzyl-2-aminopropyne;
t-BOC-Trp-Lys(ε-N-(2-methylphenyl)aminocarbonyl)-Asp-L-pyridylalanineNH₂;
t-BOC-Trp-Lys(ε-N-(2-methylphenyl)aminocarbonyl)Ψ(CH₂NH)Asp-PheNH₂; and
t-BOC-Trp-Lys(ε-N-(2-methylphenyl)aminocarbonyl)-(NMe)Asp-(2S)benzylaminoacetonitrile;
as well as pharmaceutically-acceptable salts thereof.
Preferred compounds of the invention include:
t-BOC-Trp-Lys(ε-N-(3-(4-hydroxyphenyl)propionyl))-Asp-PheNH₂;
t-BOC-Trp-Lys(ε-N-(3-(4-sulfatylphenyl)propionyl))-Asp-PheNH₂;
t-BOC-Trp-Lys(ε-N-(4-sulfatylcinnamoyl))-Asp-PheNH₂;
t-BOC-Trp-Lys(ε-N-(3-(4-methoxyphenyl)propionyl))-Asp-PheNH₂;
t-BOC-Trp-Lys(ε-N-(3-hydroxycinnamoyl))-Asp-PheNH₂;
t-BOC-Trp-Lys(ε-N-(4-methylcinnamoyl))-Asp-PheNH₂;
t-BOC-Trp-Lys(ε-N-(4-fluorocinnamoyl))-Asp-PheNH₂;
t-BOC-Trp-Lys(ε-N-(4-trifluoromethylcinnamoyl))-Asp-PheNH₂;
t-BOC-Trp-Lys(ε-N-(3-(3-pyridyl)acrylyl))-Asp-PheNH₂;
t-BOC-Trp-Lys(ε-N-(α-naphthoyl))-Asp-PheNH₂;
t-BOC-Trp-Lys(ε-N-(3-(2-thienyl)acrylyl))-Asp-PheNH₂;
t-BOC-Trp-Lys(ε-N-(4-chlorocinnamoyl))-Asp-PheNH₂;
t-BOC-Trp-Lys(ε-N-(4-(dimethylamino)cinnamoyl))-Asp-PheNH₂;
t-BOC-Trp-Lys(ε-N-(3,4-dihydroxycinnamoyl))-Asp-PheNH₂;
t-BOC-Trp-Lys(ε-N-(3,4-dichlorocinnamoyl))-Asp-PheNH₂;
t-BOC-Trp-Lys(ε-N-(3-(4-hydroxyphenyl)propionyl))-Asp-(NMe)PheNH₂;
t-BOC-Trp-Lys(ε-N-(4-hydroxycinnamoyl))-Asp-(NMe)PheNH₂;
t-BOC-Trp-Lys(ε-N-(4-chlorocinnamoyl))-Asp-(NMe)PheNH₂;
t-BOC-Trp-Lys(ε-N-(6-hydroxy-β-naphthoyl))-Asp-(NMe)PheNH₂;
t-BOC-Trp-Lys(ε-N-(6-acetoxy-β-naphthoyl))-Asp-(NMe)P: NH₂;
t-BOC-Trp-Lys(ε-N-(3-(4-hydroxyphenyl)propionyl))-Asp-α-NalNH₂;
t-BOC-Trp-Lys(ε-N-(2-hydroxycinnamoyl))-Asp-PheNH₂;
t-BOC-Trp-Lys(ε-N-(2,4-dimethoxycinnamoyl))-Asp-PheNH₂;
t-BOC-Trp-Lys(ε-N-(2-methylphenyl)aminocarbonyl)-Asp-PheNH₂;
t-BOC-Trp-Lys(ε-N-(3-methylphenyl)aminocarbonyl)-Asp-PheNH₂;
t-BOC-Trp-Lys(ε-N-(4-chlorophenyl)aminocarbonyl)-Asp-PheNH₂;
t-BOC-Trp-Lys(ε-N-(2-chlorophenyl)aminocarbonyl)-Asp-PheNH₂;

t-BOC-Trp-Lys(ε-N-(α-naphthyl)aminocarbonyl)-Asp-PheNH₂;
t-BOC-Trp-Lys(ε-N-(phenylaminocarbonyl))-Asp-PheNH₂;
t-BOC-Trp-Lys(ε-N-(cyclohexylaminocarbonyl))-Asp-PheNH₂;
t-BOC-Trp-Lys(ε-N-(3-chlorophenyl)aminocarbonyl)-Asp-PheNH₂;
t-BOC-Trp-Lys(ε-N-(t-butylaminocarbonyl))-Asp-PheNH₂;
t-BOC-Trp-Lys(ε-N-(2-methylphenyl)aminocarbonyl)-Asp-(NMe)PheNH₂;
t-BOC-Trp-Lys(ε-N-(2-nitrophenyl)aminocarbonyl)-Asp-PheNH₂;
t-BOC-Trp-Lys(ε-N-(2-triflurormethylphenyl)aminocarbonyl)-Asp-PheNH₂;
t-BOC-Trp-Lys(ε-N-(2-bromophenyl)aminocarbonyl)-Asp-PheNH₂;
t-BOC-Trp-Lys(ε-N-(2-chlorophenyl)aminothiocarbonyl)-Asp-PheNH₂;
t-BOC-Trp-Lys(ε-N-(2-methylphenyl)aminothiocarbonyl)-Asp-PheNH₂;
t-BOC-Trp-Lys(ε-N-(3-acetylphenyl)aminocarbonyl)-Asp-PheNH₂;
t-BOC-Trp-Lys(ε-N-(4-acetylphenyl)aminocarbonyl)-Asp-PheNH₂;
t-BOC-Trp-Lys(ε-N-(2-isopropylphenyl)aminocarbonyl)-Asp-PheNH₂;
t-BOC-Trp-Lys(ε-N-(4-methylphenyl)aminocarbonyl)-Asp-PheNH₂;
t-BOC-Trp-Lys(ε-N-(2-methoxyphenyl)aminocarbonyl)-Asp-PheNH₂;
t-BOC-Trp-Lys(ε-N-(β-naphthyl)aminocarbonyl)-Asp-PheNH₂;
t-BOC-Trp-Lys(ε-N-(2-(methoxycarbonyl)phenyl)aminocarbonyl)-Asp-PheNH₂;
t-BOC-Trp-Lys(ε-N-(3-(methoxycarbonyl)phenyl)aminocarbonyl)-Asp-PheNH₂;
t-BOC-Trp-Lys(ε-N-(2,6-dichlorophenyl)aminocarbonyl)-Asp-PheNH₂;
t-BOC-Trp-Lys(ε-N-(4-nitrophenyl)aminocarbonyl)-Asp-PheNH₂;
t-BOC-Trp-Lys(ε-N-(2-methylphenyl)aminocarbonyl)-Asp-hPheNH₂;
(Isobutoxycarbonyl)indolelactoyl-Lys(ε-N-(2-methylphenyl)aminocarbonyl)-Asp-PheNH₂;
Indolelactoyl-Lys(ε-N-(2-methylphenyl)aminocarbonyl)-Asp-PheNH₂;
t-BOC-Trp-hLys(ω-N-(2-methylphenyl)aminocarbonyl)-Asp-PheNH₂;
t-BOC-Trp-Lys(ε-N-(3-pyridyl-3-acrylyl))-Asp-(NMe)PheNH₂;
t-BOC-Trp-Lys(ε-N-(4-sulphatyl-cinnamoyl))-Asp-(NMe)PheNH₂;
t-BOC-Trp-Lys(ε-N-(2-methylphenyl)aminocarbonyl)-Asp(OMe)(NMe)PheNH₂;
Trp-Lys(ε-N-(2-methylphenyl)aminocarbonyl)-Asp-(NMe)PheNH₂;
D-Trp-Lys(ε-N-(2-methylphenyl)aminocarbonyl)-Asp-(NMe)PheNH₂;
Ac-Trp-Lys(ε-N-(2-methylphenyl)aminocarbonyl)-Asp-PheNH₂
t-BOC-Trp-(NMe)Lys(ε-N-(2-methylphenyl)aminocarbonyl)-Asp-(NMe)PheNH₂;
t-BOC-Trp-Lys(ε-N-(2-methylphenyl)aminocarbonyl)-(NMe)Asp-PheNH₂;
t-BOC-Trp-Lys(ε-N-(2-methylphenyl)aminocarbonyl)-(NMe)Asp-(NMe)PheNH₂;
t-BOC-Trp-Lys(ε-N-(2-methylphenyl)aminocarbonyl)Ψ(CH₂NH)-Asp-PheNH₂;
2-Fluoro-3-(indol-3-yl)propionyl-Lys(ε-N-(2-methylphenyl)aminocarbonyl)-Asp-PheNH₂;
(2-Cyano-3-(3-indolyl)propionyl)-Lys(ε-N-(2-methylphenyl)aminocarbonyl)-Asp-PheNH₂;
3-(3-Indolyl)propionyl-Lys(ε-N-(2-methylphenyl)aminocarbonyl)-(NMe)Asp-PheNH₂;
t-BOC-Trp-Lys-(ε-N-3-(2-thienyl)acrylyl)-(NMe)Asp-PheNH₂;
t-BOC-Trp-Lys-(ε-N-3-(3-pyridyl)acrylyl)-(NMe)Asp-PheNH₂;
t-BOC-Trp-Lys-(ε-N-3-(3-pyridyl)acrylyl)-(NMe)Asp-(NMe)PheNH₂;
(NMe)Trp-Lys(ε-N-(2-methylphenyl)aminocarbonyl)-(NMe)Asp-PheNH₂;
3-(Indol-3-yl)propionyl-Lys(ε-N-(2-methylphenyl)aminocarbonyl)-Asp-(NMe)PheNH₂;
t-BOC-Trp-Lys(ε-N-(4-hydroxycinnamoyl))-(NMe)Asp-PheNH₂;
t-BOC-Trp-Lys(ε-N-(4-hydroxycinnamoyl))-(NMe)Asp-(NMe)PheNH₂;
t-BOC-Trp-Lys(ε-N-(6-hydroxy-β-naphthoyl)-(NMe)Asp-(NMe)PheNH₂;
2-Adamantyloxycarbonyl-Trp-Lys(ε-N-(2-methylphenyl)aminocarbonyl)-Asp-(NMe)PheNH₂;
1-Adamantyloxycarbonyl-Trp-Lys(ε-N-(2-methylphenyl)aminocarbonyl)-Asp-(NMe)PheNH₂;
Benzyloxycarbonyl-Trp-Lys(ε-N-(2-methylphenyl)aminocarbonyl)-Asp-(NMe)PheNH₂;
Isobutyloxycarbonyl-Trp-Lys(ε-N-(2-methylphenyl)aminocarbonyl)-Asp-(NMe)PheNH₂;
Isopropyloxycarbonyl-Trp-Lys(ε-N-(2-methylphenyl)aminocarbonyl)-Asp-(NMe)PheNH₂;
Phenoxycarbonyl-Trp-Lys(ε-N-(2-methylphenyl)aminocarbonyl)-Asp-(NMe)PheNH₂;
Methoxycarbonyl-Trp-Lys(ε-N-(2-methylphenyl)aminocarbonyl)-Asp-(NMe)PheNH₂;
Methoxycarbonyl-Trp-Lys(ε-N-(2-methylphenyl)aminocarbonyl)-(NMe)Asp-PheNH₂;
t-Butylaminocarbonyl-Trp-Lys(ε-N-(2-methylphenyl)aminocarbonyl)-Asp-(NMe)PheNH₂;
Methylaminocarbonyl-Trp-Lys(ε-N-(2-methylphenyl)aminocarbonyl)-Asp-(NMe)PheNH₂;
Phenylaminocarbonyl-Trp-Lys(ε-N-(2-methylphenyl)aminocarbonyl)-Asp-(NMe)PheNH₂;
Acetyl-Trp-Lys(ε-N-(2-methylphenyl)aminocarbonyl)-Asp-(NMe)PheNH₂;
Acetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-Asp-(NMe)PheNH₂;
Trifluoroacetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-(NMe)Asp-PheNH₂;
Benzoyl-Trp-Lys(ε-N-(2-methylphenyl)aminocarbonyl)-Asp-(NMe)PheNH₂;
Benzoyl-Trp-Lys(ε-N-(2-methylphenyl)aminocarbonyl)-(NMe)Asp-PheNH₂;
Phenylacetyl-Trp-Lys(ε-N-(2-methylphenyl)aminocarbonyl)-Asp-(NMe)PheNH₂;
(3,3-Diphenylpropionyl)-Trp-Lys(ε-N-(2-methylphenyl)aminocarbonyl)-Asp-(NMe)PheNH₂;

(3-(4-Hydroxy-3-iodophenyl)propionyl)-Trp-Lys(ε-N-(2-methylphenyl)aminocarbonyl)-Asp-(NMe)-PheNH₂;
(3-Carboxylpropionyl)-Trp-Lys(ε-N-(2-methylphenyl)aminocarbonyl)-Asp-(NMe)PheNH₂;
Methylsulfonamyl-Trp-Lys(ε-N-(2-methylphenyl)aminocarbonyl)-Asp-(NMe)PheNH₂;
t-BOC-D,L-(α-methyl)Trp-Lys(ε-N-(2-methylphenyl)aminocarbonyl)-Asp-PheNH₂;
D,L-(α-Methyl)Trp-Lys(ε-N-(2-methylphenyl)aminocarbonyl)-Asp-PheNH₂;
(α-Methyl)-L-Trp-Lys(ε-N-(2-methylphenyl)aminocarbonyl)-Asp-(NMe)PheNH₂;
(α-Methyl)-L-Trp-Lys(ε-N-(2-methylphenyl)aminocarbonyl)-(NMe)Asp-PheNH₂;
(NMe)Trp-Lys(ε-N-(2-methylphenyl)aminocarbonyl)-(NMe)Asp-α-NalNH₂;
(NMe)Trp-Lys(ε-N-(2-methylphenyl)aminocarbonyl)-Asp-(NMe)PheNH₂;
(3-(3-Indolyl)propionyl-Lys(ε-N-(2-methylphenyl)aminocarbonyl)-(NMe)Asp-(NMe)PheNH₂;
(3-(3-Indolyl)propionyl)-Lys(ε-N-(2-methylphenyl)aminocarbonyl)-(NMe)Asp-α-NalNH₂;
(2-Methyl-3-(3-indolyl)propionyl)-Lys(ε-N-(2-methylphenyl)aminocarbonyl)-Asp-(NMe)PheNH₂;
(2-Cyano-3-(3-indolyl)propionyl)-Lys(ε-N-(2-methylphenyl)aminocarbonyl)-Asp-(NMe)PheNH₂;
(2-Aminocarbonyl-3-(3-indolyl)propionyl)-Lys(ε-N-(2-methylphenyl)aminocarbonyl)-Asp-(NMe)PheNH₂;
(2-Carboethoxy-2-methyl-3-(3-indolyl)propionyl)-Lys(ε-N-(2-methylphenyl)amino-carbonyl)-Asp-(NMe)PheNH₂;
(2-Fluoro-3-(3-indolyl)propionyl))-Lys(ε-N-(2-methylphenyl)aminocarbonyl)-Asp-(NMe)PheNH₂;
(2-Fluoro-3-(3-indolyl)propionyl)-Lys(ε-N-(2-methylphenyl)aminocarbonyl)-(NMe)Asp-PheNH₂;
(3-(β-Naphthyl)propionyl)-Lys(ε-N-(2-methylphenyl)aminocarbonyl)-Asp-PheNH₂;
(3-(α-Naphthyl)propionyl)-Lys(ε-N-(2-methylphenyl)aminocarbonyl)-(NMe)Asp-PheNH₂;
Ctp-Lys(ε-N-(2-methylphenyl)aminocarbonyl)-Asp-(NMe)PheNH₂;
t-BOC-Trp-Lys(ε-N-(3-trifluoromethylphenyl)aminocarbonyl)-Asp-PheNH₂;
t-BOC-Trp-Nle(6((2-methylphenyl)aminocarbonyl)oxy)-Asp-(NMe)PheNH₂;
t-BOC-Trp-Lys(ε-N-(2-methylphenyl)aminocarbonyl)-Asp-(S)-α-benzylprolinamide;
t-BOC-Trp-Lys(ε-N-(2-methylphenyl)aminocarbonyl)-Asp-ChaNH₂;
t-BOC-Trp-Lys-(ε-N-3-(3-pyridyl)acrylyl))-(NMe)Asp-(OMe)-(NMe)Phe-NH₂;
(NMe)Trp-Lys(ε-N-(2-methylphenyl)aminocarbonyl)-(NMe)Asp(OMe)-(NMe)Phe-NH₂;
Isobutyloxycarbonyl-Trp-Lys(ε-N-(2-methylphenyl)aminocarbonyl)-Asp(OBn)-(NMe)PheNH₂;
t-BOC-Trp-Lys(ε-N-(2-methylphenyl)aminocarbonyl)-Asp(β-2-(1-morpholino)ethyl)-(NMe)PheNH₂;
t-BOC-Trp-Lys(ε-N-(2-methylphenyl)aminocarbonyl)-Asp(β-(OCH₂—CO—N(CH₃)₂))-(NMe)PheNH₂;
(N-((morpholinocarbonylmethyl)oxycarbonyl)-Trp-Lys(ε-N-(2-methylphenyl)aminocarbonyl)-Asp(OMe)-(NMe)PheNH₂;
α-Methyl-Trp-Lys((ε-N-(2-methylphenyl)aminocarbonyl)-(NMe)Asp(OMe)-PheNH₂;
Methoxycarbonyl-Trp-Lys((ε-N-(2-methylphenyl)aminocarbonyl)-(NMe)Asp-(NMe)PheNH₂;
Methoxycarbonyl-Trp-Lys((ε-N-3-(thienyl)acrylyl)-(NMe)Asp-(NMe)PheNH₂;
Methoxycarbonyl-Trp-Lys((ε-N-3-(thienyl)acrylyl)-(NMe)Asp-PheNH₂;
2-Carboethoxy-2-methyl-3-(indol-3-yl)propionyl-Lys(ε-N-(2-methylphenyl)aminocarbonyl)-Asp(OBn)-(NMe)PheNH₂;
t-BOC-Trp-Lys(ε-N-(4-trifluoromethylphenyl)aminocarbonyl)-Asp-PheNH₂;
t-BOC-Trp-Lys(ε-N-(2,4-dichlorophenyl)aminocarbonyl)-Asp-PheNH₂;
(3-Carboxylpropionyl)-Trp-Lys(ε-N-(2-methylphenyl)aminocarbonyl)-Asp(OBn)-(NMe)PheNH₂;
t-BOC-Trp-Lys(ε-N-(2-methylphenyl)aminocarbonyl)-(R)-α-benzylprolamide;
t-BOC-Trp-Lys(ε-N-(2-methylphenyl)aminocarbonyl)-Asp-phenylalaninol;
3-(3-Indolyl)propionyl-Lys(ε-N-(2-methylphenyl)aminocarbonyl)-Asp-PheNH₂;
(NMe)Trp-Lys(ε-N-(2-methylphenyl)aminocarbonyl)-Asp-PheNH₂;
t-BOC-Trp-hLys(ω-N-(6-hydroxy-2-naphthyl)carbonyl)-Asp-PheNH₂;
t-BOC-Trp-Lys(3-quinolinecarbonyl)-(NMe)Asp-PheNH₂;
t-BOC-Trp-Lys(ε-N-(2-thienylacryloyl)-(NMe)Asp-(NMe)PheNH₂;
t-BOC-Trp-Lys(ε-N-(2-methylphenyl)aminocrbonyl)-Asp(OBn)-(NMe)PheNH₂;
Propionylyl-Trp-Lys-(ε-N-(2-methylphenyl)aminocarbonyl)-Asp-(NMe)PheNH₂;
Isobutyloxycarbonyl-Trp-Lys(ε-N-(2-methylphenyl)aminocarbonyl)-(NMe)Asp-PheNH₂;
as well as pharmaceutically-aceptable salts thereof.

More preferred compounds of the present invention include:
t-BOC-Trp-Lys(ε-N-(2-methylphenyl)aminocarbonyl)-Asp-PheNH₂;
t-BOC-Trp-Lys(ε-N-(2-methylphenyl)aminocarbonyl)-Asp-(NMe)PheNH₂;
t-BOC-Trp-Lys(ε-N-(2-methylphenyl)aminocarbonyl)-(NMe)Asp-PheNH₂;
t-BOC-Trp-Lys(ε-N-(2-methylphenyl)aminocarbonyl)-(NMe)Asp-(NMe)PheNH₂;
3-(3-Indolyl)propionyl-Lys(ε-N-(2-methylphenyl)aminocarbonyl)-(NMe)Asp-PheNH₂;
t-BOC-Trp-Lys-(ε-N-3-(2-thienyl)acrylyl)-(NMe)Asp-PheNH₂;
t-BOC-Trp-Lys-(ε-N-3-(3-pyridyl)acrylyl)-(NMe)Asp-PheNH₂;
t-BOC-Trp-Lys-(ε-N-3-(3-pyridyl)acrylyl)-(NMe)Asp-(NMe)PheNH₂;
(NMe)Trp-Lys(ε-N-(2-methylphenyl)aminocarbonyl)-(NMe)Asp-PheNH₂;
3-(3-Indolyl)propionyl-Lys(ε-N-(2-methylphenyl)aminocarbonyl)-Asp-(NMe)PheNH₂;
t-BOC-Trp-Lys(ε-N-(4-hydroxycinnamoyl))-(NMe)Asp-PheNH₂;
t-BOC-Trp-Lys(ε-N-(4-hydroxycinnamoyl))-(NMe)Asp-(NMe)PheNH₂;
t-BOC-Trp-Lys(ε-N-(6-hydroxy-β-naphthoyl)-(NMe)Asp-(NMe)PheNH₂;
1-Adamantyloxycarbonyl-Trp-Lys(ε-N-(2-methylphenyl)aminocarbonyl)-Asp-(NMe)PheNH₂;
Benzyloxycarbonyl-Trp-Lys(ε-N-(2-methylphenyl)aminocarbonyl)-Asp-PheNH₂;
Isobutyloxycarbonyl-Trp-Lys(ε-N-(2-methylphenyl)aminocarbonyl)-Asp-(NMe)PheNH₂;

Isopropyloxycarbonyl-Trp-Lys(ε-N-(2-methylphenyl)aminocarbonyl)-Asp-(NMe)PheNH₂;
Methoxycarbonyl-Trp-Lys-(ε-N-(2-methylphenyl)aminocarbonyl)-Asp-(NMe)PheNH₂;
Methoxycarbonyl-Trp-Lys(ε-N-(2-methylphenyl)aminocarbonyl)-(NMe)Asp-PheNH₂;
t-Butylaminocarbonyl-Trp-Lys(ε-N-(2-methylphenyl)aminocarbonyl)-Asp-(NMe)PheNH₂;
Methylaminocarbonyl-Trp-Lys(ε-N-(2-methylphenyl)aminocarbonyl)-Asp-(NMe)PheNH₂;
Phenylaminocarbonyl-Trp-Lys(ε-N-(2-methylphenyl)aminocarbonyl)-Asp-(NMe)PheNH₂;
Acetyl-Trp-Lys(ε-N-(2-methylphenyl)aminocarbonyl)-Asp-(NMe)PheNH₂;
Acetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-Asp-(NMe)PheNH₂;
Trifluoroacetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-(NMe)Asp-PheNH₂;
Benzoyl-Trp-Lys(ε-N-(2-methylphenyl)aminocarbonyl)-Asp-(NMe)PheNH₂;
Benzoyl-Trp-Lys(ε-N-(2-methylphenyl)aminocarbonyl)-(NMe)Asp-PheNH₂;
(3,3-Diphenylpropionyl)-Trp-Lys(ε-N-(2-methylphenyl)aminocarbonyl)-Asp-(NMe)PheNH₂;
(3-Carboxylpropionyl)-Trp-Lys(ε-N-(2-methylphenyl)aminocarbonyl)-Asp-(NMe)PheNH₂;
t-BOC-D,L-(α-methyl)Trp-Lys(ε-N-(2-methylphenyl)aminocarbonyl)-Asp-PheNH₂;
D,L-(α-Methyl)Trp-Lys(ε-N-(2-methylphenyl)aminocarbonyl)-Asp-PheNH₂;
(α-Methyl)-L-Trp-Lys(ε-N-(2-methylphenyl)aminocarbonyl)-Asp-(NMe)PheNH₂;
(α-Methyl)-L-Trp-Lys(ε-N-(2-methylphenyl)aminocarbonyl)-(NMe)Asp-PheNH₂;
(NMe)Trp-Lys(ε-N-(2-methylphenyl)aminocarbonyl)-(NMe)Asp-α-NalNH₂;
(NMe)Trp-Lys(ε-N-(2-methylphenyl)aminocarbonyl)-Asp-(NMe)PheNH₂;
(3-(3-Indolyl)propionyl)-Lys(ε-N-(2-methylphenyl)aminocarbonyl)-(NMe)Asp-(NMe)PheNH₂;
(3-(3-Indolyl)propionyl)-Lys(ε-N-(2-methylphenyl)aminocarbonyl)-(NMe)Asp-α-NalNH₂;
(2-Methyl-3-(3-indolyl)propionyl)-Lys(ε-N-(2-methylphenyl)aminocarbonyl)-Asp-(NMe)PheNH₂;
(2-Cyano-3-(3-indolyl)propionyl)-Lys(ε-N-(2-methylphenyl)aminocarbonyl)-Asp-(NMe)PheNH₂;
(2-Carboethoxy-2-methyl-3-(3-indolyl)propionyl)-Lys(ε-N-(2-methylphenyl)amino-carbonyl)-Asp-(NMe)PheNH₂;
(2-Fluoro-3-(3-indolyl)propionyl)Lys(ε-N-(2-methylphenyl)aminocarbonyl)-Asp-(NMe)PheNH₂;
(2-Fluoro-3-(3-indolyl)propionyl)-Lys(ε-N-(2-methylphenyl)aminocarbonyl)-(NMe)Asp-PheNH₂;
Ctp-Lys(ε-N-(2-methylphenyl)aminocarbonyl)-Asp-(NMe)PheNH₂;
t-BOC-Trp-Nle(6-((2-methylphenyl)aminocarbonyl)oxy)-Asp-(NMe)PheNH₂;
t-BOC-Trp-Lys(ε-N-(2-methylphenyl)aminocarbonyl)-Asp-ChaNH₂; Asp(OBn)-(NMe)PheNH₂;
t-BOC-Trp-Lys(ε-N-(2-methylphenyl)aminocarbonyl)-Asp(β-2-(1-morpholino)ethyl)-(NMe)PheNH₂;
α-Methyl-Trp-Lys((ε-N-(2-methylphenyl)aminocarbonyl)-(NMe)Asp(OMe)-PheNH₂;
Methoxycarbonyl-Trp-Lys((ε-N-3-(thienyl)acrylyl)-(NMe)Asp-(NMe)PheNH₂;
Methoxycarbonyl-Trp-Lys((ε-N-3-(thienyl)acrylyl)-(NMe)Asp-PheNH₂;
t-BOC-Trp-Lys(3-quinolinecarbonyl)-(NMe)Asp-PheNH₂;
t-BOC-Trp-Lys(ε-N-(2-thienylacryloyl)-(NMe)Asp-(NMe)PheNH₂;
Propionylyl-Trp-Lys(ε-N-(2-methylphenyl)aminocarbonyl)-Asp-(NMe)PheNH₂; and
Isobutyloxycarbonyl-Trp-Lys(ε-N-(2-methylphenyl)aminocarbonyl)-(NMe)Asp-PheNH₂;
as well as pharmaceutically-aceptable salts thereof Particularly preferred compounds of the present invention include:
t-BOC-Trp-Lys(ε-N-(2-methylphenyl)aminocarbonyl)-Asp-(NMe)PheNH₂;
t-BOC-Trp-Lys(ε-N-(2-methylphenyl)aminocarbonyl)-(NMe)Asp-PheNH₂;
t-BOC-Trp-Lys(ε-N-(2-methylphenyl)aminocarbonyl)-(NMe)Asp-(NMe)PheNH₂;
(NMe)Trp-Lys(ε-N-(2-methylphenyl)aminocarbonyl)-(NMe)Asp-PheNH₂;
Benzyloxycarbonyl-Trp-Lys(ε-N-(2-methylphenyl)aminocarbonyl)-Asp-(NMe)PheNH₂;
Isopropyloxycarbonyl-Trp-Lys(ε-N-(2-methylphenyl)aminocarbonyl)-Asp-(NMe)PheNH₂;
Methoxycarbonyl-Trp-Lys(ε-N-(2-methylphenyl)aminocarbonyl)-Asp-(NMe)PheNH₂;
Methoxycarbonyl-Trp-Lys(ε-N-(2-methylphenyl)aminocarbonyl)-(NMe)Asp-PheNH₂;
Acetyl-Trp-Lys(ε-N-(2-methylphenyl)aminocarbonyl)-Asp-(NMe)PheNH₂;
Acetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-Asp-(NMe)PheNH₂;
Trifluoroacetyl-Trp-Lys(ε-N-(2-methylphenyl)aminocarbonyl)-(NMe)Asp-PheNH₂;
t-Butylacetyl-Trp-Lys(ε-N-(2-methylphenyl)aminocarbonyl)-(NMe)Asp-PheNH₂;
Benzoyl-Trp-Lys(ε-N-(2-methylphenyl)aminocarbonyl)-(NMe)Asp-PheNH₂;
D,L-(α-Methyl)Trp-Lys(ε-N-(2-methylphenyl)aminocarbonyl)-Asp-PheNH₂;
(NMe)Trp-Lys(ε-N-(2-methylphenyl)aminocarbonyl)-(NMe)Asp-α-NalNH₂;
(NMe)Trp-Lys(ε-N-(2-methylphenyl)aminocarbonyl)-Asp-(NMe)PheNH₂;
(3-(3-Indolyl)propionyl)-Lys(ε-N-(2-methylphenyl)aminocarbonyl)-(NMe)Asp-α-NalNH₂;
t-BOC-Trp-Lys(ε-N-(2-methylphenyl)aminocarbonyl)-Asp-ChaNH₂;
α-Methyl-Trp-Lys((ε-N-(2-methylphenyl)aminocarbonyl)-(NMe)Asp(OMe)-PheNH₂;
Methoxycarbonyl-Trp-Lys((ε-N-3-(thienyl)acrylyl)-(NMe)Asp-(NMe)PheNH₂;
Propionylyl-TrpLys(ε-N-(2-methylphenyl)aminocarbonyl)-Asp-(NMe)PheNH₂;
Isobutyloxycarbonyl-Trp-Lys(ε-N-(2-methylphenyl)aminocarbonyl)(NMe)Asp-PheNH₂;
as well as pharmaceutically-acceptable salts thereof.

The compounds of the present invention, represented by formula (I), may be prepared via a number of processes which have been developed for peptide synthesis. A detailed description of these methods is contained in "The Peptides, Vol. 1", Gross and Meinenhofer, Eds., Academic Press, New York, 1979. Coupling methods employed include the carbodiimide method (1,3-dicyclohexylcarbodiimide [DCC], 1-(3-dimethylaminopropyl-3-ethylcarbodiimide hydrochloride [EDCl]) with the option of racemization preventing additives (l-hydroxybenzotriazole [HOBT]), the mixed anhydride method, the azide method, the acid chloride method, the symmetrical anhydride method, the use of bis(2-oxo-3-oxazolidinyl)phosphinic chloride (BOP-Cl), and the active ester method (N-hydroxysuccinimide esters, 4-nitrophenol esters, 2,4,5-trichlorophenol esters, and the like).

The compounds of the invention are prepared by stepwise coupling of the amino acids or by coupling together fragments of dipeptide length or greater. Thus, the free carboxylic acid moiety from one amino acid or peptide fragment is activated and allowed to condense with the free nitrogen group of the second amino acid or peptide fragment. The coupling reactions are conducted in solvents such as methylene chloride ($CH_2Cl_2$), tetrahydrofuran (THF), dimethylformamide (DMF) or other such solvents under an inert atmosphere such as nitrogen ($N_2$) or argon (Ar).

During the coupling process, the non-participating carboxylic acids or amines on the reacting set of amino acids or peptide fragments are protected by a protecting group which can be selectively removed at a later time if desired. A detailed description of these groups and their selection and chemistry is contained in "The Peptides, Vol. 3", Gross and Meinenhofer, Eds., Academic Press, New York, 1981. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Examples of useful protective groups for the carboxylic acid include esters, such as methyl, ethyl, benzyl, t-butyl, 2,2,2-trichloroethyl, allyl, 4-nitrobenzyl, and the like. Removal of these protecting groups may be accomplished selectively by employing various acid or base catalyzed hydrolytic, hydrogenolytic, thermal or dissolving metal conditions.

For the production of a compound of the invention where any one or several of the constituent amino acids bear an N-alkyl group, specifically methyl, the corresponding N-alkyl amino acid can be prepared via the method described by Benoiton (*Can. J. Chem.*, 1977, 55:906) or Shuman ("Peptides: Proceedings of the 7th American Peptide Symposium", D. Rich, E. Gross, Eds., Pierce Chemical Co., Rockford, Ill. 1981, p 617) wherein the t-BOC- or Cbz-protected amino acid is treated with a base in the presence of a chelating agent such as a crown ether and then quenched with methyl iodide. An alternative method described by Freidinger (*J. Org. Chem.*, 1983, 48:77) in which triethylsilane reduction of the oxazolidinone of an amino acid directly produces the N-methyl derivative may also be utilized.

The reduced carbonyl amide bond surrogates can be prepared in a manner similar to that described by Martinez (*J. Med. Chem.* 1987, 30:1366). The N-α-t-BOC protected amino acid (with appropriate protection of side chain functional groups) is converted to the 3,5-dimethylpyrazolide, which is then reduced with lithium aluminum hydride. The resulting aldehyde is then allowed to condense with an amino acid or peptide bearing a free amino terminus. Reduction of the Schiff base which is formed as a result of the condensation is accomplished using sodium cyanoborohydride to yield the desired compound having a reduced amide bond.

Functionalization of the ε-amino group of the lysine (Lys) or homologous (e.g., Orn) residue is achieved via activation of the acid fragment as the active ester (N-hydroxysuccinimide, 2,4,5-trichlorophenol, etc.) or, if no other free carboxylic acid function is present on the peptide, coupling using any of the methods mentioned above is applicable. In addition, the functionalization of the ε-amino group may be accomplished by reaction with various alkyl and aryl isocyanates, as well as alkyl and aryl isothiocyanates.

The sulfuric acid esterification of the phenolic residues may be conducted using a variety of known reagents such as the pyridine-sulfuric anhydride or the pyridine-sulfur trioxide complex. Use of pyridinium acetyl sulfate as described by Penke and Rivier ("Proceedings of the 8th American Peptide Symposium", V. Hruby, D. Rich, Eds., Pierce Chemical Company, Rockford, Ill.; 1983; p. 119) may also be applied to prepare the sulfuric acid ester derivative of the tetrapeptides.

The following examples, which are provided for illustration and not limitation of the invention, will serve to further illustrate preparation of the novel compounds of the invention. The following abbreviations are used: THF for tetrahydrofuran, DMF for N,N-dimethyl-formamide, $CDCl_3$ for deuterochloroform, DMSO-d6 for deuterodimethylsulfoxide, t-BPC for t-butyloxycarbonyl, DCC for dicyclohexylcarbodiimide, DIEA for diisopropylethylamine, EDCl for 1-(3-dimethyl-aminopropyl)-3-ethylcarbodiimide hydrochloride, IBCF for isobutyl chloroformate, HOBT for 1-hydroxybenzotriazole and NMM for N-methylmorpholine.

4-Carboethoxy-3,4,5,6-tetrahydro-1H,5H-azocin[4,5,6-c]indole

To a solution of the product of Example 112 c (53 mg, 0.19 mmol) in THF (6 mL) was added Lawesson's reagent (118 mg, 0.29 mmol) at ambient temperature. After stirring for 25 minutes, the reaction mixture was concentrated and the resulting residue was purified by flash chromatography on silica gel eluted with ethyl acetate/hexane (2:3) to give 33 mg of the corresponding thiol lactam. (TLC $Rf=0.40$ (ethyl acetate/hexane=1:1)). To a solution of the thiol lactam (33 mg, 0.11 mmol) in methylene chloride (2 mL) was added a 1M solution of triethyloxonium tetrafluoroborate in methylene chloride (130 mL, 0.13 mmol) at 0° C. under nitrogen. After stirring overnight at ambient temperature, the solvent was evaporated and ethanol (92 mL) was added to the resulting residue, followed by sodium borohydride (5 mg, 0.13 mmol) and the reaction mixture was stirred for 2 hours. The reaction mixture was washed with saturated aqueous $NaHCO_3$ solution and extracted with ethyl acetate several times. The organic phase was dried ($Na_2SO_4$), concentrated and the resulting residue purified by flash chromatography on silica gel eluted with 10% $MeOH/CHCl_3$ to give 12 mg of the title compound as a viscous oil. TLC $Rf=0.38$ (10% $MeOH/CHCl_3$). MS(DCl) m/e 259 $(M+H)^+$. $^1H$ NMR ($CDCl_3$, 300 MHz) δ8.07 (br, indole NH), 7.25 (m,1H) 7.12 (t,J=7.0 Hz,1H), 6.89 (d,J=2.2 Hz,1H), 6.83 (d,J=7.0 Hz,1H), 4.18 (q,J=7.0 Hz,2H), 3.89 (dd,J=7.0, 3.7 Hz,1H), 3.52 (br dd, J=15.1, 7.0 Hz,1H), 3.45–3.15 (m,4H), 2.95 (dt, J=13.0, 4.4 Hz,1H), 1.27 (t,J=7.0 Hz,3H).

EXAMPLE 1 t-BOC-Trp-Lys(ε-N-(3-(4-hydroxyphenyl)propionyl))-Asp-PheNH₂ a. t-BOC-Asp(OBn)-PheNH₂

To a solution of phenylalanineamide hydrochloride (19.4 g, 0.06 mol) in 100 mL of dimethylformamide (DMF) cooled to 0° C. were added N-methylmorpholine (NMM;7.2 mL, 0.065 mol), a solution of t-BOC-Asp β-benzyl ester (12.0 g, 0.06 mol), commercially available from Sigma Chemical Company, in methylene chloride (80 mL), 1-hydroxybenzotriazole (HOBT; 12.2 g, 0.09 mol) and 1-(3-dimethylaminopropyl)-3-ethylcarbodiimide hydrochloride (EDCl; 12.4 g, 0.065 mol). The reaction was stirred overnight with warming to ambient temperature. The solvent was removed in vacuo and the resulting residue was dissolved in ethyl acetate and washed 3× with 1M aqueous phosphoric acid solution ($H_3PO_4$), 3× with saturated aqueous sodium bicarbonate solution ($NaHCO_3$) solution and once with brine. After drying over anhydrous magnesium sulfate ($MgSO_4$), the solvent was evaporated. The residue was dissolved in hot ethyl acetate and the product precipitated with dropwise addition of hexane. The product was collected and dried to yield 25 g of the title compound as a white solid. MS(Cl/NH₃) m/e 470 (M+H)⁺, 487 (M+NH₄)⁺. ¹H NMR(CDCl₃, 300 MHz) δ1.39 (s,9H), 2.78 (dd,J=18 Hz,1H), 2.92–3.05 (m,2H), 3.21 (dd,1H), 4.38–4.45 (m,1H), 4.65 (q,J=6 Hz,1H), 5.36 (br s,1H), 5.49 (br d,J=7.5 Hz,1H), 6.09 (br s,1H), 6.82 (br d,J=7 Hz,1H), 7.21–7.40 (m,10H).

b. Asp(OBn)-PheNH₂ hydrochloride

A solution of Example 1a (16.2 g, 34 mmol) in 50 mL of 1.5M hydrogen chloride in acetic acid was stirred at ambient temperature for 1.5 hour. The reaction was quenched with the addition of diethyl ether which precipitated the product. The solid was collected, washed with fresh ether and dried to yield 12.9 g of the title compound as a white powder. MS(Cl/NH₃) m/e 370 (M+H)⁺. ¹H NMR(DMSO-d6, 300 MHz) δ2.74–2.91 (m,2H), 2.98–3.09 (m,2H), 4.08–4.12 (m,1H), 4.42–4.51 (m,1H), 5.17 (br s,2H), 7.14–7.59 (m,10H), 8.26 (br s,1H), 8.71 (br d,J=7 Hz,1H).

c. t-BOC-Lys(ε-N-benzyloxycarbonyl)-Asp(OBn)-PheNH₂

To a solution of the hydrochloride of Example 1b (12.9 g, 32 mmol) in DMF (20 mL) and methylene chloride (20 mL) cooled to −10° C. were added NMM (3.9 mL, 35 mmol), t-BOC-Lys(ε-N-benzyloxycarbonyl) (12.1 g, 32 mmol), HOBT (6.5 g, 48 mmol), and EDCl (6.7 g, 35 mmol). The reaction was stirred overnight with warming to ambient temperature. The solvents were removed in vacuo and the residue was dissolved in ethyl acetate and washed successively with solutions of 1M $H_3PO_4$ (3×), saturated $NaHCO_3$ (3×) and brine. The solvent was removed in vacuo and the solid residue was dissolved in acetone with warming. The product was precipitated with the dropwise addition of water, collected and dried to yield 22.3 g of the title compound as a white powder. MS(Cl/NH₃) m/e 732 (M+H)⁺, 749 (M+NH₄)⁺. ¹H NMR(DMSO-d6, 300 MHz) δ1.13–1.54 (m,6H), 1.37 (br s,9H), 2.51–3.05 (m,6H), 3.86 (br s,1H), 4.38 (br s,1H), 4.61 (br s,1H), 5.00 (s,2H), 5.07 (s,2H), 6.87 (br d,J=7 Hz,1H), 7.12–7.38 (m,16H), 7.85 (br d,1H), 8.15 (br d,1H). Analysis calculated for C₃₉H₄₉N₄O₉: C, 64.00; H, 6.75; N, 9.57. Found: C, 63.92; H, 6.82; N, 9.54.

d. Lys(ε-N-benzyloxycarbonyl)-Asp(OBn)-PheNH₂ hydrochloride

A solution of Example 1c (19 g, 26 mmol) in 80 mL of 1.5M hydrogen chloride in acetic acid was stirred at ambient temperature for 1.5 hour. The product was precipitated with the addition of diethyl ether (1 L), collected and dried to yield 17.2 g of the title compound as a white powder. MS(Cl/NH₃) m/e 632 (M+H)⁺. ¹H NMR(DMSO-d6, 300 MHz) δ1.21–1.43 (m,4H), 1.59–1.70 (m,2H), 2.59–2.69 (m,4H), 2.78–3.06 (m,5H), 3.69 (br s,1H), 4.36–4.45 (m,1H), 4.62–4.72 (m,1H), 5.00 (br s,2H), 5.10 (br s,2H), 7.11–7.40 (m,16H), 8.17 (br d,J=7 Hz,1H), 8.76 (br d,J=7 Hz,1H).

e. t-BOC-Trp-Lys(ε-N-benzyloxycarbonyl)-Asp(OBn)-PheNH₂

To a solution of the hydrochloride salt of Example 1d (9.8 g, 15.5 mmol) in DMF (100 mL) cooled to 0° C. were added N-methylmorpholine (1.9 mL, 17 mmol) and t-BOC-Trp N-hydroxysuccinimide ester (6.15 g, 15.5 mmol). The reaction was stirred overnight with warming to ambient temperature. The solvent was removed in vacuo and the residue partitioned between a solution of citric acid and ethyl acetate. The organic phase was further washed with solutions of $NaHCO_3$ (3×) and water (3×). After drying over $MgSO_4$, the solvent was removed in vacuo and the solid residue dissolved in ethyl acetate/acetone and precipitated with the addition of water. The product was collected and dried to yield 11.9 g of the title compound as a white solid. MS(FAB+) m/e 918 (M+H)⁺, 940 (M+Na)⁺. ¹H NMR(DMSO-d6, 300 MHz) δ1.01–1.66 (m,6H), 1.29 (br s,9H), 2.52–3.31 (m,8H), 4.18–4.31(m,2H), 4.36–4.45 (m,1H), 4.57–4.68 (m,1H), 4.99 (br s,2H), 5.06 (br s,2H), 6.82–7.39 (m,20H), 7.58 (br d,J=7 Hz,1H), 7.82 (br d,1H), 7.92 (br s,1H), 8.29 (br d,J=7 Hz,1H), 10.78 (br s,1H). Analysis calculated for C₅₀H₅₉N₇O.0.25H₂O: C, 65.09; H, 6.57; N, 10.62. Found: C, 64.80; H, 6.49; N, 10.65.

f. t-BOC-Trp-Lys-Asp-PheNH₂

A mixture of Example 1e (5.0 g, 5.45 mmol) and 10% Pd/C (1.0 g) in acetic acid (100 mL) was hydrogenated under one atmosphere of hydrogen at ambient temperature overnight. The catalyst was removed by filtration and the filtrate was concentrated in vacuo. The residue was triturated with ether to yield 3.95 g of the title compound as a light pink powder. MS(FAB+) m/e 694 (M+H)⁺. ¹H NMR(DMSO-d6, 300 MHz) δ1.11–1.62 (m, 6H), 1.32 (br s,1H), 2.25–3.18 (m, 8H), 4.10–4.43(m, 4H), 6.78–7.34 (m, 12H), 7.51–7.62 (m, 2H), 8.05 (br d,J=7 Hz, 1H), 8.17 (br d,J=7 Hz,1H), 10.91 (br s,1H). analysis calculated for C₃₅H₄₇N₇O₈.1.75CH₃CO₂H: C, 57.88; H, 6.81; N, 12.27. Found: C, 57.84; H, 6.92; N, 12.64.

g. t-BOC-Trp-Lys(ε-N-(3-(4-hydroxyphenyl)propionyl))-Asp-PheNH₂

To a solution of Example 1f (670 mg), in DMF (20 mL) cooled to 0° C. were added diisopropylethylamine (130 mg) and 3-(4-hydroxyphenyl)propionic acid N-hydroxysuccinimide ester (271 mg). The mixture was stirred overnight with warming to ambient temperature. The DMF was removed in vacuo and the residue was chromatographed on silica gel using ethyl acetate/pyridine/acetic acid/water (42:3.3:1:1.8). The solvents were removed in vacuo and the residue was dissolved in aqueous acetone and lyophilized to yield 515 mg of the title compound as a white flocculent solid. MS(FAB+) m/e 842 (M+H)⁺. ¹H NMR (DMSO-d6, 300 MHz)

δ1.12–1.58 (m,6H), 1.31 (br s,9H), 2.28 (br t,J=9 Hz,2H), 2.40–2.52 (m,2H), 2.69 (t,J=9H,2H), 2.81–3.20 (m,8H), 4.23 (br s,2H), 4.36 (m,1H), 4.49 (m,1H), 6.63 (d,J=9 Hz),1H), 6.78 (br d,J=8 Hz,1H), 6.91–7.38 (m,10H), 7.58 (br d,J=7 Hz,1H), 7.73 (br t,1H), 7.89–7.99 (m,2H), 8.23 (br d,J=7 Hz,1H), 10.81 (br s,1H). Analysis calculated for $C_{44}H_{55}N_7O_{10}.H_2O$: C, 61.45; H, 6.68; N, 11.40. Found: C, 61.12; H, 6.48; N, 11.14.

EXAMPLE 2 t-BOC-Trp-Lys($\epsilon$-N-(3-(4-sulfatylphenyl)propionyl))-Asp-PheNH$_2$

To a solution of Example 1g (103 mg, 0.12 mmol) in DMF (4 mL) and pyridine (4 mL) was added pyridinium acetyl sulfate (270 mg, 1.23 mmol). The reaction was stirred at ambient temperature for 18 hours then poured into water (50 mL) and made basic with 1M aqueous sodium hydroxide (NaOH) solution to a pH in the range of from 7.0 to 7.5. The mixture was concentrated in vacuo and the residue suspended in methanol and filtered. The filtrate was evaporated in vacuo and the residue chromatographed via preparative reverse phase HPLC using acetonitrile and 0.05M ammonium acetate buffer at pH 4.5 as eluants. The product was lyophilized to yield 52 mg of the title compound as a white flocculent powder. MS(FAB+) m/e 922 $(M+H)^+$. $^1$H NMR (DMSO-d6, 300 MHz) δ1.08–1.60 (m,6H), 1.31 (br s,9H), 2.33 (t,J=9 Hz,2H), 2.41–3.18 (m,10H), 4.23 (br s,2H), 4.38 (m,1H), 4.50 (m,1H), 6.80 (br s,1H), 6.91–7.33 (m,12H), 7.57 (br d,1H), 7.78 (br d,1H), 7.89 (br t,2H), 8.25 (m,1H), 10.66 (br s, 1H). Analysis calculated for $C_{44}H_{55}N_7O_{13}S$ NH$_4$OH: C, 55.22; H, 6.32; N, 11.71. Found: C, 55.35; H, 6.22; N, 11.52.

EXAMPLE 3 t-BOC-Trp-Lys($\epsilon$-N-(4-sulfatylcinnamoyl))-Asp-PheNH$_2$ a. 4-Hydroxycinnamic acid N-hydroxysuccinimide ester A solution of 4-hydroxycinnamic acid (300 mg: commercially available from Aldrich Chemical Company), N-hydroxysuccinimide (252 mg) and EDCl (385 mg) in methylene chloride (20 mL) was stirred at ambient temperature for 18 hours. The product was isolated as described in Example (old)1g to yield 280 mg of the title compound as a white solid. MS(Cl/NH$_3$) m/e 262 $(M+H)^+$. $^1$H NMR(DMSO-d6, 300 MHz) δ2.85 (br s,4H), 6.68 (d,J=15 Hz,1H), 6.83 (d,J=8 Hz,2H), 7.68 (d,2H), 7.85 (d,2H).

b. t-BOC-Trp-Lys($\epsilon$-N-(4-hydroxycinnamoyl))-Asp-PheNH$_2$

The tetrapeptide of Example 1f (120 mg), active ester of Example 3a (60 mg) and NMM (20 mg) were reacted under similar conditions to those described in Example 1g. The product was isolated in a similar manner to yield 96 mg of the title compound as a white flocculent powder. MS(FAB+) m/e 840 $(M+H)^+$. $^1$H NMR(DMSO-d6, 300 MHz) δ1.12–1.68 (m,6H), 1.32 (br s,9H), 2.38–2.68 (m,4H), 2.82–3.19 (m,4H), 4.19–4.31 (m,2H), 4.32–4.41 (m,1H), 4.45–4.53 (m,1H), 6.41 (d,J=15 Hz,1H), 6.76 (d,J=8 Hz,2H), 6.92–7.45 (m,13H), 7.58 (d,J=7 Hz,1H), 7.92–8.05 (m,3H), 8.25 (br d,J=7 Hz,1H), 10.82 (br s,1H). Analysis calculated for $C_{44}H_{53}N_7O_{10}$: C, 62.92; H, 6.36; N, 11.67. Found: C, 63.24; H, 6.43; N, 11.64.

c. t-BOC-Trp-Lys($\epsilon$-N-(4-sulfatylcinnamoyl))-Asp-PheNH$_2$

The tetrapeptide of Example 3b (50 mg) was treated in a manner similar to Example 2 employing pyridinium acetyl sulfate (131 mg) in a solution of DMF and pyridine. The product was isolated and purified under identical conditions to yield 34 mg of the title compound as a white solid. MS(FAB−) m/e 918 $(M-H)^-$. $^1$H NMR(DMSO-d6, 300 MHz) δ1.12–1.18 (m,6H), 1.32 (br s,9H), 2.45–2.75 (m,4H), 2.82–3.24 (m,4H), 4.21–4.32 (m,2H), 4.38–4.44 (m,1H), 4.49–4.58 (m,1H), 6.51 (d,J=15 Hz,1H), 6.78 (br s,1H), 6.92–7.46 (m,16H), 7.58 (br d,J=7 Hz,1H), 7.82 (br d,J=7 Hz,1H), 7.92 (br d,J=7 Hz,1H), 8.01 (br s,1H), 8.27 (br s,1H), 10.72 (br s,1H). Analysis calculated for $C_{44}H_{53}N_7O_{13}S.NH_4OH$: C, 53.81; H, 6.26; N, 11.41. Found: C, 53.81; H, 5.79; N, 11.24.

EXAMPLE 4 t-BOC-Trp-Lys($\epsilon$-N-(3-(4-methoxyphenyl)propionyl))-Asp-PheNH$_2$ a. 3-(4-Methoxyphenyl)propionic acid N-hydroxysuccinimide ester A solution of 3-(4-methoxyphenyl)propionic acid (512 mg; commercially available from Aldrich Chemical Company), N-hydroxy-succinimide (392 mg) and EDCl (599 mg) in methylene chloride (20 mL) was stirred at ambient temperature for 18 hours. The product was isolated as described in Example 3a to yield 650 mg of the title compound as a white solid. MS(Cl/NH$_3$) m/e 277 M$^+$, 295 $(M+NH_4)^+$. $^1$H NMR(CDCl$_3$, 300 MHz) δ2.82–2.93 (m,6H), 4.98–3.04 (m,2H), 3.29 (s,3H), 6.85 (dt,J=9 Hz,2H), 7.15 (dt,2H).

b. t-BOC-Trp-Lys($\epsilon$-N-(3-(4-methoxyphenyl)propionyl))-Asp-PheNH$_2$

The tetrapeptide of Example 1f (50 mg), active ester of Example 4a (25 mg) and NMM (8 mg) were reacted under similar conditions to those described in Example 1g. The product was isolated in a similar manner to yield 31 mg of the title compound as a white flocculent solid. MS(FAB+) m/e 878 $(M+Na)^+$. $^1$H NMR(DMSO-d6, 300 MHz) δ1.12–1.61 (m,6H), 1.32 (br s,9H), 2.25–3.25 (m,12H), 3.70 (s,3H), 4.21–4.49 (m,4H), 6.74–7.35 (m,13H), 7.58 (br d,1H), 7.29 (br s,2H), 7.95 (br d,1H), 8.13–8.30 (m,2H), 11.00 (br s,1H). Analysis calculated for $C_{45}H_{57}N_7O_{10}.0.5H_2O$: C, 62.48; H, 6.76; N, 11.34. Found: C, 62.42; H, 6.73; N, 11.26.

EXAMPLE 5 t-BOC-Trp-Lys($\epsilon$-N-(3-hydroxycinnamoyl))-Asp-PheNH$_2$ a. 3-Hydroxycinnamic acid N-hydroxysuccinimide ester The active ester was prepared in a similar manner to that described for Example 3a using 3-hydroxycinnamic acid (300 mg), N-hydroxysuccinimide (252 mg) and EDCl (385 mg). The product was isolated as described in Example 3a to yield 375 mg of the title compound as a white solid. MS(Cl/NH$_3$) m/e 279 $(M+NH_4)^+$. $^1$H NMR(DMSO-d6, 300 MHz) δ2.85 (br s,4H), 6.76–6.96 (m,2H), 7.17 (br s,1H), 7.25 (br d,2H), 7.87 (d,J=16 Hz,1H).

b. t-BOC-Trp-Lys($\epsilon$-N-(3-hydroxycinnamoyl))-Asp-PheNH$_2$

The tetrapeptide of Example 1f (97 mg), active ester of Example 5a (44 mg) and NMM (16 mg) were reacted under similar conditions to those described in Example 1g. The product was isolated in a similar manner to yield 85 mg of the title compound as a white solid. MS(FAB+) m/e 841 (M+H)+. $^1$H NMR(DMSO-d6, 300 MHz) δ1.13–1.68 (m,6H), 1.32 (br s,9H), 2.23–3.19 (m,8H), 4.21–4.48 (m,4H), 6.61 (d,J=16 Hz,1H), 6.72–7.33 (m,13H), 7.57 (br d,J=8 Hz,1H), 7.82 (br s,1H), 7.99 (br d,1H), 8.19 (br d,2H), 8.50 (br s,1H), 11.01 (br s,1H). Analysis calculated for $C_{44}H_{53}N_7O_{10}$: C, 62.92; H, 6.36; N, 11.67. Found: C, 62.59; H, 6.40; N, 11.54.

EXAMPLE 6 t-BOC-Trp-Lys(ε-N-(4-methylcinnamoyl))-Asp-PheNH$_2$ a. 4-Methylcinnamic acid N-hydroxysuccinimide ester A solution of 4-methylcinnamic acid (500 mg: commercially available from Aldrich Chemical Company), N-hydroxysuccinimide (425 mg) and EDCl (650 mg) in methylene chloride (20 mL) was stirred at ambient temperature for 18 hours. The active ester was isolated as described in Example 3a to yield 680 mg of the title compound as a white solid. MS(Cl/NH$_3$) m/e 260 (M+H)+, 277 (M+NH$_4$)+. $^1$H NMR (CDCl$_3$,300 MHz) δ2.38 (s,3H), 2.86 (br s,4H), 6.89 (d,J=16.5 Hz,1H), 7.28 (d,J=9 Hz,2H), 7.72 (d,2H), 7.92 (d,1H).

b. t-BOC-Trp-Lys(ε-N-(4-methylcinnamoyl))-Asp-PheNH$_2$

The tetrapeptide of Example 1f (75 mg), active ester of Example 6a (34 mg) and NMM (12 mg) were allowed to react under similar conditions to those described in Example 1g. The final product was isolated in a similar manner to yield 48 mg of the title compound as a white flocculent solid. MS(FAB+) m/e 860 (M+Na)+. $^1$H NMR(DMSO-d6, 300 MHz) δ1.12–1.68 (m,6H), 1.31 (br s,9H), 2.32 (s,3H), 2.38–2.69 (m,2H), 2.80–3.20 (m,6H), 4.26 (br s,2H), 4.32–4.42 (m,1H), 4.45–4.55 (m,1H), 6.57 (d,J=16.5 Hz,1H), 6.79 (br d,J=9 Hz,1H), 6.92–7.43 (m,16H), 7.50 (br d,1H), 7.92–8.00 (m,2H), 8.05 (br t,1H), 8.26 (br d,1H), 10.81 (br s,1H). Analysis calculated for $C_{45}H_{57}N_7O_{10} \cdot H_2O$: C, 63.14; H, 6.71; N, 11.45. Found: C, 63.06; H, 6.43; N, 11.34.

EXAMPLE 7 t-BOC-Trp-Lys(ε-N-(4-fluorocinnamoyl))-Asp-PheNH$_2$ a. 4-Fluorocinnamic acid N-hydroxysuccinimide ester A solution of 4-fluorocinnamic acid (500 mg: commercially available from Aldrich Chemical Company), N-hydroxysuccinimide (415 mg) and EDCl (634 mg) in methylene chloride (20 mL) was stirred at ambient temperature for 18 hours. The product was chromatographed and isolated as described in Example 3a to yield 680 mg of the title compound as a white solid. MS(Cl/NH$_3$) m/e 281 (M+NH$_4$)+. $^1$H NMR(CDCl$_3$, 300 MHz) δ2.87 (br s,4H), 6.95 (d,J=15 Hz,1H), 7.30 (t,J=10 Hz,2H), 7.91–8.01 (m,3H).

b. t-BOC-Trp-Lys(ε-N-(4-fluorocinnamoyl))-Asp-PheNH$_2$

The tetrapeptide of Example 1f (75 mg), active ester of Example 7a (34 mg) and NMM (12 mg) were allowed to react under similar conditions as those described in Example 1g. The peptide was isolated in an identical manner to yield 50 mg of the title compound as a white solid. MS(FAB+) m/e 842 (M+H)+. $^1$H NMR(DMSO-d6, 300 MHz) δ1.08–1.67 (m,6H), 1.29 (br s,9H), 2.38–2.66 (m,2H), 2.79–3.18 (m,6H), 4.17–4.40 (m,3H), 4.49 (q,J=7 Hz,1H), 6.58 (d,J=15 Hz,1H), 6.80–7.45 (m,16H), 7.54–7.62 (m,2H), 7.90–8.00 (m,2H), 8.11 (br t,1H), 8.26 (br d,1H), 10.84 (br s,1H). Analysis calculated for $C_{44}H_{52}FN_7O_9 \cdot 1.5H_2O$: C, 60.82; H, 6.38; N, 11.28. Found: C, 60.56; H, 6.09; N, 11.18.

EXAMPLE 8 t-BOC-Trp-Lys(ε-N-(4-trifluoromethylcinnamoyl))-Asp-PheNH$_2$ a. 4-Trifluoromethylcinnamic acid N-hydroxysuccinimide ester A solution of 4-trifluoromethylcinnamic acid (500 mg: commercially available from Aldrich Chemical Company), N-hydroxy-succinimide (319 mg) and EDCl (488 mg) in methylene chloride (20 mL) was stirred at ambient temperature for 18 hours. The product was isolated as previously described in Example 3a to yield 580 mg of the title compound as a white solid. MS(Cl/NH$_3$) m/e 331 (M+NH$_4$)+. $^1$H NMR(CDCl$_3$, 300 MHz) δ2.87 (br s,4H), 7.15 (d,J=16 Hz,1H), 7.82 (d,J=7 Hz,2H), 8.01–8.11 (m,3H).

b. t-BOC-Trp-Lys(ε-N-(4-trifluoromethylcinnamoyl))-Asp-PheNH$_2$

The tetrapeptide of Example 1f (75 mg), active ester of Example 8a (41 mg) and NMM (12 mg) were allowed to react under similar conditions to those described in Example 1 g. The peptide was isolated in an identical manner to yield 64 mg of the title compound as a white solid. MS (FAB+) m/e 892 (M+H)+. $^1$H NMR(DMSO-d6, 300 MHz) δ1.05–1.65 (m,6h), 1.29 (br s,9H), 2.36–2.65 (m,2H), 2.78–3.75 (m,6h), 4.16–4.41 (m,3H), 4.48 (q,J=8 Hz,1H), 6.77 (d,J=16 Hz,1H), 6.83 (d,J=9 Hz,1H), 6.92–7.34 (m,15H), 7.48 (d,1H), 7.59 (br d,1H), 7.92–8.03 (m,2H), 8.24 (br t,2H), 10.84 (br s,1H). Analysis calculated for $C_{45}H_{52}F_3N_7O_9 \cdot 1.5 H_2O$: C, 58.81; H, 6.03; N, 10.67. Found: C, 58.60; H, 5.86; N, 10.65.

EXAMPLE 9 t-BOC-Trp-Lys(ε-N-(3-(3-pyridyl)acrylyl))-Asp-PheNH$_2$ a. 3-(3-Pyridyl)acrylic acid N-hydroxysuccinimide ester A solution of 3-(3-pyridyl)acrylic acid (500 mg: commercially available from Aldrich Chemical Company), N-hydroxysuccinimide (463 mg), and EDCl (707 mg) in methylene chloride (20 mL) and DMF (10 mL) was stirred at ambient temperature for 18 hours. The product was isolated as described in Example 3a to yield 740 mg of the title compound as a white solid. MS (Cl/NH$_3$) m/e 247 (M+H)+. $^1$H NMR(CDCl$_3$, 300 MHz) δ2.87 (br s,4H), 7.15 (d,J=16 Hz,1H), 7.48–7.53 (m,1H), 8.02 (d,1H), 8.31 (dt,J=9 Hz,1H), 8.66 (dd,J=6 Hz,1H), 8.99 (d,J=2 Hz,1H).

b. t-BOC-Trp-Lys(ε-N-(3-(3-pyridyl)acrylyl))-Asp-PheNH$_2$

The tetrapeptide of Example 1f (75 mg), active ester of Example 9a (32 mg) and NMM (12 mg) were allowed to react under similar conditions to those described in Example 1g. The peptide was isolated in the usual manner to yield 53 mg of the title compound as a white solid. MS(FAB+) m/e 825 (M+H)+. $^1$H NMR(DMSO-d6, 300 MHz) $\delta$1.09–1.67 (m,6H), 1.29 (br s,9H), 2.40–2.69 (m,2H), 2.79–3.20 (m,6H), 4.16–4.41 (m,3H), 4.50 (q,J=7 Hz,1H), 6.62 (d,J=17 Hz,1H), 6.83 (br d,J=6 Hz,1H), 6.91–7.48 (m,15H), 7.58 (d,J=8 Hz,1H), 7.86–7.95 (m,2H), 8.17 (br t,1H), 8.27 (br d,1H), 8.52 (dd,J=5 Hz,1H), 8.72 (br d,1H), 10.80 (br s,1H). Analysis calculated for $C_{43}H_{52}N_8O_9$ 1.5H$_2$O: C, 60.62; H, 6.51; N, 13.15. Found: C, 60.70; H, 6.23; N, 13.05.

EXAMPLE 10 t-BOC-Trp-Lys($\epsilon$-N-($\alpha$-naphthoyl))-Asp-PheNH$_2$ a. $\alpha$-Naphthoic acid N-hydroxysuccinimide ester A solution of $\alpha$-naphthoic acid (500 mg), N-hydroxysuccinimide (400 mg) and EDCl (610 mg) in methylene chloride (20 mL) was stirred at ambient temperature for 18 hours. The active ester was isolated as described in Example 3a to yield 660 mg of the title compound as a white solid. MS(Cl/NH$_3$) m/e 270 (M+H)$^+$. $^1$H NMR(DMSO-d6, 300 MHz) $\delta$2.95 (br s,4H), 7.18–7.32 (m,3H), 8.15 (d,J=8 Hz,1H), 8.40 (t,J=9 Hz,2H), 8.65 (d,1H).

b. t-BOC-Trp-Lys($\epsilon$-N-($\alpha$-naphthoyl))-Asp-PheNH$_2$

The tetrapeptide of Example 1f (70 mg), active ester of Example 10a (33 mg) and NMM (11 mg) were allowed to react under similar conditions to those described in Example 1g. The peptide was isolated in an identical manner to yield 42 mg of the title compound as a white, flocculent solid. MS(FAB+) m/e 848 (M+H)$^+$. $^1$H NMR(DMSO-d6, 300 MHz) $\delta$1.08–1.71 (m,6H), 1.30 (br s,9H), 2.38–2.68 (m,2H), 2.78–3.18 (m,6H), 4.17–4.40 (m,3H), 4.46–4.55 (m,1H), 6.81 (d,J=7 Hz,1H), 6.92–7.62 (m,10H), 7.92–8.02 (m,2H), 8.16–8.29 (m,2H), 8.51 (br t,1H), 10.83 (br s,1H). Analysis calculated for $C_{46}H_{53}N_7O_9 \cdot H_2O \cdot 0.5CH_3CO_2H$: C, 63.00; H, 6.41; N, 10.94. Found: C, 62.93; H, 6.15; N, 11.16.

EXAMPLE 11 t-BOC-Trp-Lys($\epsilon$-N-(3-(2-thienyl)acrylyl))-Asp-PheNH$_2$ a. 3-(2-Thienyl)acrylic acid N-hydroxysuccinimide ester A solution of 3-(2-thienyl)acrylic acid (500 mg), N-hydroxysuccinimide (450 mg) and EDCl (680 mg) in methylene chloride (20 mL) was stirred at ambient temperature for 18 hours. The active ester was isolated as described in Example 3a to yield 630 mg of the title compound as a white solid. MS(Cl/NH$_3$) m/e 252 (M+H)$^+$. $^1$H NMR(CDCl$_3$, 300 MHz) $\delta$2.87 (br s,4H), 6.37 (d,J=16 Hz,1H), 7.11 (m,1H), 7.38 (d,J=3 Hz,1H), 7.50 (d,J=5 Hz,1H), 8.01 (d,1H).

b. t-BOC-Trp-Lys($\epsilon$-N-(3-(2-thienyl)acrylyl))-Asp-PheNH$_2$

The tetrapeptide of Example 1f (70 mg), active ester of Example 11a (31 mg) and NMM (11 mg) were allowed to react under similar conditions to those described in Example 1g. The product was isolated in a similar manner to yield 47 mg of the title compound as a white solid. MS(FAB+) m/e 830 (M+H)$^+$. $^1$H NMR(DMSO-d6, 300 MHz) $\delta$1.10–1.68 (m,6H), 1.30 (br s,9H), 2.36–2.68 (m,2H), 2.78–3.18 (m,6H), 4.18–4.40 (m,3H), 4.49 (q,J=7 Hz,1H), 6.38 (d,J=16 Hz,1H), 6.82 (d,J=8 Hz,1H), 6.92–7.62 (m,9H), 7.90–8.02 (m,2H), 8.10 (br t,1H), 8.24 (br d,1H), 10.83 (br s,1H). Analysis calculated for $C_{42}H_{51}N_7O_9S \cdot H_2O$: C, 59.49; H, 6.30; N, 11.56. Found: C, 59.55; H, 6.15; N, 11.49.

EXAMPLE 12 t-BOC-Trp-Lys($\epsilon$-N-(4-chlorocinnamoyl))-Asp-PheNH$_2$ a. 4-Chlorocinnamic acid N-hydroxysuccinimide ester A solution of 4-chlorocinnamic acid (0.08 g: commercially available from Aldrich Chemical Company), N-hydroxysuccinimide (0.55 g), and EDCl (0.88 g) in methylene chloride was stirred at ambient temperature for 18 hours. The product was isolated as described in Example 3a to yield 550 mg of the title compound as white crystals. m.p. 192°–193° C. MS(DCl/NH$_3$) m/e 297 (M+NH$_4$)$^+$. $^1$H NMR(DMSO-d6, 300 MHz) $\delta$2.87 (br s,4H), 7.05 (d,J=17 Hz,1H), 7.56 (d,J=9 Hz,1H), 7.92 (d,1H), 7.99 (d,1H).

b. t-BOC-Trp-Lys($\epsilon$-N-(4-chlorocinnamoyl))-Asp-PheNH$_2$

The tetrapeptide of Example 1f (100 mg), active ester of Example 12a (47 mg) and NMM (17 mg) were allowed to react under similar conditions to those described in Example 1g. The product was isolated in an identical manner to yield 85 mg of the title compound as a white solid. MS(FAB+) m/e 858 (M+H)$^+$. $^1$H NMR(DMSO-d6, 300 MHz) $\delta$1.08–1.65 (m,6H), 1.30 (br s,9H), 2.35–2.62 (m,2H), 2.78–3.20 (m,6H), 4.15–4.40 (m,3H), 4.48 (q,J=7 Hz,1H), 6.64 (d,J=16 Hz,1H), 6.83 (br d,J=7 Hz,1H), 6.91–7.62 (m,15H), 7.95 (br d,1H), 8.03 (br s,1H), 8.17 (br s,1H), 8.25 (br d,1H), 8.57 (br d,1H), 10.87 (br s,1H). Analysis calculated for $C_{44}H_{52}ClN_7O_9 \cdot H_2O$: C, 60.30; H, 6.21; N, 11.19. Found: C, 60.65; H, 6.18; N, 11.06.

EXAMPLE 13 t-BOC-Trp-Lys($\epsilon$-N-(4-(dimethylamino)cinnamoyl))-Asp-PheNH$_2$ a. 4-(Dimethylamino)cinnamic acid N-hydroxysuccinimide ester A solution of 4-(dimethylamino)cinnamic acid (0.50 g: commercially available from Aldrich Chemical Company), N-hydroxy-succinimide (0.37 g) and EDCl (0.56 g) in methylene chloride (20 mL) and DMF (5 mL) was stirred at ambient temperature for 18 hours. The product was isolated as described in Example 3a to yield 0.15 g of the title compound as a yellow solid. MS(Cl/NH$_3$) m/e 289 (M+H)$^+$. $^1$H NMR(CDCl$_3$, 300 MHz) $\delta$2.86 (br s,4H), 3.05 (s,6H), 6.32 (d,J=16 Hz,1H), 6.67 (dt,J=9 Hz,2H), 7.46 (dt,2H), 7.83 (d,1H).

b. t-BOC-Trp-Lys($\epsilon$-N-(4-(dimethylamino)cinnamoyl))-Asp-PheNH$_2$

The tetrapeptide of Example 1f (70 mg), active ester of Example 13a (37 mg) and NMM (11 mg) were allowed to react under similar conditions to those described in Example 1g. The peptide was isolated in an identical manner to yield 31 mg of the title compound as a white solid. MS(FAB+) m/e 867 (M+H)$^+$. $^1$H NMR(DMSO-d6, 300 MHz) $\delta$1.06–1.68 (m,6H), 1.30 (br s,9H), 2.41–2.71 (m,2H), 2.78–3.25 (m,6H), 4.16–4.31 (m,2H), 4.32–4.41 (m,1H), 4.51 (q,J=7 Hz,1H), 6.25 (d,J=16 Hz,1H), 6.68 (d,J=9 Hz,2H), 6.82–7.48 (m,11H), 7.59 (d,J=8 Hz,1H), 7.82–7.97 (m,3H), 8.28 (br d,1H). Analysis calculated for $C_{46}H_{58}N_8O_9 \cdot 0.5H_2O$: C, 63.07; H, 6.79; N, 12.79. Found: C, 62.97; H, 6.68; N, 12.69.

EXAMPLE 14 t-BOC-Trp-Lys(ε-N-(3,4-dihydroxycinnamoyl))-Asp-PheNH$_2$

A solution of 3,4-dihydroxycinnammic acid (80 mg: commercially available from Aldrich Chemical Company), N-hydroxy-succinimide (50 mg) and 1,3-dicyclohexylcarbodiimide (95 mg) in DMF was stirred at ambient temperature for 18 hours. The reaction mixture was cooled to 0° C. and the tetrapeptide of Example 1f (320 mg) and NMM (92 mg) were added and allowed to react for 24 hours. The product was isolated in a similar manner as described for Example 1 g to yield the title compound as a white solid. MS(FAB+) m/e 856 (M+H)+. $^1$H NMR(DMSO-d6, 500 MHz) δ1.06–1.66 (m,6H), 1.29 (br s,9H), 2.40–2.55 (m,2H), 2.81–3.17 (m,6H), 4.17–4.32 (m,2H), 4.33–4.40 (m,1H), 4.50 (q,1H), 6.13 (d,J=16 Hz,1H), 6.42–6.54 (m,1H), 6.72 (d,J=7 Hz,1H), 6.77–6.85 (m,2H), 6.92–7.42 (m,12H), 7.58 (d,1H), 7.88–7.97 (m,2H), 8.23 (d,1H). Analysis calculated for C$_{44}$H$_{53}$N$_7$O$_{11}$·H$_2$O·CH$_3$CO$_2$H: C, 59.15; H, 6.37; N, 10.50. Found: C, 59.44; H, 6.21; N, 10.52.

EXAMPLE 15 t-BOC-Trp-Lys(ε-N-(3,4-dichlorocinnamoyl))-Asp-PheNH$_2$ a. 3,4-Dichlorocinnamic acid N-hydroxysuccinimide ester A solution of 3,4-dichlorocinnamic acid (1.0 g: commercially available from Aldrich Chemical Company), N-hydroxysuccinimide (0.6 g) and EDCl (0.9 g) in methylene chloride was stirred at ambient temperature. The solvent was removed in vacuo and the residue was dissolved in ethyl acetate and washed several times with water. After drying (MgSO$_4$), the ethyl acetate was removed in vacuo and the resulting solid was recrystallized (ethyl acetate) to yield 1.19 g of the title compound as a white solid, m.p. 192°–196° C. MS(Cl/NH$_3$) m/e 314 (M+H)+. $^1$H NMR(CD3OD, 300 MHz) δ2.87 (s,4H), 6.86 (d,J=17 Hz,1H), 7.61 (d,J=8 Hz, 1H), 7.68 (dd,J=2 Hz, 1H), 7.91 (d,1H), 7.94 (d,1H).

b. t-BOC-Trp-Lys(ε-N-(3,4-dichlorocinnamoyl))-Asp-PheNH$_2$

The tetrapeptide of Example 1f (100 mg), active ester from Example 15a (43 mg) and NMM (15 mg) were allowed to react under similar conditions to those described in Example 1g. The final product was isolated as described to yield 62 mg of the title compound as a white solid. MS(FAB+) m/e 892 (M+H)+. $^1$H NMR(DMSO-d6, 500 MHz) δ1.06–1.66 (m,6H), 1.29 (br s,9H), 2.35–2.55 (m,2H), 2.81–3.18 (m,6H), 4.19–4.32 (m,2H), 4.36 (m,1H), 4.47 (q,1H), 6.72 (d,J=16 Hz,1H), 6.78 (br d,1H), 6.95 (br t,1H), 7.02–7.65 (m,12H), 7.79 (d,J=3 Hz,1H), 7.91 (br d,1H), 8.04 (br s,1H), 8.14–8.24 (m,2H). Analysis calculated for C$_{44}$H$_{51}$Cl$_2$N$_7$O$_9$·CH$_3$CO$_2$H·1.75H$_2$O: C, 56.18; H, 5.98; N, 9.97. Found: C, 55.94; H, 5.59; N, 10.23.

EXAMPLE 16 t-BOC-Trp-Lys(ε-N-(3-(4-hydroxyphenyl)propionyl))-Asp-(NMe)PheNH$_2$ a. Benzyloxycarbonyl-(NMe)PheNH$_2$ To a −10° C. solution of benzyloxycarbonyl-(NMe)-Phe (20.6 g) and NMM (7.01 g) in THF (500 mL) was added isobutylchloroformate (9.5 g: commercially available from Aldrich Chemical Company). After stirring for 5 minutes, a solution of aqueous ammonium hydroxide (12 mL) was added. After stirring an additional 15 minutes at −10° C., the reaction was allowed to warm to ambient temperature. The mixture was quenched with the addition of water and the product was collected and dried to yield 18 g of the title compound as a white solid. MS(Cl/NH$_3$) m/e 313 (M+H)+. $^1$H NMR(DMSO-d6, 300 MHz) δ2.82–2.97 (m,1H), 3.13–3.28 (m,1H), 3.35 (s,3H), 4.75–5.05 (m,3H), 7.13–7.55 (m,10H).

b. (NMe)PheNH$_2$

The title compound was prepared from Example 16a using the identical conditions described in Example 1f.

c. t-BOC-Asp(OBn)-(NMe)PheNH$_2$

To a 0° C. solution of t-BOC-(OBn)Asp (39.9 g: commercially available from Sigma Chemical Company) in methylene chloride (350 mL) was added EDCl (11.6 g). After stirring 1 hour, the amide of Example 16b (8.33 g) was added to the reaction and allowed to stand at ambient temperature for 18 hours. The solvent was removed in vacuo, the residue dissolved in ethyl acetate and washed with 1M H$_3$PO$_4$ then with saturated sodium bicarbonate solution. After drying (MgSO$_4$), the ethyl acetate was evaporated in vacuo to yield 25.4 g of the title compound as a white solid.

d. Asp(OBn)-(NMe)PheNH2 hydrochloride

The title compound was prepared from Example 16c employing similar reaction conditions to those described in Example 1b.

e. t-BOC-Lys(ε-N-benzyloxycarbonyl)-Asp(OBn)-(NMe)PheNH$_2$

The coupling of t-BOC-Lys(ε-N-benzyloxycarbonyl) and dipeptide of Example 16d was conducted under similar conditions to those described in Example 1c to afford the title compound.

f. Lys(ε-N-benzyloxycarbonyl)-Asp(OBn)-(NMe)-PheNH$_2$ hydrochloride

The title compound was prepared from Example 16e in a similar manner to that described for Example 1d.

g. t-BOC-Trp-Lys(ε-N-benzyloxycarbonyl)-Asp(OBn)-(NMe)PheNH$_2$

The coupling of t-BOC-Trp with the tripeptide of Example 16f was performed under identical conditions to those described for Example 1e to afford the title compound.

h. t-BOC-Trp-Lys-Asp-(NMe)PheNH$_2$

The title compound was prepared from Example 16g employing the procedure described for Example 1f.

i. t-BOC-Trp-Lys(ε-N-(3-(4-hydroxyphenyl)propionyl))-Asp-(NMe)PheNH$_2$

The tetrapeptide of Example 16h (43 mg), NMM (8 uL) and 3-(4-hydroxyphenyl)propionic acid N-hydroxysuccinimide ester (20 mg) were allowed to react under similar conditions to those described in Example 1g. The product was isolated in an identical manner to yield 26 mg of the title compound as a white solid. MS(FAB+) m/e 856 (M+H)+. $^1$H NMR(DMSO-d6, 300 MHz) δ1.08–1.61 (m,6H), 1.29 (br s,9H), 2.21–2.34 (m,4H), 2.62–3.25 (m,11H), 4.12–5.27 (m,4H), 6.62 (d,J=8 Hz,2H), 6.74–7.84 (m,13H), 8.18 (br d,1H), 8.58 (br d,2H). Analysis calculated for C$_{45}$H$_{57}$N$_7$O$_{10}$·CH$_3$CO$_2$H·1.5H$_2$O: C, 59.86; H, 6.84; N, 10.40. Found: C, 59.54; H, 6.52; N, 10.32.

EXAMPLE 17 t-BOC-Trp-Lys(ε-N-(4-hydroxycinnamoyl))-Asp-(NMe)PheNH₂

The tetrapeptide of Example 16h (107 mg), active ester of Example 3a (48 mg) and NMM (20 μL) were allowed to react under similar conditions to those described in Example 1g. The product was isolated in an identical manner to yield 48 mg of the title compound as a white solid. MS(FAB+) m/e 854 (M+H)+. ¹H NMR(DMSO-d6, 300 MHz) δ1.05–1.62 (m,6H), 1.29 (br s,9H), 2.26–2.54 (m,2H), 2.69–3.26 (m,9H), 4.15–5.20 (m,4H), 6.42 (d,J=16 Hz,1H), 6.72–6.85 (m,3H), 6.90–7.65 (m,14H), 7.79–8.00 (m,2H), 8.24 (br d,1H), 8.59 (m,1H), 9.82 (br s,1H). Analysis calculated for $C_{45}H_{56}N_7O_{10} \cdot CH_3CO_2H \cdot 0.5H_2O$: C, 61.09; H, 6.65; N, 10.61. Found: C, 60.66; H, 6.26; N, 11.00.

EXAMPLE 18 t-BOC-Trp-Lys(ε-N-(4-chlorocinnamoyl))-Asp-(NMe)PheNH₂

The tetrapeptide of Example 16h (113 mg), active ester of Example 12a (50 mg) and NMM (18 μL) were allowed to react under similar conditions to those described in Example 1g. The product was purified employing identical conditions to yield 44 mg of the title compound as a white powder. MS(FAB+) m/e 872 (m+H)+. ¹H NMR(DMSO-d6, 300 MHz) δ1.06–1.51 (m,6H), 1.28 (br s,9H), 2.22–2.51 (m,2H), 2.69–3.31 (m,9H), 4.13–5.18 (m,4H), 6.55–8.31 (m,18H). Analysis calculated for $C_{45}H_{57}ClN_7O_9 \cdot 1.5H_2O$: C, 60.02; H, 6.49; N, 10.89. Found: C, 60.16; H, 6.14; N, 10.88.

EXAMPLE 19 t-BOC-Trp-Lys(ε-N-(6-hydroxy-β-naphthoyl))-Asp-(NMe)PheNH₂ a. 6-Hydroxy-β-naphthoic acid N-hydroxysuccinimide ester

A solution of 6-hydroxy-β-naphthoic acid (1.0 g), N-hydroxysuccinimide (0.65 g), and EDCl (1.1 g) in methylene chloride was stirred at ambient temperature. The product was isolated as described in Example 3a to yield 0.32 g of the title compound as a white solid. MS (Cl/NH₃) m/e 303 (M+NH₃)+. ¹H NMR(DMSO-d6, 300 MHz) δ2.92 (br s,4H), 7.22–7.29 (m,2H), 7.91 (s,2H), 8.10 (d,J=8 Hz,1H), 8.71 (s,1H), 10.49 (s,1H).

b. t-BOC-Trp-Lys(ε-N-(6-hydroxy-β-naphthoyl))-Asp-(NMe)PheNH₂

The tetrapeptide of Example 16h (156 mg), active ester of Example 19a (64 mg) and NMM (24 μL) were allowed to react under similar conditions to those described for Example 1g. The product was isolated as described to yield 78 mg of the title compound as a white solid. MS(FAB+) m/e 878 (M+H)+. ¹H NMR(DMSO-d6, 300 MHz) δ1.04–1.65 (m,6H), 1.28 (br d,9H), 2.25–2.59 (m,2H), 2.69–3.35 (m,9H), 4.15–5.15 (m,4H), 6.81 (br t,1H), 6.91–7.98 (m,12H), 8.22–8.62 (m,4H). Analysis calculated for $C_{47}H_{55}N_7O_{10} \cdot H_2O$: C, 63.00; H, 6.41; N, 10.94. Found: C, 63.27; H, 6.38; N, 10.66.

EXAMPLE 20 t-BOC-Trp-Lys(ε-N-(6-acetoxy-β-naphthoyl))-Asp-(NMe)PheNH₂ a. 6-Acetoxy-β-naphthoic acid N-hydroxysuccinimide ester

A solution of 6-acetoxy-β-naphthoic acid (1.00 g), N-hydroxysuccinimide (0.53 g) and EDCl (0.95 g) in methylene chloride was stirred at ambient temperature for 18 hours. The product was isolated as described in Example 3a to yield 0.90 g of the title compound as a white solid. MS(Cl/NH₃) m/e 345 (M+NH₄)+. ¹H NMR(CDCl₃, 300 MHz) δ2.39 (s,3H), 2.94 (br s,4H), 7.36 (dd,J=9 Hz,1H), 7.66 (d,J=2 Hz,1H), 7.91 (d,J=8 Hz,1H), 8.00 (d,1H), 8.10 (dd,1H), 8.75 (br s,1H).

b. t-BOC-Trp-Lys(ε-N-(6-acetoxy-β-naphthoyl))-Asp-(NMe)PheNH₂

The tetrapeptide of Example 16h (105 mg), active ester from Example 20a (54 mg) and NMM (17 μL) were allowed to react under similar conditions employed of Example 1g. The product was purified as described to yield 59 mg of the title compound as a flocculent solid. MS(FAB+) m/e 920 (M+H)+. ¹H NMR(DMSO-d6, 300 MHz) δ1.06–1.65 (m,6H), 1.28 (br d,9H), 2.34 (s,3H), 2.68–3.95 (m,9H), 4.14–5.18 (m,4H), 6.81 (br t,1H), 6.91–8.07 (m,12H), 8.26 (br d,1H), 8.48 (br d,1H), 8.55–8.70 (m,3H). Analysis calculated for $C_{49}H_{57}N_7O_{11} \cdot 1.5H_2O$: C, 62.14; H, 6.39; N, 10.38. Found: C, 61.94; H, 6.13; N, 10.29.

EXAMPLE 21 t-BOC-Trp-Lys(ε-N-(3-(4-hydroxyphenyl)propionyl))-Asp-α-NalNH₂ a. t-BOC-α-NalNH₂

A solution of t-Boc-a-Nal-OH (1.5 g, 4.75 mmol) in THF (85 mL) was cooled to −20° C. and treated with NMM (0.63 mL, 5.7 mmol) and isobutyl chloroformate (0.75 mL, 5.7 mmol). After stirring for 5 min, 2.7 mL of conc. NH4OH was added rapidly, and the mixture was stirred and allowed to warm to ambient temperature. The mixture was concentrated and the residue was dissolved in ethyl acetate and washed with aqueous citric acid, aqueous NaHCO₃, and H₂O, dried (MgSO4) and evaporated to 1.25 g of product. Partial ¹H-NMR (300 MHz, DMSO-d6) δ1.25 (s, Boc), 3.11 (dd, J=10, 14 Hz, β-H), 3.52 (dd, J=4, 14 Hz, β-H), 4.23 (m, α-H).

b. α-NalNH₂ hydrochloride

The product of example 21a (1.2 g, 3.8 mmol) was treated with 25 mL of 4N HCl/dioxane for 1 h, then the product was precipitated by addition of ether and hexane and collected by filtration to afford 0.8 g of the hydrochloride. MS (Cl) m/e 215 (M+H)+, 232 (M+NH₄)+, 429 (2M+H)+. Partial ¹H-NMR (300 MHz, DMSO-d6) δ4.0 (m, α-H).

c. t-BOC-Asp(OBn)-α-NalNH2

The title compound was prepared via coupling of t-BOC-Asp(OBn) with the amino acid of Example 21b employing the conditions described in Example 1a.

d. Asp(OBn)-α-NalNH2 hydrochloride

The deprotection of the compound of Example 21c was conducted under similar conditions to those described in Example 1b to afford the title compound.

e. t-BOC-Lys(ε-N-benzyloxycarbonyl)-Asp(OBn)-α-NalNH₂

The title compound was prepared from coupling of t-BOC-Lys(ε-N-benzyloxycarbonyl) with the compound of Example 21d under conditions described for Example 1c.

f. Lys(ε-N-benzyloxycarbonyl)-Asp(OBn)-α-NalNH$_2$ hydrochloride

The title compound was prepared from the compound of Example 21e in an identical manner to Example 1d.

g. t-BOC-Trp-Lys(ε-N-benzyloxycarbonyl)-Asp(OBn)-α-NalNH$_2$

The title compound was prepared by coupling t-BOC-Trp with the tripeptide of Example 21f using the conditions described in Example 1e.

h. t-BOC-Trp-Lys-Asp-α-NalNH$_2$

The title compound was prepared from Example 21g using the conditions described for Example 1f.

i. t-BOC-Trp-Lys(ε-N-(3-(4-hydroxyphenyl)propionyl))-Asp-α-NalNH$_2$

The title compound was prepared from the compound of Example 21h in a similar manner to that described for Example 1g. MS(FAB+) m/e 892 (M+H)+. $^1$H NMR(DMSO-d6, 300 MHz) δ1.05–1.79 (m,6H), 1.29 (br s,9H), 2.28 (t,J=8 Hz,2H), 2.40–2.72 (m,4H), 2.85–3.64 (m,6H), 4.15–4.26 (m,2H), 4.42–4.55 (m,2H), 6.63 (d,J=8 Hz,1H), 6.83–8.35 (m,16H), 9.14 (s,1H). Analysis calculated for C$_{48}$H$_{57}$N$_7$O$_{10}$.0.5H$_2$O: C, 63.98; H, 6.49; N, 10.88. Found: C, 63.86; H, 6.44; N, 10.75.

EXAMPLE 22 t-BOC-Trp-Lys(ε-N-(2-hydroxycinnamoyl))-Asp-PheNH$_2$ a. 2-Hydroxycinnamic acid N-hydroxysuccinimide ester A solution of 2-hydroxycinnamic acid (1.00 g: commercially available from Aldrich Chemical Company), N-hydroxysuccinimide (0.72 g) and EDCl (1.20 g) in methylene chloride (15 mL) was stirred at ambient temperature for 18 hours. The title compound was isolated in an identical manner as described in Example 3a. MS(Cl/NH3) m/e 262 (M+H)+. $^1$H NMR(CDCl3, 300 MHz) δ2.90 (br s,4H), 6.72 (d,J=15 Hz,1H), 6.81 (dd,J=7 Hz,1H), 6.93 (t,1H), 7.28 (t,1H), 7.38 (dd,J=7 Hz,1H), 8.03 (d,1H).

b. t-BOC-Trp-Lys(ε-N-(2-hydroxycinnamoyl))-Asp-PheNH$_2$

The tetrapeptide of Example 1f (100 mg), active ester of Example 22a (38 mg) and NMM (28 mg) were allowed to react under identical conditions to those described in Example 1g. The product was isolated in a similar manner to yield 49 mg of the title compound as a white solid. MS(FAB+) m/e 840 (M+H)+. $^1$H NMR(DMSO-d6, 300 MHz) δ1.04–1.66 (m,6H), 1.30 (br s,9H), 2.38–2.51 (m,2H), 2.58–2.69 (m,2H), 2.79–3.17 (m,4H), 4.16–4.42 (m,3H), 4.50 (br q,1H), 6.65 (d,J=16 Hz,1H), 6.77–7.44 (m,15H), 7.58 (br s,1H), 7.62 (d,1H), 7.95 (d,1H), 8.06 (br t,1H), 8.28 (d,1H), 10.83 (br s,1H). Analysis calculated for C$_{44}$H$_{53}$N$_7$O$_{10}$.1.75H$_2$O: C, 60.64; H, 6.54; N, 11.25. Found: C, 60.48; H, 6.36; N, 10.97.

EXAMPLE 23 t-BOC-Trp-Lys(ε-N-(2,4-dimethoxycinnamoyl))-Asp-PheNH$_2$ a. 2,4-Dimethoxycinnamic acid N-hydroxysuccinimide ester A solution of 2,4-dimethoxycinnamic acid (1.00 g: commercially available from Aldrich Chemical Company), N-hydroxy-succinimide (0.56 g) and EDCl (0.95 g) in methylene chloride was allowed to stir at ambient temperature for 18 hours. The product was isolated as described in Example 3a to yield 1.04 g of the title compound as a white solid. MS(Cl/NH$_3$) m/e 306 (M+H)+. $^1$H NMR(CDCl3, 300 MHz) δ2.87 (br s,4H), 3.85 (s,3H), 3.88 (s,3H), 6.46 (d,J=2 Hz,1H), 6.52 (dd,J=9 Hz,1H), 6.62 (d,J=16 Hz,1H), 7.46 (d,1H), 8.09 (d,1H).

b. t-BOC-Trp-Lys(ε-N-(2,4-dimethoxycinnamoyl))-Asp-PheNH$_2$

The tetrapeptide of Example 1f (100 mg), active ester of Example 23a (44 mg) and NMM (29 mg) were allowed to react under the conditions described in Example 1g. The product was isolated in a similar manner to yield 77 mg of the title compound as a white solid. MS(FAB+) m/e 884 (M+H)+. $^1$H NMR(DMSO-d6, 500 MHz) δ1.06–1.61 (m,6H), 1.28 (br s,9H), 2.36–2.43 (m,1H), 2.52–2.62 (m,1H), 2.78–2.92 (m,2H), 3.00–3.15 (m,4H), 3.77 (s,3H), 3.80 (s,3H), 4.14–4.28 (m,2H), 4.30–4.37 (m,1H), 4.46 (q,1H), 6.47–6.57 (m,3H), 6.78 (d,1H), 6.92 (t,1H), 7.02 (t,1H), 7.05–7.40 (m,7H), 7.51–7.58 (m, 2H), 7.88–7.98 (m,3H), 8.21 (d,1H), 10.80 (br s,1H). Analysis calculated for C$_{46}$H$_{57}$N$_7$O$_{11}$.0.5-H$_2$O: C, 61.87; H, 6.55; N, 10.98. Found: C, 61.47; H, 6.43; N, 10.84.

EXAMPLE 24 t-BOC-Trp-Lys(ε-N-(2-methylphenyl)aminocarbonyl)-Asp-PheNH$_2$

A solution of the tetrapeptide of Example 1f (50 mg), 2-methylphenyl isocyanate (15 mg), commercially available from Aldrich Chemical Company, and NMM (18 mg) in DMF (5 mL) was stirred at ambient temperature for 18 hours. The product was isolated as described in Example 1g to yield 36 mg of the title compound as a white solid. MS(FAB+) m/e 827 (M+H)+. $^1$H NMR(DMSO-d6, 300 MHz) δ1.05–1.69 (m,6H), 1.30 (br s,9H), 2.16 (s,3H), 2.35–3.25 (m,10H), 4.16–4.40 (m,3H), 4.48 (q,1H), 6.78–7.42 (m,16H), 7.59 (br d,J=7 Hz,1H), 7.75–8.05 (m,4H), 8.26 (d,1H), 8.58 (m,1H), 10.82 (br s,1H). Analysis calculated for C$_{43}$H$_{54}$N$_8$O$_9$.CH$_3$CO$_2$H: C, 60.94; H, 6.59; N, 12.63. Found: C, 60.92; H, 6.58; N, 12.54.

EXAMPLE 25 t-BOC-Trp-Lys(ε-N-(3-methylphenyl)aminocarbonyl)-Asp-PheNH$_2$

A solution of the tetrapeptide of Example 1f (110 mg), 3-methylphenyl isocyanate (25 μL: commercially available from Aldrich Chemical Company) and NMM (33 mg) in DMF (5 mL) was allowed to react as described in Example 24. The product was isolated in a similar manner to yield 86 mg of the title compound as a white solid. MS(FAB+) m/e 827 (M+H)+. $^1$H NMR(DMSO-d6, 500 MHz) δ1.08–1.66 (m,6H), 1.31 (br s,9H), 2.22 (s,3H), 2.32–2.39 (m,1H), 2.44–2.55 (m,1H), 2.81–3.25 (m,8H), 4.16–4.29 (m,2H), 4.35 (m,1H), 4.42 (br q, 1H), 6.65 (br d,J=7.5 Hz,1H), 6.77 (br d,1H), 6.94 (br t,1H), 7.03–7.40 (m,15H), 7.54 (br d,1H), 7.88 (br d,1H), 7.98 (br d,1H), 8.09 (br d,1H). Analysis calculated for C$_{43}$H$_{54}$N$_8$O$_9$.CH$_3$CO$_2$H.0.75-H$_2$O: C, 59.96; H, 6.66;, N, 12.43. Found: C, 59.97; H, 6.31; N, 12.45.

EXAMPLE 26 t-BOC-Trp-Lys(ε-N-(4-chlorophenyl)aminocarbonyl)-Asp-PheNH$_2$

A solution of tetrapeptide of Example 1f (100 mg), NMM (40 μL), and 4-chlorophenyl isocyanate (40 mg: commercially available from Aldrich Chemical Company) in DMF (5 mL) was reacted according to the procedure in Example 24. The product was isolated under identical conditions to yield 38 mg of the title compound as a white solid. MS(FAB+) m/e 847 (M+H)+. $^1$H NMR(DMSO-d6, 500 MHz) δ1.08–1.68 (m,6H), 1.29 (br s,9H), 2.40–2.64 (m,2H), 2.80–3.16 (m,8H), 4.22 (br s,2H), 4.37 (br m,1H), 4.48 (br m,1H), 6.74 (br m,1H), 6.95 (t,1H), 7.02–7.38 (m,14H), 7.41 (d,1H), 7.57 (br d,1H), 7.75 (br d,1H), 7.88 (br s,1H), 8.14 (br s,1H). Anal calc for C$_{42}$H$_{51}$N$_8$O$_9$Cl.H$_2$O.0.5CH$_3$CO$_2$H: C, 57.68; H, 6.19; N, 12.51. Found: C, 57.67; H, 5.99; N, 12.43.

EXAMPLE 27 t-BOC-Trp-Lys(ε-N-(2-chlorophenyl)aminocarbonyl)-Asp-PheNH$_2$

A solution of tetrapeptide of Example 1f (100 mg), 2-chlorophenyl isocyanate (30 μL: commercially available from Aldrich Chemical Company) and NMM (35 μL) in DMF (5 mL) was stirred at ambient temperature for 18 hours. The product was purified as described in Example 24 to yield 72 mg of the title compound as a white solid. MS(FAB+) m/e 847 (M+H)+. $^1$H NMR(DMSO-d6, 500 MHz) δ1.10–166 (m,6H), 1.31 (br s,9H), 2.41 (dd,J=6 Hz,J=17 Hz,1H), 2.63 (dd,1H), 2.83–3.14 (m,8H), 4.20–4.30 (m,2H), 4.38 (m,1H), 4.51 (q,1H), 6.77 (br d,1H), 6.90–7.40 (m,14H), 7.58 (d,1H), 7.86 (d,1H), 7.90 (d,1H), 8.00 (s,1H), 8.14 (d,1H), 8.21 (d,1H). Analysis calculated for C$_{42}$H$_{51}$N$_8$O$_9$Cl.H$_2$O.0.5CH$_3$CO$_2$H: C, 57.68; H, 6.19; N, 12.51. Found: C, 57.68; H, 6.03; N, 12.51.

EXAMPLE 28 t-BOC-Trp-Lys(ε-N-(α-naphthyl)aminocarbonyl)-Asp-PheNH$_2$

A solution of tetrapeptide of Example 1f (100 mg), α-naphthyl isocyanate (30 μL: commercially available from Aldrich Chemical Company) and NMM (30 μL) in DMF (5 mL) was allowed to react as described in Example 24. The final product was purified in a similar manner to yield 54 mg of the title compound as a white solid. MS(FAB+) m/e 863 (M+H)+. $^1$H NMR(DMSO-d6, 500 MHz) δ1.10–1.68 (m,6H), 1.30 (br s,9H), 2.39–2.60 (m,2H), 2.82–3.18 (m,8H), 4.24 (br s,2H), 4.36 (m,1H), 4.45 (m,1H), 6.78 (br d,1H), 6.91–7.68 (m,18H), 7.84–8.05 (m,3H), 8.17 (br s,1H). Analysis calculated for C$_{46}$H$_{54}$N$_8$O$_9$.CH$_3$CO$_2$H.0.6-H$_2$O: C, 61.74; H, 6.39; N, 11.99. Found: C, 61.67; H, 6.19; N, 11.99.

EXAMPLE 29 t-BOC-Trp-Lys(ε-N-(phenylaminocarbonyl))-Asp-PheNH$_2$

A solution of tetrapeptide of Example 1f (100 mg), phenyl isocyanate (20 μL: commercially available from Aldrich Chemical Company) and NMM (30 μL) in DMF (5 mL) was reacted in a similar manner as described in Example 24. The product was purified under identical conditions to yield 47 mg of the title compound as a white powder. MS(FAB+) m/e 813 (M+H)+. $^1$H NMR(DMSO-d6, 500 MHz) δ1.08–1.66 (m,6H), 1.30 (br s,9H), 2.35–2.60 (m,2H), 2.81–3.14 (m,6H), 4.17–4.28 (br m,2H), 4.35 (m,1H), 4.45 (m,1H), 6.82 (q,2H), 6.95 (t,1H), 7.04 (t,1H), 7.09–7.45 (m,14H), 7.58 (d,1H), 7.86 (d,1H), 7.98 (br d,1H), 8.18 (br d,1H). Analysis calculated for C$_{42}$H$_{52}$N$_8$O$_9$.H$_2$O: C, 60.71; H, 6.55; N, 13.49. Found C, 60.76; H, 6.50; N, 13.14.

EXAMPLE 30 t-BOC-Trp-Lys(ε-N-(cyclohexylaminocarbonyl))-Asp-PheNH$_2$

A solution of tetrapeptide of Example 1f (100 mg), cyclohexyl isocyanate (25 μL: commercially available from Aldrich Chemical Company) and NMM (33 μL) in DMF (5 mL) was allowed to react as described in Example 24. The product was purified in a similar manner to that described to yield 44 mg of the title compound as a white solid. MS(FAB+) m/e 819 (M+H)+. $^1$H NMR(DMSO-d6, 300 MHz) δ1.00–1.76 (m,17H), 1.30 (br s,9H), 2.42 (dd,J=7 Hz,J=16 Hz,1H), 2.59 (dd,1H), 2.81–2.95 (m,4H), 3.01–3.12 (m,2H), 4.22 (m,2H), 4.36 (m,1H), 4.48 (q,1H), 6.78 (d,1H), 6.95 (t,J=7 Hz,1H), 7.04 (t, 1H), 7.08–7.38 (m,8H), 7.58 (d,1H), 7.85–7.95 (m,2H), 8.21 (d,1H), Analysis calculated for C$_{42}$H$_{58}$N$_8$O$_9$. H$_2$O.0.75CH$_3$CO$_2$H: C, 59.17; H, 7.20' N, 12.66. Found: C, 59.11; H, 6.83' N, 12.82.

EXAMPLE 31 t-BOC-Trp-Lys(ε-N-(3-chlorophenyl)aminocarbonyl)-Asp-PheNH$_2$

A solution of tetrapeptide of Example 1f (100 mg), 3-chlorophenyl isocyanate (40 μl: commercially available from Aldrich Chemical Company) and NMM (35 μl) in DMF (5 mL).was allowed to react under the conditions described in Example 24. The final product was purified under identical conditions to yield 46 mg of the title compound as a white powder. MS(FAB+) m/e 847 (M+H)+. $^1$H NMR(DMSO-d6, 500 MHz) δ1.08–1.65 (m,6H), 1.30 (br s,9H), 2.44 (dd,1H), 2.62 (dd,1H), 2.81–2.96 (m,2H), 3.00–3.15 (m,4H), 4.22 (br s,2H), 4.36 (br m,1H), 4.48 (q,1H), 6.81 (d,1H), 6.89 (m,1H), 6.95 (t,J=5 Hz,1H), 7.04 (t,1H), 7.09–7.33 (m,10H), 7.58 (d,1H), 7.67 (s,1H), 7.82 (d,1H), 7.94 (d,1H), 8.20 (d,1H), 10.76 (br s,1H). Analysis calculated for C$_{42}$H$_{51}$N$_8$O$_9$Cl.H$_2$O.0.5CH$_3$CO$_2$H: C, 57.68; H, 6.19; N, 12.51. Found: C, 57.63; H, 5.84; N, 12.48.

EXAMPLE 32 t-BOC-Trp-Lys(ε-N-(t-butylaminocarbonyl))-Asp-PheNH$_2$

A solution of tetrapeptide of Example 1f (100 mg), t-butylisocyanate (30 μL: commercially available from Aldrich Chemical Company) and NMM (30 μL) in DMF (5 mL) was allowed to react under the conditions described in Example 24. The product was purified in a similar manner to yield 67 mg of the title compound as a white solid. MS(FAB+) m/e 793 (M+H)+. $^1$H NMR(DMSO-d6, 300 MHz) δ1.03–1.58 (m,6H), 1.20 (br s,9H), 1.30 (br s,9H), 2.40 (dd,J=Hz,J=16 Hz,1H), 2.58 (dd, 1H), 2.78–2.98 (m,4H), 3.02–3.14 (m,2H), 4.15–4.29 (m,2H), 4.35 (m,1H), 4.47 (q,1H), 6.82 (d,J=8 Hz,1H), 6.91–7.49 (m,10H), 7.58 (d,1H), 7.90–8.02 (m,2H), 8.22 (d,1H), 10.85 (br s,1H). Analysis calculated for C$_{40}$H$_{56}$N$_8$O$_9$.H$_2$O.0.75CH$_3$CO$_2$H: C, 58.23; H, 7.18; N, 13.09. Found: C, 58.21; H, 6.87; N, 13.20.

EXAMPLE 33 t-BOC-Trp-Lys(ε-N-(2-methylphenyl)aminocarbonyl)-Asp-(NMe)PheNH₂

A solution of the tetrapeptide of Example 16h (219 mg), 2-methyl-phenyl isocyanate (100 μL) and NMM (35 μL) in DMF was allowed to react as described in Example 1g. The product was purified under similar conditions to yield the title compound as a white solid. MS(FAB+) m/e 841 (M+H)+. ¹H NMR(DMSO-d6, 300 MHz) δ1.14–1.56 (m,6H), 1.29 (br s,9H), 2.05–2.40 (m,2H), 2.15 (s,3H), 2.27 (s,3H), 2.67–3.29 (m,8H), 2.97 (s,3H), 4.20–4.39 (m,2H), 4.71–5.27 (m,2H), 6.78–7.98 (m,16H), 8.24 (s,1H), 8.58 (br s,1H), 10.82 (br s,1H). Analysis calculated for $C_{44}H_{56}N_8O_9 \cdot CH_3CO_2H$: C, 61.32; H, 6.61; N, 12.44. Found: C, 61.46; H, 6.22; N, 12.18.

EXAMPLE 34 t-BOC-Trp-Lys(ε-N-(2-nitrophenyl)aminocarbonyl)-Asp-PheNH₂

The tetrapeptide of Example 1f, 2-nitrophenyl isocyanate (commercially available from Aldrich Chemical Company) and NMM in DMF were allowed to react in a manner described in Example 24. Similar purification yielded the title compound as a white solid. MS(FAB+) m/e 858 (M+H)+. ¹H NMR(DMSO-d6, 300 MHz) δ1.08–1.65 (m,8H), 1.30 (s, 9H), 2.41–2.53 (d,1H), 2.66 (dd,1H), 2.70–3.13 (m,6H), 4.16–4.32 (br s,2H), 4.33–4.43 (m,1H), 4.46–4.55 (m,1H), 6.84 (d,1H), 6.95 (t,1H), 7.02–7.34 (m,9H), 7.55–7.65 (m,2H), 7.86 (d,1H), 7.95 (d,1H), 8.03 (d,1H), 8.28 (t,1H). Analysis calculated for $C_{42}H_{51}N_9O_{11} \cdot CH_3CO_2H$: C, 57.57; H, 6.04; N, 13.73. Found: C, 57.93; H, 5.90; N, 13.90.

EXAMPLE 35 t-BOC-Trp-Lys(ε-N-(2-trifluoromethylphenyl)aminocarbonyl)Asp-PheNH₂

The tetrapeptide of Example 1f (175 mg, 0.26 mmol), NMM (0.06 mL) and 2-trifluoromethylphenyl isocyanate (0.05 mL, 0.28 mmol) in DMF (5 mL) were allowed to react in a manner described in Example 24. Similar purification yielded 135 mg of the title compound as a white solid. MS(FAB+) m/e 881 (M+H)+. ¹H NMR(DMSO-d6, 500 MHz) δ1.09–1.66 (m,8H), 1.31 (s,9H), 2.47 (dd,1H), 2.65 (dd,1H), 2.82–2.96 (m,2H), 2.99–3.13 (m,4H), 4.19–4.32 (m,2H), 4.34–4.40 (m,1H), 4.48–4.54 (m,1H), 6.80 (d,1H), 6.95 (t,1H), 7.02–7.33 (m,9H), 7.51–7.61 (m,2H), 7.27 (s,1H), 7.92 (d,1H), 7.96 (d,1H), 8.25 (d,1H). Analysis calculated for $C_{43}H_{51}F_3N_8O_9$: C, 58.63; H, 5.84; N, 12.72. Found: C, 58.26; H, 5.81; N, 12.46.

EXAMPLE 36 t-BOC-Trp-Lys(ε-N-(2-bromophenyl)aminocarbonyl)-Asp-PheNH₂

A solution of the tetrapeptide of Example 1f (175 mg, 0.26 mmol), NMM (0.06 mL, 0.52 mmol) and 2-bromophenyl isocyanate (0.034 mL, 0.28 mmol: commercially available from Aldrich Chemical Company) in DMF (5 mL) was allowed to react as described in Example 24 and the product purified in a similar manner to yield 130 mg of the title compound as a white solid. MS(FAB+) m/e 893 (M+H)+. ¹H NMR(DMSO-d6, 500 MHz) δ1.07–1.66 (m,8H), 1.30 (s,9H), 2.44 (dd,1H), 2.61 (dd,1H), 2.82–2.95 (m,2H), 3.01–3.13 (m,4H), 4.19–4.30 (m,2H), 4.33–4.39 (m,1H), 4.49 (q,1H), 6.79 (d,1H), 6.95 (t,1H), 7.02–7.39 (m,8H), 7.53 (d,1H), 7.58 (d,1H), 7.88 (s,1H), 7.93 (d,1H), 8.06 (d,1H), 8.22 (d,1H). Analysis calculated for $C_{42}H_{51}BrN_8O_9 \cdot H_2O$: C, 55.44; H, 5.99; N, 12.32. Found: C, 55.70; H, 5.70; N, 12.16.

EXAMPLE 37 t-BOC-Trp-Lys(ε-N-(2-chlorophenyl)aminothiocarbonyl)-Asp-PheNH₂

A solution of the tetrapeptide of Example 1f (160 mg, 0.23 mmol), NMM (0.06 mL, 0.52 mmol) and 2-chlorophenyl isothiocyanate (0.05 mL, 0.26 mmol: commercially available from Aldrich Chemical Company) in DMF (5 mL) was allowed to react as described in Example 24. A similar purification yielded 138 mg of the title compound as a white solid. MS(FAB+) m/e 863 (M+H)+. ¹H NMR(DMSO-d6, 300 MHz) δ1.09–1.65 (m,8H), 1.30 (s,9H), 2.44 (dd,1H), 2.63 (dd,1H), 2.80–2.96 (m,2H), 3.00–3.18 (m,4H), 4.17–4.30 (m,2H), 4.31–4.40 (m,1H), 4.45–4.53 (m,1H), 6.84 (d,1H), 6.95 (t,1H), 7.11–7.34 (m,8H), 7.46 (d,1H), 7.59 (d,1H), 7.67 (d,1H), 7.87 (d,1H), 7.98 (d,1H). Analysis calculated for $C_{42}H_{51}ClN_8O_8S \cdot H_2O$: C, 57.23; H, 6.06; N, 12.71. Found: C, 57.42; H, 5.87; N, 12.63.

EXAMPLE 38 t-BOC-Trp-Lys(ε-N-(2-methylphenyl)aminothiocarbonyl)-Asp-PheNH₂

A solution of the tetrapeptide of Example 1f (160 mg, 0.23 mmol), NMM (0.06 mL, 0.52 mmol) and 2-methylphenyl isothiocyanate (0.04 mL, 0.26 mmol: commercially available from Aldrich Chemical Company) in DMF (5 mL) was allowed to react in a manner similar to that described in Example 24. Purification of the mixture yielded 54 mg of the title compound as a white solid. MS(FAB+) m/e 843 (M+H)+. ¹H NMR(DMSO-d6, 300 MHz) δ1.09–1.67 (m,8H), 1.30 (br s,9H), 2.44–2.66 (m,2H), 2.78–2.97 (m,2H), 3.01–3.19 (m,2H), 4.16–4.29 (m,2H), 4.30–4.39 (m,1H), 4.42–4.54 (m,1H), 6.82 (d,1H), 6.95 (t,1H), 7.10–7.37 (m,7H), 7.58 (d,1H), 7.87 (d,1H), 7.98 (d,1H), 8.22 (d,1H). Analysis calculated for $C_{43}H_{54}N_8O_8S \cdot H_2O$: C, 59.99; H, 6.32; N, 13.02. Found: C, 60.15; H, 6.34; N, 12.96.

EXAMPLE 39 t-BOC-Trp-Lys(ε-N-(3-acetylphenyl)aminocarbonyl)-Asp-PheNH₂

The tetrapeptide of Example 1f (160 mg, 0.23 mmol), NMM (0.06 mL, 0.52 mmol) and 3-acetylphenyl isocyanate (0.05 mL, 0.26 mmol) were allowed to react in DMF (5 mL) as described in Example 24. A similar purification yielded 96 mg of the title compound as a white solid. MS(FAB+) m/e 855 (M+H)+. ¹H NMR(DMSO-d6, 300 MHz) δ1.08–1.66 (m,8H), 1.31 (br s,9H), 2.52 (s,3H), 2.39–2.66 (m,2H), 2.79–2.96 (m,2H), 2.98–3.15 (m,4H), 4.18–4.28 (m,2H), 4.31–4.40 (m,1H), 4.43–4.53 (m,1H), 6.85 (d,1H), 6.95 (t,1H), 7.05 (t,1H), 7.11–7.41 (m,9H), 7.47 (d,1H), 7.55–7.66 (m,2H), 7.86 (d,1H), 7.95–8.04 (m,2H), 8.24 (d,1H). Analysis calculated for $C_{44}H_{54}N_8O_{10} \cdot H_2O$: C, 60.54; H, 6.47; N, 12.84. Found: C, 60.32; H, 6.28; N, 12.64.

EXAMPLE 40 t-BOC-Trp-Lys(ε-N-(4-acetylphenyl)aminocarbonyl)-Asp-PheNH₂

A solution of the tetrapeptide of Example 1f (160 mg, 0.23 mmol), NMM (0.06 mL, 0.52 mmol) and 4-acetylphenyl isocyanate (0.05 mL, 0.26 mmol) in DMF (5 mL) was allowed to react as described in Example 24. The product was purified in an identical manner to yield 125 mg of the title compound as a white solid. MS(FAB+) m/e 855 (M+H)+. ¹H NMR(DMSO-d6, 300 MHz) δ1.09-1.65 (m,8H), 1.30 (br s,9H), 2.33-2.67 (m,2H), 2.47 (s,3H), 2.80-2.95 (m,2H), 3.01-3.14 (m,4H), 4.17-4.28 (m,2H), 4.32-4.40 (m,1H), 4.43-4.53 (m,1H), 6.85 (d,1H), 6.95 (t,1H), 7.05 (t,1H), 7.10-7.35 (m,8H), 7.52 (d,1H), 7.58 (d,1H), 7.79-7.87 (m,2H), 7.99 (d,1H). Analysis calculated for $C_{44}H_{54}N_8O_{10} \cdot 1.25H_2O$: C, 60.22; H, 6.46; N, 12.77. Found: C, 60.07; H, 6.24; N, 12.62.

EXAMPLE 41 t-BOC-Trp-Lys(ε-N-(2-isopropylphenyl)aminocarbonyl)-Asp-PheNH₂

A solution of the tetrapeptide of Example 1f (160 mg, 0.23 mmol), 2-isopropylphenyl isocyanante (0.042 mL) and NMM in DMF was allowed to react as described in Example 24. The product was isolated in a similar manner to yield 60 mg of the title compound as a white solid. MS(FAB+) m/e 855 (M+H)+. ¹H NMR(DMSO-d6, 300 MHz) δ1.09-1.65 (m,8H), 1.14 (d,J=7 Hz,6H), 1.30 (s,9H), 2.78-3.17 (m,6H), 4.18-4.29 (m,2H), 4.31-4.40 (m,1H), 4.42-4.51 (m,1H), 6.83 (d,1H), 6.91-7.33 (m,8H), 7.40 (br s,1H), 7.55-7.66 (m,2H), 7.97 (t,1H), 8.22 (d,1H). Analysis calculated for $C_{45}H_{58}N_8O_9 \cdot H_2O \cdot 0.75CH_3CO_2H$: C, 60.90; H, 6.91; N, 12.25. Found: C, 60.90; H, 6.76; N, 12.30.

EXAMPLE 42 t-BOC-Trp-Lys(ε-N-(4-methylphenyl)aminocarbonyl)-Asp-PheNH₂

A solution of the tetrapeptide of Example 1f (100 mg, 0.15 mmol), NMM (0.035 mL) and 4-methylphenyl isocyanate (0.08 mL: commercially available from Aldrich Chemical Company) in DMF was reacted under the conditions described in Example 24 and isolated to yield 31 mg of a white solid. MS(FAB+) m/e (M+H)+. ¹H NMR(DMSO-d6, 500 MHz) δ1.11-1.66 (m,8H), 1.32 (s,9H), 2.19 (s,3H), 2.34-2.43 (m,1H), 2.47-2.59 (m,1H), 2.82-3.15 (m,4H), 4.17-4.27 (m,2H), 4.32-4.39 (m, 1H). 4.41-4.47 (m,1H), 6.79 (d,1H), 6.92-7.33 (m,10H), 7.57 (d,1H), 7.85 (d,1H), 7.97 (d,1H), 8.15 (d,1H). Analysis calculated for $C_{43}H_{54}N_8O_9 \cdot C_2H_4O_2 \cdot 1.75H_2O$: C, 58.90; H, 6.74; N, 12.21. Found: C, 58.80; H, 6.36; N, 12.44.

EXAMPLE 43 t-BOC-Trp-Lys(ε-N-(2-methoxyphenyl)aminocarbonyl)-Asp-PheNH₂

A solution of the tetrapeptide of Example 1f (100 mg, 0.15 mmol), NMM (0.35 mL) and 2-methoxyphenyl isocyanate (0.05 mL: commercially available from Aldrich Chemical Company) in DMF was allowed to react as described in Example 24. Purification yielded 47 mg of the title compound as a white solid. MS(FAB+) m/e 843 (M+H)+. ¹H NMR(DMSO-d6, 500 MHz) δ1.11-1.66 (m,8H), 1.31 (s,9H), 2.44 (dd, 1H), 2.61 (dd,1H), 2.81-2.95 (m,2H), 2.99-3.14 (m,3H), 3.79 (s,3H), 4.19-4.31 (m,2H), 4.33-4.40 (m,1H), 4.47-4.53 (m,1H), 6.76-6.88 (m,3H), 6.91-6.99 (m,2H), 7.04 (t,1H), 7.08-7.41 (m,5H), 7.58 (d,1H), 7.85-7.96 (m,2H), 8.08 (dd,1H), 8.22 (d,1H). Analysis calculated for $C_{43}H_{54}N_8O_8 \cdot 0.5CH_3CO_2H$: C, 60.68; H, 6.46; N, 12.92. Found: C, 60.85; H, 6.60; N, 12.84.

EXAMPLE 44 t-BOC-Trp-Lys(ε-N-(β-naphthyl)aminocarbonyl)-Asp-PheNH2

A solution of the tetrapeptide of Example 1f (100 mg, 0.14 mmol), NMM and β-naphtyl isocyanate (0.03 mL) was allowed to react as described in Example 24. Purification yielded 50 mg of the title compound as a white solid. MS(FAB+) m/e 863 (M+H)+. ¹H NMR(DMSO-d6, 500 MHz) δ1.07-1.49 (m,8H), 1.30 (s,9H), 2.45 (dd,1H), 2.64 (dd,1H), 2.78-3.17 (m,4H), 4.17-4.30 (m,2H), 4.31-4.41 (m,1H), 4.40-4.55 (m,1H), 6.87 (d,1H), 6.95 (t,1H), 7.05 (t,1H), 7.11-7.46 (m,10H), 7.59 (m,1H). Analysis calculated for $C_{46}H_{56}N_8O_9 \cdot H_2O$: C, 62.71; H, 6.41; N, 12.72. Found: C, 62.34; H, 6.21; N, 12.35.

EXAMPLE 45 t-BOC-Trp-Lys(ε-N-(2-(methoxycarbonyl)phenyl)aminocarbonyl)-Asp-PheNH₂

A solution of the peptide of Example 1f (100 mg, 0.14 mmol), 2-(methoxycarbonyl)phenyl isocyanate (0.03 mL) and NMM in DMF was allowed to react as described in Example 24. The product was purified in a similar manner to yield 50 mg of the title compound as a white solid. MS(FAB+) m/e 871 (M+H)+. ¹H NMR(DMSO-d6, 300 MHz) δ1.08-1.66 (m,8H), 1.30 (s,9H), 2.45 (dd,1H), 2.64 (dd,1H), 2.79-3.14 (m,4H), 3.83 (s,3H), 4.16-4.31 (m,2H), 4.32-4.42 (m,1H), 4.46-4.57 (m,1H), 6.83 (d,1H), 6.91-7.38 (m,10H), 7.44-7.53 (m,3H), 7.58 (d,1H), 7.86-7.98 (m,3), 8.28 (d,1H), 8.37 (d,1H). Analysis calculated for $C_{44}H_{54}N_8O_{11} \cdot 0.5H_2O \cdot 0.5CH_3CO_2H$: C, 59.52; H, 6.31; N, 12.40. Found: C, 59.54; H, 6.24; N, 12.39.

EXAMPLE 46 t-BOC-Trp-Lys(ε-N-(3-(methoxycarbonyl)phenyl)aminocarbonyl)-Asp-PheNH₂

The procedure described for Example 45 using 3-(methoxycarbonyl)phenyl isocyanate in place of 2-(methoxycarbonyl)-phenyl isocyanate yielded the title compound as a white solid. MS(FAB+) m/e 893 (M+Na)+. ¹H NMR(DMSO-d6, 300 MHz) δ1.08-1.46 (m,8H), 1.30 (s,9H), 2.43 (dd,1H), 2.62 (dd,1H), 2.78-3.83 (m,6H), 3.82 (s,3H), 4.18-4.28 (m,2H), 4.31-4.39 (m,1H), 4.41-4.53 (m,1H), 6.87 (d,1H), 6.95 (t,1H), 7.04 (t,1H), 7.10-7.38 (m,10H), 7.46 (d,1H), 7.59 (d,2H), 7.36 (d,1H), 8.00 (d,1H). Analysis calculated for $C_{44}H_{54}N_8O_{11} \cdot H_2O \cdot 0.75CH_3CO_2H$: C, 58.45; H, 6.37; N, 11.96. Found: C, 58.59; H, 6.04; N, 12.28.

EXAMPLE 47 t-BOC-Trp-Lys(ε-N-(2,6-dichlorophenyl)aminocarbonyl)-Asp-PheNH₂

A solution of the tetrapeptide of Example 1f (100 mg), 2,6-dichlorophenyl isocyanate and NMM in DMF was allowed to react as described in Example 24. The product was purified to yield 66 mg of the title compound as a white solid. MS(FAB+) m/e 881 (M+H)+. 1H NMR(DMSO-d6, 300 MHz) δ1.10-1.47 (m,8H), 1.31 (s,9H), 2.42 (dd,1H), 2.79-3.17 (m,4H), 4.14-4.29 (m,2H), 4.31-4.41 (m,1H), 4.43-4.52 (m,1H), 6.81 (d,1H), 6.95 (t,1H), 7.04 (t,1H), 7.10-7.38(m,8H), 7.47 (d,1H), 7.57 (d,1H), 7.86-7.98 (m,3H), 8.22 (d,1H). Anal calc for $C_{42}H_{50}N_8O_9Cl_2 \cdot H_2O$: C, 56.06; H, 5.83; N, 12.45. Found: C, 56.04; H, 5.69; N, 12.11.

EXAMPLE 48 t-BOC-Trp-Lys(ε-N-(4-nitrophenyl)aminocarbonyl)-Asp-PheNH$_2$

A solution of the tetrapeptide of Example 1f (100 mg), 4-nitrophenyl isocyanate (24 mg) and NMM (0.03 mL) was allowed to react as described in Example 24. The reaction was chromatographed to yield 70 mg of the title compound as a white solid. MS(FAB+) m/e 858 (M+H)+. 1H NMR(DMSO-d6, 300 MHz) δ1.05-1.69 (m,8H), 1.29 (s,9H), 2.43 (dd,1H), 2.61 (dd,1H), 2.80-3.16 (m,4H), 4.15-4.28 (m,2H), 4.31-4.40 (m,1H), 4.42-4.53 (m,1H), 6.86 (d,1H), 6.95 (t,1H), 7.04 (t,1H), 7.10-7.35 (m,10H), 7.58 (d,1H), 7.62 (d,1H), 7.84 (d,1H), 8.00 (d,1H), 8.10 (d,1H), 8.20 (d,1H). Analysis calculated for $C_{42}H_{51}N_9O_{11} \cdot 0.5H_2O \cdot 0.5CH_3CO_2H$: C, 57.47; H, 6.08; N, 14.03. Found: C, 57.48; H, 5.94; N, 14.14.

EXAMPLE 49 t-BOC-Trp-Lys(ε-N-(2-methylphenyl)aminocarbonyl)-Asp-hPheNH$_2$ a. t-BOC-homophenylalanine amide A solution of homophenylalanine (95 mg), triethylamine (0.18 mL), and di-t-butyl dicarbonate (180 mg) in 10 mL water and 10 mL acetone was stirred at ambient temperature overnight. The acetone was removed in vacuo, the aqueous phase diluted with water and extracted with ethyl acetate three times. The organic phase was washed with 1M phosphoric acid (3×), saturated sodium bicarbonate solution (3×), brine and dried over magnesium sulfate. The solvent was removed in vacuo to yield 127 mg (86%) of a viscous oil. The oil (127 mg) was dissolved in THF (15 mL) and cooled to −15° C. to which NMM (0.051 mL) and isobutylchloroformate (0.60 mL) were added and stirred for 5 minutes at −10° C. A solution of ammonium hydroxide (2 mL) was then added, the solution stirred for 15 minutes and then allowed to warm to ambient temperature. After 4 hours, the reaction mixture was diluted with ethyl acetate, washed successively with 1M phosphoric acid, saturated sodium bicarbonate solution and brine. After drying over magnesium sulfate, the solvent was removed in vacuo to yield 116 mg of the title compound as a white solid. 1H NMR(CDCl3, 300 MHz) δ1.46 (s,9H), 1.87-2.00 (m,1H), 2.13-2.28 (m,1H), 2.72 (t,J=7 Hz,2H), 4.05-4.16 (m,1H), 7.16-7.33 (m,5H).

b. HCl-Asp(OBn)-hPheNH$_2$

A solution of the compound of Example 49a (112 mg) in 10 mL hydrogen chloride in acetic acid was stirred at ambient temperature for 2 hours. The product was precipitated with addition of diethyl ether, collected and dried. The salt (35 mg) was then coupled with t-BOC-Asp(OBn) activated with isobutylchloroformate in the presence of NMM. A similar work-up as described in Example 49a yielded the dipeptide which was deprotected using hydrogen chloride in acetic acid to yield the hydrochloride salt. MS(CDl/NH3) m/e 384 (M+H)+. 1H NMR(DMSO-d6, 300 MHz) δ1.77-1.91 (m,1H), 1.93-2.03 (m,1H), 2.55-2.69 (m,2H), 2.88 (dd,1H), 3.07 (dd,1H), 4.19-4.30 (m,1H), 5.17 (s,2H), 7.14-7.47 (m,5H).

c. t-BOC-Trp-Lys(ε-N-(2-methylphenylaminocarbonyl))-OH

A solution of H-Lys(benzyloxycarbonyl)-OH in MeOH is treated with 1 equivalent of N-benzyltrimethylammonium hydroxide, and the solvent is evaporated and the residue dissolved in dimethylformamide and treated with 1 equivalent of commercially available t-Boc-tryptophan N-hydroxysuccinimide ester. After 18 h at ambient temperature, the solvent is evaporated, the residue is partitioned between ethyl acetate and 10% citric acid, and the organic layer is washed successively with H2O and brine, then dried and concentrated to an oily residue. Crystallization from ethyl acetate/heptane affords a white solid in 88% yield. This dipeptide (6.05 g, 10.7 mmol) in DMF was subjected to hydrogenolysis for 3 h in the presence of 1.21 g of 10% Pd/C. after which the catalyst was removed by filtration and the filtrate was cooled to 0° C. and treated with NMM (1.29 mL, 11.8 mmol) and O-tolyl isocyanate (1.46 mL, 11.8 mmol). The mixture was allowed to warm to ambient temperature and stir overnight. The solvent was evaporated and the residue partitioned between ethyl acetate and water, and the organic layer was washed successively with 10% citric acid, water and brine, then dried and concentrated. The residue was recrystallized from ethyl acetate heptane to afford 4.77 g (79%) of the title compound.

d. t-BOC-Trp-Lys(ε-N-(2-methylphenyl)aminocarbonyl)-Asp-hPheNH$_2$

To a −10° C. solution of t-BOC-Trp-Lys(ε-N-(2-methylphenylaminocarbonyl)-OH (99 mg), from Step c, in 10 mL THF were added NMM (0.02 mL) and isobutylchloroformate (0.024 mL). The heterogeneous suspension was stirred for 3 minutes and a solution of compound of Example 49b (70 mg) and NMM (0.02 mL) in THF (5 mL) was added. After stirring for 15 minutes at −10° C., the reaction was warmed to ambient temperature, allowed to stand for 4 hours and worked up by dilution with ethyl acetate and washing successively with 1M phosphoric acid, saturated sodium bicarbonate solution and brine followed by drying over magnesium sulfate. After solvent evaporation, the residue was chromatographed on silica gel using ethyl acetate/pyridine/water:/acetic acid to yield a white solid after lyopholization. The peptide was then hydrogenolyzed as in example 1f and the crude product was purified on silica gel eluting with ethyl acetate/pyridine/acetic acid/water to yield the title compound as a white solid after lyopholization. MS(FAB+) m/e 841 (M+H)+. 1H NMR(DMSO-d6, 300 MHz) δ1.11-1.42 (m,6H), 1.30 (s,9H), 1.49-1.72 (m,2H), 1.77-1.89 (m,1H), 1.94-2.06 (m,2H), 2.30 (dd,1H), 4.02-4.13 (m,1H), 4.18-4.34 (m,2H), 4.50-4.58 (m,1H), 6.82 (t,1H), 6.94 (t,1H), 7.01-7.35 (m,10H), 7.58 (d,1H), 7.81 (d,1H). Analysis calculated for $C_{44}H_{56}N_8O_9 \cdot H_2O \cdot 1.5CH_3CO_2H$: C, 59.53; H, 6.84; N, 12.07. Found: C, 59.58; H, 6.38; N, 12.47.

EXAMPLE 50

(Isobutoxycarbonyl)indolelactoyl-Lys(ε-N-(2-methylphenyl)aminocarbonyl)-Asp-PheNH$_2$ To a −10° C. solution of indolelactic acid (100 mg) in 10 mL THF were added NMM (0.059 mL) and isobutylchloroformate (0.07 mL) to form a heterogeneous suspension that was stirred for five minutes. To this mixture was added HCl.Lys(benzyloxycarbonyl)-Asp(OBn)-PheNH$_2$ (325 mg), the product of Example 1c, and NMM (0.06 mL) in 2 mL DMF and stirred an additional 15 minutes at $-10°$ C. The reaction was allowed to warm to ambient temperature and stirred for 4 hours. The product was precipitated by addition of methylene chloride, collected then hydrogenolyzed as in example 1f. The resulting peptide was then dissolved in DMF to which NMM and 2-methylphenyl isocyanate were added and allowed to stand overnight. The product was purified by chromatography in silica gel eluting with ethyl acetate/pyridine/acetic acid/water to yield the title compound as a white solid upon lyopholyzation. MS(FAB+) m/e 828 (M+H)$^+$. $^1$H NMR(DMSO-d6, 500 MHz) δ0.80–0.85 (m,6H), 1.08–1.63 (m,6H), 1.75–1.85 (m,1H), 2.15 (s,1.5H), 2.17 (s,1.5H), 2.38–2.66 (m,2H), 2.80–2.87 (m,1H), 2.97–3.25 (m,6H), 3.75–3.81 (m,1H), 4.19–4.28 (m,1H), 4.32–4.38 (m,1H), 4.43–4.52 (m,1H), 5.08–5.15 (m,1H), 6.83 (t,1H), 6.97 (t,1H), 7.03–7.26 (m,1H), 7.32 (d,1H), 7.61–7.65 (m,1H), 7.78–7.88 (m,2H). Analysis calculated for C$_{43}$H$_{53}$N$_7$O$_{10}$.H$_2$O: C, 61.05; H, 6.55; N, 11.59. Found: C, 61.05; H, 6.38; N, 11.59.

EXAMPLE 51

Indolelactoyl-Lys(ε-N-(2-methylphenyl)aminocarbonyl)-Asp-PheNH$_2$

The title compound was prepared in an identical manner described in Example 50 using benzylchloroformate instead of isobutylchloroformate in the coupling of indolelactic acid with HCl.Lys(benzyloxycarbonyl)-Asp(OBn)-PheNH$_2$, the product of Example 1d. MS(FAB+) m/e 728 (M+H)$^+$. $^1$H NMR(DMSO-d6, 500 MHz) δ1.00–1.65 (m,6H), 2.17 (br s,3H), 2.38–2.48 (m,1H), 2.61 (dd,1H), 2.78–3.36 (m,6H), 4.15–4.20 (m,1H), 4.22–4.28 (m,1H), 4.32–4.38 (m,1H), 4.43–4.52 (m,1H), 6.85 (t,1H), 6.94 (q,1H), 7.01–7.39 (m,9H), 7.53 (dd,1H), 7.59 (d,1H), 7.72–7.92 (m,3H). Analysis calculated for C$_{38}$H$_{45}$N$_7$O$_8$.H$_2$O: C, 61.20; H, 6.35; N, 13.15. Found: C, 60.88; H, 6.11; N, 12.97.

EXAMPLE 52 t-BOC-Trp-hLys(ω-N-(2-methylphenyl)aminocarbonyl)-Asp-PheNH$_2$ a. Nα-t-BOC,Nω-(2-methylphenyl)aminocarbonyl)-L-homolysine Nα-t-BOC-3,4-dehydro-L-homolysine (0.153 g, 0.59 mmol) prepared from t-Boc-D-serine by a modification of the method of Schiller and Beaulieu, *Tetrahedron Lett.*, 1988, 29:2019 was dissolved in DMF (2 mL) containing disopropylethylamine (DIEA) (0.115 ml, 0.65 mmol) and treated with 2-methylphenyl isocyanate (0.085 ml, 0.67 mmol). The flask was capped with a drierite filled drying tube and the contents allowed to stir at ambient temperature overnight. The reaction mixture was subsequently partitioned between ethyl acetate and dilute aqueous HCl. The organic phase was dried (MgSO4), filtered and concentrated in vacuo to give the crude product which was purified by flash chromatography on silica gel eluting first with ethyl acetate/hexane/acetic acid and then ethyl acetate/acetone/acetic acid to give 0.131 g (0.355 mmol) of an oil. MS (EI) m/e 392 (M+H)$^+$. The unsaturated product was dissolved in ethyl acetate and hydrogenated (10% Pd/C, 4 atm. H$_2$) at ambient temperature. Filtration through Celite® filter aid and concentration in vacuo gave 0.102 g (0.26 mmol) of the title compound as an oil.

b. N-α-t-BOC,Nω-(2-methylphenyl)aminocarbonyl)hLys-Asp-PheNH$_2$

The product from Example 52a (0.098 g, 0.25 mmol) was coupled to the hydrochloride salt of Asp-PheNH$_2$ (0.08 g, 0.25 mmol) (prepared as described by J. M. Davey, et al., in *J. Chem. Soc.* (C), 1966, 555) via standard mixed anhydride methodology (M. Bodanszky, A. Bodanszky, "The Practice of Peptide Chemistry" Springer Verlag, Berlin, 1984 p. 109). The reaction mixture was subsequently added dropwise to a large volume of dilute aqueous hydrochloric acid with vigorous agitation. The crude product was collected by vacuum filtration, water washed and dried in vacuo at ambient temperature to give 0.102 g (0.155 mmol) of the title compound as a solid product sufficiently pure for further use as isolated. MS (FAB+) m/e 655 (M+H)$^+$ m/e 677 (M+Na)$^+$.

c. t-BOC-Trp-hLys(Nω-(2-methylphenyl)aminocarbonyl)-Asp-PheNH$_2$

The product from Example 52b (0.102 g, 0.155 mmol) was treated with 1.5N hydrogen chloride in glacial acetic acid (7 mL) at ambient temperature in a tightly capped flask. After 45 minutes the reaction mixture was frozen and lyophilized. The hydrochloride (0.155 mmol) was combined with t-BOC-Trp-OSu (0.062 g, 0.155 mmol) in DMF (2 mL) containing DIEA (0.06 mL, 0.34 mmol) under nitrogen at ambient temperature and allowed to stir overnight. The reaction mixture was subsequently added dropwise to a large volume of dilute aqueous hydrochloric acid solution and the crude product collected by vacuum filtration, water washed and dried in vacuo at ambient temperature. Purification by recrystallization from aqueous ethanol gave 0.110 g (0.131 mmol) of the title compound as a granular off-white solid. MS (FAB+) m/e 841 (M+H)$^+$ m/e, 863 (M+Na)$^+$. $^1$H NMR (DMSO-d6, 300 MHz) δ1.1–1.7 (m,8H), 1.31 (s,9H), 2.4–3.15 (m,8H), 4.15–4.45 (m,3H), 4.52 (m,1H), 6.52 (t,1H), 6.8–7.35 (m,15H), 7.55–7.65 (m,2H), 7.8–8.0 (m,3H), 8.29 (db,J=7.5 Hz,1H), 10.8 (s,1H). Analysis calculated for C$_{44}$H$_{56}$N$_8$O$_9$.H$_2$O: C, 61.51; H, 6.82; N, 13.05. Found: C, 61.61; H, 6.73; N, 12.95.

EXAMPLE 53 t-BOC-Trp-Lys(ε-N-(3-pyridyl-3-acrylyl))-Asp-(NMe)-PheNH$_2$

The product of Example 16h (0.153 g), the active ester of Example 9a (0.059 g), and NMM were allowed to react as in example 1g. The crude product was chromatographed on silica gel eluting with ethyl acetate/pyridine/acetic acid/water to obtain 80 mg of the title compound as a white solid after lyopholyzation. MS(FAB+) m/e 839 (M+H)$^+$. $^1$H NMR(DMSO-d6, 300 MHz) δ1.08–1.48 (m,15H), 2.74–3.35 (m,11H), 4.14–4.25 (m,2H), 4.62–4.68 (m,1H), 4.84–5.02 (m,2H), 5.10–5.20 (m,1H), 6.68–6.83 (m,2H), 6.93–7.50 (m,12H), 7.57–7.63 (m,1H), 7.90–7.93 (m,1H), 8.12–8.25 (m,2H), 8.52–8.54 (m,1H), 8.71–8.73 (m,1H), 10.75–10.82 (m,1H). Analysis calculated for C$_{44}$H$_{54}$N$_8$O$_9$.1.5H$_2$O: C, 61.03, H, 6.63, N, 12.95. Found: C 61.00, H 6.35, N 12.82.

EXAMPLE 54 t-BOC-Trp-Lys(ε-N-(4-sulphatyl-cinnamoyl))-Asp-(NMe)PheNH₂

The tetrapeptide of Example 17 was allowed to react as described in Example 3. Purification under identical conditions yielded the title compound as a white solid. MS(FAB-) m/e 932 (M−H)⁺. ¹H NMR(DMSO-d6, 300 MHz) δ1.04–1.43 (m,15H), 2.02–2.12 (m,1H), 2.34–2.42 (m,1H), 2.73–2.94 (m,5H), 3.03–3.32 (m,4H), 4.16–4.30 (m,2H), 4.61–4.70 (m,1H), 4.84–4.92 (m,1H), 4.93–5.02 (m,1H), 5.09–5.17 (m,1H), 6.43–6.57 (m,2H), 6.78–6.84 (m,1H), 6.93–7.52 (m,12H), 7.58–7.64 (m,1H), 7.80–7.93 (m,1H), 8.00–8.09 (m,2H), 8.27–8.31 (m,1H), 8.59–8.63 (m,1H). Analysis calculated for C₄₅H₅₅N₇O₁₃S.2H₂O.0.9NH₃: C, 54.85; H, 6.31; N, 11.23. Found: C, 54.61; H, 6.08; N, 10.85.

EXAMPLE 55 t-BOC-Trp-Lys(ε-N-(2-methylphenyl)aminocarbonyl)-Asp(OMe)(NMe)PheNH₂

The title compound was prepared in a similar process to that described for Example 21 except that t-BOC-Asp(OMe) was used instead of t-BOC-Asp(OBn) in the preparation of the tetrapeptide. MS(FAB+) m/e 855 (M+H)⁺. ¹H NMR(DMSO-d6, 300 MHz) δ1.10–1.46 (m,15H), 1.91 (s,3H), 2.72–2.94 (m,7H), 3.00–3.36 (m,5H), 3.454 (d,2H), 4.48–4.53 (m,1H), 4.90–5.00 (m,2H), 5.38–5.43 (m,1H), 6.48–6.53 (m,1H), 8.81–7.01 (m,3H), 7.02–7.28 (m,9H), 7.29–7.34 (m,2H), 7.47 (s,1H), 7.54–7.63 (m,3H), 7.78–7.98 (m,2H), 8.28–8.32 (m,1H). Analysis calculated for C₄₅H₅₈N₈O₉.0.5H₂O: C, 62.42; H, 6.83; N, 12.66. Found: C, 62.26; H, 6.80; N, 12.90.

EXAMPLE 56

Trp-Lys(ε-N-(2-methylphenyl)aminocarbonyl)-Asp-(NMe)PheNH₂ hydrochloride a. t-Boc-Lys(ε-N-(2-methylphenylaminocarbonyl)-Asp-(NMe)PheNH₂ Boc-Lys(ε-N-(methylphenyl)aminocarbonyl)-OH, the product of Example 74b, is coupled to HClAsp(OBn)-(NMe)Phe-NH₂, the product of Example 16d, using the mixed anhydride procedure of Example 52b. The product is debenzylated as in Example 1f b. Lys(ε-N-(2-methylphenylaminocarbonyl)-Asp-(NMe)PheNH₂ trifluoroacetate.

The product of step a. (12.3 g, 18.8 mmol) in methylene chloride (100 mL) was treated with trifluoroacetic acid (40 mL) at 17° C. for 2 hours. The solution was concentrated, treated with isopropyl alcohol (50 mL) and again concentrated. The residue was treated with anhydrous ethyl ether to give a white solid which was collected by filtration to afford 11.7 g (93%) of the trifluoroacetate salt.

c. Trp-Lys(ε-N-(2-methylphenyl)aminocarbonyl)-Asp-(NMe)PheNH₂ hydrochloride

N-Benzyloxycarbonyl-Trp was coupled with the product of Step b via the standard mixed anhydride coupling procedure of Example 52b. The product was subjected to hydrogenolysis as in Example 1f, and the crude product was dissolved in HCl in acetic acid and lyopholyzed to give the title compound as a white powder. MS(FAB+) m/e 741 (M+H)⁺. ¹H NMR(DMSO-d6,300 MHz) δ1.20–1.48 (m,6H), 2.72–3.27 (m,14H), 4.03–4.10 (m,1H), 4.20–4.38 (m,1H), 4.62–4.93 (m,1H), 4.97–5.09 (m,1H), 6.61–6.72 (m,1H), 6.83–6.87 (m,1H), 6.93–7.28 (m,1H), 7.47–7.52 (m,1H), 7.70–7.83 (m,4H), 7.84–7.89 (m,1H), 7.98–8.03 (m,2H), 8.48–8.52 (m,1H), 8.70–8.72 (m,1H), 10.97–11.02 (m,1H). Analysis calculated for C₃₉H₄₈N₈O₇.2HCl.1.5H₂O: C, 55.71; H, 6.35; N, 13.33. Found: C, 55.53; H, 6.22; N, 13.15.

EXAMPLE 57

D-Trp-Lys(ε-N-(2-methylphenyl)aminocarbonyl)-Asp-(NMe)PheNH₂ hydrochloride

The title compound was prepared in an identical manner as described in Example 56 using benzyloxycarbonyl-D-Trp. MS(FAB+) m/e 741 (M+H)⁺. ¹H NMR(DMSO-d6, 300 MHz) δ1.00–1.38 (m,6H), 2.25–2.41 (m,1H), 2.72–3.28 (m,13H), 4.03–4.10 (m,1H), 4.19–4.34 (m,1H), 4.55–5.01 (m,1H), 4.94–5.14 (m,1H), 6.58–6.68 (m,1H), 6.84 (t,1H), 6.95–7.50 (m,16H), 7.62–7.84 (m,2H), 8.04–8.12 (m,1H), 8.40–8.43 (m,1H), 8.68–8.84 (m,1H), 11.02 (m,1H). Analysis calculated for C₃₉H₄₈N₈O₇.2HCl.NH₃.H₂O: C, 52.93; H, 6.62; N, 14.25. Found: C, 52.97; H, 6.29; N, 14.17.

EXAMPLE 58

Ac-Trp-Lys(ε-N-(2-methylphenyl)aminocarbonyl)-Asp-PheNH₂

To a solution of t-BOC-Trp-Lys(ε-N-benzyloxycarbonyl)-Asp(OBn)-PheNH₂ (0.52 g), the product of Example 1e, in acetic acid (5 mL) was added 1.4N hydrogen chloride in acetic acid (5 mL). The mixture was stirred for 2 hours, the acetic acid removed in vacuo and the resulting residue taken up in THF (10 mL) and cooled to 0° C. Acetic anhydride (0.064 mL) and NMM (0.075 mL) were added, the reaction allowed to warm to ambient temperature and stirred overnight. The reaction was poured into water and extracted three times with ethyl acetate which was washed with phosphoric acid solution, bicarbonate solution and brine followed by drying with sodium sulfate. After removal of solvent by evaporation, the residue was subjected to hydrogenolysis as in Example 1f, and the crude product was lyopholyzed from water. The resulting product was reacted with 2-methylphenyl isocyanate and NMM in DMF for 16 hours. The reaction mixture was diluted with 25% isopropanol in chloroform and washed with phosphoric acid. After drying over sodium sulfate, the solvents were evaporated and the residue purified on a preparative reverse phase C-18 column using acetonitrile and 0.05M ammonium acetate solution (pH 4.5) as the eluants to give the title compound. MS(FAB+) m/e 769 (M+H)⁺. ¹H NMR(DMSO-d6, 300 MHz) δ1.20–1.55 (m,6H), 1.78 (s,3H), 2.16 (s,3H), 2.43–2.75 (m,3H), 2.80–3.19 (m,5H), 4.16–4.27 (m,1H), 4.31–4.38 (m,1H), 4.45–4.58 (m,2H), 6.50–6.53 (m,1H), 6.85 (t,1H), 6.95 (t,1H), 7.02–7.34 (m,14H), 7.58–7.63 (m,1H), 7.78–7.86 (m,1H), 8.07 (t,1H), 8.18 (d,1H), 10.78 (s,1H). Analysis calculated for C₄₀H₄₈N₈O₈.4.5H₂O: C, 56.86; H, 6.20; N, 13.26. Found: C, 57.19; H, 5.95; N, 12.77.

EXAMPLE 59 t-BOC-Trp-(NMe)Lys(ε-N-(2-methylphenyl)aminocarbonyl)-Asp-(NMe)PheNH₂ a. t-BOC-(NMe)Lys(ε-N-(2-methylphenyl)aminocarbonyl)-OH

A solution of 1.25 g, 3.1 mmol of benzyloxycarbonyl(NMe)Lys(phthaloyl)-OH (Freidinger, R. M.; Hinkle, J. S.; Perlow, D. S.; Arison, B. H. *J. Org. Chem.* 1983, 48:77–81) in 4 mL of MeOH was added to a suspension of 100 mg of 10% Pd/C in 4 mL of MeOH, and the mixture was stirred under an atmosphere of hydrogen for about 18 hours. The resultant mixture was diluted with 8 mL of water, treated with triethylamine (457 mL, 3.3 mmol) and di-t-butyl dicarbonate (720 mg, 3.3 mmol), and stirred overnight. The mixture was diluted with aqueous acetic acid (HOAc) and filtered. The filtrate was concentrated, and the remaining aqueous solution was extracted with ethyl acetate. The combined organic extracts were washed with brine, dried ($Na_2SO_4$) and evaporated to 280 mg of oily residue. A 239 mg (0.64 mmol) sample of the product was dissolved in absolute ethanol and treated with 34 μL (0.7 μmol) of hydrazine hydrate. The solution was heated under reflux for 1 hours, whereupon an additional 34 μL of hydrazine hydrate was added and heating under reflux was continued for 2 hours. The mixture was concentrated under vacuum, diluted with aqueous HOAc, and filtered to remove precipitated phthalhydrazide. The filtrate was washed with ethyl acetate, and lyophilized to afford 190 mg of white powder, which was dried under reduced pressure at 50° C. A 185 mg (0.76 mmol) portion of the product was suspended in dry DMF and treated with triethylamine (115 mL, 0.83 mmol) and 2-methylphenyl isocyanate (104 μL, 0.83 mmol). The mixture was stirred for 1 hour, then treated with additional triethylamine (115 mL, 0.83 mmol) and 2-methylphenyl isocyanate (104 mL, 0.83 mmol) and stirred for an additional 0.25 hour, whereupon the mixture was diluted with ethyl acetate and aqueous $NaHCO_3$. The layers were mixed and separated, then the aqueous layer was acidified with aqueous $KHSO_4$ and extracted with ethyl acetate. The organic layer which contained acidic product was dried over $Na_2SO_4$ and evaporated to 258 mg of crude product, which was chromatographed over silica gel eluting with hexane/ethyl acetate/acetic acid (10:9:1) to afford 125 mg of pure title compound. MS ($Cl/NH_3$) m/e 394 $(M+H)^+$, 411. $^1$H NMR($CDCl_3$) δ1.32 (m,2H), 1.45 (s,9H), 1.52 (m,1H), 1.75 (m,1H), 1.97 (m, 1H), 2.29 (s,3H), 2.80 (br s,3H), 3.22 (m,2H), 4.43 (m,0.4H), 4.70 (m,1.6H), 7.0 (s,1H), 7.07–7.35 (m,4H).

b. (NMe)Lys(ε-N-(2-methylphenyl)aminocarbonyl)-Asp(OBn)(NMe)PheNH$_2$·CF$_3$CO$_2$H The product of Example 59a (67 mg, 0.17 mmol) was coupled to the hydrochloride salt of Asp(OBn)-(NMe)-PheNH$_2$ (107 mg, 0.26 mmol), the product of Example 16d, by the usual mixed isobutylcarbonic anhydride procedure indicated in Example 52b to afford the crude product in quantitative yield. Treatment with 1:1 trifluroacetic acid/methylene chloride at ambient temperature for 1 hour, followed by evaporation of volatile components and precipitation of the product with anhydrous diethyl ether provided 96 mg (72% yield) of the title compound. MS (FAB+) m/e 659 $(M+H)^+$, 681 $(M+NH_4)^+$. $^1$H NMR(DMSO-d6) (two conformers) δ1.2 (m,2H), 1.4 (m,2H), 1.57 (m,1H), 1.7 (m,1H), 2.15 and 2.17 (two s,3H), 2.4 (two br s,3H), 2.65 (dd,J=8 and 16 Hz, 1H), 2.8 (s,1H), 2.9 (m,1H), 2.95 (s,2H), 3.04 (m,2H), 3.15-3.3 (m,2H, partially obscured), 3.62 (m,1H), 4.22 (m,1H), 4.33 (m,1H), 5.02–5.11 (m,2H), 5.13 (m,1H), 6.52 (m,1H), 6.87 (t,J=6.5 Hz, 1H), 7.1 (m,3H), 7.2 (m,5H), 7.4 (m,5H), 7.6 (m,2H), 7.8 (m,1H), 8.8 (br s), 9.0 (d,J=9 Hz, 0.5H), 9.19 (d, J=6 Hz, 0.5H).

c. t-BOC-Trp-(NMe)Lys(ε-N-(2-methylphenyl)aminocarbonyl)-Asp(OBn)(NMe)PheNH$_2$

A solution of Boc-Trp-OH (79 mg, 0.26 mmol) in methylene chloride (4 mL) at 0° C. was treated with 1-cyclohexyl-3-(2-morpholinoethyl)carbodiimide metho-p-toluenesulfonate(CMC). After stirring for 0.5 h, the resulting solution of the symmetrical anhydride was added to a DMF solution of the product of Example 59b (50 mg, 0.065 mmol) at 0° C. The mixture was allowed to warm to ambient temperature and stir overnight, then diluted with ethyl acetate and subjected to acid-base work-up followed by chromatography over silica gel (2% MeOH/CHCl$_3$ to afford 46 mg of the title compound. MS (FAB+) m/e 945 $(M+H)^+$, 928, 845 $(M+H-Boc)^+$.

d. t-BOC-Trp-(NMe)Lys(ε-N-(2-methylphenyl)aminocarbonyl)-Asp-(NMe)PheNH$_2$

The product of Example 59c (42 mg, 0.044 mmol) in MeOH (2 mL) was stirred for 2 h under a hydrogen atmosphere in the presence of 20 mg of 10% Pd/C. The catalyst was separated by filtration and the crude product was purified by chromatography over silica gel eluting with ethyl acetate/pyridine/water/acetic acid (62:3:2:1) to afford the title compound in a 50% overall yield. MS (FAB+) m/e 855 $(M+H)^+$, 755,562. $^1$H NMR(DMSO-d6, 148° C.) δ1.15–1.45 (m,13H, includes δ1.32 (s,9H)), 1.75 (m,2H), 2.05 (s,0.5H), 2.16 (s,2.5H), 2.35 (m,1H), 2.6–2.85 obscured, 2.9 (s,3H), 2.95 (dd,J=5 and 9 Hz,1H), 3.05 (m,1H), 3.10 (dd,J=3 and 9 Hz,1H), 3.28 (dd,J=3 and 9 Hz,1H), 4.7 (m,2H), 4.95 (m,1H), 5.05 (m,1H), 6.03 (br m,1H), 6.10 (br m,1H), 6.61 (m,2H), 6.87 (m,1H), 6.96 (t,J=4 Hz,1H), 7.05 (t, J=4.5 Hz,2H), 7.08 (br s,2H), 7.15–7.30 (m,7H), 7.32 (d,J=5 Hz, 1H), 7.64 (d,J=5 Hz,1H), 10.35 (br s,1H). Anal. Calcd for $C_{45}H_{58}N_8O_9 \cdot H_2O$: C, 61.91; H, 6.93; N, 12.84. Found: C, 61.96; H, 6.81; N, 12.62.

EXAMPLE 60 t-BOC-Trp-Lys(ε-N-(2-methylphenyl)aminocarbonyl)-(NMe)Asp-PheNH$_2$ a. 9-Fluorenylmethoxycarbonyl-(NMe)Asp(OBn)-OH According to the general procedure described in Freidinger, R. M.; Hinkle, J. S.; Perlow, D. S.; Arison, B. H. *J. Org. Chem.* 1983, 48:77–81, 15 g of 9-fluorenylmethoxycarbonyl-Asp(OBn)-OH was converted to the title compound (obtained as a solid after trituration with diethyl ether/hexane) in 78% yield. MS (FAB+) m/e 460 $(M+H)^+$, 482 $(M+Na)^+$. $^1$H NMR (CDCl$_3$) (two conformers) δ2.35 (dd,J=7.5 and 17 Hz,0.5H), 2.72 (dd,J=6 and 16 Hz,0.5H), 2.6 (s,1.5H), 2.95 (1H, obscured), 3.0 (s,1.5H), 3.18 (dd,J=6 and 17 Hz,0.5H), 4.15 (m,0.5H), 4.25 (t,J=7.5 Hz,0.5H), 4.42 (m,1.5H), 4.5 (dd,J=5 and 10.5 Hz,0.5H), 4.62 (m,0.5H), 4.8 (dd,J=6 and 8 Hz,0.5H), 5.13 (m,2H), 7.3 (m,9H), 7.52 (m,2H), 7.68 (d,J=7.5 Hz,0.5H), 7.75 (d,J=7.5 Hz,1.5H).

b. 9-Fluorenylmethoxycarbonyl-(NMe)Asp(OBn)-PheNH$_2$

The product of Example 60a (4.45 g, 9.69 mmol) was coupled to PheNH$_2$ (1.6 g, 9.69 mmol) using bis(2-oxo-3-oxazolidinyl)phosphinic chloride (BOP-Cl) (5 g, 11 mmol) and NMM (1.1 mL, 10 mmol) in DMF, with stirring at 0° C. followed by warming to ambient temperature and stirring overnight. The mixture was concentrated, diluted with ethyl acetate, and the solution was washed with aqueous citric acid, aqueous NaHCO$_3$, and brine, dried (MgSO$_4$) and evaporated to 2.88 g (49% yield) of title compound. MS (FAB+) m/e 606 $(M+H)^+$, 628 $(M+Na)^+$. $^1$H NMR (CDCl$_3$) (two conformers) δ2.34 (m,1H), 2.46–2.70 (m,4H, includes 2.59,s), 2.99 (m,1H), 3.1–3.3 (m,2H), 4.22 (m,2H), 4.48 (m,1H), 4.70 (m,1H), 5.0–5.15 (m,2H), 5.32 (major) and 5.41 (br m's,1H), 6.05 (major) and 6.25 (br m's,1H), 6.51 (d,J=7.5 Hz,1H), 6.9–7.5 (m,14H), 7.56 (d,J=7.5 Hz,1H), 7.8 (d,J=7.5 Hz,1H).

c. t-BOC-Lys($\epsilon$-N-(2-methylphenyl)aminocarbonyl)-(NMe)Asp(OBn)-PheNH$_2$ The product of Example 60b (510 mg, 0.84 mmol) was treated with 50% diethylamine/acetonitrile for 40 minutes, then the volatile components were evaporated under reduced pressure. Additional acetonitrile was added and evaporated to afford 438 mg of crude product. A 225 mg portion of the crude product in 2 mL of DMF at 0° C. was treated with a solution of the symmetrical anhydride prepared by treating t-BOC-Lys($\epsilon$-N-[2-methylphenylaminocarbonyl])-OH (407 mg, 1.075 mmol) in methylene chloride (4 mL) with EDCl (103 mg, 0.54 mmol) for 0.5 h at 0° C. The solution was allowed to warm to ambient temperature and stir for about 18 hours. After extractive work-up, the crude product was chromatographed over silica gel, eluting with 5% MeOH/CHCl$_3$ to afford 160 mg (50% yield) of pure protected tripeptide, MS (FAB+) m/e 745, 767.

d. t-BOC-Trp-Lys($\epsilon$-N-(2-methylphenyl)aminocarbonyl)-(NMe)Asp-PheNH$_2$

The product of Example 60c (86 mg, 0.12 mmol) was treated with 1:1 trifluoroacetic acid/methylene chloride and allowed to stand at ambient temperature for 1 h. The volatiles were evaporated and the residue was kept under vacuum in the presence of KOH pellets for 2 h. The salt in methylene chloride at 0° C. was treated with Boc-Trp-OSu (51 mg, 0.13 mmol) and DIEA (0.022 mL, 0.13 mmol); additional DIEA was added until the solution was basic, then after stirring overnight, the mixture was diluted with ethyl acetate and subjected to acid-base work-up. The crude tetrapeptide was then subjected to benzyl ester cleavage by hydrogenolysis in MeOH as in Example 59d. The product was purified by chromatography over silica gel, eluting with ethyl acetate/pyridine/water/acetic acid (56:3:2:1). Pure fractions were combined, concentrated, diluted with water and lyophilized to afford 42 mg of pure title compound. MS (FAB+) m/e 841 (M+H)+, 741, 577. $^1$H NMR(DMSO-d6) (two conformers) δ1.05–1.9 (m,15H, includes 1.30, s and 1.31, s, total 9H), 2.10–2.25 (m,5H, includes 2.15, s, and 2.20, s), 2.58 (m,1.5H), 2.7 (dd,J=6 and 9 Hz,0.5H), 2.75–3.2 (m,3H), 3.41 (0.5H, obscured), 4.21 (m,0.5H), 4.32 (m,1H), 4.40 (m,0.5H), 4.59 (br m,1H), 4.9 (m,0.5H), 5.08 (m,0.5H), 5.22 (m,0.5H), 6.67 (m,0.5H), 6.82 (m,1H), 6.87 (m,0.5H), 6.95 (m,1H), 7.05 (m,4H), 7.11–7.28 (m,5.5H), 7.30 (d,J=5 Hz, 1H), 7.45 (s,0.5H), 7.50 (s,0.5H), 7.57 (t,J=4 Hz,1H), 7.18 (d,J=5 Hz,0.5H), 7.63 (br s,0.5H), 7.81 (d,J=5 Hz,0.5H), 8.02 (d,J=5 Hz,0.5H), 8.10 (br m,0.5H), 8.26 (br m,0.5H), 8.35 (m,1H), 8.45 (br m,0.5H), 8.59 (br m,0.5H), 8.81 (br m,0.5H), 10.8 (s,0.5H), 10.97 (br s,0.5H). Analysis calculated for C$_{44}$H$_{56}$N$_8$O$_9$·0.8. CH$_3$CO$_2$H·1.2H$_2$O: C, 60.14; H, 6.81; N, 12.31. Found C, 60.06; H, 6.49; N, 12.37.

EXAMPLE 61 t-BOC-Trp-Lys($\epsilon$-N-(2-methylphenyl)aminocarbonyl)(NMe)Asp-(NMe)PheNH$_2$ a. 9-Fluorenylmethoxycarbonyl-(NMe)Asp(OBn)-(NMe)PheNH$_2$ The product of Example 60a (540 mg, 1.18 mmol), CF$_3$COOH—(NMe)PheNH$_2$ (344 mg, 1.18 mmol) and triethylamine (538 mL, 3.89 mmol) were combined in methylene chloride at 0° C. then BOP-Cl was added. The mixture was allowed to warm to ambient temperature and stirred overnight. The solution was diluted with ethyl acetate and subjected to standard acid-base extractive work-up, followed by chromatography of the crude product over silica gel, eluting with hexane-/acetone (2:1) to afford 360 mg (49% yield) of the title compound. MS (FAB+) m/e 642 (M+Na)+. $^1$H NMR(CDCl$_3$) (multiple conformers) δ1.9–3.0 (m,11H, methyl singlets at 1.92, 2.09, 2.21, and 2.82), 3.12 (m,1H), 3.40 (m,1H), 4.19 (m,1H), 4.35–4.45 (m,2H), 4.6–4.8 (m,1H), 4.98–5.18 (m,2H), 5.32–5.68 (m,2H), 6.08–6.29 (m,1H), 6.98–7.62 (m,15H), 7.65–7.87 (m,3H).

b. t-BOC-Trp-Lys($\epsilon$-N-(2-methylphenyl)aminocarbonyl)-(NMe)Asp-(NMe)PheNH2

The product of Example 61a was extended to the title compound by a procedure analogous to that described in Example 60c and d. MS(FAB+) m/e 577 (M+H)+. $^1$H NMR(DMSO-d6) δ1.15 (m,1H), 1.20–1.35 (m,10H, includes 1.30 (s, 9H)) 1.35–1.52 (m,4H), 2.0 (dd,J=2 and 10 Hz,1H), 2.06 (s,3H), 2.17 (m,4H, includes s,3H), 2.75 (m,1H and s,3H), 2.9 (m,2H), 3.04 (dd J=3 and 9 Hz,1H), 3.1 (m,1H), 3.21 (dd,J=3 and 9 Hz,1H), 4.2 (m,1H), 4.42 (q,J=4 Hz, 1H), 5.33 (dd,J=2 and 7 Hz,1H), 5.51 (dd,J=3 and 9 Hz,1H), 6.58 (t,J=3 Hz,1H), 6.73 (d, J=5 Hz,1H), 6.85 (t,J=4 Hz,1H), 6.95 (t,J=5 Hz,1H), 7.08 (m,6H), 7.15–7.4 (m,9H), 7.59 (m,2H), 7.83 (d,J=5 Hz,1H), 7.95 (d,J=5 Hz,1H), 10.8 (s,1H). Analysis calculated for C$_{45}$H$_{58}$N$_8$O$_9$·1.2CH$_3$CO$_2$H: C, 61.41; H, 6.82; N, 12.09. Found: C, 61.36; H, 6.64; N, 12.17.

EXAMPLE 62 t-BOC-Trp-Lys($\epsilon$-N-(2-methylphenyl)aminocarbonyl)ψ(CH$_2$NH)-Asp-PheNH$_2$ a. t-BOC-Lys($\epsilon$-N-benzyoxycarbonyl)-3,5-dimethylpyrazolide t-BOC-Lys($\epsilon$-N-benzyloxycarbonyl) (2.00 g), 3,5-dimethylpyrazole (0.61 g), HOBT (0.85 g), and EDCl (1.11 g) were allowed to react as described in Example 3a to yield 2.32 g of the title compound as a white solid. MS(DCl/NH$_3$) m/e 458 (M+H)+. $^1$H NMR(DMSO-d6, 300 MHz) δ1.13–1.77 (m,6H), 2.18 (s,3H), 2.44 (s,3H), 2.99 (br s,2H), 5.00 (s,2H), 5.17 (br m,1H), 6.20 (s,1H), 7.20–7.40 (m,5H).

b. t-BOC-Trp-Lys($\epsilon$-N-benzyloxycarbonyl)ψ(CH$_2$NH)Asp(OBn)-PheNH$_2$

The pyrazolide of Example 62a (403 mg) was reacted with lithium aluminum hydride (52 mg) then condensed with the free base of Example 1b (287 mg) followed by reaction with acetic acid (50 μL) and sodium cyanoborohydride (62 mg) according to the procedure described by J. Martinez et al. in *J. Med. Chem*, 1985, 28:1874–1879, to yield 326 mg of the title compound as a white solid. MS(FAB+) m/e 718 (M+H)+. $^1$H NMR(DMSO-d6, 300 MHz) δ1.10–1.40 (m,6H), 1.37 (br s,9H), 1.98 (br m,1H), 2.09–2.24 (m,2H), 2.37 (dd,1H), 2.56 (dd,1H), 2.75–3.07 (m,3H), 4.43–4.52 (m,1H), 5.00 (s,2H), 5.06 (s,2H), 6.40 (br d,1H), 7.08–7.41 (m,15H), 8.14 (d,1H).

c. Lys($\epsilon$-N-benzyloxycarbonyl)ψ(CH$_2$NH)Asp-(OBn)-PheNH$_2$ dihydrochloride The peptide of Example 62b (250 mg) was stirred in a solution of hydrogen chloride (g) in acetic acid for 2 hours. The solvent was removed in vacuo and the residue dissolved in water and lyopholyzed to yield 239 mg of the title compound as a white solid. MS(FAB+) m/e 618 (M+H)+.

d. t-BOC-Trp-Lys(ε-N-benzyloxycarbonyl)ψ(CH₂N-H)Asp(OBn)-PheNH₂

A solution of peptide of Example 62c (150 mg), NMM (50 μL) and t-BOC-Trp N-hydroxysuccinimide ester (96 mg) in methylene chloride (15 ml) was stirred at ambient temperature for 18 hours. The reaction mixture was diluted with methylene chloride then washed with water and dried over sodium sulfate. The solvent was removed in vacuo and the residue chromatographed on silica gel eluted with 3% methanol in chloroform to yield 152 mg of the title compound as a white solid. MS(FAB+) m/e 905 (M+H)+. ¹H NMR(DMSO-d6, 300 MHz) δ1.08-1.46 (m,6H), 1.29 (br s,9H), 2.28-2.62 (m,2H), 2.76-3.11 (m,4H), 3.64 (br s,1H), 4.16 (br m,1H), 4.49 (br m,1H), 4.99 (s,2H), 5.02 (s,2H), 6.74 (br d,1H), 6.92-7.66 (m,21H), 8.13 (br d,1H).

e. t-BOC-Trp-Lysψ(CH₂NH)Asp-PheNH₂

The peptide of Example 62d (135 mg) was reacted as described in Example 59d to yield 82 mg of the title compound as a white solid. MS(FAB+) m/e 680 (M+H)+.

f. t-BOC-Trp-Lys(ε-N-(2-methylphenyl)aminocarbonyl)ψ(CH₂NH)-Asp-PheNH₂

The peptide of Example 62e, NMM and 2-methylphenyl isocyanate were reacted as described in Example 1g to yield, after a similar purification procedure, the title compound. MS(FAB+) m/e 813 (M+H)+. ¹H NMR(DMSO-d6, 500 MHz) δ1.04-1.42 (m,6H), 1.23 (br s,9H), 1.98-2.00 (m,1H), 2.10 (s,3H), 2.19-2.29 (m,2H), 2.39 (dd,1H), 2.73 (dd,1H), 2.83-2.91 (m,1H), 2.95-3.12 (m,4H), 3.38 (t,1H), 3.66 (m,1H), 4.10-4.17 (m,1H), 4.45 (dd,1H), 6.89 (t,1H), 6.95 (t,1H), 7.02-7.22 (m,11H), 7.32 (d,1H), 7.56 (br t,2H). Analysis calculated for $C_{43}H_{56}N_8O_8 \cdot C_2H_4O_2 \cdot 1.5H_2O$: C, 60.05; H, 7.06; N, 12.45. Found: C, 60.17; H 6.65; N, 12.75.

EXAMPLE 63

2-Fluoro-3-(indol-3-yl)propionyl-Lys(ε-N-(2-methylphenyl)aminocarbonyl)-Asp-PheNH₂ a. 2-Fluoro-3-(indol-3-yl)-2-propenoic acid ethyl ester

To a solution of triethyl-α-fluoro-phosphonoacetate (4.6 g, 19 mmol), lithium chloride (860 mg, 20 mmol) and diazabicycloundecane (DBU; 3.2 mL, 23 mmol) was added indole-3-carboxaldehyde (2.9 g, 20 mmol: commercially available from Aldrich Chemical Company). The reaction was left at ambient temperature overnight then added to 10% citric acid and extracted with methylene chloride. After drying over anhydrous sodium sulfate, the solution was filtered and solvent was removed in vacuo. The crude product was chromatographed on silica gel eluting with ethyl acetate/hexane (1:6 to 1:4 gradient) then recrystallized (diethyl ether/hexane) to yield 3.1 g (66% yield) of the title compound as a white solid. MS(CI) 251 (M+NH₄)+. ¹H NMR(CDCl₃, 300 MHz) δ1.40 (2 t,3H), 4.37 (q,2H), 7.20-7.32 (m,4H), 7.38-7.45 (m,1H), 7.78-83 (m,1H), 8.52 (br d,1H).

b. 2-Fluoro-3-(indol-3-yl)propionic acid

The product from Example 63a (500 mg, 2.14 mmol) and 10% Pd/C (50 mg) in methanol (20 mL) was hydrogenated at ambient temperature overnight. The catalyst was filtered and the solvent was removed in vacuo. The residue was redissolved in methanol (4 mL) then cooled to 0° C. Aqueous 1N NaOH (4 mL) was added and the reaction stirred at ambient temperature for 10 hours, acidified to pH from about 2 to about 3 and extracted with ethyl acetate (4×). After drying over Na₂SO₄, the solution was filtered and the solvent was removed in vacuo. The residue was chromatographed on silica gel eluting with ethyl acetate/hexane containing 5% acetic acid (1:3 to 1:2 gradient) with 2% acetic acid to yield 160 mg (36% yield) of the title compound. MS(CI) 225 (M+NH₄)+. ¹H NMR(CD₃OD, 300 MHz) δ3.20-3.48 (m,2H), 5.17 (ddd,1H), 7.01 (br t,1H), 7.08 (br t,1H), 7.13 (br s,1H), 7.32 (br d,1H), 7.54 (br d,1H).

c. 2-Fluoro-3-(indol-3-yl)propionic acid 2,4,5-trichlorophenyl ester

To a solution of Example 63b (104 mg, 0.5 mmol) in 2 mL anhydrous methylene chloride was added 2,4,5-trichlorophenol (150 mg, 0.75 mmol), HOBT (81 mg, 0.6 mmol) and EDCl (120 mg, 0.6 mmol). The solution was stirred at ambient temperature for 24 hours then washed with 10% citric acid (1×), water (1×) and brine. After drying over Na₂SO₄, the solution was filtered and the solvent evaporated. The residue was chromatographed on silica gel eluting with ethyl acetate/hexane (1:5) to yield 125 mg of the title compound as a white solid. MS(CI) 403, 405, 409 (M+NH₄)+. ¹H NMR(CDCl₃, 300 MHz) δ3.56 (ddd,2H), 5.45(ddd, 1H), 7.13-7.30 (b m, 5H), 7.42(br d,1H), 7.64(br d,1H), 8.15(br s,1H).

d. Lys(ε-N-(2-methylphenyl)aminocarbonyl)-Asp-PheNH₂ trifluoroacetate

Boc-Lys(ε-N-(2-methylphenyl)aminocarbonyl)-OH, the product of Example 74b, is coupled to Asp-Phe-NH₂ hydrochloride, obtained as described in Example 52b, using the standard mixed anhydride procedure indicated in Example 52b. The product is treated with trifluoroacetic acid/methylene chloride (1:1) and isolated as described in Example 59b.

e. 2-Fluoro-3-(indol-3-yl)propionyl-Lys(ε-N-(methylphenyl)aminocarbonyl)-Asp-PheNH₂

To a solution of the trifluoroacetic acid salt of Example 63d (210 mg, 0.32 mmol) in DMF (2 mL) at 4° C. was added diisopropylethylamine (0.12 mL, 0.69 mmol) and the active ester of Example 63c (124 mg, 0.32 mmol). The reaction mixture was stirred at ambient temperature for 10 hours, then was poured into a cold, rapidly stirring solution of 10% citric acid causing a white precipitate which was collected by filtration. The crude product was suspended in hot ethyl acetate for 30 minutes with vigorous stirring, cooled to ambient temperature and the solid was collected by filtration to yield 170 mg (73% yield) of the title compound as a white solid. HPLC analysis (C-18-ultrasphere octadecylsilane (ODS) with acetonitrile/50 mM ammonium acetate buffer as eluent) showed a diastereomeric ratio of 1/1 at the carbon that bears the fluorine atom. MS(FAB+) m/e 730(M+H)+. ¹H NMR(DMSO-d6/D₂O, 300 MHz) δ1.21-1.62(m,6H), 2.15(2s,3H), 2.30-3.32(m,8H), 4.26(m,1H), 4.37(m,1H), 4.51(m,1H), 5.18(2m,1H), 6.87(br t,1H), 6.97(br t,1H), 7.06-7.30(m,9H), 7.34(br d,1H), 7.55(br t,1H), 7.84(2d,1H). Analysis calculated for $C_{38}H_{44}FN_7O_7 \cdot 0.5H_2O$: C, 61.78; H, 6.14; N, 13.27. Found: C, 61.48; H, 6.09; N, 12.91.

EXAMPLE 64

(2-Cyano-3-(3-indolyl)propionyl)-Lys($\epsilon$-N-(2-methylphenyl)aminocarbonyl)-Asp-PheNH$_2$ a. 2-Cyano-3-(3-indolyl)propionic acid Ethyl 2-cyano-3-(3-indolyl)propionate (350 mg, 1.45 mmol) (S. Masanori, et al., *Heterocycles*, 1981, 16: 941–9) was dissolved in ethanol (6 mL). 2N Sodium hydroxide solution (4 mL) was added and the reaction mixture was stirred at ambient temperature for 20 hours. Water (10 mL) was added and the ethanol was removed under reduced pressure. The pH of the aqueous solution was adjusted to approximately 1 with 6N hydrochloric acid solution and it was extracted with ethyl acetate. The ethyl acetate solution was concentrated in vacuo to give the title compound which was carried on to the next step without purification.

b. 2-Cyano-3-(3-indolyl)propionic acid 2,4,5-trichlorophenyl ester

2-Cyano-3-(3-indolyl)propionic acid from Step a, 2,4,5-trichlorophenol (394 mg, 2 mmol) and EDCl (392 mg, 2 mmol) were combined in methylene chloride (10 mL) and the reaction mixture was stirred at ambient temperature overnight. The reaction mixture was added to 20 mL of 10% citric acid solution and the aqueous mixture was extracted with methylene chloride. The methylene chloride was evaporated under reduced pressure and the residue was purified by flash chromatography on silica gel eluting with ethyl acetate/hexane (1:4 to 1:2) to give 210 mg (37% yield from ethyl 2-cyano-3-(3-indolyl)propionate) of the title compound.

c. (2-Cyano-3-(3-indolyl)propionyl)-Lys($\epsilon$-N-(2-methylphenyl)aminocarbonyl)-Asp-PheNH$_2$ 2-Cyano-3-(3-indolyl)propionic acid 2,4,5-trichlorophenyl ester (210 mg, 0.53 mmol) from Example 64b and the TFA salt of Lys($\epsilon$-N-(2-methylphenyl)aminocarbonyl)-Asp-PheNH$_2$ (200 mg, 0.3 mmol), the product of Example 63d, were dissolved in 4 mL of DMF. DIEA (110 µL, 0.6 mmol) was added and the reaction mixture was stirred at ambient temperature overnight. The reaction mixture was then added to 40 mL of ice-cold 10% citric acid solution. The precipitate was filtered and dried in a vacuum oven at ambient temperature overnight. The solid was suspended in ethyl acetate and the suspension was stirred for 1 hour and filtered. The solid was washed with diethyl ether, suspended in acetic acid (5 mL) and lyopholized to give 160 mg of the title compound, m.p. 211°–214° C. MS (FAB+) m/e 737 (M+H)+. $^1$H NMR (DMSO/D$_2$O): (mixture of a pair of diastereomers and two conformers) δ Ar—CH$_3$: 2.14, 2.16 (2s,3H); α-protons: 4.12–4.41, 4.47–4.56 (4H). Analysis calculated for C$_{39}$H$_{44}$N$_8$O$_7$.1.0H$_2$O: C,62.06; H. 6.14; N, 14.85. Found: C, 61.89; H; 5.97; N, 14.60.

EXAMPLE 65

3-(3-Indolyl)propionyl-Lys($\epsilon$-N-(2-methylphenyl)aminocarbonyl)-(NMe)Asp-PheNH$_2$ 3-Indolyl-3-propionic acid (34 mg, 0.17 mmol) was coupled to TFA.Lys($\epsilon$-N-(2-methylphenyl)aminocarbonyl)-(NMe)Asp(OBn)-PheNH$_2$ (90 mg, 0.11 mmol), (obtained as described in Example 60d) by the mixed carbonic anhydride procedure of Example 52b. The crude product in DMF was stirred under a hydrogen atmosphere in the presence of 30 mg of 10% Pd-C for 18 hours, then filtered, rinsing with methanol. The solution was concentrated, dissolved in ethyl acetate, and washed sequentially with saturated aqueous KHSO$_4$, water and brine, then concentrated. The crude product was chromatographed on silica gel eluting with EtOAC/S2, S2=8:1:1 MeOH/HOAc/water) (8:1), and pooled pure fractions were lyophilized to afford 47 mg of the title compound as a powder. MS (FAB+) m/e 748 (M+Na)+, 726 (M+H)+. $^1$H NMR (DMSO-d6, 500 MHz) (two conformers, ca. 1:1) δ1.20–1.65 (m,5H), 1.76 (m,1H), 2.10 (s,1.5H), 2.25 (s,1.5H), 2.26 (s,1.5H), 2.40 (m,1H), 2.40–3.18 (m,7.5H, partially obscured by solvent), 3.30 (m,1H, visible after addition of DCl), 4.32 (m,0.5H), 4.42 (m,0.5H), 4.52 (m,0.5H), 4.83 (m,0.5H), 5.08 (m,0.5H), 5.29 (m,0.5H), 6.60 (br m,0.5H), 6.83 (m,1H), 6.95 (t,J=7.5 Hz, 1H), 7.00–7.30 (m,8H), 7.30–7.37 (m,1.5H), 7.45–7.52 (m, 1.5H), 7.66 (m, 0.5H), 7.71 (m, 0.5H), 7.81 (d, J=9 Hz,0.5H), 7.92 (br m,0.5H), 8.08 (d, J=9 Hz,0.5H), 8.51 (d, J=9 Hz,0.5H), 8.58 (d, J=6 Hz,0.5H), 10.75 (s,0.5H), 10.79 (s,0.5H). Analysis calculated for C$_{39}$H$_{47}$N$_7$O$_7$.0.8H$_2$O.1.1CH$_3$CO$_2$H: C, 61.37; H, 6.62; N, 12.16. Found: C, 61.27; H, 6.35; N, 12.15.

EXAMPLE 66 t-BOC-Trp-Lys-($\epsilon$-N-3-(2-thienyl)acrylyl)-(NMe)Asp-PheNH$_2$ a. t-BOC-Lys($\epsilon$-N-benzyloxycarbonyl)-(NMe)Asp-(OBn)-PheNH2

(NMe)Asp(OBn)-PheNH$_2$, obtained as described in Example 60c (3.31 mmol), was treated with the symmetrical anhydride prepared from t-BOC-Lys($\epsilon$-N-benzyloxycarbonyl)-OH (2.65 g, 6.96 mmol) and EDCl (667 mg, 3.48 mmol) in methylene chloride at 0° C. The solution was allowed to warm to ambient temperature and stir for about 18 hours. After extractive work-up, the crude product was chromatographed over silica gel, eluting with 3% HOAc/50% hexane in ethyl acetate followed by 3% HOAc/25% hexane in ethyl acetate. Pure fractions were combined, concentrated, diluted with water and lyophilized to afford 706 mg (30% yield) of the title compound as a white solid. MS (FAB+) m/e 768 (M+Na)+, 746 (M+H)+. $^1$H NMR (DMSO-d6) (two conformers ca. 1:1) δ1.20–1.55 (m,15H, includes 1.31 (s), 1.36 (s), 1.43 (s)), 2.08 (s, 1.5H), 2.23–2.50 (m, 2.5H, includes 2.35 (s), 2.70–3.25 (m, 4.5H), 3.45 (dd, J=5 and 14 Hz, 1H, partially obscured), 4.12 (m, 0.5H), 4.30 (m, 0.5H), 4.38 (m, 0.5H), 4.48–4.53 (m,1H), 4.72 (m, 0.5H), 4.97–5.10 (m, 4.5H), 5.15–5.28 (m, 1.5H), 7.12–7.43 (m, 15.5H), 7.51 (d, J=6 Hz, 0.5H), 7.97 (d, J=9 Hz, 0.5H), 8.32 (d, J=9 Hz, 0.5H).

b. t-BOC-Trp-Lys-(NMe)AspPheNH$_2$

The product of Example 66a (545 mg, 0.73 mmol) was N-deprotected with trifluoroacetic acid as in Example 60d, then coupled to the symmetrical anhydride prepared from t-BOC-Trp-OH (466 mg, 1.53 mmol) and EDCl (147 mg, 0.77 mmol) using the procedure analogous to that described in Example 59c. Following extractive work-up the crude product was combined with material from a trial reaction (0.14 mmol). Purification was effected by silica gel chromatography, eluting with 3% HOAc/25% hexane in ethyl acetate and the pure fractions were combined and lyophilized in the same manner as described to afford 555 mg (68% yield) of pure t-BOC-Trp-Lys($\epsilon$-benzyloxycarbonyl)-(NMe)Asp(OBn)-PheNH$_2$. This material (522 mg) was then subjected to hydrogenolysis using 10% Pd-C in DMF. Following filtration, the mixture was diluted with water and HOAc, and the mixture was lyophilized. Recrystallization from EtOH/hexane gave pure title compound isolated as the acetic acid salt (290 mg, 67% yield). MS (FAB+) m/e 730 (M+Na)+, 708 (M+H)+. $^1$H NMR (DMSO-d6) δ1.10–1.70 (m, 15H, includes 1.30, s), 2.03–2.15 (m, 4H, includes 2.08, s), 2.21–2.38 (m, 2H), 2.63–3.17 (m, 7H), 4.22–4.38 (m, 3H), 4.79 (m, 1H), 5.31 (d, J=10 Hz, 1H), 6.89–7.35 (m, 11.5H), 7.49–7.68 (m, 1.5H), 8.22 (d, J=9 Hz, 0.5H), 8.54 (d, J=6 Hz, 0.5H), 10.83 (br s, 1H).

c. t-BOC-Trp-Lys-(ε-N-3-(2-thienyl)acrylyl)-(NMe)Asp-PheNH$_2$

The tetrapeptide of Example 66b (88 mg, 0.115 mmol), the active ester of Example 11a (29 mg, 0.115 mmol) and NMM (0.025 ml) were allowed to react under similar conditions to those described in Example 1 g. The DMF was removed in vacuo and the residue was purified by preparative reverse phase HPLC, and the product isolated in a manner similar to that described in Example 2 to give 60 mg (62% yield) of the title compound as a white solid. MS (FAB+) m/e 866 (M+Na)+, 844 (M+H)+. $^1$H NMR (DMSO-d$_6$) (two conformers ca. 1:1) δ1.04–1.75 (m, 15H, includes 1.31 (s)), 2.09–2.17 (m, 2.5H, includes 2.14 (s)), 2.34–2.56 (m, 2.5H, partially obscured, includes 2.38 (s)), 2.68–2.97 (m, 3H), 3.01–3.44 (m, 3H, partially obscured), 4.19 (m, 0.5H), 4.29–4.38 (m, 1H), 4.44 (m, 0.5H), 4.53 (m, 0.5H), 4.84 (m, 0.5H), 5.14 (dd, J=5 and 10 Hz, 0.5H), 5.21 (m, 0.5H), 6.36–6.44 (m, 1H), 6.72 (br d, J=10 Hz, 0.5H), 6.87 (d, J=10 Hz, 0.5H), 6.92–7.59 (m, 16H), 7.98 (br d, J=9 Hz, 0.5H), 8.04–8.13 (m, 1.5H), 8.26–8.55 (m, 1H), 10.78 (br s, 0.5H), 10.87 (br s, 0.5H). Analysis calculated for C$_{43}$H$_{53}$N$_7$O$_9$S.0.6CH$_3$CO$_2$H. 0.3NH$_4$OAc: C, 59.58; H, 6.42; N, 11.32; S, 3.55. Found: C, 59.52; H, 6.27; N, 11.62; S, 2.95.

EXAMPLE 67 t-BOC-Trp-Lys-(ε-N-3-(3-pyridyl)acrylyl)-(NMe)Asp-PheNH$_2$

The tetrapeptide of Example 66b (87 mg, 0.113 mmol) and the active ester of Example 9a (28 mg, 0.113 mmol) and NMM (0.025 ml) were reacted under the same conditions as described in Example 140c and the product was isolated in the same manner to give 63 mg (64% yeild) of the title compound as a white solid. MS (FAB+) m/e 839 (M+H)+. $^1$H NMR (DMSO-d6) (two conformers ca. 1:1) δ0.99–1.68 (m, 15H, includes 1.22 (s)), 2.03–2.10 (m, 1.5H, includes 2.08 (s)), 2.28–2.4 (m, 1.5H, includes 2.3 (s)), 2.63–2.93 (m, 4H), 2.95–3.43 (m, 4H, partially obscured), 4.14 (m, 0.5H), 4.23–4.34 (m, 1H), 4.40 (m, 0.5H), 4.47 (m, 0.5H), 4.79 (m, 0.5H), 5.07 (dd, J=5 and 10 Hz, 0.5H), 5.16 (m, 0.5H), 6.63–7.40 (m, 13H), 7.48–7.55 (m, 1H), 7.82–8.00 (m, 2H), 8.08–8.13 (m, 1H), 8.31–8.48 (m, 2H), 8.65 (br s, 1H), 10.72–10.78 (m, 1H). Analysis calculated for C$_{44}$H$_{54}$N$_8$O$_9$.H$_2$O.0.3CH$_3$CO$_2$H: C, 61.22; H,6.59; N, 12.81. Found: C, 61.24; H, 6.44; N, 12.82.

EXAMPLE 68 t-BOC-Trp-Lys-(ε-N-3-(3-pyridyl)acrylyl)-(NMe)Asp-(NMe)PheNH$_2$ a. t-BOC-Lys(ε-N-benzyloxycarbonyl)-(NMe)Asp-(OBn)-(NMe)PheNH$_2$ H-(NMe)Asp(OBn)-(NMe)PheNH$_2$ (1.04 g, 2.40 mmol), obtained as described in Example 61b, was treated with the symmetrical anhydride prepared from t-BOC-Lys(ε-benzyloxycarbonyl)-OH (1.92 g, 5.04 mmol) and EDCl (483 mg, 2.52 mmol) using a procedure similar to that described in Example 66a. After extractive work-up, the crude material was triturated with EtOH/hexane to afford pure title compound in quantitative yield (1.82 g). MS (FAB+) m/e 782 (M+Na)+, 760 (M+H)+. $^1$H NMR (DMSO-d6, two conformers, ca. 2:1) δ t-Boc singlet (major): 1.32; methyl singlets (major): 2.02, 2.71; α protons (major): 4.02 (m, includes Hα overlap with signal from minor conformer), 5.36 (dd, J=5 and 12 Hz), 5.60 (dd, J=6 and 12 Hz); t-Boc singlet (minor): 1.37; methyl singlets (minor) 2.66, 2.94; α protons (minor): 4.02 (m, includes overlap with signal from major conformer), 4.14 (t, J=6 Hz), 4.33 (t, 5 Hz).

b. t-BOC-Trp-Lys-(NMe)Asp-(NMe)PheNH$_2$

The product of Example 68a (900 mg, 1.19 mmol) was N-deprotected with trifluoroacetic acid in the usual manner and then coupled to the symmetrical anhydride prepared from t-BOC-Trp-OH (905 mg, 2.98 mmol) and EDCl (285 mg, 1.49 mmol) in a fashion similar to that used in Example 66a. Following extractive work-up the crude product was combined with material from a trial reaction (0.13 mmol) and purified by silica gel chromatography eluting with 50:1 ethyl acetate: S1 (S1=20: 11:6 pyridine: H$_2$O:CH$_3$CO$_2$H). The pure fractions were combined, concentrated, diluted with water and lyophilized to afford 730 mg (58% yield) of protected tetrapeptide, which was then subjected to hydrogenolysis and isolation in a manner similar to that used in Example 66b to remove to afford the title compound as an acetic acid salt (506 mg, 86% yield). MS (FAB+) m/e 744 (M+Na)+722 (M+H)+. $^1$H NMR (MeOH-d$_4$) (major and minor conformers discernible in N-Me signals) δ1.27–1.46 (m, 12H, includes 1.40 (br s)), 1.50–1.71 (m, 3H), 2.03–2.17 (m, 4H, includes 2.11 (br s, major conformer)), 2.58–3.25 (m, 8H, partially obscured, includes 2.86 (s with shoulder, major and minor conformers), and 2.98 (s, minor conformer)), 3.38 (d, J=6 Hz, 1H), 4.43 (d, J=6 Hz, 1H), 4.28 (m, 1H), 4.41 (m, 1H), 5.31 (m, 1H), 5.54 (m, 1H), 6.93–7.38 (m, 9H), 7.38 (br d, J=9 Hz, 1H), 7.97 (br s, minor conformer).

c. t-BOC-Trp-Lys-(ε-3-(3-pyridyl)acrylyl))-(NMe)Asp-(NMe)PheNH$_2$

The tetrapeptide of Example 68b (80 mg, 0.102 mmol) and the active ester of Example 9a (25 mg, 0.102 mmol) were reacted and isolated in the same manner as was described in Example 66c to afford 57 mg (66% yield) of title compound. MS (FAB+) m/e 875 (M+Na)+, 853 (M+H)+. $^1$H NMR (DMSO-d6) δ1.08–1.57 (m, 15H, includes 1.28 (s)), 1.95–2.07 (m, 3H, includes 2.04 (br s)), 2.42–2.97 (m, 5H, includes 2.73 (s)), 3.04 (dd, J=5 and 15 Hz, 2H), 3.14–3.25 (m, 3H, partially obscured), 4.17 (m, 1H), 4.40 (m, 1H), 5.32 (dd, J=5 and 13 Hz, 1H), 5.50 (dd, J=4 and 10 Hz, 1H), 6.68–6.77 (m, 2H), 6.91–7.32 (m, 11H), 7.39 (m, 1H), 7.43 (s, 0.5H), 7.47 (s, 0.5H), 7.56 (m, 1H), 7.89–7.96 (m, 2H), 8.21 (m, 1H), 8.53 (d, J=5 Hz, 1H), 8.71 (br s, 1H), 10.79 (br s, 1H). Analysis calculated for C$_{45}$H$_{56}$N$_8$O$_9$.0.8-H$_2$O.0.2CH$_3$CO$_2$H: C, 62.01; H, 6.69; N, 12.74. Found: C, 62.05; H, 6.74; N, 12.72.

EXAMPLE 69

HCl-(NMe)Trp-Lys(ε-N-(2-methylphenyl)aminocarbonyl)-(NMe)Asp-PheNH$_2$ a. t-BOC-(NMe)Trp-OH To a solution of (NMe)Trp (5 g, 23 mmol) in water/dioxane (1:1) was added diisopropylethylamine (9 ml) and di-t-butyl dicarbonate (6 g, 27.6 mmol) and the mixture was stirred overnight at ambient temperature. The solvents were removed under reduced pressure and resulting residue was diluted with water and acidified to pH 2 using 1N HCl. The mixture was extracted with ethyl acetate, and the combined ethyl acetate extracts were washed successively with water and brine, then dried (MgSO4) to give 7.26 g (90% yield) of the title compound as a white foamy product which was carried on to the next step without purification. MS (FAB+) m/e 319 (M+H)+. $^1$H NMR (DMSO-d6, 300 MHz) $\delta$ 1.06 (s, 9H), 2.65 (bs, 3H), 3.02–3.30 (m, 2H), 4.28 (m, 2H), 6.98 (t, J=9 Hz, 1H), 7.1 (m, 3H), 7.32 (d, J=12 Hz, 1H), 7.53 (d, J=12 Hz, 1H), 10.82 (bs, 1H), 12.85 (bs, 1H).

b. HCl-(NMe)Trp-Lys($\epsilon$-N-(2-methylphenyl)aminocarbonyl)-(NMe)Asp-PheNH$_2$ t-BOC-Lys($\epsilon$-N-(2-methylphenylaminocarbonyl))-(NMe)Asp(OBn)-PheNH$_2$ of Example 60c (135 mg, 0.19 mmol) was N-deprotected with 4N HCl/dioxane in the usual manner. The resultant hydrochloride salt was coupled to t-BOC-(NMe)Trp using EDCI and HOBT as in Example 1c. Precipitation from acetone/water afforded 115 mg of product. The crude tetrapeptide was subjected to benzyl ester cleavage by hydrogenation in methanol as described in Example 59d. A solution of the resultant tetrapeptide (0.05 g, 0.0585 mmol) in 8 mL of 1.5M HCl in acetic acid was stirred at ambient temperature for 1.5 hour. The product was precipitated with diethyl ether. The solid was collected, washed with fresh ether and dried to yield 35 mg (79% yield) of the title compound. m.p. 169°–171° C. MS (FAB+) m/e 755 (M+H)+, 777 (M+Na)+. $^1$H NMR (DMSO-d6, 300 MHz) $\delta$ 1.3–1.68 (m, 6H), 2.20 (s, 3H), 2.25 (s, 3H), 2.43 (s, 3H), 2.5 (m, 2H), 2.68–2.85 (m, 2H), 3.02–3.24 (m, 6H), 4.1 (m, 1H), 4.5 (m, 2H), 5.1 (m, 1H), 6.84 (t, J=7 Hz, 1H), 6.88–7.02 (m, 2H), 7.09–7.12 (m, 3H), 7.13–7.3 (m, 6H), 7.32 (m, 1H), 7.60 (d, J=10 Hz, 1H), 7.84 (m, 2H), 8.00 (s, 1H), 8.85 (d, J=10 Hz, 1H), 8.93–9.30 (m, 2H), 10.98 (s, 1H). Anal.Calcd. for C$_{40}$H$_{50}$N$_8$O$_7$.2H$_2$O.2HCl: C, 55.61; H, 6.50; N, 12.97. Found: C, 55.84; H, 6.02; N, 12.92.

EXAMPLE 70

3-(Indol-3-yl)propionyl-Lys($\epsilon$-N-(2-methylphenyl)aminocarbonyl)-Asp-(NMe)PheNH$_2$ To a solution of Lys($\epsilon$-N-(2-methylphenyl)aminocarbonyl)-Asp-(NMe)PheNH$_2$ trifluoracetate (205 mg, 3 mmol), prepared as described in Example 56b, in DMF(2 mL) at 4° C. was added diisopropylethylamine (0.068 mL, 0.62 mmol) and 3-(indol-3-yl)propionic acid 2,4,5-trichlorophenyl ester (113 mg, 0.31 mmol), which was prepared according to the procedure described in Example 63c, replacing 2-fluoro-3-(indol-3-yl)propionic acid with 3-(indol-3-yl)propionic acid. The reaction mixture was stirred at ambient temperature for 10 hours, then was poured into a cold, rapidly stirring solution of 10% citric acid. The resultant white precipitate was collected by filtration. The crude product was suspended in hot ethyl acetate for 30 minutes with vigorous stirring. The suspension was cooled to ambient temperature and solid was collected by filtration to yield 97 mg (43% yield) the title compound as a white solid. MS(FAB+) m/e 726 (M+H)+, $^1$H NMR (DMSO-d6/D$_2$O, 300 MHz) $\delta$ 1.21–1.62 (m, 6H), 2.14 & 2.16 (2s, 3H), 2.33–2.57 (m, 4H), 2.72 & 2.92 (2s, 3H), 2.75–3.30 (m, 6H), 4.12(t) & 4.19–5.13 (5m, 3H), 6.85 (br.t, 1H), 6.96 (br.t, 1H), 7.06–7.26 (m, 9H), 7.32 (d, 1H), 7.52 (br.d, 1H), 7.72–7.38 (m, 1H). Anal calc for C$_{39}$H$_{47}$N$_7$O$_7$.2.1H$_2$O: C, 61.34; H, 6.76; N, 12.84. Found: C, 61.51; H, 6.46; N, 12.44.

EXAMPLE 71 t-BOC-Trp-Lys($\epsilon$-N-(4-hydroxycinnamoyl))-(NMe)Asp-PheNH$_2$

The tetrapeptide of Example 66b, the active ester of Example 3a and NMM were allowed to react as described in Example 1 g to afford the title compound. MS (FAB+) m/e 876 (M+Na)+, 854 (M+H)+. $^1$H NMR (DMSO-d6) (two conformers, ca. 1:1) $\delta$ 0.94–1.73 (m, 14H, includes 1.20 (s)), 2.02–2.13 (m, 2H, includes 2.11 (s)), 2.24–2.41 (m, 2H, partially obscured, includes 2.40 (s)), 2.61–3.12 (m, 8H, partially obscured), 4.14 (m, 0.5H), 4.19–4.32 (m, 1H), 4.37 (m, 0.5H), 4.49 (m, 0.5H), 4.80 (m, 0.5H), 5.05–5.16 (m, 1H, includes 5.07 (dd, J=5, 10 Hz, 0.5H)), 6.34 (d, J=15 Hz, 0.5H), 6.46 (br d, J=15 Hz, 0.5H), 6.59 (m, 0.5H), 6.67–6.76 (m, 1H), 6.81 (m, 0.5H), 6.89 (m, 0.5H), 6.94–7.65 (cm, 15.5H), 7.87–8.03 (m, 1H), 8.22–8.48 (m, 1H), 10.74 (s, 0.5H), 10.94 (br s, 0.5H). Analysis calculated for C$_{45}$H$_{55}$N$_7$O$_{10}$.2.6H$_2$O: C, 60.00; H, 6.74; N, 10.88. Found: C, 59.90; N, 6.47; N, 11.04.

EXAMPLE 72 t-BOC-Trp-Lys($\epsilon$-N-(4-hydroxycinnamoyl))-(NMe)Asp-(NMe)PheNH$_2$

The tetrapeptide of Example 68b, the activated ester of Example 3a and NMM were allowed to react as described in Example 1 g to give the title compound. MS (FAB+) m/e 890 (M+Na)+, 868 (M+H)+. $^1$H NMR (DMSO-d6) $\delta$ t-Boc singlet: 1.28; methyl singlets: 2.06, 2.77; $\alpha$ protons: 4.19 (m), 4.42 (m), 5.34 (dd, J=5, 15 Hz), 5.51 (dd, J=5, 13 Hz). Analysis calculated for C$_{46}$H$_{57}$N$_7$O$_{10}$.1.7H$_2$O.0.5CH$_3$CO$_2$H: C, 60.79; H, 6.77; N, 10.56. Found: C, 60.74; H, 6.38; N, 10.71.

EXAMPLE 73 t-BOC-Trp-Lys($\epsilon$-N-(6-hydroxy-$\beta$-naphthoyl)-(NMe)Asp-(NMe)PheNH$_2$ a. 6-Hydroxy-$\beta$-naphthoic acid N-hydroxysuccinimide ester A solution of 6-hydroxy-$\beta$-naphthoic acid (1.0 g), N-hydroxysuccin-imide (0.65 g) and EDCI (1.1 g) in methylene chloride was stirred at ambient temperature. The product was isolated as described in Example 3a to yield 0.32 g of the title compound as a white solid. MS (CI/NH$_3$) m/e 303 (M+NH$_3$)+. $^1$H NMR (DMSO-d6, 300 MHz) $\delta$ 2.92 (br s, 4H), 7.22–7.29 (m, 2H), 7.91 (s, 2H), 8.10 (d, J=8 Hz, 1H), 8.71 (s, 1H), 10.49 (s, 1H).

b. t-BOC-Trp-Lys($\epsilon$-N-(6-hydroxy-$\beta$-naphthoyl)-(NMe)Asp-(NMe)PheNH$_2$ The tetrapeptide of Example 68b, the activated ester of Example 73a and NMM were allowed to react as described in Example 1 g to give the title compound. MS (FAB−) m/e 891 (M-H)−. $^1$H NMR (DMSO-d6) $\delta$ t-Boc singlet: 1.21; methyl singlets: 1.99, 2.67; $\alpha$ protons: 4.13 (m), 4.36 (m), 5.26 (dd, J=6, 14 Hz), 5.44 (dd, J=5, 12 Hz). Analysis calculated for C$_{48}$H$_{57}$N$_7$O$_{10}$.0.6-H$_2$O.0.5CH$_3$CO$_2$H: C, 63.09; H, 6.50; N, 10.51. Found: C, 63.06; H, 6.35; N, 10.58.

EXAMPLE 74

2-Adamantyloxycarbonyl-Trp-Lys(ε-N-(2-methylphenyl)aminocarbonyl)Asp-(NMe)PheNH$_2$ a. 2-Adamantyl chloroformate To a solution of 2-adamantanol (912 mg, 5.99 mmol) in methylene chloride (15 mL), at 0° C. under nitrogen, was added a solution of triphosgene (653 mg, 2.2 mmol) and pyridine (484 μL, 5.99 mmol) in methylene chloride. The reaction mixture was stirred at ambient temperature for 3 hours and then concentrated to dryness under reduced pressure. Ethyl acetate was added to the residue and the resultant mixture was filtered. The filtrate was concentrated in vacuo to give 980 mg of the title compound as a white powder. $^1$H NMR (CDCl$_3$) δ1.5-2.2 (m, 14H), 5.02 (m, 1H).

b. t-BOC-Lys(ε-N-(2-methylphenyl)aminocarbonyl)-OH

To a solution of N$^\alpha$-Boc-Lys-OH (1.0 g, 4.1 mmol) in H$_2$O (5 mL), dioxane (7 mL) and 2N NaOH (2 mL) at 0° C. were added in portions o-tolyl isocyanate (1.12 g, 8.4 mmol) and additional 2N NaOH (4.2 mL, 8.4 mmol). The mixture was stirred and allowed to warm to ambient temperature, then made basic with additional aq. NaOH. The solution was washed with ethyl acetate, then acidified with aq. KHSO$_4$. The solution was again extracted with ethyl acetate and the latter organic phase was dried (Na$_2$SO$_4$) and concentrated. The residue was crystallized from ether/hexane to afford 1.2 g of product: MS (CI) m/e 380 (M+H)$^+$. NMR (300 MHz, CDCl3) d 1.41 (s, 9H), 1.30-1.55 (m, 3H), 1.70-1.90 (m, 3H), 2.28 (s, 3H), 3.22 (m, 2H), 4.29 (m, 1H), 4.90 (br m, 2H), 5.23 (br d, J=7.5 Hz, 1H), 7.10-7.31 (m, 4H).

c. t-BOC-Lys(ε-N-(2-methylphenyl)aminocarbonyl)-Asp(OBn)-(NMe)PheNH$_2$

The product of Step b (1.36 g, 3.57 mmol) was coupled to HClAsp(OBn)-(NMe)PheNH$_2$ from Example 16d (1.50 g, 3.57 mmol) using the mixed isobutyl carbonic anhydride method as in Example 52b. The reaction mixture was concentrated, dissolved in ethyl acetate and subjected to acid/base work-up, then the crude product was purified by chromatography over silica gel, eluting with 2% MeOH/CHCl$_3$ to afford the pure product as a white solid (1.97 g, 74%). MS (FAB+) m/e745 (M+H)$^+$, 7.67 (M-Na)$^+$. $^1$H-NMR (DMSO-d6) two conformers ca 1:1; 1.35 (s,9H), methyl singlets δ2.15, 2.16 (s, 3H); 2.72, 2.88 (3H); α protons 3.84, 4.65, 4.90, 4.98-5.12 (m,3).

d. Lys(2-methylphenylaminocarbonyl)-Asp(OBn)-N(Me)PheNH$_2$ trifluoroacetate

To a solution of Boc-Lys(2-methylphenylaminocarbonyl)-Asp(OBn)N(Me)PheNH2 (297 mg, 0.4 mmol) in methylene chloride (3 mL) at 0° C. was added trifluoroacetic acid (3 mL) and the reaction mixture stirred for 2.5 hours at room temperature. The reaction mixture was then concentrated in vacuo and lyophilized from MeOH/H$_2$O to afford the product as a white powder (263 mg, 86%). MS (FAB+) m/e645 (M+H)$^+$, 628 (M-NH$_2$)$^+$. $^1$H-NMR (DMSO-d6) two conformers ca 1:1; methyl singlets δ2.13, 2.15 (s, 3H); 2.74, 2.92 (3H); α protons 4.65, 4.77, 4.97-5.18 (m,3).

e. t-BOC-Trp-Lys(ε-N-(2-methylphenyl)aminocarbonyl)-Asp(OBn)-(NMe)PheNH$_2$

To a solution of Lys(2-methylphenylaminocarbonyl)-Asp(OBn)-N(Me)Phe-NH2 trifluoroacetate from step d (2.27 g, 3.0 mmol) and Boc-TrpOH (913 mg, 3 mmol) in DMF (12 mL) was added HOBt (405 mg, 3.0 mmol), N-methylmorpholine (395 ml, 3.6 mmol) and EDCl (632 mg, 3.3 mmol) and the reaction mixture stirred for 22 hours at room temperature. The reaction mixture was then diluted with 10% citric acid (150 mL) and filtered, and the white precipitate washed with H$_2$O (2×50 mL) and hexane (50 mL) to afford the tetrapeptide (2.72 g, 95%). MS (FAB+) m/e931 (M+H)$^+$, 914 (M−NH$_2$)$^+$. $^1$H-NMR (DMSO-d6) two conformers ca 1:1; methyl singlets δ2.15 (s, 3H); 2.74, 2.89 (3H); α protons 4.22, 4.28, 4.66, 4.88, 4.98-5.12 (m,2); 10.78 (br. s., 1). Analysis calcd. for C$_{50}$H$_{61}$N$_8$O$_9$×1.5 H$_2$O: C, 64.00; H, 6.74; N, 11.71. Found: C, 64.14; H, 6.56; N, 12.10.

f. Trp-Lys(ε-N-(2-methylphenyl)aminocarbonyl)-Asp(OBn)-(NMe)PheNH$_2$ trifluoroacetate To a solution of t-BOC-Trp-Lys(ε-N-(2-methylphenyl)aminocarbonyl)-. Asp(OBn)-(NMe)PheNH$_2$ (930 mg, 1 mmol), from Step e, in methylene chloride (10 mL) at 0° C., was added water (1.0 mL), followed by trifluoroacetic acid (10 mL). The reaction mixture was allowed to warm to ambient temperature over a 1 hour period and was then concentrated in vacuo to afford a foam. The foam was triturated with diethyl ether (3×10 mL) to give 873 mg (92% yield) of the title compound as a white solid. MS (FAB+) m/e 831 (M+H)$^+$, 814 (M−NH$_2$)$^+$. $^1$H-NMR (DMSO-d6) two conformers ca 1:1; methyl singlets δ2.15, 2.16 (s, 3H); 2.75, 2.92 (3H); α protons 4.05, 4.24, 4.33, 4.68, 4.87.

g. 2-Adamantyloxycarbonyl-Trp-Lys(ε-N-(2-methylphenyl)aminocarbonyl)-Asp(OBn)-(NMe)PheNH$_2$ To a solution of 2-adamantyl chloroformate (14.5 mg, 0.067 mmol), from Step a, and Trp-Lys(ε-N-(2-methylphenyl)aminocarbonyl)-Asp(OBn)-(NMe)PheNH$_2$ (58 mg, 0.061 mmol) from step f, in DMF (500 μL) was added diisopropylethylamine (26.7 μL, 0.153 mmol) at ambient temperature. After stirring for 3 hours, the reaction mixture was quenched with water (2 mL), sonicated for 30 minutes and then filtered. The white precipitate was dried to give 47 mg of the title compound as a white powder. MS(FAB+) m/e 1010 (M+H)$^+$, 1048 (M+K)$^+$; $^1$H NMR(DMSO-d6) (two conformers ca. 1:1) δ methyl singlets: 2.14, 2.15 (2s,3H), 2.74, 2.90 (2s,3H).

h. 2-Adamantyloxycarbonyl-Trp-Lys(ε-N-(2-methylphenyl)aminocarbonyl)-Asp-(NMe)PheNH$_2$ The tetrapeptide of Step g was debenzylated by hydrogenolysis as described in Example 1f to give the title compound. MS (FAB+) m/e 902 (M-NH$_2$)$^+$, 919 (M+H)$^+$, 941 (M+H+Na)$^+$. $^1$H-NMR (DMSO-d6) (two conformers ca 1:1) δ methyl singlets: 2.6 (3H); 2.74, 2.95 (3H); α protons: 4.21, 4.28, 4.54, 4.71, 4.88, 4.96, 5.15 (5H). Analysis calculated for C$_{50}$H$_{62}$N$_8$O$_9$.2-H$_2$O.0.6CH$_3$CO$_2$H: C, 62.05; H, 6.96; N, 11.31. Found: C, 61.98; H, 6.60; N, 11.40.

EXAMPLE 75

1-Adamantyloxycarbonyl-Trp-Lys(ε-N-(2-methylphenyl)aminocarbonyl)-Asp-(NMe)PheNH$_2$ The title compound was prepared by the method described in Example 74 g and h, replacing 2-adamantyl chloroformate with the commercially available 1-adamantyloxyfluoroformate. MS(FAB+) m/e 919 (M+H)$^+$, 902 (M−NH$_2$)$^+$; $^1$H NMR(DMSO-d6) (two conformers ca 1:1) δ methyl singlets: 2.13, 2.14 (2s,3H), 2.72, 2.88 (2s,3H); α protons: 4.18, 4.29, 4.67, 4.85, 4.97, 5.11 (4H). Analysis calculated for C$_{50}$H$_{62}$N$_8$O$_9$.2H$_2$O:

C, 62.88; H, 6.96; N, 11.73. Found: C, 63.13; H, 6.74; N, 11.76.

EXAMPLE 76

Benzyloxycarbonyl-Trp-Lys(ε-N-(2-methylphenyl)aminocarbonyl)-Asp-(NMe)PheNH$_2$

The title compound was prepared from the tripeptide of Example 56b and benzyloxycarbonyl-Trp-OSu by the method described in Example 1e. MS (FAB+) m/e 875(M+H)+, 897(M+Na)+. $^1$H NMR (DMSO-d$_6$/D$_2$O): (two conformers ca. 1:1) δ Ar—CH$_3$: 2.15, 2.17 (2s, 3H); N—CH$_3$: 2.76, 2.94 (2s,3H); α-protons: 4.17–4.35, 4.63–4.71, 4.83–5.02 & 5.07–5.15 (4H). Analysis calculated for C$_{47}$H$_{54}$N$_8$O$_{11}$.3H$_2$O: C, 60.76; H. 6.51; N, 12.06. Found: C, 60.42; H; 6.09; N, 11.80.

EXAMPLE 77

Isobutyloxycarbonyl-Trp-Lys(ε-N-(2-methylphenyl)aminocarbonyl)-Asp-(NMe)PheNH$_2$ The title compound was prepared from the tetrapeptide of Example 119b by the debenzylation procedure described in Example 1f. MS (FAB+) m/e 841 (M+H)+. $^1$H NMR (DMSO-d6): (two conformers ca. 1:1) δ(CH$_3$)$_2$C—: 0.70, 0.71 (2s,6H); Ar—CH$_3$: 2.14, 2.15 (2s,3H); N—CH$_3$: 2.73, 2.94 (2s,3H); α-Protons and (CH$_3$)$_2$CH—CH$_2$—O—: 4.17–4.30, 4.65–4.72, 4.83–4.89, 4.93–5.00, 5.09–5.13 (6H). Analysis calculated for C$_{44}$H$_{56}$N$_8$O$_9$.0.5H$_2$O.0.5CH$_3$CO$_2$H: C, 61.42; H. 6.76; N, 12.73. Found: C, 61.23; H; 6.54; N, 12.88.

EXAMPLE 78

Isopropyloxycarbonyl-Trp-Lys(ε-N-(2-methylphenyl)aminocarbonyl)-Asp-(NMe)PheNH$_2$ The title compound was prepared by the method described in Example 63e, replacing the active ester of Example 63c with isopropyloxycarbonyl-Trp-OTCP ester, which was prepared by the procedure described in Example 63c. MS (FAB+) m/e 827 (M+H)+. $^1$H NMR (DMSO-d6/D20): (two conformers ca. 1:1) δ(CH$_3$)$_2$C—: 0.99, 1.08 (2d,6H); Ar—CH$_3$: 2.10, 2.11 (2s,3H); N—CH$_3$: 2.70, 2.90 (2s,3H); α-Protons and (CH$_3$)$_2$CH—O—: 4.08–4.14, 4.16–4.24, 4.53–4.63, 4.80–4.85, 4.87–4.92, 5.07–5.13 (5H). Analysis calculated for C$_{43}$H$_{54}$N$_8$O$_9$.1.5CH$_3$CO$_2$H: C, 60.25; H. 6.60; N, 12.22. Found: C, 60.42; H; 6.37; N, 12.68.

EXAMPLE 79

Phenoxycarbonyl-Trp-Lys(ε-N-(2-methylphenyl)aminocarbonyl)-Asp-(NMe)PheNH$_2$

The title compound was prepared by the method described in Example 74 g and h, replacing 2-adamantyl chloroformate with the commercially available phenyl chloroformate. MS (FAB+) m/e 861 (M+H)+. $^1$H NMR (DMSO-d6): (two conformers ca 1:1) δ methyl singlets: 2.1–2.18, 2.73, 2.97; 3.43; α protons: 4.22, 4.32, 4.38, 4.5, 4.62, 4.71, 4.9, 4.98, 5.18 (4H), NH-indole: 10.83, 10.88 (1H). Analysis calculated for C$_{46}$H$_{52}$N$_8$O$_9$2.4H$_2$O: C, 61.10; H, 6.33; N, 12.39. Found: C, 60.81; H, 5.95; N, 12.33.

EXAMPLE 80

Methoxycarbonyl-Trp-Lys(ε-N-(2-methylphenyl)aminocarbonyl)-Asp-(NMe)PheNH$_2$

The title compound was prepared by the method described in Example 74 g and h, replacing 2-adamantyl chloroformate with the commercially available methyl chloroformate. MS (FAB+) m/e (M+H)+, (M+Na)+. $^1$H NMR (DMSO-d6) (two conformers ca 1:1) δ methyl singlets: 2.13, 2.15 (3H); 2.73, 2.92 (3H); 3.43 (s,3); α protons: 4.18, 4.26, 4.66, 4.86, 4.98, 5.10 (4H). Analysis calculated for C$_{41}$H$_{50}$N$_8$O$_9$.1.5H$_2$O: C, 59.63; H, 6.47; N, 13.57. Found: C, 59.51; H, 6.37; N, 13.51.

EXAMPLE 81

Methoxycarbonyl-Trp-Lys(ε-N-(2-methylphenyl)aminocarbonyl)-(NMe)Asp-PheNH$_2$ a. Methoxycarbonyl-Trp-OH A solution of L-tryptophan (1.0 g, 4.9 mmol), DIEA (0.94 mL, 5.4 mmol), and dimethyl pyrocarbonate (0.58 mL, 5.4 mmol) in 15 mL of 1:1 water/dioxane was stirred at ambient temperature overnight. Isolation of the acidic product by standard extractive procedures gave 740 mg of crude product which was crystallized from diethyl ether/hexane to afford 580 mg of the title compound as colorless crystals. 1H NMR (300 MHz, CDCl$_3$) δ3.35 (m,2H), 3.65 (s, 3H), 4.70 (m, 1H), 5.20 (m, 1H), 7.05–7.40 (aromatic), 7.60 (d, J=7.5 Hz, 1H), 8.10 (br s, 1H).

b. Methoxycarbonyl-Trp-Lys(ε-N-(2-methylphenyl)aminocarbonyl)-(NMe)Asp-PheNH$_2$ The product of Example 81a (47 mg, 0.18 mmol) was coupled to the tripeptide salt TFA.Lys(2-methylphenylaminocarbonyl)-(NMe)Asp(OBn)-Phe-NH$_2$ (125 mg, 0.16 mmol), obtained as described in example 60d, using the standard mixed isobutyl carbonic anhydride procedure as described in Example 52b. Standard acid-base extractive work-up provided 155 mg of crude product, which was subjected to debenzylation as described in Example 1f. Purification by preparative reverse-phase HPLC with CH$_3$CN/50 mM NH$_4$OAc as the mobile phase afforded after lyophilization 71 mg of the title compound. MS (FAB+) m/e 799 (M+H)+, 821 (M+Na)+. $^1$H NMR (DMSO-d$_6$) (two conformers ca. 1:1) δ methyl singlets: 2.11, 2.17 (3H), 2.35, 3.42, 3.46; α protons: 4.27, 4.32, 4.41, 4.48, 4.51, 4.85, 5.14, 5.25. Analysis calculated for C$_{41}$H$_{50}$N$_8$O$_9$.H$_2$O.0.5CH$_3$CO$_2$H: C, 59.56; H, 6.43; N, 13.23. Found: C, 59.62; H, 6.18; N, 13.33.

EXAMPLE 82 t-Butylaminocarbonyl-Trp-Lys(ε-N-(2-methylphenyl)aminocarbonyl)-Asp(NMe)PheNH$_2$ a. H-Trp-Lys(2-methylphenylaminocarbonyl)-AspN(Me)PheNH2 trifluoroacetate:

To a solution of Boc-Trp-Lys(2-methylphenylaminocarbonyl)AspN(Me)PheNH2, the product of Example 33 (2.0 g, 2.37 mmol), in methylene chloride (16 mL) was added anisole (2.6 mL, 23.7 mmol), dimethylphosphite (2.16 mL, 23.7 mmoL) and trifluoroacetic acid (16 mL) and the reaction mixture stirred at room temperature for 6 hours. The solvents were then removed in vacuo and the crude product titurated with ether (3×50 mL) to afford the product as an off-white solid (2.0 g, 98%). MS (FAB+) m/e741 (M+H)+, 724 (M-NH$_2$)+. $^1$H-NMR (DMSO-d6) two conformers ca 1:1; methyl singlets δ2.15, 2.16 (s, 3H); 2.74, 2.95 (3H); α protons 4.04, 4.22, 4.33, 4.68, 4.86, 5.01, 5.14.

b. t-Butylaminocarbonyl-Trp-Lys(ε-N-(2-methylphenyl)aminocarbonyl)-Asp-(NMe)PheNH$_2$ To a solution of the TFA salt of Trp-Lys(ε-N-(2-methylphenyl)aminocarbonyl)-Asp-(NMe)PheNH$_2$ (85 mg, 0.1 mmol) from Step a, and pyridine (28 μL, 0.35 mmol) in DMF (1 mL), at ambient temperature under argon, was added t-butyl isocyanate (12.5 μL, 0.11 mmol). The reaction was incomplete after 1 day, and a catalytic amount of N,N-dimethylaminopyridine (DMAP) was added. After stirring for an additional day at ambient temperature, a second portion (12 μL) of t-butyl isocyanate was added and the reaction mixture was stirred for another day. The reaction mixture was then quenched with 10% citric acid (6 mL) and filtered. The precipitate was washed successively with 2 mL portions of 10% citric acid (2×), water (2×) and hexane (2×) to obtain the crude product (55 mg). Chromatographic purification of the crude product on silica gel eluted with 6:1 ethyl acetate/S3 (S3=20/11/6 pyridinewater/acetic acid) afforded the title compound (16.3 mg) as a white powder. MS(FAB+) m/e 840 (M+H)+, 862 (M-Na)+; $^1$H NMR(DMSO-d6, T=135° C.) δ methyl singlets: 120 (s,9H), 2.17 (s,3H); α protons: 4.22, 4.38, 4.92, 5.01 (4s,4H). Analysis calculated for $C_{44}H_{57}N_9O_8 \cdot 0.5H_2O \cdot 0.5CH_3CO_2H$: C, 61.49; H, 6.88; N, 14.38. Found: C, 61.36; H, 6.71; N, 14.40.

EXAMPLE 83

Methylaminocarbonyl-Trp-Lys(ε-N-(2-methylphenyl)aminocarbonyl)-Asp-(NMe)PheNH$_2$ a. Methylaminocarbonyl-Trp-Lys(ε-N-(2-methylphenyl)aminocarbonyl)-Asp(OBn)-(NMe)PheNH$_2$ To a solution of the trifluoroacetic acid salt of Trp-Lys(ε-N-(2-methylphenyl)aminocarbonyl)-Asp(OBn)-(NMe)PheNH$_2$ (125 mg, 0.13 mmol), the product of Example 74f, in DMF (2 mL) at ambient temperature, was added diisopropylethylamine (0.065 mL, 0.4 mmol), followed by the addition of methyl isocyanate (0.01 mL, 0.16 mmol). After stirring overnight, water was added to the reaction mixture and the precipitate was collected by filtration. The precipitate was washed with 10% aqueous citric acid solution and dried at 40° C. in vacuo to give 105 mg (88% yield) of the title compound as a white solid. MS(FAB+) m/e 888 (M+H)+; $^1$H NMR(DMSO-d6) (two conformers ca. 1:1) δ methyl singlets: 2.14, 2.15 (2s,3H), 2.42, 2.43 (2s,3H), 2.69, 2.72 (2s,3H).

b. Methylaminocarbonyl-Trp-Lys(ε-N-(2-methylphenyl)aminocarbonyl)-Asp-(NMe)PheNH$_2$ The product of Example 83a was debenzylated by the procedure described in Example 1f to give the title compound. MS(FAB+): m/e 796 (M+H)−, 798 (M+H)+. $^1$H NMR (DMSO-d6) (two conformers ca. 2:1) δ methyl singlets: 2.14, 2.15 (3H), α protons 4.18, 4.24, 4.41, 4.72, 4.88, 4.92, 5.16 (4H), indole NH 10.78, 10.84 (1H).

EXAMPLE 84

Phenylaminocarbonyl-Trp-Lys(ε-N-(2-methylphenyl)aminocarbonyl)-Asp-(NMe)PheNH$_2$ a. Phenylaminocarbonyl-Trp-Lys(ε-N-(2-methylphenyl)aminocarbonyl)-Asp(OBn)-(NMe)PheNH$_2$ Following the procedure described in Example 83a, replacing methyl isocyanate with the commercially available phenyl isocyanate, the title compound was prepared.

b. Phenylaminocarbonyl-Trp-Lys(ε-N-(2-methylphenyl)aminocarbonyl)-Asp-(NMe)PheNH$_2$ The product of Example 84a was debenzylated by the procedure described in Example 1f to give the title compound. MS(FAB+): m/e 860 (M+H)+, 862 (M+Na)+. $^1$H NMR (DMSO-d6) (two conformers ca. 2:1) δ2.14, 2.15 (2s,3H), 2.72, 2.84 (2s,3H), 4.21, 4.28, 4.57, 4.58, 4.72, 4.9, 5.00, 5.15 (α,4H), 6.22 (NH,1H), 6.6 (NH,1H), 10.75, 10.84 (NH, indole, 1H).

EXAMPLE 85

Acetyl-Trp-Lys(ε-N-(2-methylphenyl)aminocarbonyl)-Asp-(NMe)PheNH$_2$

Following the procedure of Example 74 g and h, replacing adamantyl chloroformate with the commercially available acetyl chloride, the tetrapeptide of Example 74f was acetylated and debenzylated to give the title compound. MS (FAB+) m/e 783 (M+H)+, 766 (M-NH$_2$)+. $^1$H NMR (DMSO-d6) (two conformers ca 1:1) δ methyl singlets 1.75, 1.76 (2s,3H); 2.14, 2.15 (2s,3H); 2.74, 2.93 (2s,3H); α protons 4.16, 4.25, 4.53, 4.66, 4.87, 4.98, 5.10 (4H). Analysis calculated for $C_{41}H_{50}N_8O_8 \cdot 1.5H_2O$: C, 60.80; H, 6.60; N, 13.84. Found: C, 61.09; H, 6.44; N, 13.63.

EXAMPLE 86

Acetyl-Trp-Lys(ε-N-(2-methylphenyl)aminocarbonyl)-(NMe)Asp-PheNH$_2$

Boc-Trp-Lys(ε-N-(2-methylphenyl)aminocarbonyl)-(NMe)Asp(OBn)-PheNH$_2$, prepared as described in Example 60d, was deprotected to the TFA salt by treatment with trifluoroacetic acid/methylene chloride as described in Example 59b. A solution of the TFA salt of the tetrapeptide in DMF was treated following the procedure of Example 74g and h, replacing adamantyl chlorformate with the commercially available acetic anhydride, to effect acetylation and debenzylation to give the title compound. MS (FAB+) m/e 805 (M+Na)+, 783 (M+H)+. $^1$H NMR (DMSO-d6) (two conformers, ca. 1:1) δ1.14–1.76 (cm, 9H, includes 1.69 (s), 1.72 (s)), 2.03–2.14 (m, 4.5H, includes 2.06 (br s), 2.08 (s)), 2.24–3.12 (cm, 9.5H, includes 2.27 (br s)), 4.27 (m, 0.5H), 4.36–4.50 (m, 1.5H), 4.60 (m, 0.5H), 4.77 (m, 0.5H), 5.06 (dd, J=5, 10 Hz, 0.5H), 5.18 (m, 0.5H), 6.44 (m, 0.5H), 6.74–6.80 (m, 1H), 6.85–6.93 (m, 1H), 6.95–7.26 (cm, 11.5H), 7.35 (br s, 0.5H), 7.48–7.54 (m, 1.5H), 7.68–7.84 (m, 2H), 7.88–7.95 (m, 1.5H, includes 2.91 (d, J=10 Hz), 2.94 (d, J=10 Hz)), 8.04 (br d, J=10 Hz, 0.5H), 8.32 (br d, J=10 Hz, 0.5H), 8.55 (m, 0.5H), 10.71 (br d, J=5 Hz, 1H). Analysis calculated for $C_{41}H_{50}N_8O_8 \cdot 0.8H_2O$: C, 61.77; H, 6.52; N, 14.05. Found: C, 61.66; H, 6.53; N, 14.20.

EXAMPLE 87 t-Butylacetyl-Trp-Lys(ε-N-(2-methylphenyl)aminocarbonyl)-Asp-(NMe)PheNH$_2$

Following the procedures of Example 74g and h, replacing adamantyl chloroformate with the commercially available t-butylacetyl chloride, the tetrapeptide of Example 74f was acylated and debenzylated to give the title compound. MS (FAB+) m/e 839 (M+H)+, 861 (M+Na)+. $^1$H NMR (DMSO-d6) (two conformers ca 1) δ methyl singlets 0.81, 0.82 (2s,9H); 1.92 (m,2H); 2.15 (s,3H); 2.73, 2.95 (2s,3H); α protons 4.18, 4.26, 4.57, 4.69, 4.87, 4.94, 5.15 (4H). Analysis calculated for $C_{45}H_{58}N_8O_8 \cdot 1H_2O \cdot 0.5CH_3CO_2H$: C, 62.28; H, 7.04; N, 12.63. Found: C, 62.27; H, 6.91; N, 12.69.

EXAMPLE 88

Trifluoroacetyl-Trp-Lys(ε-N-(2-methylphenyl)aminocarbonyl)-(NMe)Asp-PheNH$_2$ and t-Butylacetyl-Trp-Lys(ε-N-(2-methylphenyl)aminocarbonyl)-(NMe)Asp-PheNH$_2$ To tetrapeptide Trp-Lys(ε-N-(2-methylphenyl)aminocarbonyl)-(NMe)Asp(OBn)-PheNH$_2$ trifluoroacetate(500 mg, 0.54 mmol), obtained as described in Example 86, in 2 mL of methylene chloride at ambient temperature were added DIEA (104 μL, 0.59 mmol) and t-butylacetyl chloride (83 μL, 0.59 mmol), followed by an additional 208 μL of DIEA. After stirring at ambient temperature for 0.5 hour, the reaction was diluted with methylene chloride and subjected to standard acid/base extractive work-up. The crude product (380 mg) was purified by chromatography on silica gel, eluting with ethyl acetate/hexane (9:1) containing 2% acetic acid, to give two products. The first product was 210 mg of the Asp(OBn) derivative of trifluoroacetyl-Trp-Lys(ε-N-(2-methylphenyl)aminocarbonyl)-(NMe)Asp-PheNH$_2$ which was debenzylated as described in Example 1f to give trifluoroacetyl-Trp-Lys(ε-N-(2-methylphenyl)aminocarbonyl)-(NMe)Asp-PheNH$_2$ (Example 88A). 88A: MS (FAB+) m/e 875 (M+K)$^+$, 859 (M+Na)$^+$, 837 (M+H)$^+$. $^1$H NMR (DMSO-d$_6$) (two conformers, ca. 2:1) δ methyl singlets: 2.15 (4H), 2.35 (2H); α protons: 4.34 (m, 0.33H), 4.45–4.56 (m, 1.33H), 4.63 (m, 0.66H), 4.74 (m, 0.33H), 4.88 (m, 0.33H), 5.16 (dd, J=5, 13 Hz, 0.66H), 5.22 (m, 0.33H). Analysis calculated for C$_{41}$H$_{47}$N$_8$O$_8$F$_3$.0.7H$_2$O: C, 57.97; H, 5.74; N, 13.19. Found: C, 58.00; H, 5.61; N, 13.27. The second product was 80 mg of the Asp(OBn) derivative of t-butylacetyl-Trp-Lys(ε-N-(2-methylphenyl)aminocarbonyl)-(NMe)Asp-PheNH$_2$ which was debenzylated as described in Example 1f to give t-butylacetyl-Trp-Lys(ε-N-(2-methylphenyl)aminocarbonyl)-(NMe)Asp-PheNH$_2$ (Example 88B). 88B: MS (FAB+) m/e 839 (M+H)$^+$. $^1$H NMR (DMSO-d6) (two conformers, ca. 2:1) δ t-butyl singlets: 0.82, 0.83; methyl singlets: 2.15 (3H), 2.16 (1.5H), 2.43 (1.5H); α protons: 4.27 (m), 4.42 (m), 4.51 (m), 4.57 (m), 4.69 (m), 4.85 (m), 5.08 (m), 5.24 (m).

EXAMPLE 89

Benzoyl-Trp-Lys(ε-N-(2-methylphenyl)aminocarbonyl)-Asp-(NMe)PheNH$_2$

Following the procedure of Example 74g and h, replacing adamantyl chlorformate with the commercially available benzoyl chloride, the tetrapeptide of Example 74f was acetylated and debenzylated to give the title compound. MS MS (FAB) m/e 845 (M+H)$^+$. $^1$H NMR (DMSO-d$_6$): two conformers ca. 2:1δ2.1, 2.13, (2s,3H), 2.72, 2.93 (2s,3H), 4.22, 4.28, 4.68, 4.72,4.75, 4.86, 4.98, 5.1 (α protons,4H), 6.5 (NH,2H), 10.71, 10.73 (NH,indole,1H). Anal.calcd.for C$_{46}$H$_{52}$N$_8$O$_8$. 1.5H$_2$O: C, 63.36; H, 6.36; N, 12.85. Found: C, 63.3; H, 6.16; N, 12.47.

EXAMPLE 90

Benzoyl-Trp-Lys(ε-N-(2-methylphenyl)aminocarbonyl)-(NMe)Asp-PheNH$_2$

Starting with Trp-Lys(ε-N-(2-methylphenyl)aminocarbonyl)-(NMe)Asp(OBn)-PheNH$_2$ trifluoroacetate, obtained as described in Example 86, the title compound was prepared following the procedure of Examples 74g and h, replacing adamantyl chloroformate with the commercially available benzoic anhydride. Final purification was accomplished by reverse phase HPLC as in Example 2. MS (FAB+) m/e 867 (M+Na)$^+$, 845 (M+H)$^+$. $^1$H NMR (DMSO-d$_6$) (two conformers, ca. 1:1) δ methyl singlets: 2.13 (3H), 2.14 (1.5H), 2.37 (1.5H); α protons: 4.35 (m, 0.5H), 4.47 (m, 0.5H), 4.55 (m, 0.5H), 4.74 (m, 0.5H), 4.84–4.94 (m, 1H), 5.16 (dd, J=7, 14 Hz, 0.5H), 5.26 (m, 0.5H). Analysis calculated for C$_{46}$H$_{52}$N$_8$O$_8$.0.8H$_2$O.0.2CH$_3$CO$_2$H: C, 63.96; H, 6.29; N, 12.86. Found: C, 63.95; H, 6.09; N, 12.91.

EXAMPLE 91

Phenylacetyl-Trp-Lys(ε-N-(2-methylphenyl)aminocarbonyl)-Asp-(NMe)PheNH$_2$

Following the procedure of Example 74g and h, replacing adamantyl chlorformate with the commercially available phenylacetyl chloride, the tetrapeptide of Example 74f was converted to the title compound. MS (FAB+) m/e 859 (M+H)$^+$. $^1$H NMR (DMSO-d$_6$) (two conformers ca 1:1) δ methyl singlets: 2.14 (s,3H); 2.74, 2.97 (2s,3H); 3.39 (br.s., 2H); α protons: 4.19, 4.26, 4.58, 4.72, 4.88, 4.95, 5.16 (4H).

EXAMPLE 92

(3,3-Diphenylpropionyl)-Trp-Lys(ε-N-(2-methylphenyl)aminocarbonyl)-Asp-(NMe)PheNH$_2$ 3,3-Diphenylpropionic acid was coupled to the tetrapeptide of Example 74f by standard procedure, using EDCl and HOBT, to afford the title compound. MS (FAB+) m/e 971 (M+Na)$^+$. $^1$H NMR (DMSO-d$_6$) (two conformers ca. 2:1) δ2.12, 2.15 (3H,CH$_3$), 2.7, 2.93 (3H,CH$_3$), 4.12, 4.18, 4.36, 4.43, 4.71, 4.88, 4.93, 5.15 (4H, α protons), 10.71, 10.75 (NH, indole). Anal.calcd. for C$_{54}$H$_{60}$N$_8$O$_8$.H$_2$O: C 67.06, H 6.46, N 11.58; Found: C 66.77, H 6.47, N 11.31;

EXAMPLE 93

(3-(4-Hydroxy-3-iodophenyl)propionyl)-Trp-Lys(ε-N-(2-methylphenyl)aminocarbonyl)-Asp-(NMe)PheNH$_2$ a. (3-(4-Hydroxy-3-iodophenyl)propionyl)-Trp-Lys(ε-N-(2-methylphenyl)aminocarbonyl)-Asp-(NMe)-PheNH$_2$ Following the procedure of Example 1e, 3-(4-hydroxy-3-iodophenyl)propionic N-hydroxysuccinimide ester (L. J. Miller et al, J. Biol. Chem. 256, 12417, 1981) and the tetrapeptide of Example 74f were coupled to afford the title compound. MS (FAB+) m/e 1015(M+H)$^+$. $^1$H NMR (DMSO-d$_6$) (two conformers ca. 1:1) δ Ar—CH$_3$: 2.09 (3s,3H); N—CH$_3$: 2.67, 2.89 (2s,3H); α-protons: 4.11, 4.18, 4.48, 4.67, 4.83, 4.89, 5.11 (4H), phenolic OH: 10.66, 10.71 (2br s,1H). Analysis calculated for C$_{48}$H$_{55}$IN$_8$O$_9$.1.5H$_2$O.1.5CH$_3$CO$_2$H: C, 56.80; H. 5.47; N, 11.04. Found: C, 58.60; H; 6.07; N, 11.42.

EXAMPLE 94

(3-Carboxylpropionyl)-Trp-Lys(ε-N-(2-methylphenyl)aminocarbonyl)-Asp-(NMe)PheNH$_2$ Following the procedure of Example 74g and h, replacing adamantyl chlorformate with commercially available succinic anhydride, the tetrapeptide of Example 74f was converted to the title compound. MS (FAB−) m/e 839 (M−H)$^+$. $^1$NMR (DMSO-d$_6$) (two conformers ca. 2:1) δ2.08, 2.13 (2s,3H,CH₃), 2.65,2.87 (2s,3H,CH₃), 4.08, 4.22, 4.31, 4.35, 4.7, 4.49, 4.82, 4.97 (α,4H), 10.68, 10.7 (NH,indole).

EXAMPLE 95

Methylsufonamyl-Trp-Lys(ε-N-(2-methylphenyl)aminocarbonyl)-Asp-(NMe)PheNH₂

The tetrapeptide of Example 74f, Trp-Lys(ε-N-(2-methylphenyl)aminocarbonyl)-Asp(OBn)-(NMe)-PheNH₂, was acylated using methanesulfonyl chloride and DIEA. After standard acid-base work-up, the crude product was chromatographed on silica gel elting with 5% ethanol in ethyl acetate. The protected tetrapeptide was hydrogenated with palladium in DMF as described in Example 65 and the crude product chromatographed on silica gel eluting with ethyl acetate/pyridine/acetic acid/water to give the title compound. MS (FAB+) m/e 841 (M+H)+. ¹H NMR (DMSO-d₆) (two conformers ca. 2:1) δ methyl singlet: 2.15 (3H), 2.72, 2.98 (3H); α-protons: 4.14, 4.21, 4.28, 4.72, 4.89, 5.18 (4H), indole NH: 10.85, 10.9. Analysis calculated for C₄₀H₅₀IN₈O₉S.1.5H₂O: C, 56.79; H. 6.26; N, 13.25. Found: C, 56.90; H; 6.11; N, 12.84.

EXAMPLE 96 t-BOC-D,L-(α-methyl)Trp-Lys(ε-N-(2-methylphenyl)aminocarbonyl)-Asp-PheNH₂ a. t-BOC-[D,L]-(α-Me)Trp-Lys(ε-N-benzyloxycarbonyl) methyl ester t-BOC-α-Me-[D.L]-Trp-OH was prepared as described in the literature (Horwell, et al, *Eur. J. Med. Chem*, 1990, 25:53–60). To a solution of HCl-Lys-(ε-N-benzyloxycarbonyl)-OCH₃ (0.78 g, 2.35 mmol) in methylene chloride (5 mL) cooled to 0° C. was added NMM (0.275 ml, 2.5 mmol), t-BOC-[D,L](α-methyl)Trp-OH (0.75 g, 2.35 mmol), HOBT (0.48 g, 3.5 mmol), and EDCl (0.58 g, 3 mmol). The reaction was stirred overnight with warming to ambient temperature. The solvents were removed in vacuo and the residue dissolved in ethyl acetate and washed successively with solutions of 1M H₃PO₄ (3×), NaHCO₃, water and brine. The solvent was removed after drying with MgSO₄ and the residue was dissolved in a minimum of ethyl acetate and precipitated with hexane to provide 1.23 g (88% yield) of the title compound as a solid. MS (Cl) m/e 595 (M+H+). ¹H NMR (CDCl₃) δ1.43, 1.45 (2s,9H), 3.66, 3.69 (2s,3H), 5.1 (s,2H).

b. t-BOC-D,L-(α-Me)Trp-Lys(ε-N-benzyloxycarbonyl)-OH

To a solution of t-BOC-[D,L]-(α-Me)Trp-Lys(ε-N-benzyloxycarbonyl)-OMe (1.2 g, 2.02 mmol), from Step a, in methanol (10 ml) was added a 2M solution KOH (1 mL) and the reaction stirred at ambient temperature for one hour (monitored by TLC). The solvent was evaporated in vacuo and the residue quenched with 0.5M HCl. The product was extracted into ethyl acetate (2×) and the combined organic layers washed with water and brine, dried (MgSO₄) and the solvents removed in vacuo to yield 1.1 g (93% yield) of the semisolid product. MS (FAB+): m/e 581 (M+H)+, 603 (M+Na)+. ¹H NMR (DMSO-d₆) δ1.43 (s,9H), 2.03 (s,3H), 4.5(s,1H,α), 5.2 (s,2H).

c. t-BOC-D,L-(α-methyl)Trp-Lys(ε-N-(2-methylphenyl)aminocarbonyl)-Asp-PheNH₂

The dipeptide acid of Example 96b was coupled to the TFA salt of Asp-Phe-NH₂ by mixed isobutyl carbonic anhydride procedure as indicated in example 52b. Hydrogenolysis as in Example 1f and urea formation as in Example 24 afforded the title compound. MS (FAB+): m/e 863 (M+Na)+. ¹H NMR (DMSO-d₆) (two diastereoisomers ca. 1:1) δ1.18, 1.22 (2s, α methyl,3H), 1.42, 1.44 (2s, 9H), 2.16, 2.17 (2s,3H), 4.03, 4.33, 4.48 (3m, α protons, 3H), 7.25 (1H, NH), 7.3 (2H, NH), 8.05 (1H,NH). Analysis calculated for C₄₄H₅₆N₈O₉.2.1H₂O.2.1CH₃CO₂H: C, 57.61; H, 6.88; N, 11.15. Found: C, 57.20; H, 6.25; N, 11.50.

EXAMPLE 97

D,L-(α-Methyl)Trp-Lys(ε-N-(2-methylphenyl)aminocarbonyl)-Asp-PheNH₂

The t-BOC group was removed from the tetrapeptide of Example 96c according to the procedure described in Example 74f to give the title compound. MS (FAB+) m/e 741 (M+H)+. ¹H NMR (DMSO-d₆) (two diastereoisomers ca. 1:1) δ1.49, 1.51 (2 s, 3H, α-methyl), 2.08, 2.10 (2s, 3H), 4.29, 4.38, 4.40, 4.20, 4.50, 4.59 (α-protons), 6.22 (s, 1H, NH), 7.95 (bs, 1H, NH), 8.03 (bs, 1H, NH), 8.30 (d, J=7 Hz, 1H,NH), 8.5 (d, J=7 Hz, 1H, NH), 11.04, 11.08 (s, 1H, indole NH).

EXAMPLE 98

(α-Methyl)Trp-Lys(ε-N-(2-methylphenyl)aminocarbonyl)-Asp-(NMe)PheNH₂ (Isomer A)

a. (α-Methyl)Trp-Lys(ε-N-(2-methylphenyl)aminocarbonyl)-Asp(OBn)-(NMe)PheNH₂

To a solution of Boc-α-methyl-TrpOH (48 mg, 0.15 mmol) and the TFA salt of Lys(ε-N-(2-methylphenyl)aminocarbonyl)-Asp(OBn)-N(Me)PheNH₂ (113 mg, 0.15 mmol) in methylene chloride (2 mL) cooled to 0° C. was added N-methylmorpholine (20 μL, 0.18 mmol) followed by EDCl (31 mg, 0.165 mmol), and the reaction allowed to warm to ambient temperature. After one day the solvent was removed in vacuo and the crude product washed with 1-mL portions of 10% citric acid (4×), and water (2×) and dried to afford the title compound (mixture of diastereomers) as a white solid (97 mg). These isomers can be separated by flash chromatography on silica gel (eluted with ethyl acetate).

ISOMER A: (Higher Rf material) MS (FAB+) m/e 845 (M+H)+, 883 (M+K)+. ¹H-NMR (DMSO-d6) (two conformers ca 1:1) δ methyl singlets: 1.20 (3H); 2.15, 2.16 (3H); 2.71, 2.85 (3H); α protons: 4.12, 4.62, 4.87 (3H). Analalysis calculated for C₄₇H₅₆N₈O₇.1.0-H₂O: C, 65.41; H, 6.77; N, 12.98. Found: C, 65.18; H, 6.77; N, 12.71.

ISOMER B: (Lower Rf material) MS (FAB+) m/e 845 (M+H)+, 867 (M+Na)+, 883 (M+K)+. ¹H-NMR (DMSO-d6) (two conformers ca 1:1) methyl singlets: δ1.15 (3H); 2.14, 2.16 (3H); 2.72, 2.86 (3H); α protons: 4.20, 4.62, 4.88 (3H).

b. (α-Methyl)Trp-Lys(ε-N-(2-methylphenyl)aminocarbonyl)-Asp-(NMe)PheNH₂ (Isomer A)

The benzyl protecting group was removed from Isomer A of the tetrapeptide from Step a, as described in Example 1f, to give the title compound. MS (FAB+) m/e 755 (M+H)+, 738 (M-NH₂)+. ¹H NMR (DMSO-d6) (two conformers ca 1:1) δ methyl singlets: 1.23, 1.26 (2s,3H); 2.16, 2.17 (2s,3H); 2.71, 2.92 (2s,3H); α protons: 4.15, 4.64, 4.86, 4.94, 5.12 (3H). Analysis calculated for C₄₀H₅₀N₈O₇.2.2H₂O: C, 60.47; H, 6.90; N, 14.10. Found: C, 60.56; H. 6.66; N, 13.73.

EXAMPLE 99

(α-Methyl)Trp-Lys(ε-N-(2-methylphenyl)aminocarbonyl)-Asp-(NMe)PheNH$_2$ (Isomer B)

The benzyl protecting group was removed from Isomer B of the tetrapeptide from Example 174a, as described in Example 1f, to give the title compound. MS (FAB+) m/e 755 (M+H)+, 738 (M-NH$_2$)+. $^1$H-NMR (DMSO-d6) (two conformers ca 1:1) δ methyl singlets: 1.23, 1.25 (3H); 2.14, 2.15 (3H); 2.73, 2.94 (3H); α protons: 4.19, 4.25, 4.65, 4.86, 4.91, 5.16 (3H).

EXAMPLE 100

(NMe)Trp-Lys(ε-N-(2-methylphenyl)aminocarbonyl)-(NMe)Asp-α-NalNH$_2$ a. t-BOC-(NMe)Asp(OBn)-OH The product of Example 60a (83 g) in 300 mL of methylene chloride was treated with piperidine (100 mL) followed by isopropyl ether (1000 mL). After ca. 2 hours, additional isopropyl ether was added to precipitate the product which was collected by filtration to afford 31.3 g of material. A suspension of this intermediate in methylene chloride (200 mL) was added to a stirred mixture of di-t-butyl dicarbonate (42.33 g), methylene chloride (200 mL), water (100 mL) and DIEA (to maintain pH 8–8.3). After stirring at 35° C. for 1 h, the acidic product was isolated by standard extractive procedures, followed by crystallization from ethyl acetate/heptane to afford 32.6 g of the title compound. $^1$H NMR (CDCl$_3$, 300 MHz) (two conformers, ca. 1:1) δ1.41 (s) and 1.43 (s) (total 9H), 2.83 (m, 1H), 2.39 (s) and 2.45 (s) (total 3H), 3.15 (dd, J=6, 16 Hz, 1H), 4.60 (m) and 4.75 (m) (total 1H), 5.15 (s, 2H), 7.35 (m, 5H). MS (Cl) m/e 338 (M+H)+, 355 (M+NH$_4$)+.

b. t-BOC-(NMe)Asp(OBn)-α-NalNH$_2$

The hydrochloride salt of α-Nal-NH$_2$ (the product of Example 21b) was coupled to the product of Step a according to the method described in Example 1a.

c. t-BOC-Lys(ε-N-(2-methylphenyl)aminocarbonyl)-(NMe)Asp(OBn)-α-NalNH$_2$ t-BOC-(NMe)Asp(OBn)-α-Nal-NH$_2$, from Step a, was treated with 1.3N hydrogen chloride in glacial acetic acid as described in Example 1d, to give the corresponding hydrochloride salt of the dipeptide. The dipeptide was then coupled with t-BOC-Lys(ε-N-(2-methylphenyl)aminocarbonyl-OH, the product of Example 74b, according to the procedure described in Example 1a, to give the title compound.

d. t-BOC-(NMe)Trp-Lys(ε-N-(2-methylphenyl)aminocarbonyl)-(NMe)Asp(OBn)-α-NalNH$_2$ t-BOC-Lys(ε-N-(2-methylphenyl)-(NMe)Asp(OBn)-α-NalNH$_2$, from Step c, was treated with 1.5N hydrogen chloride in glacial acetic acid as described in Example 1d, to give the corresponding hydrochloride salt of the tripeptide. The tripeptide was then coupled with t-BOC-(NMe)Trp-OH, the product of Example 69a, according to the procedure described in Example 1a, to give the title compound.

e. t-BOC-(NMe)Trp-Lys(ε-N-(2-methylphenyl)aminocarbonyl)-(NMe)Asp(OBn)-α-NalNH$_2$ To a suspension of 55 mg of 10% palladium on carbon in acetic acid, under nitrogen atmosphere, was added a solution of the benzyl ester of Step d (50 mg, 0.53 mmol) in 10 mL of acetic acid and 300 μL of cyclohexadiene. The reaction was monitored by TLC for the disappearance of starting material. When the reaction was complete according to the TLC analysis, the reaction mixture was filtered through Celite® and refiltered through a membrane filter. The filtrate was concentrated in vacuo and the residue was lyopholized to give 35 mg (73% yield) of the title compound.

f. (NMe)Trp-Lys(ε-N-(2-methylphenyl)aminocarbonyl)-(NMe)Asp-α-NalNH$_2$

A solution of t-BOC-(NMe)Trp-Lys(ε-N-(2-methylphenyl)aminocarbonyl)-Asp-(NMe)-α-NalNH$_2$ (0.03 g, 0.033 mmol) in 2–3 mL of 1.5N HCl in acetic acid was stirred at ambient temperature approximately 0.5 hour. Slow dropwise addition of diethyl ether precipitated the product, which was collected by filtration and dried to yield the crude product. Preparative HPLC (acetonitrile/50 mM ammonium acetate) afforded the pure title compound (10 mg, 37% yield). MS (FAB+) m/e 805 (M+H)+, 827 (M+Na)+. $^1$H NMR (DMSO-d$_6$) (two conformers ca 2:1) methyl singlets: δ2.09, 2.13 (2s,3H), 2.4, 2.48 (2s,3H), 3.13, 3.16 (2s,3H); α-protons: 3.55, 3.65, 4.05, 4.15, 4.41, 4.53, 4.95, 5.0.

EXAMPLE 101

(NMe)Trp-Lys(ε-N-(2-methylphenyl)aminocarbonyl)-Asp-(NMe)PheNH$_2$ a. t-BOC-(NMe)Trp-Lys(ε-N-(2-methylphenyl)aminocarbonyl)-Asp(OBn)-(NMe)PheNH$_2$ The tripeptide of Example 74d, Lys(ε-N-(2-methylphenyl)aminocarbonyl)-Asp(OBn)-(NMe)PheNH$_2$, was coupled with t-BOC-(NMe)Trp-OH, the product of Example 69a, according to the procedure described in Example 1a, to give the title compound. MS (FAB+) m/e 945 (M+H)+, 967 (M+Na)+. $^1$H NMR (DMSO-d$_6$) (two conformers ca 2:1) δ methyl singlets: 2.15, 2.17 (2s,3H), 2.72, 2.89 (2s,3H); α-protons: 4.18–432, 4.61–469, 4.85–4.96 (4H), β-CH2-benzyl protons: 5.1–5.15 (2H), indole NH proton 10.8 (1H).

b. t-BOC-(NMe)Trp-Lys(ε-N-(2-methylphenyl)aminocarbonyl)-Asp-(NMe)PheNH$_2$

The tetrapeptide of Step a was debenzylated by hydrogenolysis according to the procedure described in Example 1f to give the title compound. MS (FAB+) m/e 855 (M+H)+. $^1$H NMR (DMSO-d$_6$) (two conformers ca 1:1) δ methyl singlets: 2.14, 2.16 (2s,3H), 2.68, 2.69 (2s,3H); α-protons: 4.12, 428, 4.68, 489, 4.96, 5.12 (4H), NH proton: 6.56 (1H), indole NH proton 10.28 (1H). Analysis calculated for C$_{45}$H$_{58}$N$_8$O$_9$.2.8-H$_2$O: C, 59.69; H, 7.05; N, 12.38. Found: C, 59.51; H, 6.53; N, 12.48.

c. (NMe)Trp-Lys(ε-N-(2-methylphenyl)aminocarbonyl)-Asp-(NMe)PheNH$_2$

Following the procedure described in Example 69b, replacing t-BOC-Lys(ε-N-(2-methylphenylaminocarbonyl))-(NMe)Asp(OBn)-PheNH$_2$ with the tetrapeptide of Step b, t-BOC-(NMe)Trp-Lys(ε-N-(2-methylphenyl)aminocarbonyl)-Asp-(NMe)PheNH$_2$, the title compound was prepared. MS (FAB+) m/e 755 (M+H)+, 777 (M+Na)+. $^1$H NMR (DMSO-d$_6$) (two conformers ca 1:1) δ methyl singlets: 2.22, 2.28 (2s,3H), α-protons: 4.25, 4.95, 5.05 (4H), indole NH proton 10.4 (1H). Analysis calculated for C$_{40}$H$_{50}$N$_8$O$_7$.1.0HCl.2.8H$_2$O: C, 59.23; H, 6.61; N, 13.81. Found: C, 59.29; H, 6.62; N, 13.44.

EXAMPLE 102

(3-(3-Indolyl)propionyl-Lys(ε-N-(2-methylphenyl)aminocarbonyl)-(NMe)Asp-(NMe)PheNH₂

3-Indolyl-3-propionic acid-N-hydroxysuccinimide ester was coupled to Lys(ε-benzyloxycarbonyl)-(NMe)AspOBn)-(NMe)PheNH₂, (obtained as described in Example 59b) from the petide of Example 68a, by a procedure analogous to that described in Example 1e. Hydrogenolysis as in Example 1f and acylation with 2-methyl-phenyl isocyanate and NMM in DMF as described in Example 1g provided the title compound. MS (FAB+) m/e 762 (M+Na)+, 740 (M+H)+. ¹H NMR (DMSO-d₆) δ methyl singlets: 2.09, 2.17, 2.24; α protons: 4.41 (m), 5.34 (dd, J=5, 15 Hz), 5.52 (dd, J=5, 10 Hz). Analysis calculated for C₄₀H₄₉N₇O₇.0.5NH₄OAc: C, 63.26; H, 6.80; N, 13.50. Found: C, 63.19; H, 6.59; N, 13.55.

EXAMPLE 103

(3-(3-Indolyl)propionyl-Lys(ε-N-(2-methylphenyl)aminocarbonyl)-(NMe)Asp-α-NalNH₂ a. (3-(3-Indolyl)propionyl)-Lys(ε-N-(2-methylphenyl)aminocarbonyl)-(NMe)Asp(OBn)-α-NalNH₂

(3-(3-Indolyl)propionyl) N-hydroxysuccinimide was coupled to HCl.Lys(ε-N-(2-methylphenyl)aminocarbonyll-(NMe)Asp(OBn)-α-NalNH₂, from Example 100e, under standard conditions using N-methylmorpholine in methylene chloride and DMF to give the title compound.

b. (3-(3-Indolyl)propionyl)-Lys(ε-N-(2-methylphenyl)aminocarbonyl)-(NMe)Asp-α-NalNH₂

The tetrapeptide of Step a was debenzylated as described in Example #100d with cyclohexadiene in the presence of palladium on carbon catalyst and a trace amount of ammonium formate, to give the title compound. MS (FAB+) m/e 776 (M+H)+. ¹H NMR (DMSO-d₆) (two conformers ca. 1:1): δ2.03, 2.10 (2s,3H), 4.36, 4.88, 5.32 (3m,3H, α protons), 7.5 (1H,NH), 7.65 (2H,NH), 8.5 (1H,NH), 8.65 (1H,NH), 10.78 (1H, indole NH). Analalysis calculated for C₄₃H₄₉N₇O₇.1.0H₂O.1.5CH₃CO₂H: C, 61.50; H, 6.49; N, 11.09. Found: C, 61.18; H, 6.28; N, 11.14.

EXAMPLE 104

(2-Methyl-3-(3-indolyl)propionyl)-Lys(ε-N-(2-methylphenyl)aminocarbonyl)-Asp-(NMe)PheNH₂ a. 2-carboethoxy-3-(3-indolyl)-2-methylpropionic acid

Ethyl 2-carboethoxy-3-(3-indolyl)-2-methylpropionate (1.8 g, 5.95 mmol) (S. Masanori, et al., *Heterocycles*, 1981, 16:941-9), was added to a solution of potassium hydroxide (380 mg, 5.76 mmol) in 4 mL of ethanol. The reaction mixture was stirred at ambient temperature overnight and then heated on a steam bath for 2 hours. The ethanol was evaporated and water (20 mL) was added. The aqueous mixture was extracted with diethyl ether (3×20 mL). The pH of the aqueous layer was adjusted to approximately 1 and it was then extracted with ethyl acetate. The ethyl acetate solution was dried over anhydrous sodium sulfate, filtered and concentrated in vacuo to give 1.5 g (92% yield) of the title compound.

b. 3-(3-Indolyl)-2-methylpropionic acid 2,4,5-trichlorophenyl ester

The product of Step a was added to diglyme (15 mL) and the reaction mixture was heated at reflux for 6 hours. The diglyme was removed by vacuum distillation. The residue was purified by flash chromatography on silica gel eluting with ethyl acetate/hexane (1:4) to give ethyl 3-(3-indolyl)-2-methylpropionate. The ethyl ester was the converted to the carboxylic acid as described in Example 64a and subsequently converted to the TCP active ester as described in Example 64b to give the title compound.

c. (2-Methyl-3-(3-indolyl)propionyl)-Lys(ε-N-(2-methylphenyl)aminocarbonyl)-Asp-(NMe)PheNH₂

The ester of Step b (300 mg, 0.83 mmol), the TFA salt of Lys(ε-N-(2-methylphenyl)aminocarbonyl)-Asp-(NMe)Phe (553 mg, 0.83 mmol), the product of Example 74d, and NMM (182 μL, 0.83 mmol) were combined in 4.5 mL of DMF and the reaction mixture was allowed to stir at ambient temperature for approximately 18 hours. The reaction was then quenched by pouring into phosphoric acid/brine solution. The precipitate was filtered, dissolved in acetic acid and lyopholized to give 267 mg of crude product. The crude product was chromatographed on silica gel eluting with 20% and then 30% Bodansky stock solution in ethyl acetate (Bodansky stock solution=pyridine/water/acetic acid, 20:11:6). The fractions containing the desired product were combined and concentrated and the residue was dissolved in toluene. The toluene solution was concentrated to a yellow oil in vacuo and the yellow oil was dissolved in DMF (1 mL). The DMF solution was added dropwise to cold phosphoric acid solution. The solid was filtered, dissolved in acetic acid and lyopholized to give 41 mg of the title compound. MS (FAB+) m/e 740 (M+H)+. ¹H NMR (DMSO/D₂O) (mixture of a pair of diastereomers and two conformers) δ Ar—CH₃: 2.15, 2.17 (2s, 3H); N—CH₃: 2.73, 2.75, 2.91, 2.94 (4s, 3H); α-Protons: 4.07-4.30, 4.55-4.68, 4.81-5.00, 5.05-5.15 (4H). Analysis calculated for C₄₀H₄₉N₇O₇.1.0H₂O: C, 63.39; H, 6.78; N, 12.94. Found: C, 63.59; H; 6.55; N, 12.75.

EXAMPLE 105

(2-Cyano-3-(3-indolyl)propionyl)-Lys(ε-N-(2-methylphenyl)aminocarbonyl)-Asp-(NMe)PheNH₂

Following the procedure of Example 64, replacing the tripeptide Lys(ε-N-(2-methylphenyl)aminocarbonyl)-Asp-PheNH₂, with the tripeptide of Example 56a, Lys(ε-N-(2-methylphenyl)aminocarbonyl)-Asp-(NMe)PheNH₂, the title compound was prepared. MS (FAB+) m/e 773 (M+Na)+. ¹H NMR (DMSO-d₆/D₂O) (mixture of a pair of diastereomers and two conformers) δ Ar—CH₃: 2.13, 2.15,2.17 (3s,3H); N—CH₃: 2.74, 2.76, 2.93, 2.94 (4s,3H); α-protons: 4.08-4.30, 4.57-4.66, 4.84-5.02, 5.08-5.17 (4H). Analysis calculated for C₄₀H₄₆N₈O₇.1H₂O: C, 62.49; H. 6.29; N, 14.57. Found: C, 62.32; H; 6.17; N, 14.31.

EXAMPLE 106

(2-Aminocarbonyl-3-(3-indolyl)propionyl)-Lys(ε-N-(2-methylphenyl)aminocarbonyl)-Asp-(NMe)PheNH₂ a. Ethyl 2-aminocarbonyl-3-(3-idolyl)propionate

The title compound was prepared in 83% yield (2.6 g) from gramine and malonate monamide mono ethyl ester in a similar manner to the procedure used by S. Masanori, et al., (*Heterocycles*, 1981, 16:941-9) to make ethyl 2-cyano-3-(3-indolyl)propionate.

b. 2-Aminocarbonyl-3-(3-idolyl)propionic acid 2,4,5-trichlorophenyl ester

Following the procedure described in Example 64 a and b, the ethyl 2-aminocarbonyl-3-(3-indolyl)propionate from Step a (300 mg) was converted to the corresponding trichlorophenyl (tcp) ester in 14% yield (65 mg).

c. (2-Aminocarbonyl-3-(3-indolyl)propionyl)-Lys($\epsilon$-N-(2-methylphenyl)aminocarbonyl)-Asp-(NMe)-PheNH$_2$ The tripeptide of Example 56b, Lys($\epsilon$-N-(2-methylphenyl)aminocarbonyl)-Asp-(NMe)PheNH$_2$ (116 mg, 0.174 mmol) was condensed with the top ester of Step b (65 mg, 0.16 mmol) by the procedure similar to that described in Example 1e. The product was adsorbed onto silica gel and purified by flash chromatography on silica gel eluting with 1:4 Bodansky stock solution in ethyl acetate (Bodansky stock solution=pyridine/water/acetic acid 20:11:6) and lyopholized from acetic acid to give 70 mg of the title compound. MS (FAB+) m/e 769 (M+H)$^+$, 791 (M+Na)$^+$. $^1$H NMR (DMSO/D$_2$O): Mixture of a pair of diastereomers and two conformers Ar—CH$_3$: 2.11, 2.12 (2s,3H); N—CH$_3$: 2.69, 2.71, 2.90, 2.92 (4s,3H); $\alpha$-Protons: 4.03–4.22, 4.57–4.63, 4.81–4.91, 5.08–5.15 (4H). Analysis calculated for C$_{40}$H$_{48}$N$_8$O$_8$.1.5H$_2$O.1.5CH$_3$CO$_2$H: C, 58.30; H. 6.48; N, 12.65. found: C, 58.20; H; 6.01; N, 12.95.

EXAMPLE 107

(2-Carboethoxy-2-methyl-3-(3-indolyl)propionyl)-Lys($\epsilon$-N-(2-methylphenyl)amino-carbonyl)-Asp-(NMe)PheNH$_2$ a. (2-Carboethoxy-2-methyl-3-(3-indolyl)propionyl)-Lys($\epsilon$-N-(2-methylphenyl)amino-carbonyl)-Asp(OBn)-(NMe)PheNH$_2$ 2-Carboethoxy-3-(3-indolyl)-2-methylpropionic acid (151 mg, 0.55 mmol), from Example 104a, the TFA salt of Lys($\epsilon$-N-(2-methylphenyl)aminocarbonyl)-Asp(OBn)-(NMe)Phe (553 mg, 0.83 mmol), the product of Example 74d, NMM (0.26 mL, 2.4 mmol) and HOBT (81 mg, 0.6 mmol) were dissolved in methylene chloride and the resultant solution was cooled to 0° C. EDCl (0.23 g, 1.2 mmol) was added and the reaction mixture was allowed to warm to ambient temperature. The reaction mixture was stirred over the weekend and then diluted with methylene chloride, washed with 1N hydrochloric acid solution and saturated aqueous sodium bicarbonate solution, dried over anhydrous magnesium sulfate, filtered and concentrated in vacuo. The residue was dissolved in ethyl acetate and filtered through a pad of silica gel. The ethyl acetate was evaporated in vacuo to give 0.34 g (69% yield) of the title compound.

b. (2-Carboethoxy-2-methyl-3-(3-indolyl)propionyl)-Lys($\epsilon$-N-(2-methylphenyl)amino-carbonyl)-Asp-(NMe)PheNH$_2$ The tetrapeptide product of Step a (0.28 g, 0.31 mmol) from Step a, was dissolved in ethanol and hydrogenolyzed over 10% palladium on carbon. The reaction mixture was filtered through Celite ® and the filtrate was concentrated in vacuo to give 152 mg (60% yield) of the title compound. MS (FAB+) m/e 812 (M+H)$^+$, 834 (M+Na)$^+$. $^1$H NMR (DMSO-d$_6$/D$_2$O): (mixture of a pair diastereomers and two conformers) $\delta$ —O—CH2CH$_3$: 1.11(t,3H); 2—CH$_3$: 1.13, 1.16, 1.24, 1.27(3s,3H); Ar—CH$_3$: 2.16, 2.17 (3s,3H); N—CH$_3$: 2.75, 2.76, 2.95, 2.96 (4s,3H); —O—CH$_2$—CH3: 3.98–4.11 (2H); $\alpha$-protons: 4.16–4.30, 4.60–4.70, 4.85–5.03, 5.12–5.20 (4H). Analysis calculated for C$_{43}$H$_{53}$N$_3$O$_9$.1.5H$_2$O: C, 61.56; H. 6.73; N, 11.69. Found: C, 61.66; H; 6.70; N, 11.36.

EXAMPLE 108

(2-Fluoro-3-(3-indolyl)propionyl)-Lys($\epsilon$-N-(2-methylphenyl)aminocarbonyl)-Asp-(NMe)PheNH$_2$ 2-Fluoro-3-(indol-3-yl)propionic acid 2,4,5-trichlorophenyl ester, the product of Example 63c, was coupled to the tripeptide of Example 56b, Lys($\epsilon$-N-(2-methylphenyl)aminocarbonyl)-Asp-(NMe)PheNH$_2$, according to the procedure described in Example 63d to give the title compound. MS (FAB+) m/e 766 (M+Na)$^+$. $^1$H NMR (DMSO-d$_6$): (mixture of a pair diastereomers and two conformers) $\delta$ Ar—CH$_3$: 2.15, 2.16,2.17 (3s,3H); N—CH$_3$: 2.74, 2.75, 2.91, 2.92 (4s,3H); three $\alpha$-protons and CH—F: 4.13–4.17, 4.19–4.24, 4.59–4.66, 4.81–4.90, 4.92–4.98, 5.06–5.14, 5.16–5.24 (4H). Analysis calculated for C$_{39}$H$_{46}$N$_7$O$_7$F.1.5-H$_2$O.1.5CH$_3$CO$_2$H: C, 58.60; H. 6.44; N, 11.39. Found: C, 58.60; H; 6.07; N, 11.42.

EXAMPLE 109

(2-Fluoro-3-(3-indolyl)propionyl)-Lys($\epsilon$-N-(2-methylphenyl)aminocarbonyl)-(NMe)Asp-PheNH$_2$ 2-Fluoro-3-(indol-3-yl)propionic acid 2,4,5-trichlorophenyl ester, the product of Example 63c, was coupled to Lys($\epsilon$-N-(2-methylphenyl)aminocarbonyl)-(NMe)Asp-PheNH$_2$, prepared as described in Example 60d, according to the procedure described in Example 64c, to give the title compound. MS (FAB+) m/e 744 (M+H)$^+$766 (M+Na)$^+$. $^1$H NMR (DMSO-d$_6$) at 80° C.: (mixture of a pair diastereomers and two conformers) Ar—CH$_3$: 2.12, 2.13 (2s,3H); N—CH$_3$: 2.49 (s,3H); Three $\alpha$-protons and CH—F: 4.38–4.53, 4.71–4.78, 4.93–5.19 (4H).

EXAMPLE 110

(3-($\beta$-Naphthyl)propionyl)-Lys($\epsilon$-N-(2-methylphenyl)aminocarbonyl)-Asp-PheNH$_2$ a. 3-($\beta$-Naphthyl)propionic acid 2,4,5-trichlorophenyl ester To a solution of 388 mg (2.43 mmol) $\beta$-naphthaldehyde (commercially available from Aldrich Chemical Company) in THF (10 mL) was added (carbethoxymethylene)triphenylphosphorane and then the reaction was left at ambient temperature for two days. The solvent was evaporated in vacuo and the residue chromatographed on silica gel eluted with ethyl acetate/hexanes (1:2) to afford a product which was then dissolved in a mixture of ethyl acetate/methanol and 10% Pd/C was added. The reaction mixture was vigorously stirred under 1 atmosphere of hydrogen for 2.5 hours after which time the catalyst was removed by filtration through Celite ® and the solvents evaporated. The residue was dissolved in a mixture of 1N sodium hydroxide/THF/methanol and left at ambient temperature for 1 hour. The reaction mixture was acidified with 1N hydrochloric acid and the product extracted with ethyl acetate. Evaporation of the solvents in vacuo gave 200 mg of a residue which was dissolved in a mixture of ethyl acetate, methylene chloride and THF. To the solution was added dicyclohexylcarbodiimide (DCC; 205 mg, 1 mmol) and 2,4,5-trichlorophenol (200 mg, 1 mmol) and the reaction mixture was stirred at ambient temperature for 2 hours. The solvents were evaporated in vacuo and the product purified by chromatography on silica gel eluting with ethyl acetate/hexanes (2:3) to afford 355 mg of the title compound as a colorless oil. $^1$H NMR (CDCl$_3$, 300 MHz) δ3.03 (t,2H, J=7.0 Hz), 3.25 (t,2H, J=7.0 Hz), 7.15 (s,1H), 7.35-7.51 (m,3H), 7.52 (s,1H), 7.70 (br s, 1H), 7.78-7.84 (m,3H).

b. (3-(β-Naphthyl)propionyl)-Lys(ε-N-(2-methylphenyl)aminocarbonyl)-Asp-PheNH$_2$ The ester of Step a and the tripeptide TFA.Lys(ε-N-(2-methylphenyl)aminocarbonyl)-Asp-PheNH$_2$ of Example 63d and NMM were allowed to react under the reaction conditions described in Example 1 g. The final peptide was isolated in a similar manner to give the title compound. MS (FAB+) m/e 723 (M+H)+. $^1$H NMR (DMSO-d$_6$) δ1.2 (m,2H), 1.35 (m,2H), 1.45 (m,1H), 1.55 (m,1H), 2.15 (s,3H), 2.5-2.68 (m,2H), 2.92-3.08 (m,4H), 4.18, 4.35, 4.48 (3H, α protons), 6.48 (bs, NH), 6.82 (t, 1H, J=7 Hz), 7.08 (m, 2H), 7.12-7.28 (m, 5H), 7.33 (d, 1H,J=7 Hz), 7.45 (m,2H), 7.5 (s,NH), 7.66 (s, 1H), 7.8 (m,4H), 7.95 (s, 1H), 8.04 (d,J=6 Hz,NH), 8.23 (d,J=6 Hz,NH). Analysis calculated for C$_{40}$H$_{46}$N$_6$O$_7$.H$_2$O: C, 64.85; H, 6.53; N, 11.34. Found: C, 64.10; H, 6.19; N, 11.31.

EXAMPLE 111

(3-(α-Naphthyl)propionyl)-Lys(ε-N-(2-methylphenyl)aminocarbonyl)-Asp-(NMe)PheNH$_2$ a. 3-(α-Naphthyl)propionic acid 2,4,5-trichlorophenyl ester Following the procedure described by Shiosaki, et al in European Application Number 405,506, published Jan. 2, 1991, (Example 11a) replacing quinoline-3-carboxaldehyde with α-naphthaldehyde (commercially available from Aldrich Chemical Company), the title compound was prepared.

b. (3-(α-Naphthyl)propionyl)-Lys(ε-N-(2-methylphenyl)amino-carbonyl)Asp(OBn)-(NMe)PheNH$_2$ Following the procedure described in Example 64c the activated ester of Example 111a and the tripeptide of Example 74d were coupled to give the title compound.

c. (3-(α-Naphthyl)propionyl)-Lys(ε-N-(2-methylphenyl)aminocarbonyl)Asp-(NMe)PheNH$_2$ Following the procedure of Example 74h, the product of Example 111b was debenzylated by hydrogenolysis, to give the title compound.

EXAMPLE 112

Ctp-Lys(ε-N-(2-methylphenyl)aminocarbonyl)-Asp-(NMe)PheNH$_2$ a-d; Alternative preparation of 4-Carboxy-6-oxo-3,4,5,6-tetrahydro-1H.5H-azocin[4,5,6-c]indole (CtpOH)

a. Ethyl α-(hydroxyimino)-β-(4-(carboethoxymethyl)indol-3-yl)-propanoate

To a solution of 4-(carboethoxymethyl)indole (830 mg, 4.12 mmol) and ethyl bromopyruvate 2-oxime (866 mg, 4.12 mmol) in methylene chloride (40 mL) was added anhydrous Na$_2$CO$_3$ (2.40 g, 22.66 mmol) at ambient temperature. After stirring at ambient temperature for 16 hours, the mixture was filtered and concentrated to dryness. The residue was chromatographed on silica gel eluted with 10% MeOH in CHCl$_3$/hexane (1:1→2:1) to give 0.98 g of the title compound. TLC Rf=0.61 (10%MeOH/CHCl$_3$). MS(DCI) m/e 333 (M+H)+. $^1$H NMR (CDCl$_3$, 300 MHz) δ1.25(t, J=7.4 Hz, 3H), 1.30(t, J=7.4 Hz,3H), 4.13(s,2H), 4.18(q, J=7.4 Hz,2H), 4.28(q, J=7.4 Hz,2H), 4.28(q, J=7.4 Hz,2H), 4.30(s,2H), 6.92(br s, 1H), 6.98(d, J=7.4 Hz, 1H), 7.12(t, J=7.4 Hz, 1H), 7.26(d,J=7.4 Hz, 1H), 8.03(br s, —OH), 8.17 (br s, —NH).

b. Ethyl α-(amino)-β-(4-(ethoxycarbonylmethyl)indol-3-yl)-propanoate

Aluminum strips (797 mg, 29.5 mmol) were amalgamated by immersing in a solution of mercuric chloride (216 mg, 0.80 mmol) in water (80 mL) for 15 seconds, then rinsed successively in ethanol and in diethyl ether, and added to a solution of the product of Example 112a (0.98 g, 2.95 mmol) in THF/water (10:1, 49.5 mL). After stirring for 3 hours, the mixture was dried with Na$_2$SO$_4$ and filtered through Celite ®. The filtrate was concentrated in vacuo to give 0.82 g of the title compound as a yellow oil. TLC Rf=0.45 (10% MeOH/CHCl$_3$). MS(DCI) m/e 319 (M+H)+. $^1$H NMR (CDCl$_3$, 300 MHz) δ1.26 (t,J=7.2 Hz,3H), 1.25 (t, J=7.2 Hz,3H), 3.00 (ddd, J=14.7,8.5,0.7 Hz, 1H), 3.25 (m, 1H), 3.50 (ddd,J=14.7, 4.8,0.7 Hz, 1H), 4.03 (d,J=15.5 Hz, 1H), 7.09 (br d,J=2.2 Hz,2H), 7.14 (t, J=8.1 Hz, 1H), 7.30 (dd,J=8.1,0.9 Hz, 1H), 8.12 (br m, indole —NH).

c. 4-Carboethoxy-6-oxo-3,4,5,6-tetrahydro-1H,5H-azocin[4,5,6-c]indole

A solution of the product of Example 112b (794 mg, 2.94 mmol) in o-xylene (50 mL) was heated at 145° C. for 3 days under nitrogen. The reaction mixture was filtered through a thin layer of silica gel (60 mm) and the filter cake was washed with 5% MeOH in CHCl$_3$. The filtrate was concentrated and the residue was taken up in MeOH/CHCl$_3$/toluene to precipitate the product. The first two crops provided 353 mg of the title compound as a yellow solid. TLC Rf=0.50 (10% MeOH/CHCl$_3$). m.p. 229°-230° C. MS(DCI) m/e 273 (M+H)+. $^1$H NMR (CDCl$_3$, 300 MHz) δ1.34 (t, =7.0 Hz,3H), 3.55-3.65 (m,2H), 3.76 (d,J=12.7 Hz,1H), 4.20 (d,J=12.7 Hz, 1H), 4.28 (q,J=7.0 Hz,2H), 4.47 (dd,J=9.9,7.7 Hz, 1H), 6.87 (d, 1H), 7.01 (t, 1H), 7.12 (s, 1H), 7.24 (d,J=7.6 Hz, 1H). Analysis calculated for C$_{15}$H$_{16}$N$_2$O$_3$.0.2H$_2$O: C, 65.30; H, 5.99; N, 10.15. Found: C, 65.35; H, 5.89; N, 10.09.

d. 4-Carboxy-6-oxo-3,4,5,6-tetrahydro-1H,5H-azocin[4,5,6-c]indole (CtpOH)

To a solution of the product of Example 112c (40 mg, 0.147 mmol) in methanol (1.5 mL) was added 2N NaOH 981 ml, 0.162 mmol) solution at ambient temperature. After stirring for 2 hours, the mixture was concentrated and the resulting residue was taken up in saturated NaHCO$_3$ solution and extracted with CHCl$_3$ (2×). The aqueous layer was acidified carefully with 4N HCl to pH 2 and then extracted with ethyl acetate (10×). The ethyl acetate extracts were dried over Na$_2$SO$_4$ and concentrated in vacuo to give 31 mg of the title compound as an off-white solid. TLC Rf=0.14 ((pyridine/water/CH$_3$CO$_2$H=20:11:6):ethyl acetate=1:3). m.p. 278°-280° C. (dec.). MS(DCI/NH$_3$) m/e 245 (M+H)+, 262 (M+NH$_4$)+. Analysis calculated for C$_{13}$H$_{12}$N$_2$O$_3$.0.10C$_4$H$_8$O$_2$: C, 63.60; H, 5.10; N, 11.07. Found: C, 64.00; H, 5.41; N, 10.77.

e. Ctp-Lys(ε-N-(2-methylphenyl)aminocarbonyl)-Asp(OBn)-(NMe)PheNH$_2$

The Ctp acid was converted to the N-hydroxysuccinimide ester as described in Example 3a and the activated ester was condensed with the tripeptide of Example 74d according to the procedure described in Example 62d to give the title compound. MS (FAB+) m/e 871 (M+H+), 893(M+Na+). $^1$HNMR (DMSO-d6)

(mixture of conformers ca. 1:1) δ Ar—CH$_3$: 2.15, 2.17 (2s, 3H); N—CH$_3$: 2.74, 2.91 (2s, 3H); α-Protons, OCO$_2$CH$_2$Ph: 4.06–4.34, 4.60–4.70, 4.83–5.13 (6H).

f. Ctp-Lys(ε-N-(2-methylphenyl)aminocarbonyl)-Asp-(NMe)PheNH$_2$

The product of Example 191a was debenzylated by hydrogenolysis as described in Example 1f to give the title compound, m.p. 155°–200° C., [α]$_D^{230}$= −97.43° (c 0.35, MeOH). MS (FAB+) m/e 781 (M+H)+, 813(M+Na)+. $^1$HNMR (DMSO-d6; T=30° C.): (mixture of conformers ca. 1:1) δ Ar—CH$_3$: 2.15, 2.17 (2s, 3H); N—CH$_3$: 2.63, 2.94 (2s, 3H); α-Protons & Ctp β-protons: 4.11–4.34, 4.63–4.71, 4.87–4.92, 4.95–5.03, 5.08–5.17 (6H). Analysis calculated for C$_{41}$H$_{48}$N$_8$O$_8$.2.5 H$_2$O.0.5CH$_3$CO$_2$H: C, 58.94; H. 6.47; N, 13.09. Found: C, 58.69; H; 5.97; N, 13.25.

EXAMPLE 113 t-BOC-Trp-Lys(ε-N-(3-trifluoromethylphenyl)aminocarbonyl)-Asp-PheNH$_2$

A solution of tetrapeptide of Example 1f (50 mg), 3-trifluoromethylphenyl isocyanate (commercially available from Aldrich Chemical Company) and NMM in DMF was stirred at ambient temperature for 18 hours. The product was isolated as described in Example 1 g to yield the title compound as a white solid.

EXAMPLE 114 t-BOC-Trp-Nle(6-((2-methylphenyl)aminocarbonyl)oxy)-Asp-(NMe)PheNH$_2$ a. N-benzyloxycarbonyl-2-aminoadipic acid A solution of L-2-aminoadipic acid (920 mg, 5.71 mmol), triethylamine (2.85 mL, 20.5 mmol) and water (3 mL) in 12 mL of dioxane was cooled to 0° C. and N-benzyloxycarbonyloxysuccinimide (Cbz-OSu: 1.71 g, 6.85 mmol) was added. The reaction mixture was stirred at 0° C. for 2 hours and at ambient temperature for 0.5 hours. The reaction mixture was washed with ethyl acetate and then acidified with aqueous potassium hydrogen sulfate. The acidic solution was extracted with ethyl acetate and the ethyl acetate solution was washed with brine, dried over anhydrous sodium sulfate, filtered and concentrated in vacuo to give 1.80 g of the title compound. MS (FAB+) m/e 296 (M+H)+.

b. 4-(N-Benzyloxycarbonyl-4-oxo-isoxazol-5-yl)butyric acid

To a solution of N-benzyloxycarbonyl-2-aminoadipic acid (1.72 g, 5.83 mmol), from Step a, in 50 mL of toluene was added paraformaldehyde (0.29 g) and p-touenesulfonic acid (0.06 g). The reaction mixture was heated at reflux for 3 hours and water was collected using a Dean-Stark trap. Ethyl acetate was added to the reaction mixture and it was washed with water and extracted with dilute aqueous sodium bicarbonate solution. The aqueous layer was quickly acidified and extracted with ethyl acetate. The combined ethyl acetate layers were dried over anhydrous sodium sulfate, filtered and concentrated in vacuo to give 848 mg (47% yield) of the title compound. MS (DCl/NH$_3$) m/e 308 (M+H)+, 325 (M+NH$_4$)+.

c. N-Benzyloxycarbonyl-5-(4-hydroxybutyl)-4-oxo-isoxazole

To a solution of 4-(N-benzyloxycarbonyl-4-oxo-isoxazol-5-yl)butyric acid (327 mg, 1.06 mmol), from Step b, in 10 mL of THF at 0° C. was added 1.1 mL (2.13 mmol) of a 2M solution of borane-methyl sulfide complex in THF. The reaction mixture was stirred at ambient temperature for 1.5 hours, diluted with ethyl acetate and extracted with water. The aqueous layer was acidified with potassium hydrogen sulfate and extracted with ethyl acetate. The ethyl acetate solution was washed with brine, dried over anhydrous sodium sulfate, filtered and concentrated in vacuo to give 324 mg of the title compound. MS (DCl/NH$_3$) m/e 294 (M+H)+, 311 (M+NH$_4$)+.

d. N-Benzyloxycarbonyl-5-(4-(2-methylphenyl)carbamoyloxybutyl)-4-oxo-isoxazole

To a solution of N-benzyloxycarbonyl-5-(4-hydroxybutyl)-4-oxo-isoxazole (170 mg, 0.58 mmol) in dry toluene was added 2-methylphenyl isocyanate (76 μL, 0.61 mmol). The reaction mixture was heated at approximately 80° C. under nitrogen for 0.5 hour. One drop of pyridine was added and heating was continued for an additional 1.5 hours. A second portion (25 μL) of 2-methylphenyl isocyanate was added and the reaction mixture was heated for another 2 hours. The reaction mixture was then allowed to cool to ambient temperature and diluted with ethyl acetate and extracted with water. The aqueous layer was acidified with potassium hydrogen sulfate and extracted with ethyl acetate. The ethyl acetate solution was washed with brine, dried over anhydrous sodium sulfate, filtered and concentrated in vacuo to give 240 mg of the title compound. MS (FAB+) m/e 427 (M+H)+.

e. 2-Benzyloxycarbonylamino-6-((2-methylphenyl)carbamoyloxyhexanoic acid

To a solution of N-benzyloxycarbonyl-5-(4-(2-methylphenyl)carbamoyloxybutyl)-4-oxo-isoxazole (220 mg, 0.52 mmol) in 10 mL of methanol was added 2.9 mL (0.52 mmol) of a saturated aqueous barium hydroxide solution and the reaction mixture was stirred at ambient temperature for 2.5 hours. The reaction mixture was then diluted with water and extracted with ethyl acetate. The aqueous layer was acidified with 3N hydrochloric acid and extracted with ethyl acetate. The second ethyl acetate extract dried over anhydrous sodium sufate, filtered and concentrated in vacuo. The first ethyl acetate extracted was washed with 3N hydrochloric acid, concentrated in vacuo, and combined with the product obtained from the second extraction. The combined product was washed with water and brine, dried over anhydrous sodium sulfate, filtered and concentrated in vacuo to a oily semisolid (224 mg). This material was dissolved in ethyl acetate and the ethyl acetate solution was extracted with five portions of sodium bicarbonate solution. The aqueous layer was acidified and extracted with ethyl acetate. The ethyl acetate solution was washed with water and brine, dried over anhydrous sodium sulfate, filtered and concentrated in vacuo to give 176 mg of the title compound. MS (FAB+) m/e 415 (M+H)+, 437 (M+Na)+.

f. 2-(S)-benzyloxycarbonylamino-6-(2-methylphenyl)aminocarbamoyloxyhexanoyl-Asp(OBn)-(NMe)-PheNH$_2$ A cooled solution (−15° C. to −20° C.) of 2-benzyloxycarbonylamino-6-((2-methylphenyl)aminocarbamoyloxyhexanoic acid (50 mg, 0.12 mmol), from Step e, isobutylchloroformate (16 mg, 0.116 mmol) and NMM (12 mg, 0.12 mmol) in 2 mL of methylene chloride was stirred for 5 minutes. The hydrochloride salt of Asp(OBn)-(NMe)PheNH$_2$ (67 mg, 0.16 mmol), the product of Example 16d, was added, followed by diisopropylethylamine (21 mg, 0.16 mmol) and the reaction mixture was stirred at from about −15° C. to about −20° C. for 1 hour. The reaction mixture was allowed to warm to ambient temperature and stirred overnight. The mixture was diluted with ethyl acetate and washed successively with aqueous potassium hydrogen sulfate, H2O, aqueous sodium bicarbonate, and brine, then dried and concentrated to afford 96 mg of the product. MS (DCl/isobutane) m/e 780 (M+H)+, 763.

g. 2-(S)-amino-6-(2-methylphenyl)aminocarbamoyloxyhexanoyl-Asp-(NMe)PheNH2

To a solution of 2-(S)-benzyloxycarbonylamino-6-(2-methylphenyl)aminocarbamoyloxyhexanoyl-Asp(OBn)-(NMe)PheNH2 (91 mg, 0.12 mmol), from Step f, in 4 mL of acetic acid, was added 40 mg of 10% palladium on carbon and the reaction mixture was stirred under an atmosphere of hydrogen for 8 hours. The reaction mixture was filtered and the solid was rinsed with methanol. The filtrate was concentrated under reduced pressure to remove the methanol and 4N hydrochloric acid/dioxane (100 μL) was added. Diethyl ether was added and the resultant precipitate was collected by filtration and dried in vacuo to give 56 mg (79% yield) of the title compound. The product was carried on to the final step without purification.

h. t-BOC-Trp-2-(S)-amino-6-(2-methylphenyl)aminocarbamoyloxyhexanoyl-Asp-(NMe)PheNH2

To a solution of 2-(S)-amino-6-(2-methylphenyl)aminocarbamoyloxyhexanoyl-Asp-(NMe)PheNH2 (51 mg, 0.086 mmol) in DMF (3 mL) at 0° C. was added DIEA (22 μL, 0.13 mmol) and t-BOC-Trp N-hydroxysuccinimide ester. The reaction mixture was allowed to warm to ambient temperature and was then stirred overnight. The reaction mixture was diluted with water and acidified with 1 mL of saturated aqueous potassium hydrogen sulfate. The white solid was filtered and purified by chromatography on silica gel eluting with ethyl acetate/S1 (10:1; S1 = 20:11:6 pyridine/H2O/HOAc) to give 49 mg of the title compound. MS (FAB+) m/e 842 (M+H)+. $^1$H NMR (DMSO-d6) (mixture of diastereomers ca. 2:1) δ methyl singlets: 2.17, 2.18, 2.72, 2.95. α-protons, —CH2O—: 3.99, 4.20, 4.30 (0.3H), 4.69 (0.3H), 4.88 (0.3H), 4.98 (0.6H), 5.16 (0.6H). Analysis calculated for $C_{44}H_{55}N_7O_{10} \cdot H_2O \cdot 0.5CH_3CO_2H$: C, 60.73; H, 6.68; N, 11.02. Found: C, 60.62; H, 6.29; N, 11.15.

EXAMPLE 115 t-BOC-Trp-Lys(ε-N-(2-methylphenyl)aminocarbonyl)-Asp-(S)-α-benzylprolinamide a. N-Trifluoroacetyl-L-Phe A suspension of L-phenylalanine (25 g, 152 mmol) in DMF (100 mL) containing triethylamine (23.3 mL, 182 mmol) and methyl trifluoroacetate (15.8 mL, 167 mmol) was stirred at 0° C., then at ambient temperature overnight. The homogeneous solution was acidified with saturated aqueous potassium hydrogen sulfate, then extracted with two portions of ethyl acetate. The combined organic phase was washed successively with water and brine, dried over anhydrous magnesium sulfate, filtered and concentrated in vacuo. The residue was crystallized from diethyl ether/hexane to give 32 g (99% yield) of the title compound as fine needles, m.p. 119°-120° C.; $[a]_D^{23} = 16°$ (c 2%, EtOH) $^1$H NMR (CDCl3) δ3.22 (dd,J=6 and 15 Hz,1H), 3.31 (dd,J=6 and 14 Hz,1H), 4.93 (m,1H), 6.72 (br d,J=7 Hz,1H), 7.13 (m,2H), 7.32 (m,3H). MS (DCl/NH3) m/e 262 (M+H)+, 279 (M+NH4)+.

b. N-Trifluoroacetyl-L-phenylalanine allyl ester

A mixture of N-trifluoroacetyl-L-Phe (7.6 g, 29.1 mmol), from Step a, p-toluenesulfonic acid monohydrate (0.55 g, 2.9 mmol), allyl alcohol (7.9 mL, 116 mmol) and toluene (100 mL) was heated at reflux for 4 hours with azeotropic removal of water using a Dean-Stark apparatus. The cooled reaction mixture was diluted with ethyl acetate, washed successively with saturated aqueous sodium bicarbonate and brine, dried over anhydrous magnesium sufate, filtered and concentrated in vacuo. The residue was crystallized from ethanol/water to give 6.7 g (76% yield) of the title compound as off-white needles, m.p. 44°-45° C.; $[a]_D^{23} = 68°$ (c 1.1, CHCl3) $^1$H NMR (CDCl3) δ3.21 (m,2H), 4.17 (m,J=16 Hz,2H), 4.90 (dd,J=6 and 16 Hz,1H), 5.36 (m,2H), 5.89 (m,1H), 6.73 (br d,1H), 7.09 (m,2H), 7.30 (m,3H). MS (DCl/NH3) m/e 319 (M+NH4)+. Analysis calculated for $C_{14}H_{14}NO_5F_3$: C, 55.82; H, 4.68; N, 4.65. Found: C, 55.65; H, 4.65; N, 4.64.

c. N-Trifluoroacetyl-α-allyl phenylalaninamide

To a solution of N-trifluoroacetyl-L-phenylalanine allyl ester (4.24 g, 14.1 mmol), from Step b, and triethylamine (10 mL, 72 mmol) in anhydrous acetonitrile (50 mL) at 0° C. under nitrogen, was added, dropwise over a 0.5 hour period, a solution of phosgene in toluene (32 mL, nominal concentration 12.5%, 32 mmol). The reaction mixture was stirred for an additional 2 hours at 0° C., then poured into ice water and extracted with ethyl acetate. The organic layer was washed successively with water and brine and then concentrated in vacuo. The residue was dissolved in 200 mL of THF. A 150 mL portion was treated with 10 mL of concentrated ammonium hydroxide, stirred at ambient temperature overnight and then concentrated in vacuo. The residue was subjected to standard workup and purified by chromatography on silica gel eluting with ethyl acetate/hexane (1:2 then 1:1) to give 2.8 g of product was crystallized from diethyl ether/hexane to give 2.21 g (70% yield) of the title compound, m.p. 124°-125° C.; $^1$H NMR (CDCl3) δ2.56 (dd,J=6 and 14 Hz,1H), 5.12 (m,1H), 5.20 (m,2H), 5.80 (br m,1H), 7.12 (m,2H), 7.28 (m,3H), 7.32 (br s,1H). MS (DCl/NH3) m/e 205 (M+H)+. Analysis calculated for $C_{12}H_{15}N_2O_2F_3$: C, 56.00; H, 5.04; N, 9.33. Found: C, 55.73; H, 5.02; N, 9.33.

d. α-Allylphenylalaninamide

To a solution of N-trifluoroacetyl-α-allyl phenylalaninamide (500 mg, 0.67 mmol), from Step c, in methanol (13 mL) was added saturated aqueous barium hydroxide (13 mL, 2.3 mmol) and the mixture was stirred at ambient temperature overnight. The methanol was evaporated, the residual phase was extracted with ethyl acetate (4×), then the ethyl acetate was evaporated to give the imidazolidinone intermediate ($^1$H NMR (CDCl3) δ1.90 (broad), 2.68 (t,J=7.5 Hz,2H), 3.08 (d,J=13 Hz,1H), 3.19 (d,J=13 Hz,1H), 5.09-5.24 (m,2H), 5.60 (m,1H), 7.12 (m,2H), 7.21 (m,2H), 7.28 (m,1H)). The imidazolinone was dissolved in methanol (10 mL) and 3N hydrochloric acid (10 mL) and this solution was allowed to stand at ambient temperature overnight and then concentrated. An equal volume of ethyl acetate was added to the residual aqueous solution and the pH was adjusted to approximately 10-11 by cautious addition of solid sodium carbonate. The layers were separated and the aqueous phase was extracted with ethyl acetate (3×). The combined organic phase was dried over anhydrous sodium sulfate, filtered and concentrated to give 340 mg (100% yield) of the title compound as a white solid, m.p. 120°-121° C.; $^1$H NMR (CDCl3/D2O) δ2.19 (dd,J=9 and 13 Hz,1H), 2.65

(d,J=14 Hz,1H), 2.80 (dd,J=7 and 13 Hz,1H), 3.36 (d,J=14 Hz,1H), 5.10-5.21 (m,2H), 5.81 (m,1H), 7.12 (m,2H), 7.20 (m,2H), 7.30 (m,3H). MS (DCl/NH$_3$) m/e 301 (M+H)$^+$, 318 (M+NH$_4$)$^+$. Analysis calculated for C$_{12}$H$_{16}$N$_2$O.0.4H$_2$O: C, 68.15; H, 8.01; N, 13.25. Found: C, 67.84; H, 7.63; N, 13.01.

e. t-BOC-Asp(OBn)-α-allylphenylalaninamide

A mixed carbonic anhydride procedure analogous to that described in Example 49d was used to convert α-allylphenylalaninamide (270 mg, 1.32 mmol), from Step d, to the title compound. The crude product was crystallized from diethyl ether/hexane to give 460 mg (67% yield) of a 1:1 mixture of diastereomers, m.p. 102°-108° C.; $^1$H NMR (CDCl$_3$/D$_2$O) δ1.37 (s) and 1.39 (s) (total of 9H), 2.45 (m,1H), 2.59 (m,1H), 2.73-2.90 (m,1H), 2.90-3.10 (m,1H), 3.13 (d,J=14 Hz,0.5H), 3.22 (d,J=14 Hz,0.5H), 3.45 (d,J=14 Hz,0.5H), 3.58 (d,J=14 Hz,0.5H), 4.38 (m,1H), 5.05-5.20 (m,4H), 5.39 (br m,1H), 5.72 (m,1H), 6.52 (br m,1H), 6.70 (br s) and 6.80 (br s) (total 1H), 7.15 (m,2H), 7.22-7.40 (m,8H). MS (FAB+) m/e 510 (M+H)$^+$. Analysis calculated for C$_{28}$H$_{35}$N$_3$O$_6$: C, 65.99; H, 6.92; N, 8.25. Found: C, 65.65; H, 6.94; N, 8.15.

f. t-BOC-Asp(OBn)-α-(3-hydroxy-n-propyl)-phenylalaninamide

To a solution of borane in THF (1.44 mL of a 1M solution, 1.44 mmol) at 0° C. under nitrogen, was added cyclohexene (0.29 mL, 2.88 mmol) by syringe, and the mixture was stirred for 0.5 hour, during which time a white precipitate formed. A prechilled (0° C.) solution of t-BOC-Asp(OBn)-α-allylphenylalaninamide (480 mg, 0.92 mmol), from Step e, in anhydrous THF (4 mL) was added and stirring was continued for 2 hours at 0° C., then at ambient temperature overnight. The solution was diluted with pH 7 buffer and ethanol and treated with excess 30% aqueous H$_2$O$_2$ and stirred overnight. The reaction mixture was then partitioned between ethyl acetate and brine and the aqueous phase was extracted with two portions of ethyl acetate. The ethyl acetate solutions were combined, dried over anhydrous sodium sufate, filtered and concentrated. The residue (514 mg) was chromatographed on silica gel eluting with hexane/acetone (1:1) to give 266 mg (54% yield) of the title compound (1:1 diastereomeric mixture) as a colorless solid, m.p. 75°-79° C.; $^1$H NMR (CDCl$_3$) δ1.37 (s) and 1.40 (s) (total of 9H), 1.50-1.71 (m,2H), 1.92-2.12 (m) and 2.13-2.27 (m) (total 2H), 2.21-2.38 (overlapping dd's,J=6 and 18 Hz and J=5 and 16 Hz,total 2H), 3.10 (dd,J=4.5 and 17 Hz,2H), 3.25-3.48 (m,2H), 3.61 (m,2H), 4.60 (m,1H), 5.10 (s) and 5.12 (s) (total 2H), 5.32 (br m,1H), 5.45 (br t,J=9 Hz,1H), 6.42 (br m,1H), 7.12 (m,2H), 7.16-7.40 (m,8H). MS (DCl/NH$_3$) m/e 528 (M+H)$^+$, 545 (M+NH$_4$)$^+$. Analysis calculated for C$_{28}$H$_{37}$N$_3$O$_7$.0.1H$_2$O: C, 63.52; H, 7.08; N, 7.94. Found: C, 63.21; H, 7.03; N, 7.68.

g. t-BOC-Asp(OBn)-(R,S)-α-benzylprolinamide

A solution of t-BOC-Asp(OBn)-α-(3-hydroxy-n-propyl)phenylalaninamide (171 mg, 0.32 mmol), from Step f, and triphenylphosphine (2 equivalents) in anhydrous THF, under nitrogen, was treated with diisopropyl azodicarboxylate (DIAD: 134 mg, 0.66 mmol) and the reaction mixture was stirred at ambient temperature for 24 hours. The solution was concentrated and standard work-up conditions were employed to give the crude product. The product was purified by radial thin layer chromatography on silica gel (2 mm thickness) eluting with hexane/acetone (3:1 to 1:1) to give 36 mg (21% yield) of the more mobile isomer (Isomer 1), 73 mg (43% of a mixture of the diastereomers) and 35 mg (21% yield) of the less mobile isomer (Isomer 2).

Isomer 1: Rf 0.44 (1:1 hexane/acetone). $^1$H NMR (300 MHz, CDCl$_3$/MeOH) δ1.21 (m,1H), 1.43 (s,9H), 1.73 (m,1H), 2.20 (m,2H), 2.68 (dd,J=7.5 and 16.5 Hz,1H), 2.80 (dd,J=6 and 16.5 Hz,1H), 3.16 (m,1H), 3.24 (d,J=13.5 Hz,1H), 3.78 (d,J=13.5 Hz,1H), 3.86 (m,1H), 4.63 (m,1H), 5.16 (s,2H), 7.11 (m,2H), 7.20-7.35 (m,4H), 7.36 (m,4H). HRMS calculated for C$_{28}$H$_{36}$N$_3$O$_6$: 510.2604; found: 510.2604. [a]$_D^{23o}$=−87.7° (c 2, CHCl$_3$).

Isomer 2: Rf 0.40 (1:1 hexane/acetone). $^1$H NMR (300 MHz, CDCl$_3$/MeOH) δ1.13 (m,1H), 1.49 (s,9H), 1.68 (m,1H), 2.20 (m,2H), 2.72 (dd,J=4 and 17 Hz,1H), 3.13 (dd,J=10.5 and 17 Hz,1H), 3.21 (d,J=14 Hz,1H), 3.30 (m,1H), 4.88 (m,1H), 5.12 (m,2H), 7.13 (m,2H), 7.20-7.33 (m,4H), 7.36 (m,4H). HRMS calculated for C$_{28}$H$_{36}$N$_3$O$_6$: 510.2604; found: 510.2599. [a]$_D^{23o}$=44.0° (c 2, CHCl$_3$)

h. t-BOC-Trp-Lys(ε-N-(2-methylphenyl)aminocarbonyl)-Asp(OBn)-(R,S)-α-benzyl-prolinamide The product of Step g was deprotected as in Example 59b, then coupled to t-BOC-Trp-Lys(ε-N-(2-methylphenyl)aminocarbonyl)-OH as described in Example 52b to give 81 mg of the title compound.

i. t-BOC-Trp-Lys(ε-N-(2-methylphenyl)aminocarbonyl)-Asp-(S)-α-benzyl-prolinamide t-BOC-Trp-Lys(ε-N-(2-methylphenyl)aminocarbonyl)-Asp(OBn)-(R,S)-α-benzyl-prolinamide (80 mg, 0.083 mmol), from Step h, was debenzylated according to the procedure described in Example 1f. The product was purified by chromatography on silica gel eluting with 3% acetic acid in ethyl acetate to give 40 mg of the title compound. MS (FAB+) m/e 867 (M+H)$^+$, 889 (M+Na)$^+$. $^1$H NMR (DMSO-d$_6$) δ methyl singlet: 2.10. PhCH$_2$: 3.0 (d,J=14.5 Hz), 3.5 (d,J=14.5 Hz). α-protons: 4.13, 4.19, 4.54. Analysis calculated for C$_{46}$H$_{58}$N$_8$O$_9$.H$_2$O.1.8 CH$_3$CO$_2$H: C, 59.99; H, 6.82; N, 11.28. Found: C, 59.65; H, 6.43; N, 11.68.

EXAMPLE 116 t-BOC-Trp-Lys(ε-N-(2-methylphenyl)aminocarbonyl)-Asp-ChaNH$_2$ a. t-BOC-ChaNH$_2$ To a solution of t-BOC-cyclohexylalanine (2.48 g, 9.2 mmol) in THF (20 mL) cooled to −20° C. and NMM (0.105 ml, 9.5 mmol) was added isobutyl chloroformate (1.6 mL, 12 mmol) and stirred for 10 minutes. Four equivalents of 30% ammonium hydroxide (5.3 mL, 37 mmol)) was added and the reaction was stirred overnight with warming to ambient temperature. The solvent was removed in vacuo and the residue partitioned between a solution of 1M phosphoric acid and ethyl acetate. The organic phase was further washed with aqueous NaHCO$_3$ (2×) and water. After drying (MgSO$_4$) the solvent was removed in vacuo and the solid residue dissolved in ethyl acetate and precipitated with the addition of hexane to afford pure title compound (2.1 g, 84% yield). MS (Cl/NH$_3$) m/e 271 (M+H)$^+$, 288 (M+NH$_4$)$^+$ $^1$NMR (CDCl$_3$): δ0.92 (m,4H), 1.1-1.22 (m,2H), 1.44 (s,9H), 1.6-1.75 (m,7H), 4.18 (m, 1H), 4.80 (br s, 1H), 4.91 (d,J=8 Hz, 1H), 5.59 (br s, 1H), 6.21 (br s, 1H).

b. Cyclohexylalanine amide hydrochloride

A solution of t-BOC-Cha-NH$_2$ (2 g.7.4 mmol) in 10 ml 1.5M hydrogen chloride in acetic acid was stirred at ambient temperature 1.5 hour. The reaction was quenched with the addition of diethyl ether which precipitated the product. The solid was collected, washed with fresh ether and dried (MgSO$_4$) and to yield 1.31 g (85% yield) of the title compound as a white powder. MS (Cl/NH$_3$) m/e 171 (M+H)$^+$, 188 (M+NH$_4$)$^+$. $^1$H NMR (DMSO-d6): δ0.8–0.95 (m,2H), 1.08–1.28 (m,3H), 1.38 (m,1H), 1.52–1.82 (m,7H), 3.7 (t,1H,), 7.5 (s,NH), 8.24 (bs,2H).

c. t-BOC-Trp-Lys(ε-N-(2-methylphenyl)aminocarbonyl)-Asp(OBn)-OH

A solution of Boc-Trp-Lys(ε-N-(2-methylphenyl)aminocarbonyl)-OH, the product of Example 49c (21.5 g, 38 mmol) and N-hydroxysuccinimide (4.6 g, 39.9 mmol) in DMF (100 mL) at 0° C. was treated with dicyclohexylcarbodiimide (8.23 g, 39.9 mmol) The reaction was stirred for 1 h at 0° C. and 1 h at ambient temperature. The solution was filtered and the filtrate was added to a suspension of H.Asp(OBn)-OH (11.0 g, 49.4 mmol) and triethylamine (10.6 mL, 76 mmol) in DMF (40 mL). The reaction was stirred for 1 h, then filtered and concentrated. The residue in ethyl acetate was subjected to acid-base work-up, then the product was crystallized from ethyl acetate/heptane to afford 32.5 g. Further purification was effected by chromatography over silica gel, eluting with MeOH/methylene chloride systems, to afford, after crystallization from ethyl acetate/hexane, 24.2 g (83%) of the title compound. MS (FAB+) m/e 809 (M+K)$^+$, 709 (M-Boc+K)$^+$.

d. t-BOC-Trp-Lys(ε-N-(2-methylphenyl)aminocarbonyl)-Asp(OBn)-ChaNH$_2$

The tripeptide of Step b was coupled to HCl.ChaNH$_2$ from Step b according to the procedure described in Example 1a to give the title compound.

e. t-BOC-Trp-Lys(ε-N-(2-methylphenyl)aminocarbonyl)-Asp-ChaNH$_2$

The tetrapeptide of Step d was debenzylated by hydrogenolysis according to the procedure described in Example 176d to give the title compound. MS (FAB+) m/e 833 (M+H)$^+$, 855 (M+Na)$^+$. $^1$H NMR (DMSO-d$_6$) δ2.18 (s,3H, methyl), 4.12–4.28, 4.45 (m,4H, α protons), 6.75 (d, J=9 Hz, NH), 6.9 (bs,1H, NH), 7.42 (bs,1H, NH), 7.84 (bd,J=9 Hz,NH) 8.03 (bd, J=9 Hz, NH), 8.11 (bd, J=9 Hz, NH), 10.82 (s, indole-NH).

EXAMPLE 117 t-BOC-Trp-Lys-(ε-N-3-(3-pyridyl)acrylyl))-(NMe)Asp-(OMe)-(NMe)Phe-NH$_2$ t-BOC-Trp-Lys-(ε-N-3-(3-pyridyl)acrylyl))-(NMe)Asp-(NMe)Phe-NH$_2$ (62 mg, 0.07 mmol) in DMF, prepared as described in Example 68, was treated with excess diazomethane in ether. Reaction was immediate and the excess diazomethane was quenched with acetic acid. After evaporation of the ether and addition of water, the mixture was lyopholized. Purification by preparative reverse phase HPLC, eluting with 0.1% aqueous trifluoroacetic acid, afforded 22 mg (0.016 mmol) of product. MS (FAB+) m/e 905 (M+K)$^+$, 889 (M+Na)$^+$, 867 (M+H)$^+$. $^1$H NMR (DMSO-d$_6$) δ Boc singlet: 1.27; methyl singlets: 1.97, 2.71, 3.43; α protons: 4.18 (m), 4.42 (m), 5.32 (dd, J=5, 15 Hz), 5.57 (m). Analysis calculated for C$_{48}$H$_{62}$N$_8$O$_{11}$.1.1H$_2$O.3.7CF$_3$CO$_2$H.1.2CH$_3$CN: C, 49.35; H, 5.01; N, 9.49. Found: C, 49.38; H, 5.02; N, 9.49.

EXAMPLE 118

(Nme)Trp-Lys(ε-N-(2-methylphenyl)aminocarbonyl)-(NMe)Asp(OMe)-(NMe)Phe-NH$_2$ a. t-BOC-(NMe)Trp-Lys(ε-N-benzyloxycarbonyl)-(NMe)Asp(Bzl)-(NMe)Phe-NH$_2$ A two-fold excess of the symmetrical anhydride, obtained from t-BOC-(NMe)Trp-OH (prepared in a manner similar to that described in Example 66b), was coupled to Lys(ε-benzyloxycarbonyl)-(NMe)Asp-(OBn)-(NMe)PheNH$_2$ (TFA salt, 0.159 mmol, prepared as described in Example 60d). After extractive work-up, the crude mixture was allowed to stand in methanol, then the solution was concentrated and the residue dissolved in ethyl acetate and washed with aqueous acid to remove (NMe)Trp-OMe side-product. The organic phase was dried and concentrated to afford crude product which was combined with similar material from a trial reaction (0.03 mmol scale) and from a trial using the EDCl/HOBt method (0.33 mmol scale). This combined product (145 mg, 0.151 mmol) was then carried on without further purification.

b. (NMe)Trp-Lys(ε-N-(2-methylphenyl)aminocarbonyl)-(NMe)Asp(OMe)-(NMe)Phe-NH$_2$ The product of Step a was subjected to hydrogenolysis in DMF as described in Example 65 to afford crude t-BOC-(NMe)Trp-Lys-(NMe)Asp-(NMe)PheNH$_2$ (112 mg, 0.14 mmol) which was treated with 2-methylphenyl isocyanate (0.016 mL, 0.128 mmol) in DMF in the presence of N-methylmorpholine. The crude product was treated with aqueous acetic acid, lyophilized and then chromatographed (silica gel, 90:5:5 ethyl acetate/MeOH/S1, S1=20:11:6 pyridine/H$_2$O/HOAc) to afford t-BOC-(NMe)Trp-Lys(ε-N-(2-methylphenylaminocarbonyl))-(NMe)Asp-(NMe)Phe-NH$_2$ (70 mg, 0.08 mmol). This intermediate (50 mg, 0.06 mmol) was treated with 2 mL of 2M hydrogen chloride in methanol to effect simultaneous BOC removal and esterification. Purification by preparative reverse phase HPLC in a manner similar to that described in Example 2 and combination with material from a subsequent similar run (0.02 mmol) afforded 13 mg (0.014 mmol) of product. MS(FAB+) m/e 783 (M+H)$^+$. $^1$H NMR (DMSO-d$_6$) (two conformers ca. 9:1) δ methyl singlets (major): 2.07, 2.13, 2.63, 3.41; α protons (major): 4.37 (m), 5.26 (dd,J=5, 13 Hz), 5.47 (m); α protons (minor): 4.49 (m), 4.66 (m), 4.81 (m). Analysis calculated for C$_{42}$H$_{55}$ClN$_8$O$_7$.1.5CH$_3$CO$_2$H: C, 59.43; H, 6.76; N, 12.32. Found: C, 59.31; H, 6.37; N, 12.45.

EXAMPLE 119

Isobutyloxycarbonyl-Trp-Lys(ε-N-(2-methylphenyl)aminocarbonyl)-Asp(OBn)-(NMe)PheNH$_2$ a. Isobutyloxycarbonyl-Trp-OH To a cold (0° C.) solution of tryptophan (408 mg, 2 mmol) in 0.2N sodium hydroxide (10 mL) was added saturated aqueous sodium bicarbonate (10 mL). Isobutyl chloroformate (0.3 mL) was then added dropwise and the reaction mixture was stirred for 30 minutes at 0° C. and 2 hours at ambient temperature. The reaction mixture was cooled to 0° C. and the pH was adjusted to about 1 with 6N aqueous hydrochloric acid. The reaction mixture was then extracted with methylene chloride. The methylene chloride solution was dried over anhydrous sodium sulfate, filtered and concentrated under reduced pressure. The residue was triturated with hexane to give 510 mg of the title compound as a white solid. ¹H NMR (300 MHz, CDCl₃) δ0.9 (d, J=7 Hz, 6H), 1.87 (hep, J=7 Hz, 1H), 3.35 (m, 2H), 3.85 (m, 2H), 4.72 (m, 1H), 5.22 (m, 1H), 7.02–7.22 (aromatic, 3H), 7.35 (d, J=7.5 Hz, 1H), 7.61 (d, J=7.5 Hz, 1H), 8.12 (br s, 1H).

b. Isobutyloxycarbonyl-Trp-Lys(ε-N-(2-methylphenyl)aminocarbonyl)-Asp(OBn)-(NMe)PheNH₂

The tripeptide product of Example 74d, Lys(ε-N-(2-methylphenyl)aminocarbonyl)-Asp(OBn)-(NMe)-PheNH₂, was coupled to the isobutyloxycarbonyl-Trp-OH from Step a, using the procedure of Example 1a to give the protected tetrapeptide which was deprotected by hydrogenolysis as described in Example 65 to give the title compound. MS (FAB+) m/e 931 (M+H)+. ¹H NMR (CDCl₃/D₂O) (two conformers ca. 1:1) δ(CH₃)₂C—: 0.86, 0.87, 0.89 (6H); (CH₃)₂CH—CH₂—O—: 1.82–1.91 (m,1H); Ar—CH₃: 2.18, 2.23 (2s,3H); N—CH₃: 2.89, 3.04 (4s,3H); O—CH2-Ph & (CH₃)₂CH—CH₂—O—: 4.97–5.16 (4H) α-Protons: 4.17–4.27, 4.47–4.60, 4.88–4.95, 5.31–5.40 (4H). Analysis calculated for C₅₁H₆₂N₈O₉.2H₂O: C, 63.34; H. 6.88; N, 11.59. Found: C, 63.24; H; 6.53; N, 11.27.

EXAMPLE 120 t-BOC-Trp-Lys(ε-N-(2-methylphenyl)aminocarbonyl)-Asp(β-2-(1-morpholino)ethyl)-(NMe)PheNH₂ a. t-BOC-Asp(β-2-(1-morpholino)ethyl)-(NMe)PheNH₂ t-BOC-Asp-(NMe)PheNH₂ (566 mg, 1.44 mmol), EDCl (412 mg, 2.16 mmol) and 4-(2-hydroxyethyl)morpholine (262 mL, 2.16 mmol) were combined in methylene chloride (10 mL). The reaction mixture was stirred at ambient temperature for 4 days and then diluted with methylene chloride, washed with saturated aqueous sodium bicarbonate (3×) and brine (2×), dried over anhydrous sodium sulfate, filtered and concentrated to give 606 mg of crude product. The product was purified by chromatography on silica gel eluting with ethanol in toluene to give 321 mg (44% yield) of the title compound. MS (Cl/NH₃) m/e 507 (M+H)+. ¹H NMR(CDCl₃) δ1.39, 1.41 (2s,9H), 2.43–2.67 (m,6H), 2.83–3.05 (m,2H), 2.96, 3.04 (2s,3H), 3.66–3.76 (m,4H), 4.18 (m,2H), 4.77–4.97 (m,2H), 5.32–5.41, 5.48–5.56 (m,2H), 7.13–7.32 (m,5H).

b. t-BOC-Trp-Lys(ε-N-(2-methylphenyl)aminocarbonyl)-Asp(β-2-(1-morpholino)ethyl)-(NMe)PheNH₂

Boc-Asp(β-2-(1-morpholino)ethyl)-(NMe)PheNH₂ from Step a was dissolved in acetic acid and treated with an acetic acid solution of anhydrous hydrogen chloride to remove the t-BOC group, affording Asp(β-2-(1-morpholino)ethyl)-(NMe)PheNH₂. A solution of t-BOC-Trp-Lys(ε-N-(2-methylphenyl)aminocarbonyl)-OH (71 mg, 0.13 mmol), the product of Example 49c, (mg, mmol) in 1:1 DMF/methylene chloride (4 mL) was cooled in a dry ice/CCl₄ bath and Asp(β-2-(1-morpholino)ethyl)-(NMe)PheNH₂ (52.6 mg, 0.119 mmol) was added, followed by HOBT (20 mg, 1.1 equivalents), EDCl (2.6 mg, 0.137 mmol) and NMM (13 μL, 1.05 equivalents). The reaction was stirred in dry ice bath for 0.5 hour and then allowed to warm to ambient temperature. The reaction was quenched with cold saturated aqueous sodium bicarbonate and extracted with ethyl acetate. The ethyl acetate solution was dried over anhydrous sodium sulfate, filtered and concentrated in vacuo. The residue was chromatographed on silica gel pretreated with NMM eluting with a gradient of methanol in methylene chloride to give 83.5 mg (74% yield) of the title compound. MS (FAB+) m/e 954 (M+H)+. ¹H NMR (DMSO-d6): mixture of conformers δ Boc: 1.29 (s,9H) AR—CH₃: 2.15, 2.16 (2s,3H); N—CH₃: 2.74, 2.91 (2s,9H); Analysis calculated for C₅₀H₆₇N₉O₁₀.1.0-H₂O: C, 61.77; H. 7.15; N, 12.97. Found: C, 61.77; H; 6.28; N, 12.99.

EXAMPLE 121 t-BOC-Trp-Lys(ε-N-(2-methylphenyl)aminocarbonyl)-Asp(β-(OCH₂—CO—N(CH₃)₂))-(NMe)PheNH₂ a. t-BOC-Asp(β-(OCH₂—CO—N(CH₃)₂)) benzyl ester

A solution of t-BOC-Asp benzyl ester (1.4 g, 4.33 mmol), N,N-dimethyl-2-hydroxyacetamide (0.50 g, 4.33 mmol) and 50 mg of DMAP in ethyl acetate (50 mL) was cooled to 0° C. and DCC (0.89 g, 4.33 mmol) was added. The reaction mixture was allowed to warm to ambient temperature and stir overnight. The reaction mixture was then filtered and the filtrate was concentrated in vacuo. The residue was chromatographed on silica gel eluting with ethyl acetate in hexane (50%, 70% and 100%) to give 1.38 g (78% yield) of the title compound. MS (FAB+) m/e 409 (M+H)+. ¹H NMR(DMSO-d6) δ1.37 (s,9H), 2.82 & 2.90 (2s,6H), 2.80–2.87 (2H, Asp-β-H), 4.42–4.49 (m,1H), 4.75 (q,2H), 5.13(s,2H), 7.37 (m,5H).

b. t-BOC-Asp(β-(OCH₂—CO—N(CH₃)₂))

To a solution of t-BOC-Asp(β-(OCH₂—CO—N(CH₃)₂)) benzyl ester (1.38 g, 3.38 mmol), from Step a, in 50 mL of methanol at ambient temperature, was added 23 mg of 10% palladium on carbon. The reaction mixture was degassed and then stirred under a hydrogen atmosphere for approximately 1 hour. The catalyst was removed by filtration and the filtrate was concentrated to give the title compound. ¹H NMR(DMSO-d6) δ1.35, 1.36 (2s,9H), 2.73, 2.81, 2.84, 2.90, 2.92 (9H, N—CH₃), 4.40–4.51, 4.52–4.86, 5.00–5.09 (4H, 2-α-H & O—CH₂—CO).

c. [t-BOC-Asp(β-(OCH₂—CO—N(CH₃)₂))]₂ anhydride

A solution of DCC (100 mg, 0.465 mmol) in minimum amount of ethyl acetate was added to a solution of the product from Step b (0.3 g, 0.93 mmol), in 15 mL of ethyl acetate at approximately 0° C.–5° C. The reaction mixture was stirred at approximately 0° C.–5° C. for 1 hour and then it was filtered. The solid was washed with ice-cold ethyl acetate and carried on to the next step.

d. t-BOC-Asp(β-(OCH₂—CO—N(CH₃)₂))-(NMe)PheNH₂

A solution of the hydrochloride salt of (NMe)PheNH₂ (100 mg, 0.465 mmol) in 4 mL of DMF was added to the ice-cold filtrate (the symmetrical anhydride) from Step c. The clear solution was allowed to warm to ambient temperature and stirred for 4 hours. A catalytic amount of DMAP was added and stirring was continued for 20 hours. The reaction mixture was then partitioned between ethyl acetate (100 mL) and water. The organic layer was washed with 10% aqueous hydrochloric acid and brine. The aqueous layer was extracted with ethyl acetate. The combined organic layers were dried over anhydrous magnesium sulfate, filtered and concentrated in vacuo. The residue was purified by flash chromatography on silica gel eluting with ethyl acetate and ethyl acetate/acetone (1:1) to give 128 mg (58% yield) of the title compound. MS (FAB+) m/e:

479 (M+H)+, 501 (M+Na)+. ¹H NMR(DMSO-d6) δ1.46, 1.47 (2s,9H), 2.15, 2.16, 2.18 (3s,3H), 2.73, 2.81, 2.84, 2.89, 2.90 [9H,—CO—(N—CH3)2 & N—CH3], 4.65–4.88, 5.00–5.12, (5H, 3-α-H & O—CH2—CO).

e. HCl-Asp(β-(OCH2—CO—N(CH3)2))-(NMe)-PheNH2

The dipeptide from Step d was deprotected as described in Example 1d with hydrochloric acid/acetic acid to give the title compound.

f. t-BOC-Lys(ε-N-(2-methylphenyl)aminocarbonyl)-Asp(β-(OCH2—CO—N(CH3)2))-(NMe)PheNH2

The dipeptide of Step e (0.33 mmol) was then coupled with t-BOC-Lys(ε-N-(2-methylphenyl)aminocarbonyl)-OH (0.12 g, 0.33 mmol), the product of Example 74, by the mixed anhydride procedure of Example 52b to give the title compound. The mass spectral data and the ¹H NMR spectrum were consistent with the desired product and the tripeptide was carried on to the next step without purification.

g. HCl-Lys(ε-N-(2-methylphenyl)aminocarbonyl)-Asp(β-(OCH2—CO—N(CH3)2))-(NMe)PheNH2

The title compound was prepared as described in Example 1d and carried on to the final product without purification.

h. t-BOC-Trp-Lys(ε-N-(2-methylphenyl)aminocarbonyl)-Asp(β-(OCH2—CO—N(CH3)2))-(NMe)-PheNH2

To a solution of HCl.Lys(ε-N-(2-methylphenyl)aminocarbonyl)-Asp(β-(OCH2—CO—N(CH3)2))-(NMe)PheNH2 (0.33 mmol) and t-BOC-Trp hydroxysuccinimide (0.13 g, 0.33 mmol), commercially available from Sigma Chemical Company, in 3 mL of DMF at ambient temperature under nitrogen, was added DIEA (63 μL, 0.36 mmol). The reaction mixture was stirred for 5 hours and then poured into a solution of 150 mL of water and 30 mL of 10% hydrochloric acid solution. The precipitate was collected by filtration, washed with water and dried in vacuo at ambient temperature to give 0.261 g (85% yield) of the title compound as a white solid. A 130 mg sample was purified by preparative HPLC on a Dynamax C-18 column eluting with a gradient from 0% to 70% acetonitrile/water over 5 minutes). MS (FAB+) m/e 926 (M+H)+, 948 (M+Na)+. ¹H NMR (DMSO-d6): mixture of conformers δ Boc: 1.29 (s,9H) Ar—CH3: 2.15, 2.17 (2s,3H); N—CH3: 2.74, 2.79, 2.83, 2.86, 2.88, 2.90 (6s,9H); α-Protons and —O—CH2—CO—N—: 4.15–4.30, 4.67–4.84, 5.02–5.13 (6H). Analysis calculated for C48H63N9O10.1.5H2O: C, 61.05; H. 6.95; N, 13.35. Found: C, 60.97; H; 6.76; N, 13.46.

EXAMPLE 122

(N-((morpholinocarbonylmethyl)oxycarbonyl)-Trp-Lys(ε-N-(2-methylphenyl)aminocarbonyl)-Asp(OMe)-(NMe)PheNH2 a. (N-((morpholinocarbonylmethyl)oxy))-(4-nitrophenyl)carbonate

To a solution of 4-nitrophenyl chloroformate (0.54 g, 2.66 mmol) in 50 mL of ethyl acetate at ambient temperature was added, dropwise over a 20 minute period, a solution of 2-hydroxyacetic acid morpholino amide (0.386 g, 2.66 mmol) and pyridine (0.22 mL, 2.66 mmol) in 15 mL of ethyl acetate. The reaction mixture was stirred overnight at ambient temperature and then filtered. The filter cake was rinsed with ethyl acetate to afford the title compound. ¹H NMR (CDCl3): 3.33–3.46, 3.60–3.71 (m, 8H), 4.89 (s, 2H), 7.42–7.49 (2H0, 8.24–8.33(2H).

b. (N-((morpholinocarbonylmethyl)oxycarbonyl)-Trp-Lys(ε-N-(2-methylphenyl)aminocarbonyl)-Asp(OMe)-(NMe)PheNH2 t-BOC-Trp-Lys(ε-N-(2-methylphenyl)aminocarbonyl)-Asp(OMe)PheNH2, the tetrapeptide of Example 55, was treated with hydrochloric acid/acetic acid as described in Example 1d affording the hydrochloride salt. To a solution of the hydrochloride salt of the tetrapeptide (152 mg, 0.192 mmol) (N-((morpholinocarbonylmethyl)oxy))-(4-nitrophenyl)carbonate (59.6 mg, 0.192 mmol) in 3 mL of DMF at ambient temperature under nitrogen, was added DIEA (37 μL, 0.211 mmol) and a catalytic amount of DMAP. The reaction mixture was stirred overnight and then added dropwise to 200 mL of water containing 30 mL of 5% sodium bicarbonate solution. The precipitate was filtered and washed with water. The solid (114.5 mg) was purified by preparative-scale HPLC on reverse phase column eluting with acetonitrile in water to give after lyophilization 65.1 mg (37% yield) of the title compound. MS (FAB+) m/e 9.26 (M+H)+. ¹H NMR (DMSO-d6) (mixture of conformers ca. 1:1) δ Ar—CH3: 2.15, 2.17 (2s,3H); N—CH3: 2.74, 2.80 (2s,3H); CO2CH3: 3.55, 3.57 (2s,3H); α-Protons: 4.09–4.32, 4.46–4.63, 4.78–4.92, 4.96–5.10 (4H). Analysis calculated for C47H59N9O11.2-H2O: C, 58.66; H. 6.61; N, 13.10. Found: C, 58.67; H; 6.22; N, 12.97.

EXAMPLE 123

α-Methyl-Trp-Lys((ε-N-(2-methylphenyl)aminocarbonyl)-(NMe)Asp-PheNH2

To a stirred solution of t-BOC-α-methyl-D,L-Trp-OH (200 mg, 0.66 mmol), from Example 96a, and NMM (145 μL, 1.32 mmol) in 1 mL of dry THF at −15° C. was added diphenylphosphinic chloride. After 20 minutes, a solution of the TFA salt of Lys(ε-N-(2-methylphenyl)aminocarbonyl)-(NMe)Asp(OBn)-PheNH2 (450 mg, 0.6 mmol), from Example 60d, and NMM (72 μL, 0.66 mmol) in 3 mL of DMF at 0° C. was added. The solution was allowed to warm slowly to ambient temperature and stir for 3 days. Acid-base extractive work-up afforded 520 mg of crude product, which was subjected directly to treatment with 1:1 trifluoroacetic acid/methylene chloride for 1 hour at ambient temperature to effect removal of the t-BOC protecting group. After evaporation of volatile components, dry diethyl ether was added to precipitate the product (440 mg), which was collected and dried. The isomers were separated by chromatography over silica gel eluted with ethyl acetate/pyridine/water after which fractions containing the more mobile isomer were combined and lyopholized twice from ethanol/water and once from ethanol/aqueous hydrochloric acid to afford 165 mg of the hydrochloride salt of the benzyl-protected product. Hydrogenolysis of 160 mg of the benzyl ester hydrochloride over 10% palladium-on-carbon in isopropanol, followed by preparative reverse-phase HPLC (mobile phase=acetonitrile/50 mM ammonium acetate) afforded 86 mg of the title compound after final lyophilization from aqueous trifluoroacetic acid. MS (FAB+) m/e 755 (M+H)+. ¹H NMR (DMSO-d6) δ Ar—CH3: 1.50 (s, 3H, α-methyl), 2.16 (s, 3H, Me—Ar), 2.40 (s,3H, N—CH3), 4.50, 4.57, 5.22 (3H, α-Protons):. Analysis calculated for C42H51F3N8O9.0.9CF3COOH.1.1H2O:

C, 58.66; H. 6.61; N, 13.10. Found: C, 58.67; H, 6.22; N, 12.97.

EXAMPLE 124

Methoxycarbonyl-Trp-Lys(($\epsilon$-N-(2-methylphenyl)aminocarbonyl)-(NMe)Asp-(NMe)PheNH$_2$ The tripeptide of Example 68b, Lys($\epsilon$-N-benzyloxycarbonyl)-(NMe)Asp(OBn)-(NMe)PheNH$_2$ trifluoro acetate and methoxycarbonyl-Trp, of Example 81a, were coupled according to standard mixed anhydride method described in Example 52b to give the diprotected tetrapeptide, methoxycarbonyl-Trp-Lys($\epsilon$-N-benzyloxycarbonyl)-(NMe)Asp(OBn)-(NMe)PheNH$_2$. Hydrogenolysis as described in Example 1f and addition of the 2-methylphenylaminocarbonyl group were carried out as described in Example 24b to afford the title compound. MS (FAB+) m/e 835 (M+Na)+, 813 (M+H)+. $^1$H NMR (DMSO-d6) (two conformers ca. 9:1) $\delta$ methyl singlets: 2.04 (s, 3H), 2.17 (s, 3H), 2.76 (s,3H), 3.44 (s, 3H); $\alpha$ protons: 4.23–4.28 (m, 1H), 4.46–4.54 (m, 1H), 5.27–5.35 (m, 1H), 5.47–5.54 (m, 1H); a protons (minor conformer) 4.48–4.56 (m), 4.64–4.68 (m), 4.96–5.03 (m), 5.22–5.27 (m, partially obscured). Analysis calculated for C$_{42}$H$_{52}$N$_8$O$_9$.0.9H$_2$O: C, 60.84; H. 6.54; N, 13.52. Found: C, 60.79; H; 6.38; N, 13.52.

EXAMPLE 125 t-BOC-Trp-Lys($\epsilon$-N-(2,3-dichlorophenyl)aminocarbonyl)-Asp-PheNH$_2$

A solution of the tetrapeptide of Example 1f, 2,3-dichloromethylphenyl isocyanate (commercially available from Aldrich Chemical Company) and NMM in DMF was stirred at ambient temperature for 18 hours as described in Example 24. The product was isolated as described in Example 1 g to yield the title compound as a white solid, m.p. 178°–181° C. Analysis calculated for C$_{42}$H$_{50}$N$_8$O$_9$Cl$_2$. 0.5H$_2$O: C, 56.63; H. 5.77; N, 12.58. Found: C, 56.47; H; 5.73; N, 12.40.

EXAMPLE 126

Methoxycarbonyl-Trp-Lys(($\epsilon$-N-3-(thienyl)acrylyl)-(NMe)Asp-PheNH$_2$

Boc-Trp-Lys($\epsilon$-N-benzyloxycarbonyl)-(NMe)Asp-(OBn)-Phe-NH$_2$, prepared as described in Example 66b was treated with trifluoroacetic acid/methylene chloride in a procedure similar to that described in Example 60d. The resulting trifluoroacetate (230 mg, 0.243 mmol) was dissolved in DMF and treated with NMM (0.267 mmol) and dimethyl pyrocarbonate (0.534 mmol), and the mixture was allowed to stir at ambient temperature for 3 hours. The mixture was diluted with ethyl acetate and subjected to acid-base work-up, then the crude product was purified by silica gel chromatograpy, eluting with ethyl acetate/hexane/acetic acid (78:20:2) to afford 115 mg (0.129 mmol) of the protected tetrapeptide. Hydrogenolysis of this material (107 mg, 0.120 mmol) in DMF as described in Example 65 afforded a quantitative yield of methoxycarbonyl-Trp-Lys-(NMe)Asp-Phe-NH$_2$ acetate, which was treated with the active ester of Example 11a in a manner analogous to that described in Example 1 g. The crude material was purified by preparative reverse phase HPLC, eluting with acetonitrile/50 mM ammonium acetate buffer (pH 4.5), to afford 45 mg (0.05 mmol) of product. MS (FAB+) m/e 802 (M+H)+. $^1$H NMR (DMSO-d$_6$) (two conformers, ca. 1:1) $\delta$ methyl singlets: 2.16, 2.46, 3.26, 3.44; $\alpha$ protons 4.23–4.34 (m, 1H), 4.36–4.45 (m, 1H), 4.53 (m), 4.83 (m), 5.14 (dd, J=5, 10 Hz), 5.19 (m). Analysis calculated for C$_{40}$H$_{47}$N$_7$O$_9$S.0.9 CH$_3$CO$_2$NH$_4$.0.9 CH$_3$CO$_2$H: C, 56.59; H, 6.20; N, 11.96. Found: C, 56.50; H, 5.67; N, 11.96.

EXAMPLE 127

2-Carboethoxy-2-methyl-3-(indol-3-yl)propionyl-Lys($\epsilon$-N-(2-methylphenyl)aminocarbonyl)-Asp(OBn)-(NMe)-PheNH$_2$ The preparation of the title compound is described in Example 107a. MS (FAB) m/e 902(M+H)+. $^1$H NMR (CDCl$_3$/D$_2$O): (two diastereomers and conformers) $\delta$1.52, 1.53, 1.54, 1.55 (3s,3H),2.20, 2.22, 2.34 (s,3H, Ar—CH$_3$), 2.89, 2.92, 2.99, 3.07 (4s,3H,N—CH3). Analysis calculated for C$_{50}$H$_{59}$N$_7$O$_9$.1.0H$_2$O: C, 65.27; H, 6.68; N,.10.27. Found: C, 65.31; H, 6.78; N, 10.27.

EXAMPLE 128 t-BOC-Trp-Lys($\epsilon$-N-(4-trifluoromethylphenyl)aminocarbonyl)-Asp-PheNH$_2$ A solution of the tetrapeptide of Example 1f, 4-trifluoromethylphenyl isocyanate (commercially available from Alfa Products) and NMM in DMF was stirred at ambient temperature for 18 hours as described in Example 24. The product was isolated as described in Example 1 g to yield the title compound as a white solid, m.p. 194°–197° C. Analysis calculated for C$_{43}$H$_{51}$N$_8$O$_9$F$_3$.H$_2$O.CH$_3$COOH: C, 56.36; H. 5.99; N, 11.68. Found: C, 56.26; H; 6.00; N, 11.66.

EXAMPLE 129 t-BOC-Trp-Lys($\epsilon$-N-(2,4-dichlorophenyl)aminocarbonyl)-Asp-PheNH$_2$

A solution of the tetrapeptide of Example 1f, 2,4-dichloromethylphenyl isocyanate (commercially available from Aldrich Chemical Company) and NMM in DMF was stirred at ambient temperature for 18 hours as described in Example 24. The product was isolated as described in Example 1 g to yield the title compound as a white solid, m.p. 183°–187° C. Analysis calculated for C$_{24}$H$_{50}$N$_8$O$_9$Cl$_2$.H$_2$O: C, 56.06; H. 5.83; N, 12.45. Found: C, 56.37; H; 5.72; N, 12.39.

EXAMPLE 130

(3-Carboxylpropionyl)-Trp-Lys($\epsilon$-N-(2-methylphenyl)aminocarbonyl)-Asp(OBn)-(NMe)PheNH$_2$ A solution of Lys(2-methylphenylaminocarbonyl)-Asp(OBn)-(NMe)PHeNH$_2$ trifluoroacetate, the product of Example 74d (150 mg, 0.16 mmol), succinic anhydride (18 mg, 0.18 mmol), and DIEA (52 $\mu$L, 32 $\mu$mol) in DMF was stirred overnight at room temperature. The reaction mixture was then diluted with cold aqueous citric acid, filtered, and the white precipitate washed several times with water to afford the tetrapeptide as a white solid (130 mg, 95%). MS (FAB+) m/e931 (M+H)+, 914 (M-NH$_2$)+. $^1$H-NMR (DMSO-d6) two conformers ca 1:1; methyl singlets $\delta$2.14, 2.15 (s, 3H); 2.73, 2.87 (3H); $\alpha$ protons 4.14, 4.20, 4.52, 4.67, 4.86, 4.98–5.09 (m,2). Analysis calcd. for C$_{50}$H$_{58}$N$_8$O$_{10}$.1.0H$_2$O: C, 63.27; H, 6.37; N, 11.82. Found: C, 64.84; H, 6.20; N, 11.52.

EXAMPLE 131 t-BOC-Trp-Lys(ε-N-(2-methylphenyl)aminocarbonyl)-(R)-α-benzylprolamide

During the chromatography of Example 115i, further elution with HOAc/MeOH/ethyl acetate (10:10:80) afforded 8 mg of the title compound. MS (FAB+) m/e 905 (M+K)+. Partial NMR (500 MHz, CD$_3$OD) δ1.39 (s), 2.20 (s), 3.12 (t, J=4 Hz, 2H), 3.19 (d, J=7 Hz, PhCH), 3.78 (d, J=7 Hz, PhCH), 5.05 (dd, J=2, 5 Hz, α-H).

EXAMPLE 132 t-BOC-Trp-Lys(ε-N-(2-methylphenyl)aminocarbonyl)-Asp-phenylalaninol a. HCl Asp(β-benzyl)-phenylalaninol A solution of t-BOC-Asp(OBn) (643 mg), phenylalaninol (300 mg), HOBT (407 mg) and EDCl (456 mg) in methylene chloride was stirred at ambient temperature for 18 hours. The mixture was washed with 1M phosphoric acid, saturated sodium bicabonate solution and brine then dried over magnesium sulfate. Solvent evaporation yielded a white solid. The solid (300 mg) was dissolved in a 0° C. solution of methylene chloride (20 mL) and trifluoroacetic acid (10 mL) and stirred for 3 hours. The reaction was concentrated, dissolved in water and lyopholyzed to yield the title compound as a white powder (288 mg). MS (DCl/NH$_3$) m/e 357 (M+H)+. $^1$H NMR(CDCl$_3$, 300 MHz) δ2.62-2.81 (m,2H), 2.85-3.00 (m,2H), 3.40-3.53 (m,2H), 3.97-4.08 (m,1H), 4.26-4.35 (m,1H), 5.02 (s,2H), 7.08-7.38 (m,10H), 7.83 (d,1H).

b. t-BOC-Trp-Lys(ε-N-[(2-methylphenyl)aminocarbonyl]-Asp-phenylalaninol

A solution of t-BOC-Trp-Lys(ε-N-[(2-methylphenyl)aminocarbonyl], the product of Example 49c, and the dipeptide salt of Step a were reacted to yield the title compound as a white solid. MS(FAB+) m/e 814 (M+H)+. $^1$H NMR(DMSO-d6, 300 MHz) δ1.08-1.45 (m,6H), 1.30 (s,9H), 2.15-2.70 (m,3H), 2.75-3.18 (m,6H), 3.78-3.91 (m,1H), 4.18-4.28 (m,2H), 4.45-4.52 (m,1H), 6.80-6.90 (m,1H), 6.95 (t,1H), 7.02-7.33 (m,10H), 7.59 (d,1H), 8.00 (d,1H). Analysis calculated for C$_{43}$H$_{55}$N$_7$O$_9$.H$_2$O.0.5CH$_3$CO$_2$H: C, 61.31; H, 6.90; N, 11.37. Found: C, 61.22; H, 6.50; N, 11.49.

EXAMPLE 133

3-(3-Indolyl)propionyl-Lys(ε-N-(2-methylphenyl)aminocarbonyl)-Asp-PheNH$_2$

The 2,4,5-trichlorophenyl (TCP) ester of 3-(indol-3-yl)propionic acid, prepared as described in Example 63c, and the trifluoroacetate salt of the tripeptide, Lys((ε-N-(2-methylphenyl)aminocarbonyl)-Asp-PheNH$_2$, the product of Example 63d were coupled as described in Example 63e to give the title compound. MS (FAB) m/e 712(M+H)+. $^1$H NMR (DMSO-d6): δ2.17 (s,3H, Ar—CH3), 4.13-4.24, 4.28-4.30, 4.43-4.44 (3H,3α-H). Analysis calculated for C$_{38}$H$_{45}$N$_7$O$_7$.0.5CH$_3$COOH: C, 63.81; H, 639; N, 13.92. Found: C, 63.14; H, 6.34; N, 13.36.

EXAMPLE 134

(NMe)Trp-Lys(ε-N-(2-methylphenyl)aminocarbonyl)-Asp-PheNH$_2$ a. t-BOC-(NMe)Trp-Lys(ε-N-benzyloxycarbonyl)-Asp(OBn)-PheNH$_2$ t-BOC-(NMe)TrpOH, the product of Example 69a (0.51 g, 1.59 mmol) was coupled to the tripeptide product of Example 1d using a BOP-Cl mediated coupling similar to that described in Example 60b. After 2 days, the mixture was subjected to acid-base work-up to afford 1.3 g of product. MS (FAB+) 933 (M+H)+.

b. t-BOC-(NMe)Trp-Lys(ε-N-(2-methylphenyl)aminocarbonyl)-Asp-PheNH$_2$

Hydrogenolysis of the product of Example 134a as in Example 1f and urea formation as in Example 24 afforded the title compound. MS (FAB+) m/e 863 (M+Na)+.

c. (NMe)Trp-Lys(ε-N-(2-methylphenyl)aminocarbonyl)-Asp-PheNH$_2$ hydrochloride

The product of Example 134b was treated with 4N HCl/dioxane for 1.5 hour, then the solvent was evaporated and the residue triturated with ethyl ether. The crude product was purified by preparative reverse-phase HPLC on a C-18 column. Pure fractions were lyophilized to afford 8 mg of product. Partial $^1$H NMR (500 MHz, DMSO-d6) δ2.15 (s, 3H), 2.20 (s, 3H), α-protons: 4.25 (m, 1H), 4.35 (m, 1H), 4.45 (m, 1H). MS (FAB+) m/e 741 (M+H)+

EXAMPLE 135 t-BOC-Trp-hLys(ω-N-(6-hydroxy-2-naphthyl)carbonyl)-Asp-PheNH$_2$

Starting with N-α-Boc-N-ε-Cbz-homolysine, prepared from Boc-D-serine using methodology analogous to that of Beaulieu and Schiller (Tetrahedron Lett. 1988, 29, 2019), homolysine was incorporated into the tetrapeptide using the procedures described in Examples 1c through 1e. The product was deprotected as described in Example 1f, and acylated with the product of Example 19a as described in Example 1g. The product was purified by chromatography over silica gel eluting with ethyl acetate/pyridine/HOAc/H2O to afford after lyophilization 29 mg of the product. MS (FAB+) m/e 878 (M+H)+. $^1$H-NMR (DMSO-d6) δ1.30 (s, 9H); 4.20-4.40 (m, 4H, α protons).

EXAMPLE 136 t-BOC-Trp-Lys(3-quinolinecarbonyl)-(NMe)Asp-PheNH$_2$ a. 3-quinolinecarboxylic acid N-hydroxysuccinimide ester A solution of 3-quinolinic acid (300 mg; commercially available from Aldrich Chemical Company), N-hydroxysuccinimide (245 mg) and EDCl (349 mg) in methylene chloride (20 mL) was stirred at ambient temperature for 18 hours. The product was isolated as described for Example 1g to yield 380 mg of the title compound as a white solid. MS(Cl/NH$_3$) m/e 271 (M+H)+. $^1$H NMR(CDCl$_3$, 300 MHz) δ2.97 (br s,4H), 7.18-7.22 (m,1H), 7.89-8.00 (m,2H), 8.22 (d,J=9 Hz,1H), 9.01 (m,1H), 9.49 (d,J=2 Hz,1H).

b. t-BOC-Trp-Lys(3-quinolinecarbonyl)-(NMe)Asp-PheNH$_2$ t-Boc Trp-Lys-(NMe)Asp-Phe-NH$_2$, the product of Example 66b, was treated with the active ester of step a as described in Example 1g. Purification by preparative reverse phase HPLC, eluting with acetonitrile/50 mM ammonium acetate buffer (pH 4.5), resulted in 61 mg. (0.071 mmol) of product. MS (FAB+) m/e 864 (M+H)+. $^1$H NMR (DMSO-d6) (two conformers, ca. 2:1) δ methyl singlets: 1.38 (1H), 1.89 (2H); α protons:

4.14 (m, 0.66H), 4.26–4.44 (m, 1H), 4.58 (m, 0.33H), 4.71 (m, 0.66H), 4.87 (m, 0.33H), 5.12 (m, 0.66H), 5.28 (m, 0.33H). Analysis calculated for $C_{46}H_{54}N_8O.2.7\ H_2O$: C, 60.61; H, 6.58; N, 12.29. Found C, 60.55; H, 6.23, N, 12.41.

EXAMPLE 137 t-BOC-Trp-Lys($\epsilon$-N-(2-thienylacryloyl)-(NMe)Asp-(NMe)PheNH$_2$

Boc-Trp-Lys-(NMe)Asp-(NMe)Phe-NH2, the product of Example 68b, was reacted with the active ester of Example 11a in a procedure analogous to that described in Example 1g. Purification by preparative HPLC, eluting with acetonitrile/50 mM ammonium acetate buffer (pH 4.5), resulted in 59 mg (0.069 mmol) of product. MS (FAB−) m/e 857 (M−H)$^-$. $^1$H NMR (DMSO-d$_6$) $\delta$ Boc singlet: 1.22; methyl singlets: 1.96, 2.68; $\alpha$ protons: 4.11 (m), 4.34 (m), 5.27 (dd, J=5, 13), 5.43 (dd, J=5, 10). Analysis calculated for $C_{44}H_{55}N_7O_9S.0.4CH_3CO_2H.0.1\ H_2O$: C, 60.88; H, 6.48; N, 11.09. Found: C, 60.82; H, 6.31; N, 11.11.

EXAMPLE 138 t-BOC-Trp-Lys($\epsilon$-N-(2-methylphenyl)aminocarbonyl)-Asp(OBn)-(NMe)PheNH$_2$ To a solution of Lys(2-methylphenylaminocarbonyl)-Asp(OBn)-N(Me)Phe-NH2 trifluoroacetate from step 74d (2.27 g, 3.0 mmol) and Boc-TrpOH (913 mg, 3 mmol) in DMF (12 mL) was added HOBt (405 mg, 3.0 mmol), N-methylmorpholine (395 ml, 3.6 mmol) and EDCl (632 mg, 3.3 mmol) and the reaction mixture stirred for 22 hours at room temperature. The reaction mixture was then diluted with 10% citric acid (150 mL) and filtered, and the white precipitate washed with H$_2$O (2×50 mL) and hexane (50 mL) to afford the tetrapeptide (2.72 g, 95%). MS (FAB$^+$) m/e931 (M+H)$^+$, 914 (M−NH$_2$)$^+$. $^1$H-NMR (DMSO-6) two conformers ca 1:1; methyl singlets $\delta$2.15 (s, 3H); 2.74, 2.89 (3H); $\alpha$ protons 4.22, 4.28, 4.66, 4.88, 4.98–5.12 (m,2); 10.78 (br. s., 1). Analysis calcd. for $C_{50}H_{61}N_8O_9 \times 1.5\ H_2O$: C, 64.00; H, 6.74; N, 11.71. Found: C, 64.14; H, 6.56; N, 12.10.

EXAMPLE 139

Propionyl-Trp-Lys($\epsilon$-N-(2-methylphenyl)aminocarbonyl)-Asp-(NMe)PheNH$_2$ Following the procedure of Examples 74g and h, replacing 2-adamantyl chloroformate with the commercially available propionyl anhydride, the tetrapeptide of example 74f was acylated and debenzylated to give the title compound. MS (FAB) m/e 797(M+H)$^+$. $^1$H NMR (DMSO-d$_6$): (two conformers ca. 1:1) $\delta$0.83–0.92 (2t,3H), 1.98–2.10 (2q,2H), 2.15 (s,3H, Ar—CH3), 2.79, 2.94 (2s,3H, N—CH3), 4.10–4.30, 4.48–4.58, 4.62–4.72, 4.83–5.02, 5.12–5.21 (4H,4$\alpha$-H). Anal. calcd for $C_{42}H_{52}N_8O_8$. 1 HOAc.0.5 H$_2$O: C, 61.09; H,6.63; N,12.94. Found: C, 60.94; H, 6.43; N, 13.05.

EXAMPLE 140

Isobutyloxycarbonyl-Trp-Lys($\epsilon$-N-(2-methylphenyl)aminocarbonyl)-(NMe)Asp-PheNH$_2$ Isobutyloxycarbonyl-TrpOH, the product of Example 119a, was coupled to the tripeptide of Example 60d using the mixed anhydride procedure of Example 52b. The mixture was diluted with ethyl acetate and subjected to acid-base work-up. The crude product was precipitated from ethanol/ether/hexane to afford a white solid in 84% yield. Hydrogenolysis in DMF as in Example 65 followed by chromatography of the crude product (silica gel, 90:10:5 ethyl acetate/MeOH/stock 1 (stock 1=20:11:6 pyridine/H2O/HOAc)) afforded the title compound in 82% yield after lyophilization. MS (FAB+) m/e 841 (M+H)$^+$. $^1$H NMR (DMSO-d$_6$) (two conformers, ca. 1:1) $\delta$ methyl singlets: 2.12, 2.16 (3H), 2.35; $\alpha$ protons: 4.23–4.36 (m, 1H), 4.37–4.54 (m, 1.5H), 4.85 (m), 5.13 (dd, J=5, 10), 5.24 (m). Analysis calculated for $C_{44}H_{56}N_8O_9.1.0\ H_2O.0.3\ CH_3CO_2H$: C, 61.08; H, 6.80; N, 12.78. Found: C, 61.06; H, 6.21; N, 12.89.

Other Examples of compounds of the invention which were prepared according to the synthetic methodology described in the above Examples include:

t-BOC-Trp-Lys($\epsilon$-N-(3-phenylpropionyl))-Asp-PheNH$_2$ t-BOC-Trp-Lys($\epsilon$-N-(3-carboxyquinolyl))-Asp-PheNH$_2$ t-BOC-Trp-Lys($\epsilon$-N-(4-hydroxyphenylacetyl))-Asp-PheNH$_2$ t-BOC-Trp-Lys($\epsilon$-N-(4-hydroxycinnamoyl))-Asp-PheNH$_2$ t-BOC-Trp-Lys($\epsilon$-N-(3-(3-hydroxyphenyl)propionyl))-Asp-PheNH$_2$ t-BOC-Trp-Lys($\epsilon$-N-(3-(3-sulfatylphenyl)propionyl))-Asp-PheNH$_2$;

t-BOC-Trp-Lys($\epsilon$-N-(3-(4-chlorophenyl)propionyl))-Asp-PheNH$_2$;

t-BOC-Trp-Lys($\epsilon$-N-(4-phenylbutyryl))-Asp-PheNH$_2$;

t-BOC-Trp-Lys($\epsilon$-N-(3-(4-methylphenyl)propionyl))-Asp-PheNH$_2$;

t-BOC-Trp-Lys($\epsilon$-N-(3-sulfatylcinnamoyl))-Asp-PheNH$_2$;

t-BOC-Trp-Lys($\epsilon$-N-(3-(4-fluorophenyl)propionyl))-Asp-PheNH$_2$;

t-BOC-Trp-Lys($\epsilon$-N-(3-(4-trifluoromethylphenyl)propionyl))-Asp-PheNH$_2$;

t-BOC-Trp-Lys($\epsilon$-N-(3-(3-indolyl)acrylyl))-Asp-PheNH$_2$;

t-BOC-Trp-Lys($\epsilon$-N-($\beta$-naphthoyl))-Asp-PheNH$_2$;

t-BOC-Trp-Lys($\epsilon$-N-(3-(3,4-dihydroxyphenyl)propionyl))-Asp-PheNH$_2$;

t-BOC-Trp-Lys($\epsilon$-N-(6-acetoxy-$\beta$-naphthoyl))-Asp-PheNH$_2$;

t-BOC-Trp-Lys($\epsilon$-N-($\alpha$-cyano-3-hydroxycinnamoyl))-Asp-PheNH$_2$;

t-BOC-Trp-Lys($\epsilon$-N-(cinnamoyl))-Asp-PheNH$_2$;

t-BOC-Trp-Lys($\epsilon$-N-(1-adamantanoyl))-Asp-PheNH$_2$;

t-BOC-Trp-Lys($\epsilon$-N-(4-methoxycinnamoyl))-Asp-PheNH$_2$;

t-BOC-Trp-Lys($\epsilon$-N-(4-bromocinnamoyl))-Asp-PheNH$_2$;

t-BOC-Trp-Lys($\epsilon$-N-(6-hydroxy-$\beta$-naphthoyl))-Asp-PheNH$_2$;

t-BOC-Trp-Lys($\epsilon$-N-(2,4-dichlorocinnamoyl))-Asp-PheNH$_2$;

t-BOC-Trp-Lys($\epsilon$-N-(4-nitrocinnamoyl))-Asp-PheNH$_2$;

t-BOC-Trp-Lys($\epsilon$-N-(3,4-dimethoxycinnamoyl))-Asp-PheNH$_2$;

t-BOC-Trp-Lys($\epsilon$-N-(4-(3-quinolyl)-3-butenoyl))-Asp-PheNH$_2$;

t-BOC-D-Trp-Lys($\epsilon$-N-(3-(4-hydroxyphenyl)propionyl))-Asp-PheNH$_2$;

t-BOC-D-Trp-Lys($\epsilon$-N-(4-hydroxycinnamoyl))-Asp-PheNH$_2$;

t-BOC-α-Nal-Lys(ε-N-(3-(4-hydroxyphenyl)propionyl))-Asp-PheNH₂;
t-BOC-α-Nal-Lys(ε-N-(4-hydroxycinnamoyl))-Asp-PheNH₂;
t-BOC-β-Nal-Lys(ε-N-(3-(4-hydroxyphenyl)propionyl))-Asp-PheNH₂;
t-BOC-β-Nal-Lys(ε-N-(4-hydroxycinnamoyl))-Asp-PheNH₂;
t-BOC-D-Trp-Lys(ε-N-(3-(4-hydroxyphenyl)propionyl))-Asp-(NMe)PheNH₂;
t-BOC-D-Trp-Lys(ε-N-(4-hydroxycinnamoyl))-Asp-(NMe)PheNH₂;
t-BOC-Trp-Lys(ε-N-(3-chlorocinnamoyl))-Asp-PheNH₂;
t-BOC-Trp-Lys(ε-N-((6-sulfatyl-β-naphthoyl))-Asp-PheNH₂;
t-BOC-Trp-Lys(ε-N-(4-(β-naphthyl)-3-butenoyl))-Asp-PheNH₂;
Ctp-Lys(ε-N-(3-(4-hydroxyphenyl)-propionyl))-Asp-PheNH₂;
β-Naphthoxyacetyl-Lys(ε-N-(4-hydroxycinnamoyl))-Asp-PheNH₂;
3-(3-Indolyl)propionyl-Lys(ε-N-(3-(4-hydroxyphenyl)-propionyl))-Asp-PheNH₂;
t-BOC-Trp-Lys(ε-N-(3-(3-indolyl)propionyl)-Asp-PheNH₂;
t-BOC-Trp-Lys(ε-N-(t-BOC-Tyr))-Asp-PheNH₂;
t-BOC-Trp-Lys(ε-N-(t-BOC-O-sulfatyl-tyrosyl))-Asp-PheNH₂;
t-BOC-Trp-Lys(ε-N-(t-BOC-Trp))-Asp-PheNH₂;
t-BOC-Trp-(2-aminopimelic acid(7-tyramide))-Asp-PheNH₂;
t-BOC-Trp-Lys(ε-N-(3-cyclohexylpropionyl))-Asp-PheNH₂;
t-BOC-Trp-Lys(ε-N-(8-hydroxyquinolyl-2-carbonyl))-Asp-PheNH₂;
t-BOC-Trp-Lys(ε-N-(5-methoxyindolyl-2-carbonyl))-Asp-PheNH₂;
t-BOC-Trp-Lys(ε-N-t-BOC-D-Trp)-Asp-PheNH₂;
t-BOC-Trp-Lys(ε-N-t-BOC-D-Tyr)-Asp-PheNH₂;
t-BOC-Trp-Lys(ε-N-(5-(benzyloxy)indole-2-carbonyl)Asp-PheNH₂;
t-BOC-Trp-Lys(ε-(5-chloroindole-2-carbonyl))-Asp-PheNH₂;
t-BOC-Trp-Lys(ε-N-(5-hydroxyindole-2-carbonyl))-Asp-PheNH₂;
t-BOC-Trp-Lys(ε-N-(3-methylphenyl)aminothiocarbonyl)-Asp-PheNH₂;
t-BOC-Trpψ(CH₂NH)Lys(ε-N-4-hydroxycinnamoyl)-Asp-PheNH₂;
t-BOC-Trp-Lys(ε-N-4-hydroxycinnamoyl)ψ(CH₂NH)Asp-PheNH₂.
t-BOC-Trp-Lys(ε-N-(4-phenoxyphenyl)aminocarbonyl)-Asp-PheNH₂;
t-BOC-Trp-Lys(ε-N-(S-2-(α-naphthyl)ethylaminocarbonyl))-Asp-PheNH₂;
t-BOC-Trp-Lys(ε-N-(2,6-dimethylphenyl)aminocarbonyl)-Asp-PheNH₂;
t-BOC-Trp-Lys(ε-N-(allylaminocarbonyl))-Asp-PheNH₂;
t-BOC-Trp-Lys(ε-N-(benzylaminocarbonyl))-Asp-PheNH₂;
t-BOC-Trp-Lys(ε-N-(2-methylphenyl)aminocarbonyl)-Asp-phenylalaninol;
t-BOC-Trp-Lys(ε-N-(2-methylphenyl)aminocarbonyl)-Asp-(NMe)phenylalaninol;
t-BOC-Trp-Lys(ε-N-(4-hydroxycinnamoyl))-Asp-TrpNH₂;
t-BOC-Trp-Orn(δ-N-(2-methylphenyl)aminocarbonyl)-Asp-PheNH₂;
t-BOC-Trp-Orn(δ-N-(4-hydroxycinnamoyl))-Asp-PheNH₂;
t-BOC-Trp-hLys(ω-N-(4-hydroxyphenylcinnamoyl))-Asp-PheNH₂;
t-BOC-Trp-(6-amino-1-(4-hydroxyphenethylamido)-hept-2-enoyl)-Asp-PheNH₂;
t-BOC-Trp-Lys(ε-N-(2-methylphenyl)aminocarbonyl)-β-Asp-PheNH₂;
t-BOC-Trp-(NMe)Lys(ε-N-(2-methylphenyl)aminocarbonyl)-Asp-PheNH₂;
t-BOC-Trp-Lys(ε-N-(2-methylphenyl)aminocarbonyl)-Asp-PheNHMe;
t-BOC-Trp-Lys(ε-N-(2-methylphenyl)aminocarbonyl)-Asp-PheNMe₂;
t-BOC-Trp-Lys(ε-N-(2-methylphenyl)aminocarbonyl)-Asp-PheOMe.
(2-Carbomethoxy-3-(3-indolyl)propionyl)-Lys(ε-N-(2-methylphenyl)aminocarbonyl)-Asp-(NMe)PheNH₂;
(2-Carboxy-3-(3-indolyl)propionyl)-Lys(ε-N-(2-methylphenyl)aminocarbonyl)-Asp-(NMe)PheNH₂;
t-BOC-Trp-Lys(ε-N-(2-methylphenyl)aminocarbonyl)-(NMe)Asp-α-NalNH₂;
t-BOC-(NMe)Trp-Lys(ε-N-(2-methylphenyl)aminocarbonyl)-(NMe)Asp-PheNH₂;
(2-Carboxy-2-methyl-3-(3-indolyl)propionyl)-Lys(ε-N-(2-methylphenyl)aminocarbonyl)-Asp-(NMe)-PheNH₂;
(2-Indolyl)carbonyl-Lys(ε-N-(2-methylphenyl)aminocarbonyl)-Asp-(NMe)PheNH₂;
(2-Quinolyl)carbonyl-Lys(ε-N-(2-methylphenyl)aminocarbonyl)-Asp-(NMe)PheNH₂;
3-(4-Hydroxy-3-iodophenyl)propionyl-Lys(ε-N-(2-methylphenyl)aminocarbonyl)-Asp-(NMe)PheNH₂;
t-BOC-Trp-Lys(ε-N-(2,3-dichlorophenyl)aminocarbonyl-Asp-PheNH₂;
t-BOC-Trp-Lys(ε-N-phenylmethylcarbonyl)-Asp-PheNH₂;
t-BOC-Trp-(2-aminosuberic acid(8-(2-methylphenyl amide)))-Asp-PheNH₂;
t-BOC-Trp-Lys(εN-(2-methylphenyl)aminocarbonyl)ψ(CH₂NH)Asp-PheNH₂;
t-BOC-Trp-Lys(ε-N-(2-methylphenyl)aminocarbonyl)-Asp-(2S)-2-benzyl-2-aminoacetonitrile;
t-BOC-Trp-Lys(ε-N-(2-methylphenyl)aminocarbonyl)-Asp-(2S)-2-benzyl-2-(N-methylamino)acetonitrile;
t-BOC-Trp-Lys(ε-N-(2-methylphenyl)aminocarbonyl)-(NMe)Asp-(2S)2-benzyl-2-aminoacetonitrile;
t-BOC-Trp-Lys(ε-N-(2-methylphenyl)-aminocarbonyl)-Asp-(2S)-2-benzyl-2-aminoacetonitrile;
t-BOC-Trp-Lys-(ε-N-(2-methylphenyl)-aminocarbonyl)-Asp-(2S)-2-benzyl-2-aminopropyne;
t-BOC-Trp-Lys-(ε-N-(2-methylphenyl)aminocarbonyl)-Asp-PheNHNH₂;
E-3-(1H-Indol-3-yl)-propenyl-Lys(ε-N-(2-methylphenyl)-aminocrbonyl)-Asp-PheNH₂;
t-BOC-Trp-hLys(ε-N-(2-methylphenyl)-aminocarbonyl)-Asp-(NMe)PheNH₂;
t-BOC-Trp-Lys(ε-N-(2-methylphenyl)aminocarbonyl)-Asp-L-pyridylalanineNH₂;
t-BOC-Trp-Lys(ε-N-(2-methylphenyl)aminocarbonyl)ψ(CH₂NH)Asp-PheNH₂;
t-BOC-Trp-Lys(ε-N-(2-methylphenyl)aminocrbonyl)-(NMe)Asp-(2S)-benzylaminoacetonitrile; and
Isobutyloxycarbonyl-Trp-Lys(ε-N-(2-methylphenyl)aminocarbonyl)(NMe)Asp-PheNH₂.

The compounds of formula (I) are CCK agonists which are useful in the treatment and prevention of CCK-related disorders of the gastrointestinal, central nervous,l and appetite and insulin regulatory systems of mammals, especially humans, As CCK agonists, they are useful in the treatment and prevention of neuroleptic disorders, tardive dyskinesia, disorders of memory an dcognition, Parkinson's disease, Huntington's chorea, psychosis, including schizophrenia, Gilles de la Tourette syndrome, diabetes, disorders of appetite regulatory systems, obseity, bulimia, the treatment of pain and the treatment of substance abuse. The compounds of formula (I) are also useful for the preventing or reducing the incidence of gallstones and for stimulating gallbladder emptying.

The ability of the compounds of the invention to interact with CCK receptors and to act as CCK agonists can be demonstrated in vitro using the following protocols.

CCK-8 [Asp-Tyr($SO_3$H)-Met-Gly-Trp-Met-Asp-PheNH$_2$], bestatin and phosphoramidion were purchased from Peptide International (Louisville, Ky.). EGTA (ethylene glycol-bis-($\beta$-aminoethyl) N,N,N',N'-tetraacetic acid), HEPES (4-(2-hydroxyethyl)-1-piperazine-enthanesulfonic acid) and BSA (bovine serum albumin) were purchased from Sigma Chemical Co. (St. Louis, Mo.). [$^{125}$I]-Bolton-Hunteer (BH-CCK-8) (specific activity, 2200 Ci/mmol) was obtained from New England Nuclear (Boston, Mass.). Male guinea pigs, 250 to 325 g, were obtained from Scientific Small Animal Laboratory and Farm (Arlington Heights, Ill.). Collagenase, code CLSPA was purchased from Worthington (Frehold, N.J.).

Protocol For Radioligand Binding Experiments in Guinea Pig Cerebral Cortical and Pancreatic Membrane Preparations Cortical and pancreatic membranes were prepared as described (Lin and Miller; *J. Pharmacol. Exp. Ther.* 1985, 232:775–780,). In brief, cortex and pancreas were removed and rinsed with ice-cold saline. Visible fat and connective tissues were removed from the pancreas. Tissues were weighed and homogenized separately in approximately 25 mL of ice-cold 50 mM Tris-HCl buffer, pH 7.4 at 4° C. with a Brinkman Polytron, setting 7, for 30 seconds. The homogenates were entrifuged for 10 minutes at 1075×g and pellets were discarded. The supernatants were saved and centrifuged at 38,730×g for 20 minutes. The resultant pellets were rehomogenized in 25 mL of 50 mM Tris-HCl buffer with a Teflon-glass homogenizer, 5 up and down strokes. The homogenates were centrifuged again at 38,730×g for 20 minutes. Pellets werre then resuspended in 20 mM HEPES, containing 1 mM EGTA, 118 mM NaCl, 4.7 mM KCl, 5 mM $MgCl_2$, 100 $\mu$M bestatin, 3 $\mu$M phosphoramidon, pH 7.4 at 22° C. with a Teflon-glass homogenizer, 15 up and down strokes. Resuspension volume for the cortex was 15–18 mL per gram of original wet weight and 60 mL per gram for the pancreas.

Incubation Conditions

[$^{125}$I]Bolton-Hunter CCK-8 and test compounds were diluted with HEPES-EGTA-salt buffer (see above) containing 0.5% BSA. To 1 mL Skatron polystyrene tubes were added 25 $\mu$L of test compounds, 25 $\mu$L of [$^{125}$I]BH-CCK-8 and 200 $\mu$L of membrane suspension. The final BSA concentration was 0.1%. The cortical tissues were incubated at 30° C. for 150 minutes and pancreatic tissues were incubated at 37° C. for 150 min. Incubations were terminated by filtration using Skatron Cell Harvester and SS32 microfiber filter mats. The specific binding of [$^{125}$I]BH-CCK-8, defined as the difference between binding in the absence and presence of 1 $\mu$M CCK-8, was 85–90% of total binding in cortex and 90–95% in pancreas. $IC_{50}$s were determined from the Hill analysis. The results of these binding asays are shown in Table 1.

TABLE 1

| Compound of Example | IC50 (nM) $^{125}$I-BH-CCK-8 Type-A receptor | $^{125}$I-BH-CCK-8 Type-B receptor |
|---|---|---|
| 1 | 124 | 6100 |
| 2 | 76 | 4800 |
| 3 | 13 | 470 |
| 4 | 140 | >10000 |
| 5 | 37 | 970 |
| 6 | 71 | 1500 |
| 7 | 65 | 1700 |
| 8 | 200 | 5300 |
| 9 | 21 | 87 |
| 10 | 51 | 4300 |
| 11 | 61 | 845 |
| 12 | 71 | 2900 |
| 13 | 120 | 2100 |
| 14 | 33 | 750 |
| 15 | 65 | 3000 |
| 16 | 30 | 3500 |
| 17 | 7 | 700 |
| 18 | 22 | 3000 |
| 19 | 3.8 | 730 |
| 20 | 3.4 | 570 |
| 21 | 33 | 1200 |
| 22 | 81 | 200 |
| 23 | 130 | 3000 |
| 24 | 3.8 | 1500 |
| 25 | 16 | 1900 |
| 26 | 60 | 770 |
| 27 | 3.8 | 1900 |
| 28 | 16 | 10000 |
| 29 | 26 | 1100 |
| 30 | 21 | 2100 |
| 31 | 51 | 2600 |
| 32 | 170 | 5600 |
| 33 | 4.6 | 4300 |
| 34 | 23 | 990 |
| 35 | 8 | 1500 |
| 36 | 7 | 1400 |
| 37 | 100 | 2900 |
| 38 | 230 | 1900 |
| 39 | 19 | 1300 |
| 41 | 23 | 5700 |
| 42 | 53 | 1200 |
| 43 | 23 | 3400 |
| 44 | 16 | 3200 |
| 45 | 34 | 3000 |
| 46 | 26 | 1400 |
| 47 | 160 | 7000 |
| 50 | 15 | 5200 |
| 51 | 28 | 2100 |
| 52 | 93 | 2000 |
| 56 | 12 | 3600 |
| 57 | 120 | 3000 |
| 60 | 4.3 | 10000 |
| 61 | 4.8 | 10000 |
| 63 | 20 | 4500 |
| 64 | 10 | 640 |
| 65 | 68 | 10000 |
| 66 | 35 | 8100 |
| 67 | 40 | 8300 |
| 69 | 14 | >10000 |
| 70 | 13 | >10000 |
| 71 | 4.9 | 5800 |
| 72 | 12 | >9000 |
| 73 | 15 | 3700 |
| 74 | 22 | 8000 |
| 75 | 17 | 10000 |
| 76 | 18 | 6400 |

TABLE 1-continued

| Compound of Example | IC50 (nM) $^{125}$I-BH-CCK-8 Type-A receptor | IC50 (nM) $^{125}$I-BH-CCK-8 Type-B receptor |
|---|---|---|
| 77 | 2.3 | 6500 |
| 78 | 1.6 | 5000 |
| 79 | 10 | 7200 |
| 80 | 4.8 | 5200 |
| 81 | 2.1 | >10000 |
| 82 | 4.9 | 4400 |
| 83 | 9.7 | 4900 |
| 84 | 3.0 | 3000 |
| 85 | 5.8 | 10000 |
| 86 | 6.7 | >10000 |
| 87 | 4.5 | 8400 |
| 88A | 4.4 | >10000 |
| 88B | 3.7 | >10000 |
| 89 | 1.8 | 4600 |
| 90 | 2.7 | 5100 |
| 91 | 19 | >10000 |
| 92 | 5.6 | 5000 |
| 93 | 4.6 | 4200 |
| 94 | 16 | 5600 |
| 95 | 47 | >10000 |
| 96 | 16 | 9300 |
| 97 | 11 | 2600 |
| 98 | 4.9 | 3200 |
| 99 | 67 | >10000 |
| 100 | 8.0 | 12000 |
| 101 | 9.3 | 12000 |
| 102 | 14 | 2500 |
| 103 | 6.1 | 6600 |
| 104 | 200 | 4100 |
| 105 | 20 | 1300 |
| 106 | 13 | >10000 |
| 107 | 21 | 1400 |
| 108 | 14 | 10000 |
| 109 | 15 | >10000 |
| 111 | 77 | >10000 |
| 112 | 6.3 | 900 |
| 113 | 59 | 3000 |
| 115 | 18 | >10000 |
| 116 | 10 | 4000 |
| 120 | 26 | 13000 |
| 123 | 5.9 | >10000 |
| 124 | 4.5 | 2600 |
| 125 | 2.8 | >10000 |

The results indicate that compounds of the invention possess selective affinity for Type-A CCK receptors.

Protocol for Amylase Release Assay

This assay was performed using the modified protocol of Lin et al., *J. Pharmacol. Exp. Ther.* 1986, 236:729–734.

Guinea Pig Acini Preparation

Guinea pig acini were prepared by the method of Bruzzone et al. (*Biochem. J.* 1985, 226:621–624) as follows. Pancreas was dissected out and connective tissues and blood vessels were removed. The pancreas was cut into small pieces (2 mm) by a scissor and placed in a 15 mL conical plastic tube containing 2.5 mL of Krebs-Ringer HEPES (KRH) buffer plus 400 units per mL of collagenase. The composition of the KRH buffer was: HEPES, 12.5 mM; NaCl, 118 mM; KCl, 4.8 mM; CaCl$_2$, 1 mM; KH$_2$PO$_4$, 1.2 mM; MgSO$_4$, 1.2 mM; NaHCO$_3$, 5 mM; glucose, 10 mM, pH 7.4. The buffer was supplemented with 1% MEM vitamins, 1% MEM amino acids and 0.001% aprotinin (pancreatic basic trypsin inhibitor). The tube was shaken by hand until the suspension appeared homogeneous (usually 5 to 6 minutes) 5 mL of the KRH, without collagenase and with 0.1% BSA, was added and the tube was centrifuged at 50×g for 35 seconds. The supernatant was discarded and 6 mL of the KRH was added to the cell pellet. Cells were triturated by a glass pipet and centrifuged at 50×g for 35 seconds. This wash procedure was repeated once. The cell pellet from the last centrifugation step was then resuspended in 15 mL of KRH containing 0.1% BSA. The contents were filtered through a dual nylon mesh, size 275 and 75 μm. The filtrate, containing the acini, was centrifuged at 50×g for 3 minutes. The acini were then resuspended in 5 mL of KRH-BSA buffer for 30 minutes at 37° C. under 100% O$_2$, with a change of fresh buffer at 15 minutes.

Amylase Assay

After the 30 minutes incubation time, the acini was resuspended in 100 volumes of KRH-BSA buffer, containing 3 μM phosphoramidon and 100 μM bestatin. While stirring, 400 μL of acini were added to 1.5 mL microcentrifuge tubes containing 50 μL of CCK-8, buffer, or test compounds. The final assay volume was 500 μL. Tubes were vortexed and placed in a 37° C. water bath, under 100% 0°, for 30 minutes. The tubes were then centrifuged at 10,000×g for 1 minute. Amylase activity in the supernatant and the cell pellet were separately determined after appropriate dilutions in 0.1% Triton X-100 ® (a non-ionic detergent available from Sigma Chemical Co.), 20 mM NaH$_2$PO$_4$, pH 7.4, by Abbott Amylase A-gent ® test using the Abbott Bichromatic Analyzer 200. The reference concentration for CCK-8 in determining the EC50's of the compounds of formula (I) was $3 \times 10^{-10}$M. The results of this assay are shown in Table 2.

TABLE 2

| Compound of Example | Amylase release EC50 (nM) |
|---|---|
| 3 | 3.3 |
| 6 | 72 |
| 9 | 24 |
| 16 | 40 |
| 17 | 3.0 |
| 21 | 30 |
| 24 | 1.0 |
| 33 | 0.4 |
| 56 | 4.2 |
| 60 | 0.5 |
| 61 | 0.6 |
| 64 | 7.6 |
| 65 | 9.1 |
| 66 | 15 |
| 67 | 16 |
| 69 | 3.3 |
| 71 | 3.7 |
| 72 | 1.0 |
| 73 | 1.0 |
| 74 | 1.0 |
| 76 | 0.6 |
| 79 | 0.3 |
| 80 | 0.7 |
| 83 | 1.7 |
| 84 | 0.24 |
| 85 | 1.0 |
| 86 | 0.7 |
| 89 | 0.21 |
| 93 | 0.30 |
| 96 | 6.2 |
| 97 | 5.6 |
| 98 | 1.1 |
| 100 | 1.05 |
| 103 | 1.3 |
| 104 | 8.3 |
| 105 | 1.3 |
| 107 | 5.0 |
| 108 | 3.4 |
| 112 | 3.0 |
| 113 | 8.7 |
| 114 | 3.0 |

TABLE 2-continued

| Amylase release | |
|---|---|
| Compound of Example | EC50 (nM) |
| 115 | 4.7 |
| 116 | 0.3 |
| 120 | 0.82 |

The results shown in Table 2 indicate that compounds of the invention are CCK agonists.

The ability of the compounds of the invention to increase the release of insulin in vivo can be demonstrated using the following protocol.

Measurement of Plasma Insulin in Mice Following Treatment With CCK-8 or a CCK Agonist Male mice, weighing from about 20 to about 30 g each, were used in all experiments. The animals were fed with laboratory lab chow and water ad libitum. CCK-8 or one the CCK agonist compounds of this invention was injected into the tail vein. Two minutes later, the animals were sacrificed and the blood was collected in 1.5 mL heparinized polypropylene tubes. The tubes were centrifuged at 10,000×g for 2 minutes. The insulin levels were determined in the supernatant, i.e., plasma, by radioimmuno assay (RIA) using kits obtained from Radioassay Systems Laboratory (Carson, CA.) or Novo Biolabs (Danbury, Conn.). The results of this assay are shown in Table 3 and are expressed as the percent increase in insulin secretion over insulin secretion observed in mice injected with a saline solution. Each dose was tested in at least six mice and the values presented are averages for the group of mice tested at each dose.

TABLE 3

| Effect of CCK Agonists On Insulin Secretion in Mice | | |
|---|---|---|
| Compound of Example | Dose (nmole/kg) | % Increase In Insulin Secretion Versus Saline Control |
| 24 | 10 | 41 |
|  | 100 | 112 |
| 33 | 100 | 238 |
| CCK-8 | 3 | 65 |
|  | 10 | 85 |
|  | 30 | 90 |
|  | 100 | 70 |

The results indicate that compounds of the invention stimulate insulin secretion in vivo.

The ability of the compounds of the invention to modulate central nervous system function in vivo can be demonstrated using the following protocol.

Behavioral Effect of CCK Agonists in Mice

Male Swiss CD-1 mice (Charles River) (22–27 g) are provided ample food (Purina Lab Chow) and water until the time of their injection with the test compounds.

I.P. (intraperitoneal) injections are given as a volume of 10.0 mL/kg using a 26 gauge, ⅜ inch needle. ICV injections were given by a free-hand method similar to that previously described (Haley and McCormick, Br. J. Pharmacol. Chemother., 1957, 12:12–15). The animals were placed on a slightly elevated metal grid and restrained by the thumb and forefinger at the level of the shoulders, thus immobilizing their heads. Injections were made with a 30 gauge needle with a "stop" consisting of a piece of tygon tubing to limit penetration of the needle to about 4.5 mm below the surface of the skin. The needle was inserted perpendicular to the skull at a midline point equidistant from each eye and an equal distance posterior from the level of the eyes such that the injection site and the two eyes form an equilateral triangle. The injection volume (5 ul) was expelled smoothly over a period of approximately 1 second.

Immediately after the injections the mice were placed in their cages and allowed a 15 minute recovery period prior to the beginning of behavioral observations.

For the behavioral observations, the mice were placed in clear plastic cages. Each cage measured 19×26×15 cm and contained a 60-tube polypropylene test tube rack place on end in the center of the cage to enhance exploratory activity. Observations were made every 30 seconds for a period of 30 minutes. Behavior was compared between drug treated mice and mice treated with an equal volume of carrier (usually 0.9% saline or 5% dimethylsulfoxide in water). Locomotion as reported here consisted of either floor locomotion or active climbing on the rack. Differences among groups were analyzed by Newman-Kewels analysis and a probability level of $p<0.05$ was accepted as significant. Each group tested consisted of 10 animals. The results of this test are shown in Table 4 and Table 5.

TABLE 4

| Suppression of Locomotor Activity in Mice Following IP Administration of CCK Agonists | |
|---|---|
| Compound of Example | Minimal Effective Dose |
| CCK-8 | 0.001 micromol/kg |
| 17 | 1.0 micromol/kg |
| 24 | 0.03 micromol/kg |
| 33 | 0.01 micromol/kg |

TABLE 5

| Suppression of Locomotor Activity in Mice Following ICV Administration of CCK Agonists | |
|---|---|
| Compound of Example | Minimal Effective Dose |
| CCK-8 | 3.0 nmol/mouse |
| 17 | 10.0 nmol/mouse |
| 24 | 30.0 nmol/mouse |
| 33 | 1.0 nmol/mouse |

The results of these tests indicate that compounds of the invention suppress locomotor activity and thus demonstrate pyschoactive properties.

The ability of the compounds of the invention to suppress feeding can be demonstrated using the following protocols.

Feeding Effect of CCK Agonists in Rats

Forty male, Sprague-Dawley rats were subjected to a 23 hour food deprivation schedule for four days. On the fifth day, the animals were divided into five equal groups based on their previous (4th day) food intake. Five minutes prior to their one hour free feeding (Purina Rat Chow), the animals were injected (i.p.) with either vehicle, CCK-8 or the compound of Example 17. The amount of food consumed was measured after subtraction of spillage. The results of this test are shown in Table 6.

TABLE 6

| Suppression of Feeding in Rats Following I.P. Administration of CCK Agonists | | |
|---|---|---|
| Compound | Dose | Mean Food Intake |
| vehicle | — | 9.40 grams |
| CCK-8 | 20 μg/kg | 6.56 grams |
| Example 17 | 1.0 mg/kg | 3.49 grams |

TABLE 6-continued

Suppression of Feeding in Rats Following
I.P. Administration of CCK Agonists

| Compound | Dose | Mean Food Intake |
|---|---|---|
| vehicle | — | 9.40 grams |
| Example 17 | 3.0 mg/kg | 1.80 grams |
| Example 17 | 9.0 mg/kg | 1.90 grams |

The results of this test indicate that compounds of the invention reduce food intake in rats.

Feeding Effects of Chronic Administration of CCK-8 and CCK Agonists in Rat

Adult male Sprague-Dawley rats, weighing approximately 250 g, were placed on a restricted diet. Rats were weighed every morning and were allowed access to a liquid diet (Ensure ®) for 60 minutes in the morning and 45 minutes in the late afternoon; intakes were recorded every 15 minutes. Following an 8-day diet acclimation period, the rats were weighed and injected with vehicle, CCK-8 (10 nmol/kg), or compound of Example 33 (1 or 10 nmol/kg) (ip). Six to 10 minutes later, the rats were presented with the diet, and intakes were recorded as usual. No injections were administered prior to the PM feeding. After 11 days of testing, half of the animals were sacrificed while the remaining rats were withdrawn from treatment and injected with vehicle for 4 days.

Figure 2:
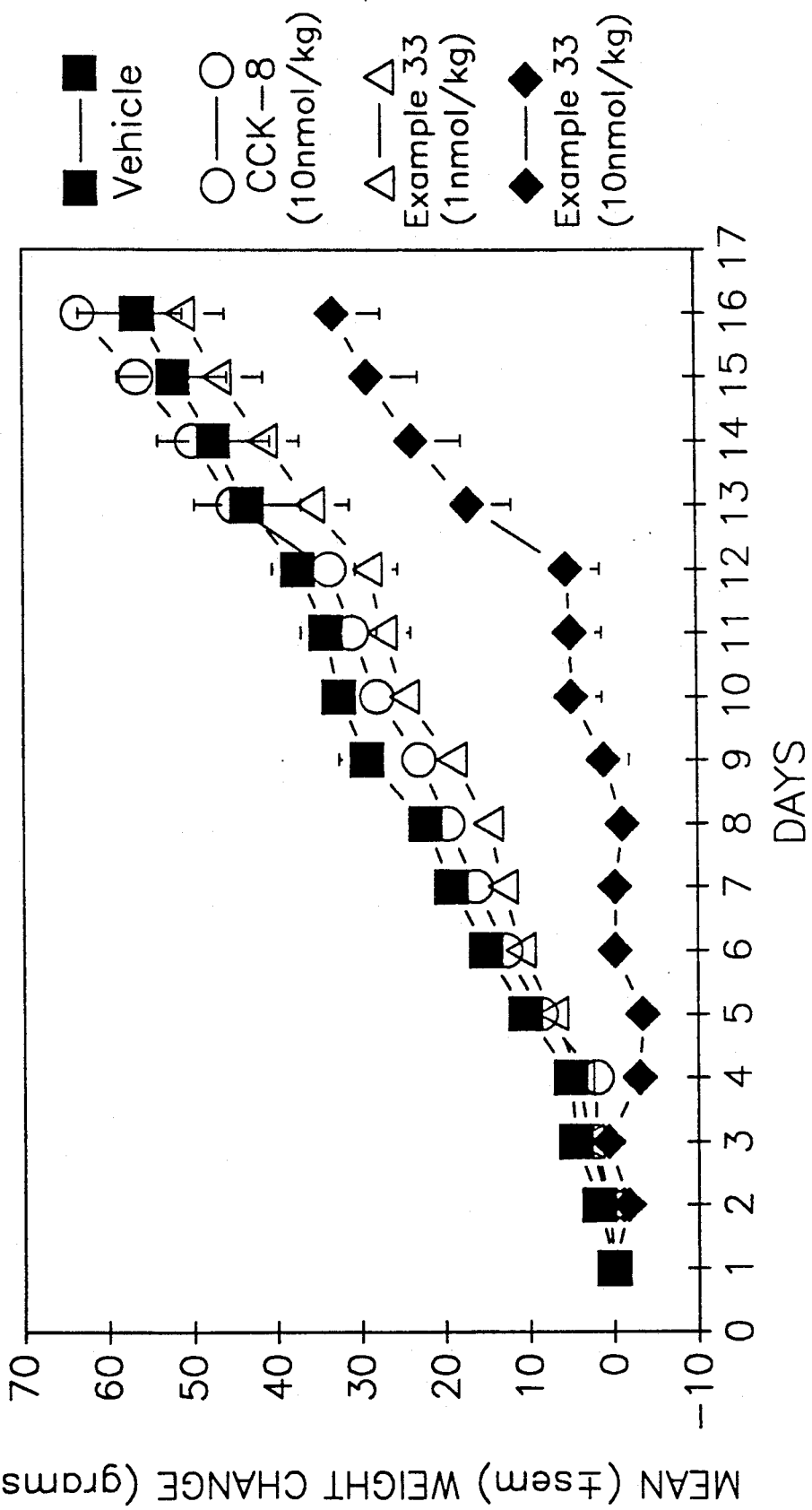
FIG. 2 is a plot comparing the mean change in body weight (grams) for rats after chronic administration of vehicle, CCK-8 (10 nmol/kg) or the compound of Example 33 (1 nmol/kg or 10 nmol/kg).

Graphs of AM food intakes and body weight changes for the various treatment groups are shown in FIGS. 1 and 2, respectively (there was no difference between groups in PM intakes so these data are not shown). Statistical analysis indicated that CCK-8 significantly reduced intakes on just the first and last treatment days and produced no significant effects on body weight gain. In contrast, the compound of Example 33 (1 nmol/kg) significantly reduced intakes on days 1,2,3,5,6,7 and 11 and animals in this groups showed significantly less weight gain than controls on days 7 and 8 of testing. Rats given the higher dose of the compound of Example 33 (10 nmol/kg) showed significantly reduced intakes on every drug injection day, and their rate of body weight gain also differed significantly from that of controls across the entire testing period.

The results of this test indicate that compounds of the invention reduce food intake when administered chronically.

Feeding Effects of Acute Administration of CCK Agonists in Rats

The experimental paradigm used in the above-mentioned chronic feeding studies was employed to establish dose reponses for CCK agonists of this invention on an acute (1 day) basis. Following an 8-day diet acclimation period, the rats were weighed and injected with vehicle. CCK-8 or test compound (see Table 7) at doses ranging from 1-1000 nmol/kg (i.p.). Six to ten minutes later, the rats were presented with the diet and intakes were recorded. No injections were administered prior to the P.M. feeding. Mean A.M. intakes as a percent of control were plotted versus log dose (nm/kg) to establish the dose response curve. All test compounds reduced the fool intake in a dose dependent manner. The dose required to decrease mean A.M. food intake by 50% (ED50) was determined for each compound and these results are presented in Table 7.

TABLE 7

Suppression of Feeding (Liquid Diet) in Rats Following
I.P. Administration of CCK Agonists

| Example Number | ED50 | ED25 |
|---|---|---|
| 17 | 300 | |
| 33 | 4.2 | 0.9 |
| 55 | 6.8 | 1.2 |
| 61 | 2.6 | 0.6 |
| 63 | 193 | 4.0 |
| 66 | 12.3 | 1.9 |
| 67 | 38 | 7.7 |
| 69 | 7.0 | 0.7 |
| 80 | 3.7 | 0.6 |
| 81 | 1.52 | 0.42 |
| 83 | 30 | 3.6 |
| 85 | 11 | 5 |
| 86 | 1.3 | 0.27 |
| 87 | 6.7 | 1.0 |
| 88A | 3.75 | 1.1 |
| 89 | 64.4 | 4.2 |
| 90 | 2.9 | 0.3 |
| 94 | 15.6 | 2.0 |
| 96 | 10.9 | 3.2 |
| 97 | 9.4 | 1.8 |
| 100 | 6.9 | 1.5 |
| 106 | 58.5 | 6.9 |
| 107 | 26.1 | 3.7 |
| 112 | 51 | 7.8 |
| 116 | 7.1 | 1.8 |
| 120 | 12.3 | 2.1 |

The results of this test indicate that compounds of the invention reduce food intake in rats when administered acutely.

The ability of the compounds of the invention to stimulate gallbladder contraction can be demonstrated using the following protocol.

Guinea Pig Gallbladder Contraction

Gallbladders were obtained from male guinea pigs (250-300 gm). The bile was emptied by a small incision and the gallbladder was suspended in an organ bath. The tissue was maintained at 37° C., suspended in Krebs-Ringer buffer (mM: NaCl, 118; KCl, 4.7; $CaCl_2$, 2.5; $MgCl_2$, 1.2; $NaH_2PO_4$, 1.2; $NaHCO_3$, 25; choline chloride, 30 mM; glucose, 11) and bubbled with 95% $O_2$-5% $CO_2$. Isometric contractions were recorded with a Grass polygraph. Baseline tension was set at 0.3 grams. After equilibration for approximately 30 minutes, CCK-8 (20 nM) was introduced and tensions were recorded. After reaching maximal contractions (about 5 minutes), the drug was washed out by overflow. The CCK-8 addition was repeated twice to ensure constant force of contraction. Then the compound of Example 33 was introduced and tensions were recorded.

The EC50 for contraction was 5.9 nM for CCK-8 and 10 nM for the compound of Example 33. (EC50 is the concentration of test compound required to produce 50% of the maximal contraction caused by the test compound). The maximal force of contraction of the compound of Example 33 was 95% higher than that of CCK-8.

The ability of the compounds of the invention to prevent or reduce gallstone formation and to stimulate gallbladder emptying can be demonstrated using the methods outlined in Poston, et al., *Gastroenterology*, 1980, 98:993-999, which is incorporated herein by reference.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The pharmaceutically acceptable salts of the present invention can be synthesized from the compounds of formula (I) which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The pharmaceutically acceptable salts of the acids of formula (I) are also readily prepared by conventional procedures such as treating an acid of formula I with an appropriate amount of a base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, trimethylamine, piperidine, pyrrolidine, benzylamine and the like, or a quaternary ammonium hydroxide such as tetramethylammonium hydroxide and the like.

When a compound of formula (I) is used as an agonist of CCK in a human subject, the total daily dose administered in single or divided doses may be in amounts, for example, from 0.001 to 1000 mg a day and more usually 1 to 1000 mg. Dosage unit compositions may contain such amounts of submultiples thereof to make up the daily dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of excretion, drug combination, and the severity of the particular disease undergoing therapy.

The compounds of the present invention may be administered sublingually, orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsion, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the tetrapeptide of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of formula

wherein,
X is selected from the group consisting of

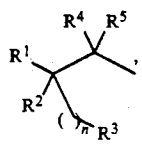

(A)

wherein n is 1 or 2;
R¹ is selected from the group consisting of
(1) hydrogen,
(2) hydroxy,
(3) halogen,
(4) $C_1$-$C_4$-alkyl,
(5) $C_1$-$C_4$-alkoxy,
(6) halo-$C_1$-$C_4$-alkyl,
(7) $C_1$-$C_4$-alkanoyl,
(8) $C_1$-$C_4$-alkoxycarbonyl,
(9) $C_1$-$C_4$-alkoxycarbonyloxy,
(10) aminocarbonyl,
(11) $C_1$-$C_4$-alkylaminocarbonyl,
(12) cyano,
(13) R⁶HN— wherein
R⁶ is selected from the group consisting of
(a) hydrogen,
(b) $C_1$-$C_6$-alkyl,
(c) —C(O)—R⁷, wherein
R⁷ is selected from the group consisting of
(i) $C_1$-$C_6$-alkyl, wherein the alkyl group may be substituted with from 1 to 3 halogens or 1 substituent selected from carboxy, $C_1$-$C_4$-alkoxycarbonyl, aminocarbonyl, $C_1$-$C_4$-alkylaminocarbonyl, ($C_1$-$C_4$-alkyl)₂-aminocarbonyl and cyano,
(ii) cyclo-$C_3$-$C_{10}$-alkyl,
(iii) $C_6$-$C_{10}$-aryl unsubstituted or substituted with 1 to 3 substituents selected from halogen, hydroxy and $C_1$-$C_4$-alkoxy,
(iv) $C_7$-$C_{14}$-arylalkyl unsubstituted or substituted with 1 to 3 substituents selected from halogen, hydroxy and $C_1$-$C_4$-alkoxy,
(v) diphenyl-($C_1$-$C_4$-alkyl),
(vi) $C_1$-$C_6$-alkoxy, wherein the alkyl group may be substituted with from 1 to 3 halogens or with a substituent selected from carboxy, $C_1$-$C_4$-alkoxycarbonyl, aminocarbonyl, $C_1$-$C_4$-alkylaminocarbonyl, ($C_1$-$C_4$)₂-alkylaminocarbonyl, hydroxy-$C_1$-$C_4$-alkylaminocarbonyl, morpholinocarbonyl, thiomorpholinocarbonyl, piperidinylcarbonyl, 4-methyl-1-piperazinylcarbonyl, hydroxy or $C_1$-$C_4$-alkoxy,
(vii) cyclo-$C_3$-$C_{10}$-alkoxy,
(viii) $C_6$-$C_{10}$-aryl unsubstituted or substituted with 1 to 3 substituents selected from halogen, hydroxy and $C_1$-$C_4$-alkoxy,
(ix) $C_7$-$C_{14}$-arylalkyl, wherein the aryl may be substituted with 1 to 3 substituents selected from halogen, hydroxy and $C_1$-$C_4$-alkoxy,
(x) $C_1$-$C_6$-alkylamino,
(xi) cyclo-$C_3$-$C_{10}$-alkylamino,
(xii) $C_6$-$C_{10}$-arylamino, wherein the aryl may be substituted with 1 to 3 substituents selected from halogen, hydroxy and $C_1$-$C_4$-alkoxy, and
(xiii) $C_6$-$C_{10}$-aryl-$C_1$-$C_4$-alkylamino, wherein the aryl may be substituted with 1 to 3 substituents selected from halogen, hydroxy and $C_1$-$C_4$-alkoxy, and
(d) —S(O)₂R⁸, wherein
R⁸ is selected from
(i) $C_1$-$C_4$-alkyl, unsubstituted or mono-, di- or trisubstituted substituted with from 1 to 3 halogens,
(ii) $C_6$-$C_{10}$-aryl, and
(iii) $C_7$-$C_{14}$-arylalkyl;
R² is hydrogen or $C_1$-$C_4$-alkyl;
R³ is bicyclic carbocycle or bicyclic heterocycle; and
R⁴ and R⁵ are each hydrogen or taken together are =O; and

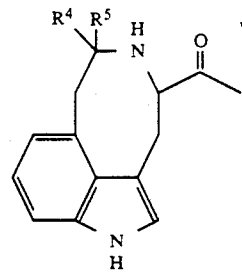

(B)

wherein R⁴ and R⁵ are as defined above, and the indole ring is unsubstituted or substituted with a substituent selected from the group consisting of hydroxy, halo, amino, $C_1$-$C_4$-alkylamino, ($C_1$-$C_4$)₂-alkylamino, $C_1$-$C_4$-alkoxy, thio-$C_1$-$C_4$-alkoxy, carboxy, $C_1$-$C_4$-alkoxycarbonyl, $C_1$-$C_4$-alkyl, $C_3$-$C_8$-cycloalkyl, —OSO₃H and halo-$C_1$-$C_4$-alkyl;
Y is selected from

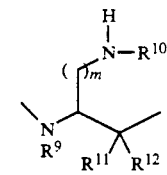

(A)

wherein m is 3, 4 or 5;
R⁹ is hydrogen or $C_1$-$C_4$-alkyl;
R¹⁰ is selected from the group consisting of

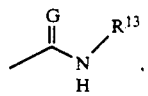

(1)

wherein G is O or S; and
R¹³ is selected from the group consisting of
(i) $C_1$-$C_6$-alkyl,
(ii) $C_2$-$C_6$-alkenyl,
(iii) cyclo-$C_3$-$C_{10}$-alkyl
(iv) monocyclic heterocycle, (v) bicyclic heterocycle,
(vi) $C_6$-$C_{10}$-aryl, and
(vii) mono- or disubstituted $C_6$-$C_{10}$-aryl wherein the 1 or 2 substituents on the aryl are selected from the group consisting of
(a) hydroxy,
(b) halogen,
(c) —$OSO_3H$,
(d) nitro,
(e) cyano,
(f) amino,
(g) $C_1$-$C_4$-alkylamino,
(h) di-$C_1$-$C_4$-alkylamino,
(i) $C_1$-$C_4$-alkyl,
(j) halo-$C_1$-$C_4$-alkyl,
(k) $C_1$-$C_4$-alkoxy,
(l) $C_1$-$C_4$-alkanoyl,
(m) $C_1$-$C_4$-alkoxycarbonyl, and
(n) phenoxy;
(2) —C(O)—$(CH_2)_p$-$R^{14}$, wherein p is 0, 1 or 2 and
$R^{14}$ is selected from the group consisting of
(i) cyclo-$C_3$-$C_{10}$-alkyl,
(ii) monocyclic heterocycle,
(iii) bicyclic heterocycle,
(iv) $C_6$-$C_{10}$-aryl, and
(v) mono- or disubstituted $C_6$-$C_{10}$-aryl wherein the 1 or 2 substituents on the aryl are selected from the group consisting of
(a) hydroxy,
(b) halogen,
(c) —$OSO_3H$,
(d) nitro,
(e) cyano,
(f) amino,
(g) $C_1$-$C_4$-alkylamino,
(h) di-$C_1$-$C_4$-alkylamino,
(i) $C_1$-$C_4$-alkyl,
(j) halo-$C_1$-$C_4$-alkyl,
(k) $C_1$-$C_4$-alkoxy,
(l) $C_1$-$C_4$-alkanoyl,
(m) $C_1$-$C_4$-alkoxycarbonyl, and
(n) phenoxy;
(3) —C(O)—$(CH_2)_q$—$CR^{15}$=CH—$R^{14}$, wherein $R^{14}$ is as defined above,
q is 0 or 1, and
$R^{15}$ is hydrogen or cyano; and
$R^{11}$ and $R^{12}$ are each hydrogen or taken together are =O, and

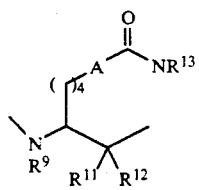 (B)

wherein A is —O— or —$CH_2$—; and
$R^9$, $R^{11}$, $R^{12}$ and $R^{13}$ are as independently defined above;
Z is

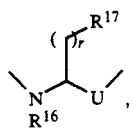

wherein U is —C(O)—, —$CH_2$, or —$CH_2C(O)$—;
r is 1 when U is —C(O)— or —$CH_2$— and r is 0 when U is —$CH_2C(O)$—;
$R^{16}$ is hydrogen or $C_1$-$C_4$ alkyl; and
$R^{17}$ is selected from
(A) —COOH,
(B) prodrug ester groups of the formula:

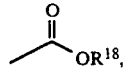

wherein $R^{18}$ is selected from
(1) $C_1$-$C_6$-alkyl,
(2) $C_2$-$C_6$-alkenyl,
(3) cyclo-$C_3$-$C_{10}$-alkyl,
(4) —$(CH_2)_t$—$NR^{19}R^{20}$ wherein t is 1, 2 or 3, and $R^{19}$ and $R^{20}$ are independently selected from hydrogen, $C_1$-$C_4$-alkyl, $C_2$-$C_4$-alkenyl and hydroxy-$C_1$-$C_4$-alkyl, or $R^{20}$ and $R^{21}$ are taken together with the nitrogen atom to which they are attached to form

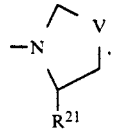

wherein V is —$CH_2$—, —$CH_2CH_2$—, —$CH_2$—O—, —$CH_2$—S— or —$CH_2$—N($CH_3$)—, and $R^{21}$ is hydrogen or carboxy, and
(5) —$(CH_2)_t$—$OR^{22}$ wherein t is as defined above and $R^{22}$ is hydrogen or $C_1$-$C_4$-alkyl,
(6) —$CH_2$—C(O)$NR^{19}R^{20}$, wherein $R^{19}$ and $R^{20}$ are as independently defined above,
(7) —$CH_2$—C(O)$OR^{19}$, wherein $R^{19}$ is selected from hydrogen, $C_1$-$C_4$-alkyl, $C_2$-$C_4$-alkenyl and hydroxy-$C_1$-$C_4$-alkyl, and
(8) benzyl; and
(C) 5-tetrazolyl; and
Q is

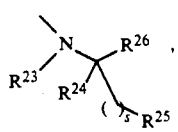

wherein s is 1 or 2,
$R^{23}$ is hydrogen or $C_1$-$C_4$-alkyl,
$R^{24}$ is hydrogen or methyl, or
$R^{23}$ and $R^{24}$ taken together form —$CH_2CH_2CH_2$—
$R^{25}$ is selected from (1) $C_6$-$C_{10}$-aryl, (2) monocyclic or bicyclic heterocycle, and (3) cyclo-$C_3$-$C_{10}$-alkyl, and
$R^{26}$ is selected from the group consisting of

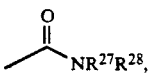

(1)

wherein $R^{27}$ and $R^{28}$ are independently hydrogen or methyl, (2) —C(O)O—$C_1$-$C_4$-alkyl,
(3) —$CH_2OH$,
(4) —C≡N,
(5) —C≡CH, and
(6) C(O)NHNH$_2$.

or a pharmaceutically-acceptable salt thereof.

2. A compound according to claim 1 having the formula:

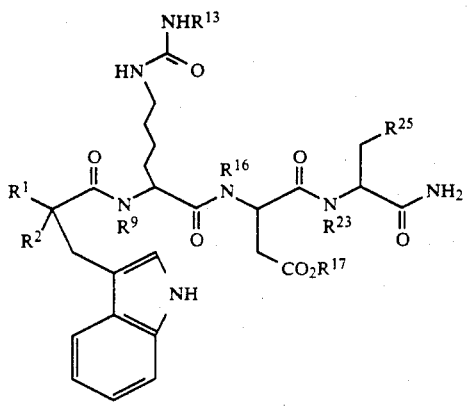

wherein $R^9$, $R^{17}$ and $R^{23}$ are independently hydrogen or methyl.

3. A compound according to claim 1 having the formula:

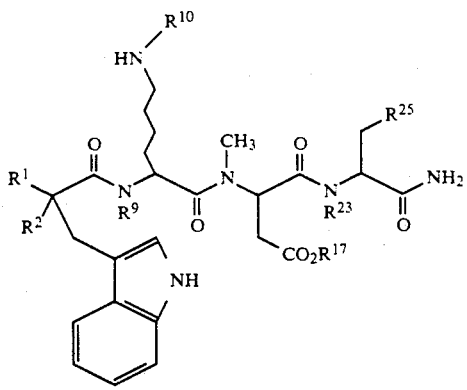

wherein $R^{10}$ is selected from options 2 and 3 in itts definition in claim 1 and $R^9$ and $R^{23}$ are independently hydrogen or methyl.

4. A compound selected from the group consisting of:
t-BOC-Trp-Lys(ε-N-(2-methylphenyl)aminocarbonyl)-Asp-PheNH$_2$;
t-BOC-Trp-Lys(ε-N-(2-methylphenyl)aminocarbonyl)-Asp-(NMe)PheNH$_2$;
t-BOC-Trp-Lys(ε-N-(2-methylphenyl)aminocarbonyl)-(NMe)Asp-PheNM$_2$;
t-BOC-Trp-Lys(ε-N-(2-methylphenyl)aminocarbonyl)-(NMe)Asp-(NMe)PheNH$_2$;
3-(3-Indolyl)propionyl-Lys(ε-N-(2-methylphenyl)aminocarbonyl)-(NMe)Asp-PheNH$_2$;
t-BOC-Trp-Lys-(ε-N-3-(2-thienyl)acrylyl)-(NMe)Asp-PheNH$_2$;
t-BOC-Trp-Lys-(ε-N-3-(3-pyridyl)acrylyl)-(NMe)Asp-PheNH$_2$;
t-BOC-Trp-Lys-(ε-N-3-(3-pyridyl)acrylyl-(NMe)Asp-(NMe)PheNH$_2$;
(NMe)Trp-Lys(ε-N-(2-methylphenyl)aminocarbonyl)-(NMe)Asp-PheNH$_2$;
(3-(3-Indolyl)propionyl-Lys(ε-N-(2-methylphenyl)aminocarbonyl)-Asp-(NMe)PheNH$_2$;
t-BOC-Trp-Lys(ε-N-(4-hydroxycinnamoyl))-(NMe)Asp-PheNH$_2$;
t-BOC-Trp-Lys(ε-N-(4-hydoxycinnamoyl))-(NMe)Asp-(NMe)PheNH$_2$;
t-BOC-Trp-Lys(ε-N-(6-hydroxy-β-naphthoyl)-(NMe)Asp-(NMe)PheNH$_2$;
1-Adamantyloxycarbonyl-Trp-Lys(ε-N-(2-methylphenyl)aminocarbonyl)-Asp-(NMe)PheNH$_2$;
Benzyloxycarbonyl-Trp-Lys(ε-N-(2-methylphenyl)aminocarbonyl)-Asp-(NMe)PheNH$_2$;
Isobutyloxycarbonyl-Trp-Lys(ε-N-(2-methylphenyl)aminocarbonyl)-Asp-(NMe)PheNH$_2$;
Isopropyloxycarbonyl-Trp-Lys(ε-N-(2-methylphenyl)aminocarbonyl)-Asp-(NMe)PheNH$_2$;
Methoxycarbonyl-Trp-Lys(ε-N-(2-methylphenyl)aminocarbonyl)-Asp-(NMe)PheNH$_2$;
Methoxycarbonyl-Trp-Lys(ε-N-(2-methylphenyl)aminocarbonyl)-(NMe)Asp-PheNH$_2$;
t-Butylaminocarbonyl-Trp-Lys(ε-N-(2-methylphenyl)aminocarbonyl)-Asp-(NMe)PheNH$_2$;
Methylaminocarbonyl-Trp-Lys(ε-N-(2-methylphenyl)aminocarbonyl)-Asp-(NMe)PheNH$_2$;
Phenylaminocarbonyl-Trp-Lys(ε-N-(2-methylphenyl)aminocarbonyl)-Asp-(NMe)PheNH$_2$;
Acetyl-Trp-Lys(ε-N-(2-methylphenyl)aminocarbonyl)-Asp-(NMe)PheNH$_2$;
Acetyl-Trp-Lys(ε-N-(2-methylphenyl)aminocarbonyl)-(NMe)Asp-PheNH$_2$;
t-Butylacetyl-Trp-Lys(ε-N-(2-methylphenyl)aminocarbonyl)-Asp-(NMe)PheNH$_2$;
Trifluoroacetyl-Trp-Lys(ε-N-(2-methylphenyl)aminocarbonyl)-(NMe)Asp-PheNH$_2$;
t-Butylacetyl-Trp-Lys(ε-N-(2-methylphenyl)aminocarbonyl)-(NMe)Asp-PheNH$_2$;
Benzoyl-Trp-Lys(ε-N-(2-methylphenyl)aminocarbonyl)-Asp-(NMe)PheNH$_2$;
Benzoyl-Trp-Lys(ε-N-(2-methylphenyl)aminocarbonyl)-(NMe)Asp-PheNH$_2$;
(3,3-Diphenylpropionyl)-Trp-Lys(ε-N-(2-methylphenyl)aminocarbonyl)-Asp-(NMe)PheNH$_2$;
(3-Carboxylpropionyl)-Trp-Lys(ε-N-(2-methylphenyl)aminocarbonyl)-Asp-(NMe)PheNH$_2$;
t-BOC-D,L-(α-methyl)Trp-Lys(ε-N-(2-methylphenyl)aminocarbonyl)-Asp-PheNH$_2$;
D,L-(α-Methyl)Trp-Lys(ε-N-(2-methylphenyl)aminocarbonyl)-Asp-PheNH$_2$;
(α-Methyl)-L-Trp-Lys(ε-N-(2-methylphenyl)aminocarbonyl)-Asp-(NMe)PheNH$_2$;
(α-Methyl)-L-Trp-Lys(ε-N-(2-methylphenyl)aminocarbonyl)-(NMe)Asp-PheNH$_2$;
(NMe)Trp-Lys(ε-N-(2-methylphenyl)aminocarbonyl)-(NMe)Asp-α-NalNH$_2$;
(NMe)Trp-Lys(ε-N-(2-methylphenyl)aminocarbonyl)-Asp-(NMe)PheNH$_2$;
(3-(3-Indolyl)propionyl)-Lys(ε-N-(2-methylphenyl)aminocarbonyl)-(NMe)Asp-(NMe)PheNH$_2$;
(3-(3-Indolyl)propionyl)-Lys(ε-N-(2-methylphenyl)aminocarbonyl)-(NMe)Asp-α-NalNH$_2$;

(2-Methyl-3-(3-indolyl)propionyl)-Lys(ε-N-(2-methylphenyl)aminocarbonyl)-Asp-(NMe)-PheNH₂;

(2-Cyano-3-(3-indolyl)propionyl)-Lys(ε-N-(2-methylphenyl)aminocarbonyl)-Asp-(NMe)-PheNH₂;

(2-Carboethoxy-2-methyl-3-(3-indolyl)propionyl)-Lys(ε-N-(2-methylphenyl)amino-carbonyl)-Asp-(NMe)PheNH₂;

(2-Fluoro-3-(3-indolyl)propionyl)-Lys(ε-N-(2-methylphenyl)aminocarbonyl)-Asp-(NMe)-PheNH₂;

(2-Fluoro-3-(3-indolyl)propionyl)-Lys(ε-N-(2-methylphenyl)aminocarbonyl)-(NMe)Asp-PheNH₂;

Ctp-Lys(ε-N-(2-methylphenyl)aminocarbonyl)-Asp-(NMe)PheNH₂;

t-BOC-Trp-Nle(6-((2-methylphenyl)aminocarbonyl)oxy)-Asp-(NMe)PheNH₂;

t-BOC-Trp-Lys(ε-N-(2-methylphenyl)aminocarbonyl)-Asp-ChaNH₂; Asp(OBn)-(NMe)PheNH₂;

t-BOC-Trp-Lys(ε-N-(2-methylphenyl)aminocarbonyl)-Asp(β-2-(1-morpholino)ethyl)-(NMe)PheNH₂;

α-Methyl-Trp-Lys((ε-N-(2-methylphenyl)aminocarbonyl)-(NMe)Asp(OMe)-PheNH₂;

Methoxycarbonyl-Trp-Lys((ε-N-3-(thienyl)acrylyl)-(NMe)Asp-(NMe)PheNH₂;

Methoxycarbonyl-Trp-Lys((ε-N-3-(thienyl)acrylyl)-(NMe)Asp-PheNH₂;

t-BOC-Trp-Lys(3-quinolinecarbonyl)-(NMe)Asp-PheNH₂;

t-BOC-Trp-Lys(ε-N-(2-thienylacryloyl)-(NMe)Asp-(NMe)PheNH₂;

Propionylyl-Trp-Lys(ε-N-(2-methylphenyl)aminocarbonyl)-Asp-(NMe)PheNH₂; and

Isobutyloxycarbonyl-Trp-Lys(ε-N-(2-methylphenyl)aminocarbonyl)-(NMe)Asp-PheNH₂, or a pharmaceutically-acceptable salt thereof.

5. A CCK agonist composition comprising a pharmaceutically-acceptable carrier and a therapeutically-effective amount of a compound according to claim 1.

6. A method for mimicking the effects of CCK on CCK Type-A receptors comprising administering to a mammalian host in need of such treatment a therapeutically-effective amount of a compound of claim 1.

7. A method for treating appetite disorders comprising administering to a mammalian host in need of such treatment a therapeutically-effective amount of a compound of claim 1.

8. A method for stimulating insulin secretion comprising administering to a mammalian host in need of such treatment a therapeutically-effective amount of a compound of claim 1.

9. A method for preventing or reducing gallstone formation comprising administering to a mammalian host in need of such treatment a therapeutically-effective amount of a compound of claim 1.

10. A method for stimulating gallbladder emptying comprising administering to a mammalian host in need of such treatment a therapeutically-effective amount of a compound of claim 1.

* * * * *